(12) United States Patent
Egawa et al.

(10) Patent No.: US 7,696,348 B2
(45) Date of Patent: Apr. 13, 2010

(54) QUINOXALINE DERIVATIVE, AND LIGHT-EMITTING ELEMENT, LIGHT-EMITTING DEVICE, ELECTRONIC DEVICE USING THE QUINOXALINE DERIVATIVE

(75) Inventors: Masakazu Egawa, Tochigi (JP); Sachiko Kawakami, Kanagawa (JP); Harue Nakashima, Kanagawa (JP); Nobuharu Ohsawa, Kanagawa (JP); Satoshi Seo, Kanagawa (JP); Ryoji Nomura, Kanagawa (JP)

(73) Assignee: Semiconductor Energy Laboratories Co., Ltd., Kanagawa-Ken (JP)

( * ) Notice: Subject to any disclaimer, the term of this patent is extended or adjusted under 35 U.S.C. 154(b) by 468 days.

(21) Appl. No.: 11/723,385

(22) Filed: Mar. 19, 2007

(65) Prior Publication Data

US 2007/0222374 A1 Sep. 27, 2007

(30) Foreign Application Priority Data

Mar. 21, 2006 (JP) .............................. 2006-077900

(51) Int. Cl.
 *C07D 241/36* (2006.01)
(52) U.S. Cl. ...................................... 544/353; 548/440
(58) Field of Classification Search .................. 544/353
 See application file for complete search history.

(56) References Cited

U.S. PATENT DOCUMENTS

| | | | |
|---|---|---|---|
| 4,760,006 | A | 7/1988 | Pawlowski |
| 6,541,129 | B1 | 4/2003 | Kawamura et al. |
| 7,034,026 | B2 | 4/2006 | Barnett et al. |
| 7,074,534 | B2 | 7/2006 | Herron et al. |
| 2005/0186446 | A1 | 8/2005 | Shitagaki et al. |
| 2007/0059553 | A1 | 3/2007 | Egawa et al. |
| 2008/0079354 | A1 | 4/2008 | Egawa et al. |

FOREIGN PATENT DOCUMENTS

| | | |
|---|---|---|
| JP | 1057261 A | 8/1989 |
| JP | 2003-040873 | 2/2003 |
| JP | 2006-016384 | 1/2006 |
| WO | WO 2004/094389 A1 | 11/2004 |
| WO | WO-2007/032258 A1 | 3/2007 |

OTHER PUBLICATIONS

K.R. Justin Thomas et al., "Quinoxalines Incorporating Triarylamines: Potential Electroluminescent Materials with Tunable Emission Characteristics", Chem. Mater. 2002, 14, pp. 2796-2802.

C.W. Tang et al., "Organic electroluminescent diodes", *Appl. Phys. Lett.*, 51 (12) Sep. 21, 1987, pp. 913-915.

C. Adachi et al., "Electroluminescence in Organic Films with Three-Layer Structure", *Japanese Journal of Applied Physics*, vol. 27, No. 2, Feb. 1988, pp. L269-L271.

Thomas, K.R. Justin, et al. "Green and Yellow Electroluminescent Dipolar Carbazole Derivatives: Features and Benefits of Electron-Withdrawing Segments", *Chemical Matter 2002*, 14, pp. 3852-3859.

International Search Report (Application No. PCT/JP2007/055335; PCT9509) Dated: Apr. 17, 2007.

Huang, T. et al., "Quinoxalines Incorporating Triarylamines: Dipolor Electrolumininescent Materials With Tunable Emission Characteristics", Journal of the Chinese Chemical Society, 2006, 53, (1), 233-242.

Burrows, H. et al., "Fluorescence Study of Dehydroabietic Acid-Based Bipolar Arylamine-quinoxalines", Journal of Fluorescence, vol. 16, No. 2, Mar. 2006, 227-231.

Written Opinion (Application No. PCT/JP2007/055335; PCT9509) dated Apr. 17, 2007.

*Primary Examiner*—James O Wilson
*Assistant Examiner*—Brian McDowell
(74) *Attorney, Agent, or Firm*—Nixon Peabody LLP; Jeffrey L. Costellia

(57) ABSTRACT

It is an object to provide a novel bipolar organic compound. In particular, it is an object to provide a bipolar organic compound excellent in thermal stability. Further, it is another object to provide a bipolar organic compound which is electrochemically stable. A quinoxaline derivative represented by a general formula (1) is provided. Further, since the quinoxaline derivative represented by the general formula (1) is bipolar, the use of the quinoxaline derivative of the present invention allows fabrication of a light-emitting element and a light-emitting device with a low driving voltage and low power consumption. Furthermore, a light-emitting element with high luminous efficiency can be obtained.

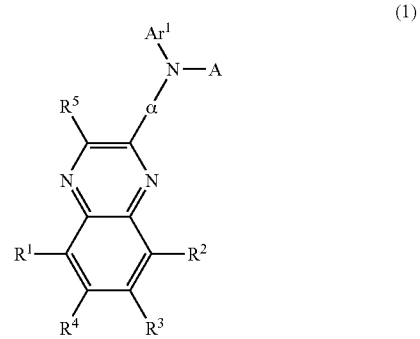

(1)

5 Claims, 76 Drawing Sheets

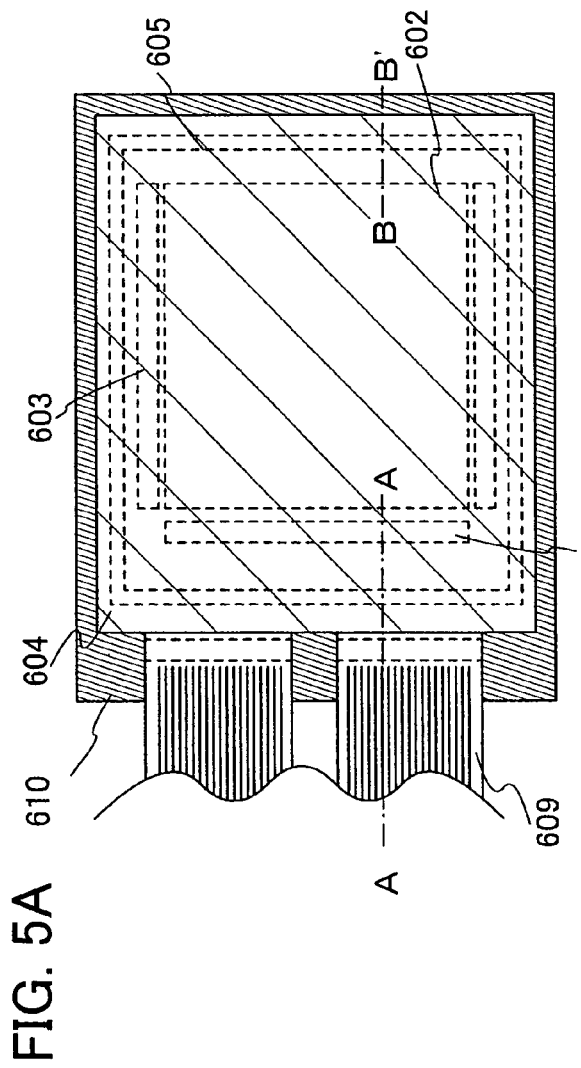
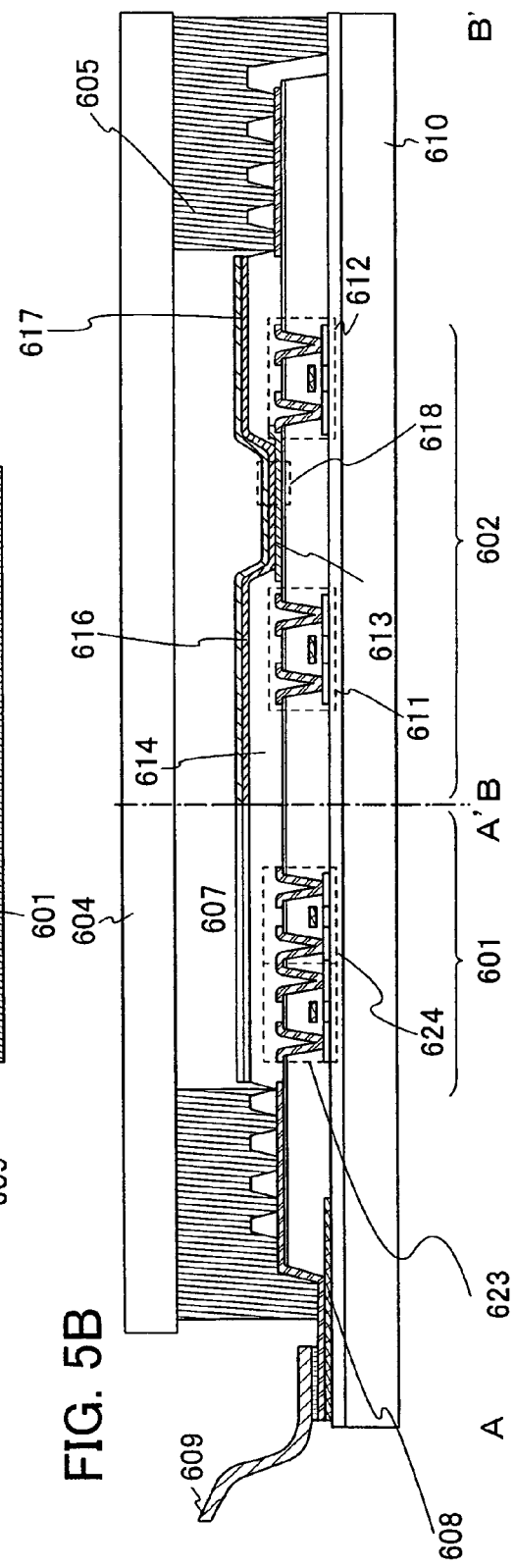
FIG. 5A
FIG. 5B

QUINOXALINE DERIVATIVE, AND LIGHT-EMITTING ELEMENT, LIGHT-EMITTING DEVICE, ELECTRONIC DEVICE USING THE QUINOXALINE DERIVATIVE

TECHNICAL FIELD

The present invention relates to a quinoxaline derivative, and a light-emitting element, a light-emitting device, an electronic device each of which uses the quinoxaline derivative.

BACKGROUND ART

Organic compounds can take various structures compared with inorganic compounds, and have possibility to provide materials having various functions by appropriate molecular design. Owing to these advantages, photo electronics and electronics which utilize functional organic materials have been attracting attention in recent years.

For example, a solar cell, a light-emitting element, an organic transistor, and the like are exemplified as an electronic device utilizing an organic compound as a functional material. These are devices taking advantage of electric properties and optical properties of the organic compound. Among them, in particular, a light-emitting element has been making remarkable development.

It is considered that light emission mechanism of a light-emitting element is as follows: when a voltage is applied between a pair of electrodes which interpose a light emitting layer, electrons injected from a cathode and holes injected from an anode are recombined in the light emission center of the light emitting layer to form a molecular exciton, and energy is released to emit light when the molecular exciton relaxes to a ground state. As excited states, a singlet excited state and a triplet excited state are known, and light emission is considered to be possible from any of these excited states.

Such a light-emitting element has a lot of problems which depend on the organic materials. In order to solve these problems, improvement of an element structure, development of a material, and the like have been carried out.

As the most basic structure of a light-emitting element, the following structure is known: a hole transporting layer, formed by an organic compound having a hole transporting property, and an electron transporting light emitting layer, formed by an organic compound having an electron transporting property, are stacked to form a thin film of approximately 100 nm thickness in total, and this thin film is interposed between electrodes (see Non-Patent Document 1, for example).

When a voltage is applied to the light-emitting element described in Non-Patent Document 1, light emission can be obtained from organic compounds having a light-emitting property and an electron transporting property.

Further, in the light-emitting element described in Non-Patent Document 1, functions are appropriately separated. That is, a hole transporting layer transports holes, and an electron transporting layer transports electrons and emits light. However, various interactions (for example, formation of exciplex, and the like) frequently occur at an interface of stacked layers. As a result, change of emission spectrum and/or decrease in luminous efficiency may take place.

In order to suppress change of emission spectrum and decrease in luminous efficiency which are caused by the interaction at an interface, a light-emitting element was developed in which functions are further separated. For example, a light-emitting element has been proposed, in which a light emitting layer is interposed between a hole transporting layer and an electron transporting layer (see Non-Patent Document 2, for example).

In such a light-emitting element described in Non-Patent Document 2, it is preferred that, in order to more effectively suppress the interaction occurring at an interface, a light emitting layer is fabricated by using a bipolar organic compound which has both an electron transporting property and a hole transporting property.

However, most organic compounds are monopolar materials having either a hole transporting property or an electron transporting property.

Therefore, a bipolar organic compound having both an electron transporting property and a hole transporting property has been required to be developed.

In Patent Document 1, a bipolar quinoxaline derivative is described. However, since their performances such as thermal stability are not satisfactory, bipolar organic compounds having high thermal stability have been required to be developed.

[Non-Patent Document 1]
C. W. Tang et al., Applied Physics Letters, vol. 51, No. 12, 913-915 (1987)

[Non-Patent Document 2]
Chihaya Adachi et al., Japanese Journal of Applied Physics, vol. 27, No. 2, L269-L271 (1988)

[Patent Document 1]
PCT International Publication No. 2004/094389

DISCLOSURE OF INVENTION

In view of the aforementioned problems, it is an object of the present invention to provide a new bipolar organic compound, in particular, a bipolar organic compound having excellent thermal stability. Further, it is another object to provide a bipolar organic compound which is electrochemically stable.

Further, it is another object to provide a light-emitting element and a light-emitting device having low driving voltage and power consumption by using the bipolar organic compound of the present invention. In addition, it is another object to provide a light-emitting element and a light-emitting device having a long lifetime by using the bipolar organic compound of the present invention.

It is still another object to provide a long-life electronic device with low power consumption and high thermal stability by using the bipolar organic compound of the present invention.

One feature of the present invention is a quinoxaline derivative represented by a general formula (1).

formula [1]

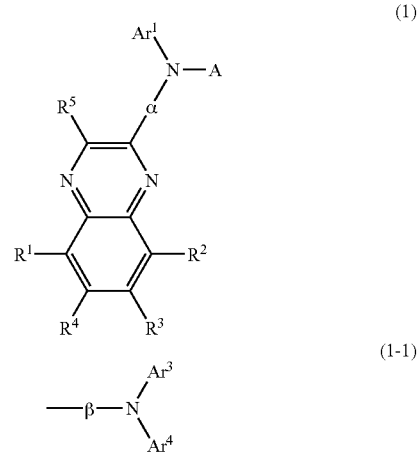

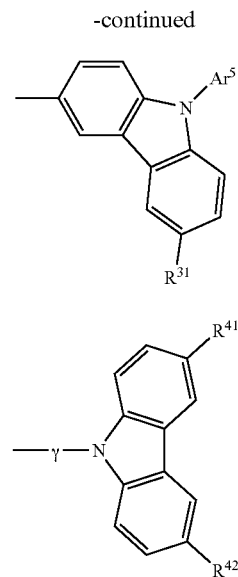

(1-2)

(1-3)

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. A represents a substituent represented by any of general formulas (1-1) to (1-3). In the general formulas (1-1) to (1-3), β represents an arylene group having 6 to 25 carbon atoms; $Ar^3$ and $Ar^4$ each represent an aryl group having 6 to 25 carbon atoms; $Ar^5$ represents an aryl group having 6 to 25 carbon atoms; $R^{31}$ represents any of a hydrogen atom, an alkyl group having 1 to 4 carbon atoms, or an aryl group having 6 to 25 carbon atoms; γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

Another feature of the present invention is a quinoxaline derivative represented by a general formula (2).

formula [2]

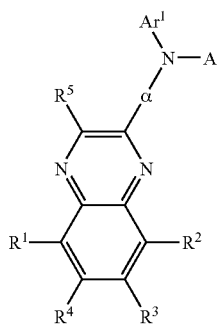

(2)

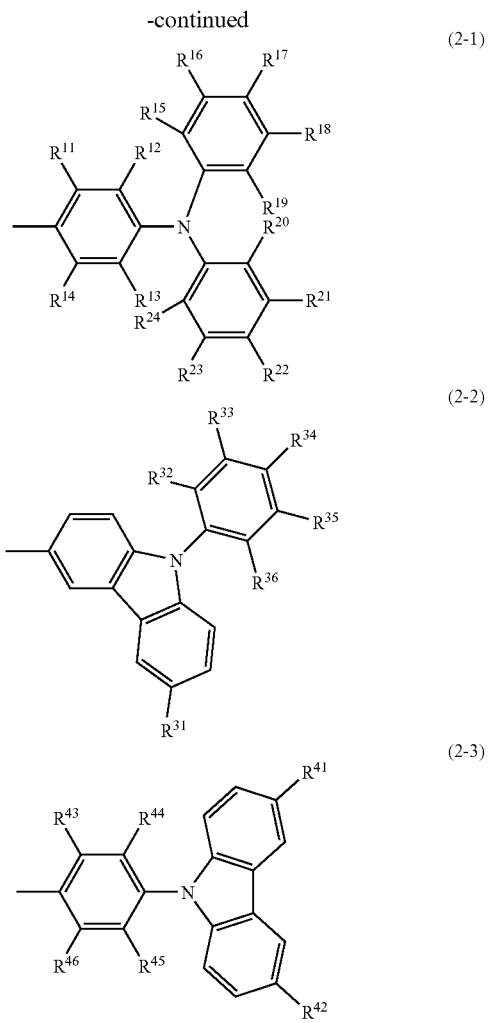

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and a represents an arylene group having 6 to 25 carbon atoms. A represents a substituent represented by any of general formulas (2-1) to (2-3). In the general formulas (2-1) to (2-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (3).

formula [3]

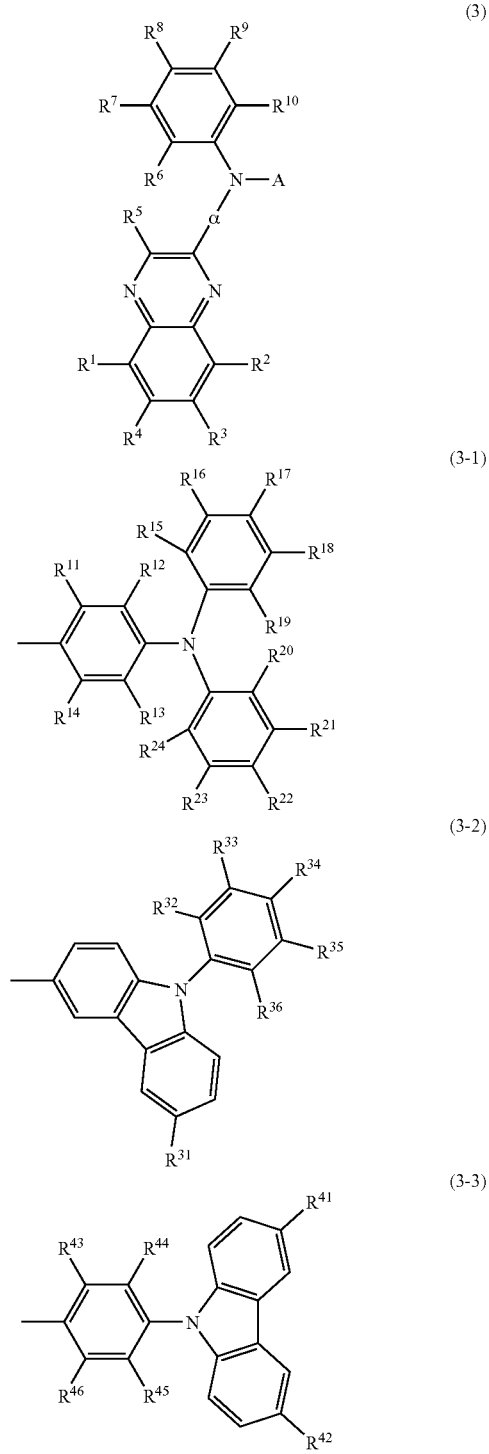

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $R^6$ to $R^{10}$ each represent any of a hydrogen atom, an alkyl group having 1 to 4 carbon atoms, or an aryl group having 6 to 15 carbon atoms; and a represents an arylene group having 6 to 25 carbon atoms. A represents a substituent represented by any of general formulas (3-1) to (3-3). In the general formulas (3-1) to (3-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (4).

formula [4]

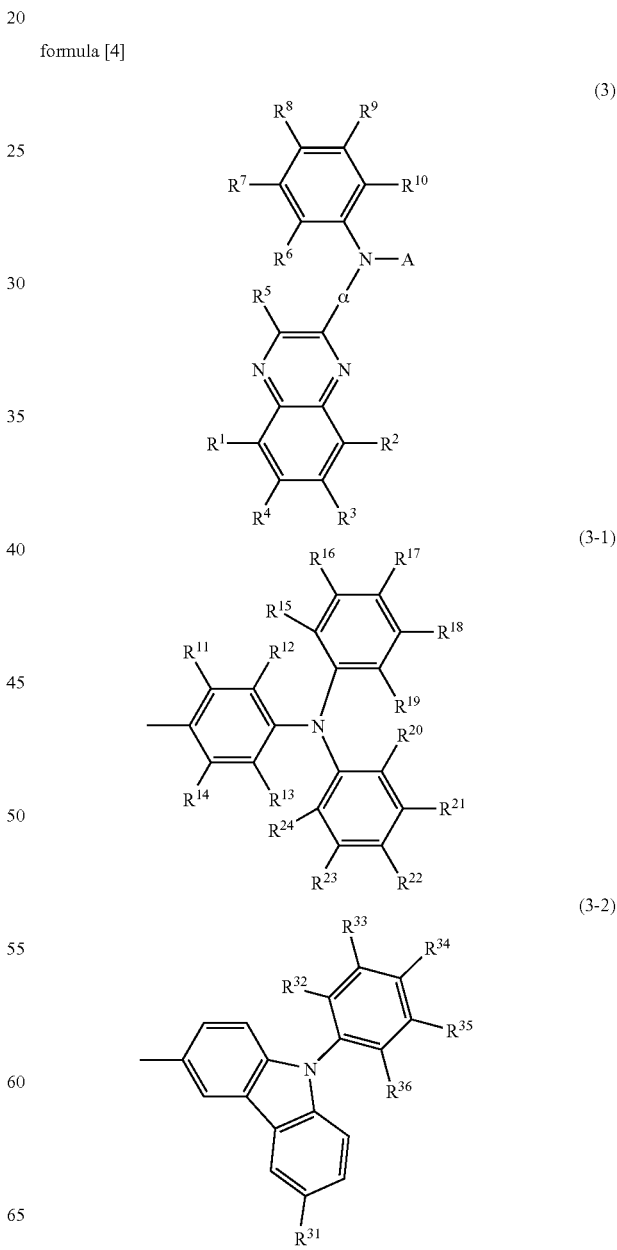

-continued

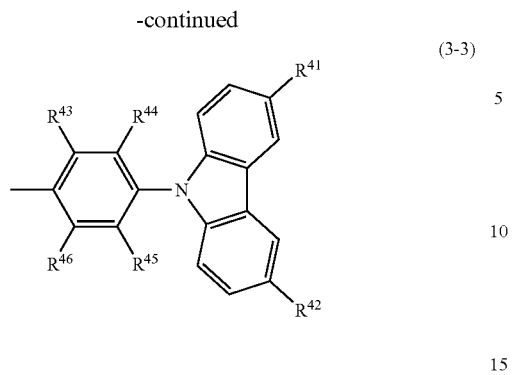

(3-3)

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (4-1) to (4-3). In the general formulas (4-1) to (4-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (5).

formula [5]

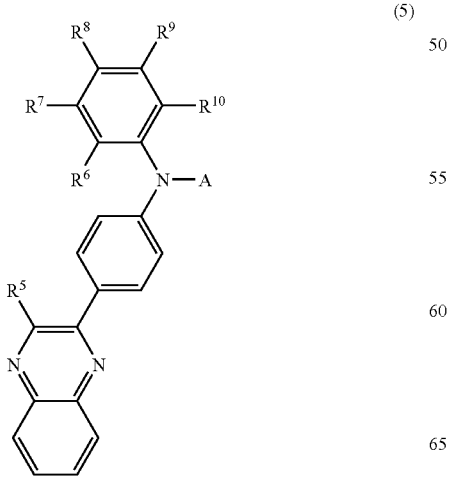

(5)

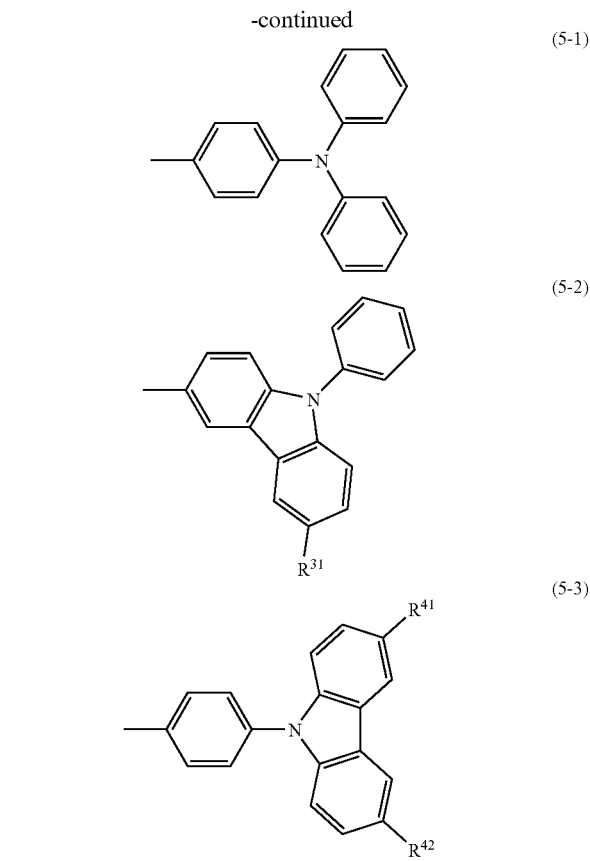

wherein $R^5$ represents any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (5-1) to (5-3). In the general formulas (5-1) to (5-3), $R^{31}$ represents any of a hydrogen atom, an alkyl group having 1 to 4 carbon atoms, or an aryl group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

Another feature of the present invention is a quinoxaline derivative represented by a general formula (6).

formula [6]

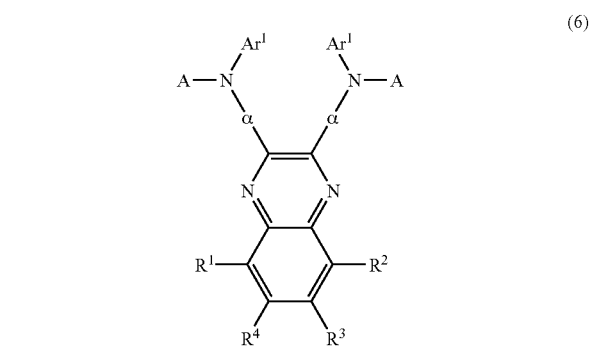

(6)

-continued

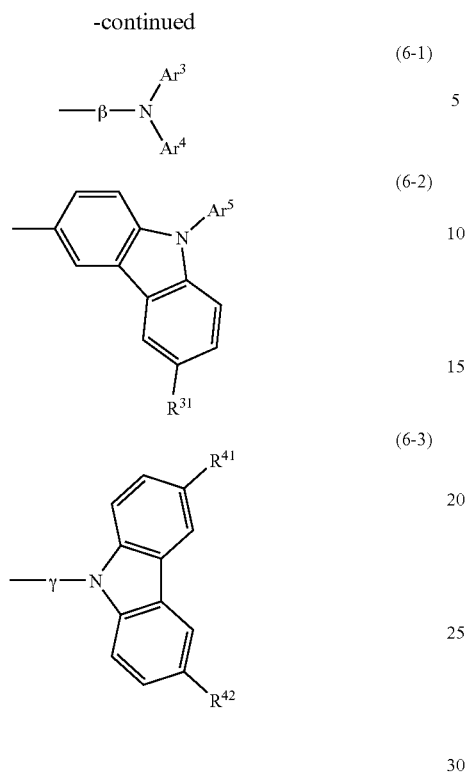

wherein R$^1$ to R$^4$ each represent any of a hydrogen atom, an alkyl group having 1 to 4 carbon atoms, or an aryl group having 6 to 25 carbon atoms; Ar$^1$ represents an aryl group having 6 to 25 carbon atoms; and a represents an arylene group having 6 to 25 carbon atoms. A represents a substituent represented by any of general formulas (6-1) to (6-3). In the general formulas (6-1) to (6-3), β represents an arylene group having 6 to 25 carbon atoms; Ar$^3$ and Ar$^4$ each represent an aryl group having 6 to 25 carbon atoms; Ar$^5$ represents an aryl group having 6 to 25 carbon atoms; R$^{31}$ represents any of a hydrogen atom, an alkyl group having 1 to 4 carbon atoms, or an aryl group having 6 to 25 carbon atoms; γ represents an arylene group having 6 to 25 carbon atoms; and R$^{41}$ and R$^{42}$ each represent any of a hydrogen atom, an alkyl group having 1 to 4 carbon atoms, or an aryl group having 6 to 25 carbon atoms.

Another feature of the present invention is a quinoxaline derivative represented by a general formula (7).

formula [7]

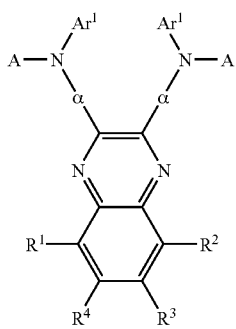

-continued

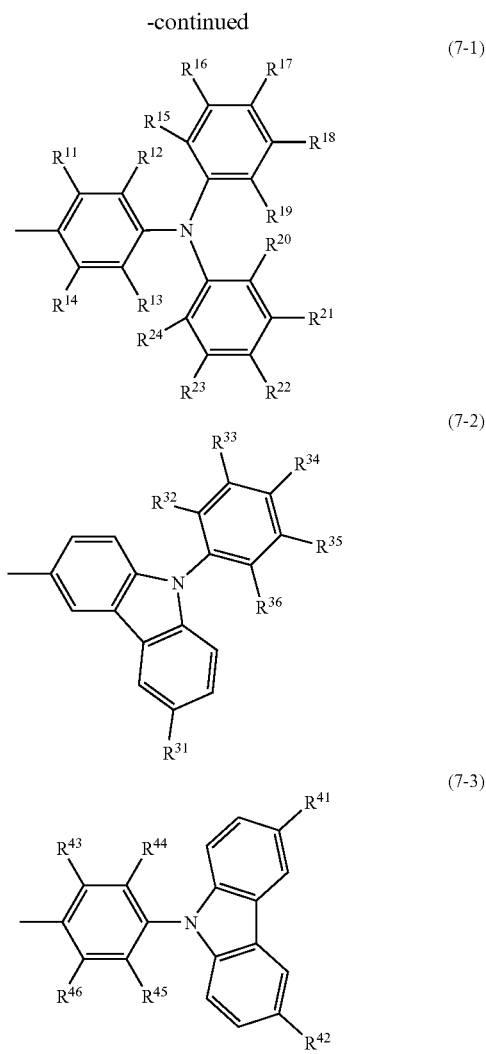

wherein R$^1$ to R$^4$ each represent any of a hydrogen atom, an alkyl group having 1 to 4 carbon atoms, or an aryl group having 6 to 25 carbon atoms; and Ar$^1$ represents an aryl group having 6 to 25 carbon atoms; and a represents an arylene group having 6 to 25 carbon atoms. A represents a substituent represented by any of general formulas (7-1) to (7-3). In the general formulas (7-1) to (7-3), R$^{11}$ to R$^{24}$ each represent any of a hydrogen atom, an alkyl group having 1 to 4 carbon atoms, or an aryl group having 6 to 15 carbon atoms; R$^{31}$ represents any of a hydrogen atom, an alkyl group having 1 to 4 carbon atoms, or an aryl group having 6 to 25 carbon atoms; R$^{32}$ to R$^{36}$ each represent any of a hydrogen atom, an alkyl group having 1 to 4 carbon atoms, or an aryl group having 6 to 15 carbon atoms; R$^{41}$ and R$^{42}$ each represent any of a hydrogen atom, an alkyl group having 1 to 4 carbon atoms, or an aryl group having 6 to 25 carbon atoms; and R$^{43}$ to R$^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (8).

formula [8]

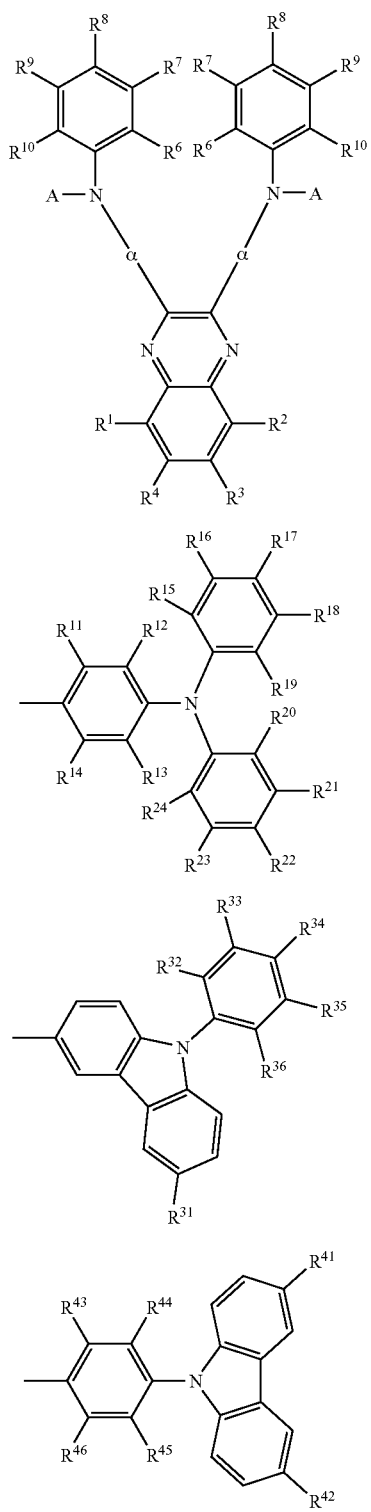

(8)
(8-1)
(8-2)
(8-3)

wherein $R^1$ to $R^4$ each represent any of a hydrogen atom, an alkyl group having 1 to 4 carbon atoms, or an aryl group having 6 to 25 carbon atoms; $R^6$ to $R^{10}$ each represent any of a hydrogen atom, an alkyl group having 1 to 4 carbon atoms, or an aryl group having 6 to 15 carbon atoms; and α represents an arylene group having 6 to 25 carbon atoms. A represents a substituent represented by any of general formulas (8-1) to (8-3). In the general formulas (8-1) to (8-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (9).

formula [9]

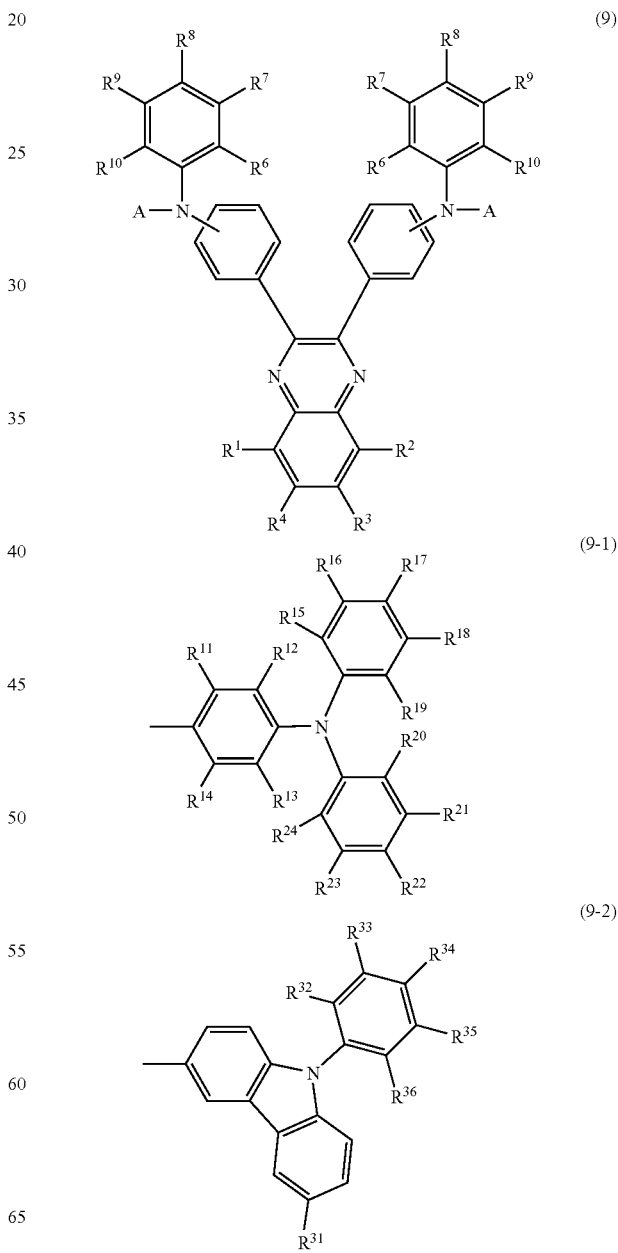

(9)
(9-1)
(9-2)

-continued (9-3)

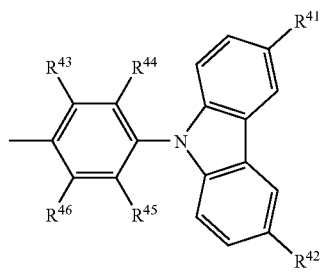

wherein $R^1$ to $R^4$ each represent any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (9-1) to (9-3). In the general formulas (9-1) to (9-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Another feature of the present invention is a quinoxaline derivative represented by a general formula (10).

formula [10]

(10)

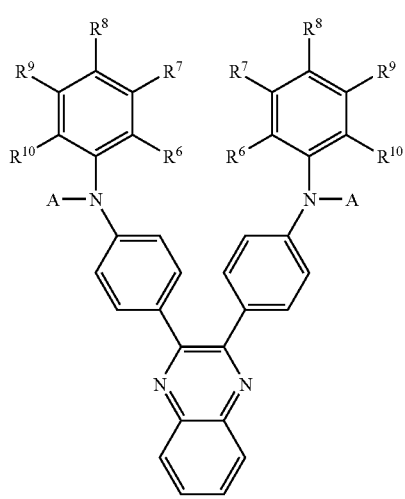

-continued (10-1)

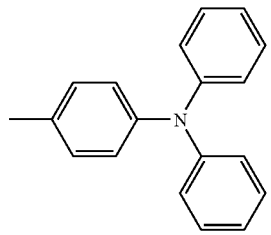

(10-2)

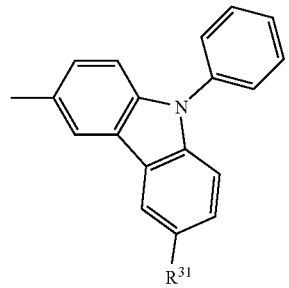

(10-3)

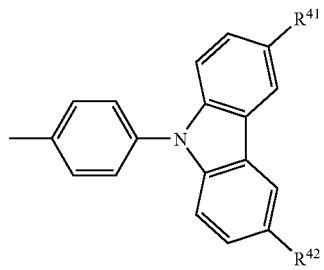

wherein $R^6$ to $R^{10}$ each represent any of a hydrogen atom, an alkyl group having 1 to 4 carbon atoms, or an aryl group having 6 to 15 carbon atoms. A represents a substituent represented by any of general formulas (10-1) to (10-3). In the general formulas (10-1) to (10-3), $R^{31}$ represents any of a hydrogen atom, an alkyl group having 1 to 4 carbon atoms, or an aryl group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

Another feature of the present invention is a light-emitting element using the quinoxaline derivative, specifically, a light-emitting element having the above-described quinoxaline derivative between a pair of electrodes.

Another feature of the present invention is a light-emitting element having a light emitting layer between a pair of electrodes, where the light emitting layer has the above-described quinoxaline derivative.

Another feature of the present invention is a light-emitting element having a light emitting layer between a pair of electrodes, where the light emitting layer has the above-described quinoxaline derivative and a substance emitting fluorescence.

Another feature of the present invention is a light-emitting element having a light emitting layer between a pair of electrodes, where the light emitting layer has the above-described quinoxaline derivative and a substance emitting phosphorescence.

The light-emitting device of the present invention possesses a light-emitting element which has a layer including light-emitting substance between a pair of electrodes, and the layer including a light-emitting substance comprises the aforementioned quinoxaline derivative. The light-emitting device of the present invention has also a means for controlling light emission from the light-emitting element. The light-emitting device in this specification includes an image display device, a light-emitting device, or a light source (including a lighting device). Further, the light-emitting device also includes a module in which a connector such as an FPC (Flexible Printed Circuit), a TAB (Tape Automated Bonding) tape, or a TCP (Tape Carrier Package) is attached to a panel on which the light-emitting element is formed. The light-emitting device in this specification also includes a module in which a printed wiring board is provided at an end of a TAB tape or a TCP, and also includes a module in which an IC (Integrated Circuit) is directly mounted on the light-emitting element by a COG (Chip On Glass) method.

Further, an electronic device using the light-emitting element of the present invention in its display portion is also included in the category of the present invention. Therefore, the electronic device of the present invention has a display portion, and this display portion is equipped with the above-described light-emitting element and a means for controlling light emission of the light-emitting element.

The quinoxaline derivative of the present invention is bipolar and excellent in both an electron transporting property and a hole transporting property. Further, the quinoxaline derivative of the present invention has a high glass transition temperature and excellent thermal stability. Furthermore, the quinoxaline derivative of the present invention is stable to electrochemical oxidation and reduction.

The quinoxaline derivative of the present invention is bipolar; therefore, by using the quinoxaline derivative of the present invention in a light-emitting element, a light-emitting element and a light-emitting device having a low driving voltage and low power consumption can be obtained. In addition, a light-emitting element with high luminous efficiency can be obtained.

Further, the quinoxaline derivative of the present invention has a high glass transition temperature; therefore, by using the quinoxaline derivative of the present invention for a light-emitting element, a light-emitting element and a light-emitting device which have high thermal stability can be obtained.

The quinoxaline derivative of the present invention is stable to electrochemical oxidation and reduction; therefore, by using the quinoxaline derivative of the present invention in a light-emitting element, a light-emitting element and light-emitting device which have a long lifetime can be obtained.

By using the quinoxaline derivative of the present invention, a long-life electronic device with low power consumption and high thermal stability can be obtained.

BRIEF DESCRIPTION OF DRAWINGS

In the accompanying drawings:

FIGS. 5A and 5B are explanatory views of a light-emitting device of the present invention;

BEST MODE FOR CARRYING OUT THE INVENTION

Figure 1A:
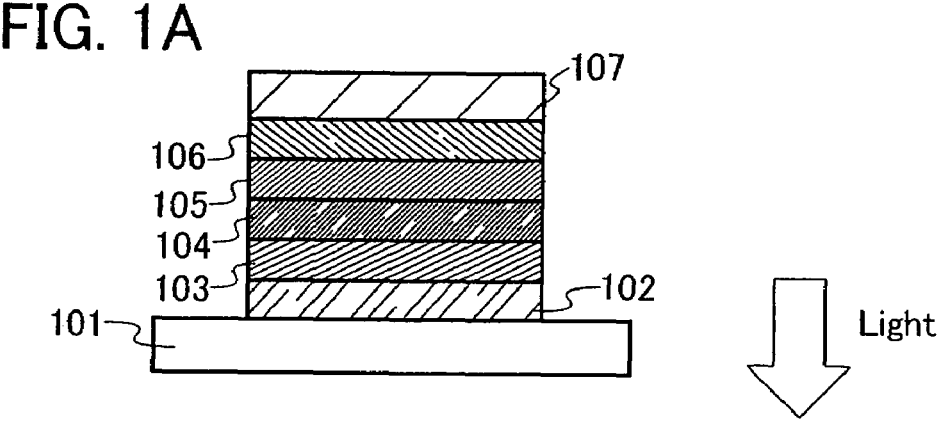
FIGS. 1A to 1C are explanatory views of light-emitting elements of the present invention.

Hereinafter, Embodiment Modes of the present invention will be explained with reference to the accompanied drawings. However, the present invention is not limited to the explanation to be given below, and it is to be easily understood that various changes and modifications in modes and details thereof will be apparent to those skilled in the art without departing from the purpose and the scope of the present invention. Therefore, the present invention should not be interpreted as being limited to the description of the embodiment modes to be given below.

Embodiment Mode 1

In this embodiment mode, a quinoxaline derivative of the present invention will be explained.

A quinoxaline derivative of the present invention is a quinoxaline derivative represented by a general formula (1).

formula [11]

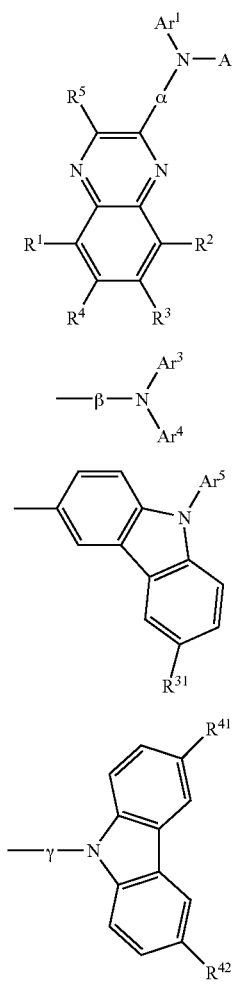

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. A represents a substituent represented by any of general formulas (1-1) to (1-3). In the general formulas (1-1) to (1-3), β represents an arylene group having 6 to 25 carbon atoms; $Ar^3$ and $Ar^4$ each represent an aryl group having 6 to 25 carbon atoms; $Ar^5$ represents an aryl group having 6 to 25 carbon atoms; $R^{31}$ represents any of a hydrogen atom, an alkyl group having 1 to 4 carbon atoms, or an aryl group having 6 to 25 carbon atoms; γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

Among the quinoxaline derivatives represented by the general formula (1), a quinoxaline derivative represented by a general formula (2) is preferable.

formula [12]

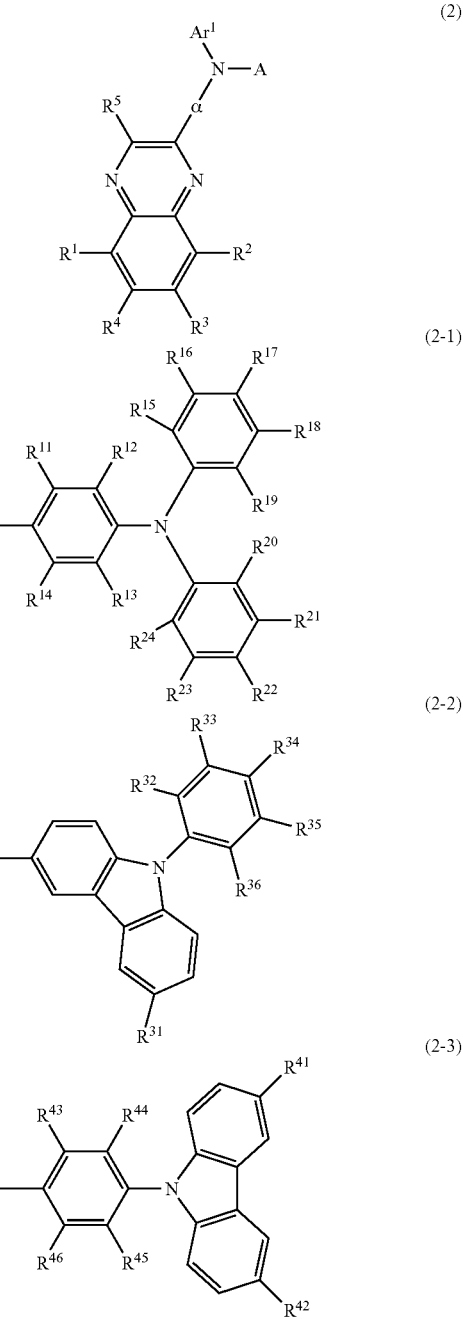

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and a represents an arylene group having 6 to 25 carbon atoms. A represents a substituent represented by any of general formulas (2-1) to (2-3). In the general formulas (2-1) to (2-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Among the quinoxaline derivatives represented by the general formula (1), a quinoxaline derivative represented by a general formula (3) is more preferable.

formula [13]

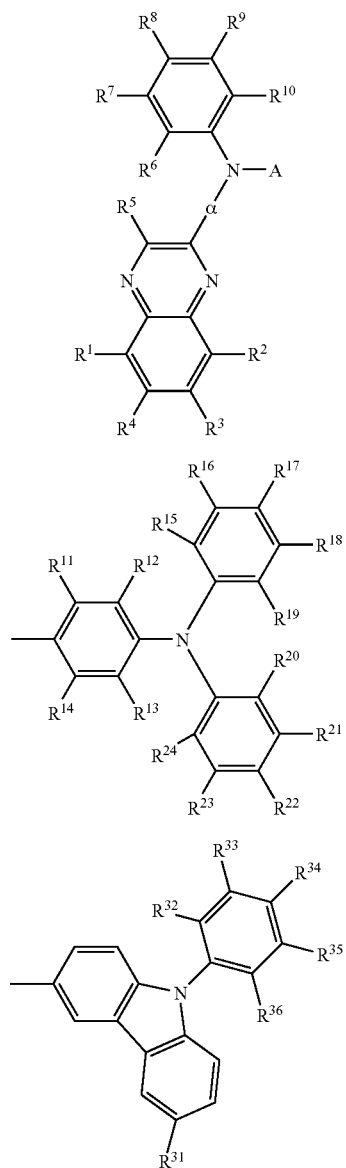

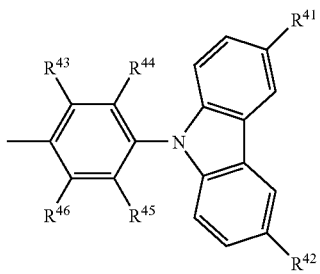

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $R^{11}$ to $R^{10}$ each represent any of a hydrogen atom, an alkyl group having 1 to 4 carbon atoms, or an aryl group having 6 to 15 carbon atoms; and a represents an arylene group having 6 to 25 carbon atoms. A represents a substituent represented by any of general formulas (3-1) to (3-3). In the general formulas (3-1) to (3-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Among the quinoxaline derivatives represented by the general formula (1), a quinoxaline derivative represented by a general formula (4) is more preferable.

formula [14]

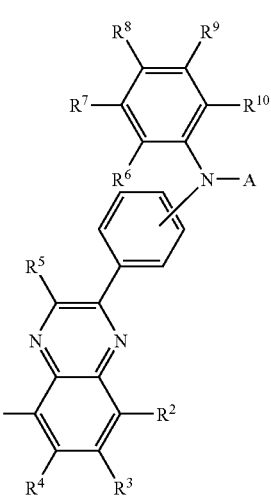

-continued

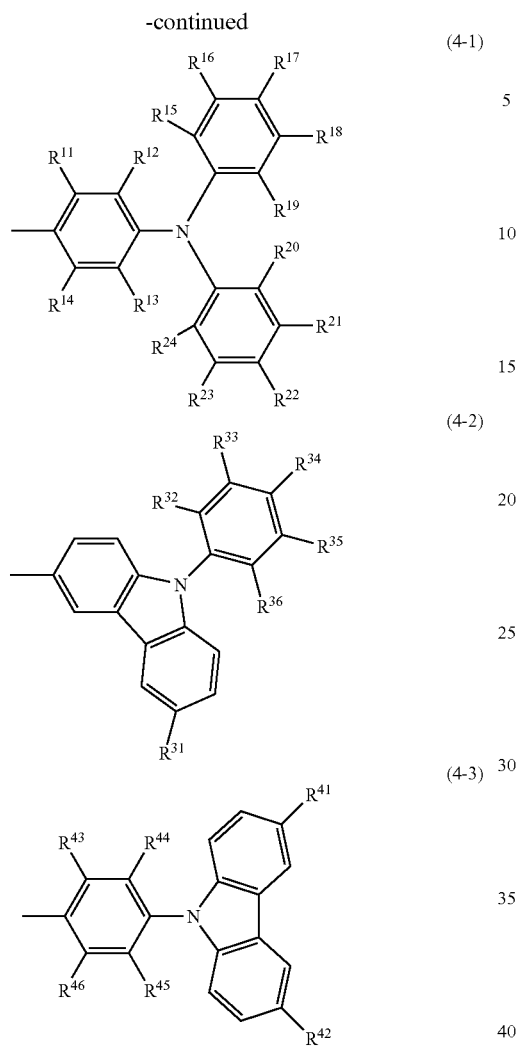

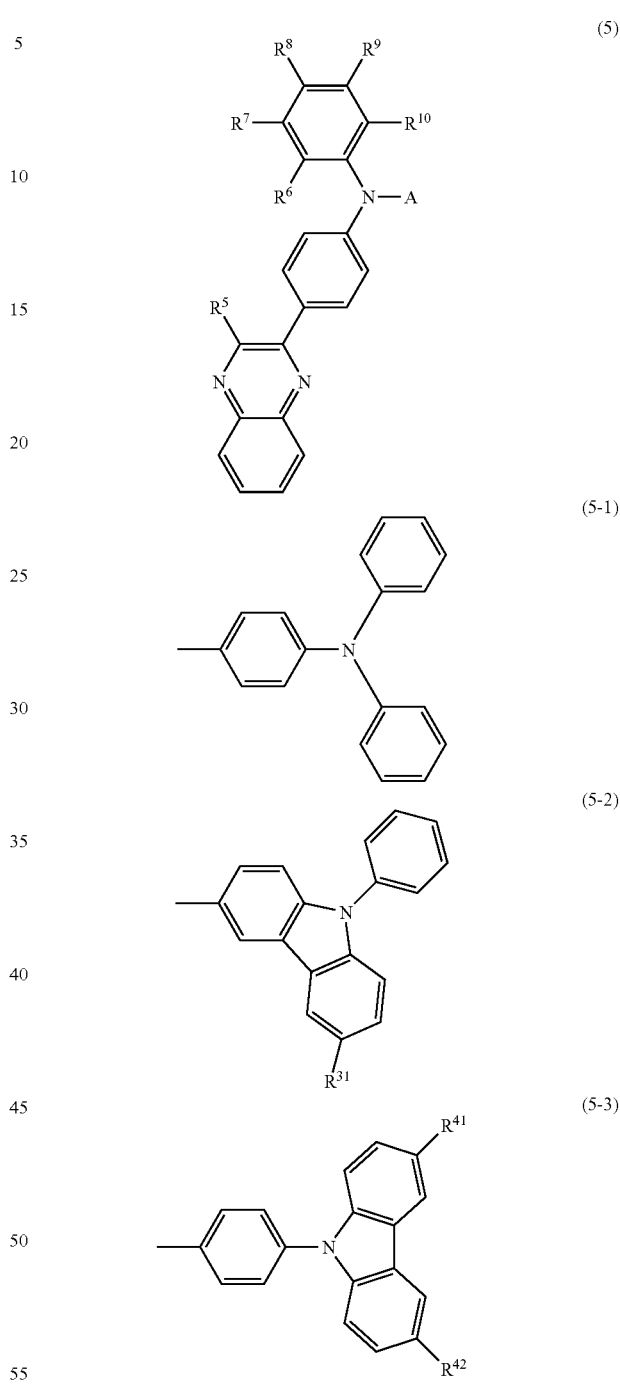

wherein $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (4-1) to (4-3). In the general formulas (4-1) to (4-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Furthermore, among the quinoxaline derivatives represented by the general formula (1), a quinoxaline derivative represented by a general formula (5) is more preferable.

wherein $R^5$ represents any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (5-1) to (5-3). In the general formulas (5-1) to (5-3), $R^{31}$ represents any of a hydrogen atom, an alkyl group having 1 to 4 carbon atoms, or an aryl group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

A quinoxaline derivative of the present invention is a quinoxaline derivative represented by a general formula (6).

formula [16]

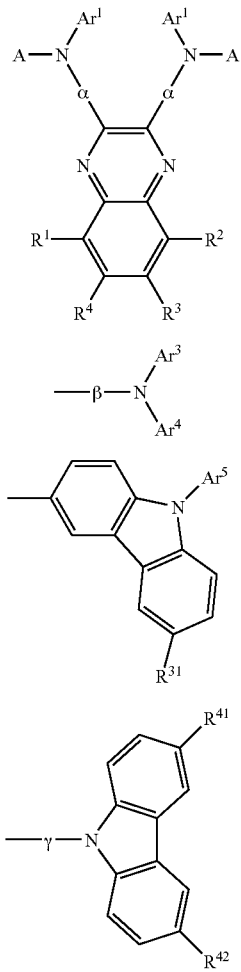

(6)

(6-1)

(6-2)

(6-3)

wherein $R^1$ to $R^4$ each represent any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. A represents a substituent represented by any of general formulas (6-1) to (6-3). In the general formulas (6-1) to (6-3), β represents an arylene group having 6 to 25 carbon atoms; $Ar^3$ and $Ar^4$ each represent an aryl group having 6 to 25 carbon atoms; $Ar^5$ represents an aryl group having 6 to 25 carbon atoms; $R^{31}$ represents any of a hydrogen atom, an alkyl group having 1 to 4 carbon atoms, or an aryl group having 6 to 25 carbon atoms; γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

Among the quinoxaline derivatives represented by the general formula (6), a quinoxaline derivative represented by a general formula (7) is preferable.

formula [17]

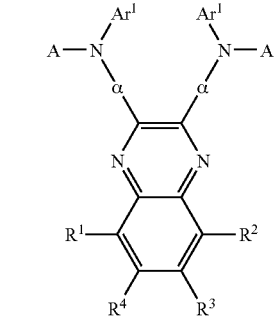

(7)

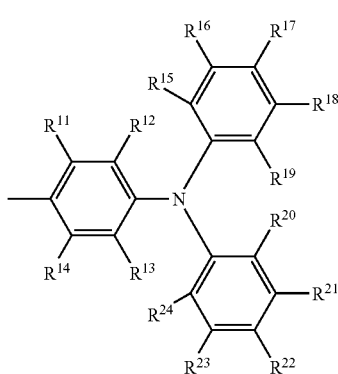

(7-1)

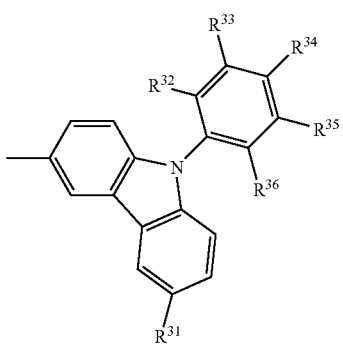

(7-2)

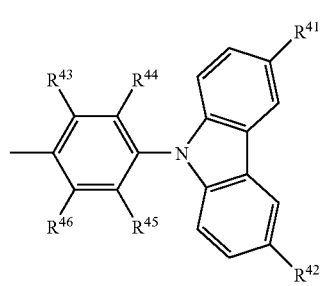

(7-3)

wherein $R^1$ to $R^4$ each represent any of a hydrogen atom, an alkyl group having 1 to 4 carbon atoms, or an aryl group having 6 to 25 carbon atoms; and $Ar^1$ represents an aryl group having 6 to 25 carbon atoms; and α represents an arylene group having 6 to 25 carbon atoms. A represents a substituent represented by any of general formulas (7-1) to (7-3). In the general formulas (7-1) to (7-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Among the quinoxaline derivatives represented by the general formula (6), a quinoxaline derivative represented by a general formula (8) is more preferable.

formula [18]

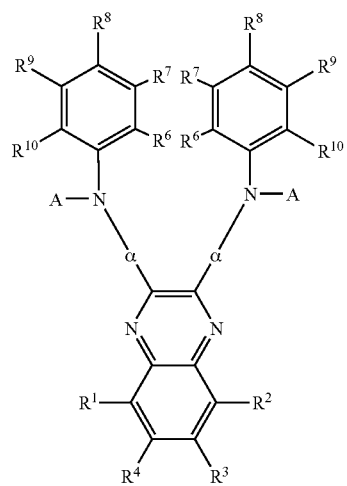
(8)

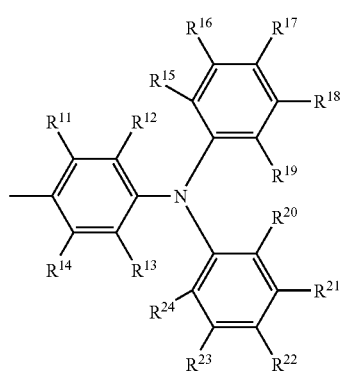
(8-1)

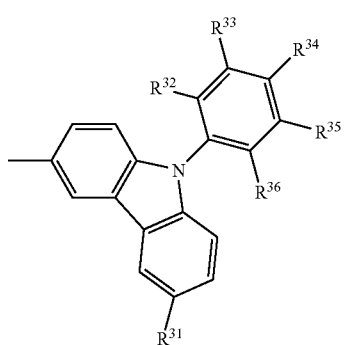
(8-2)

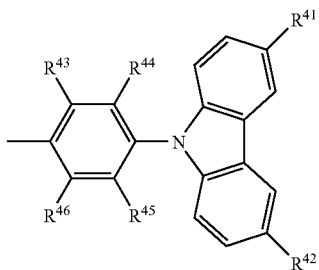
(8-3)

wherein $R^1$ to $R^4$ each represent any of a hydrogen atom, an alkyl group having 1 to 4 carbon atoms, or an aryl group having 6 to 25 carbon atoms; $R^6$ to $R^{10}$ each represent any of a hydrogen atom, an alkyl group having 1 to 4 carbon atoms, or an aryl group having 6 to 15 carbon atoms; and α represents an arylene group having 6 to 25 carbon atoms. A represents a substituent represented by any of general formulas (8-1) to (8-3). In the general formulas (8-1) to (8-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Among the quinoxaline derivatives represented by the general formula (6), a quinoxaline derivative represented by a general formula (9) is more preferable.

formula [19]

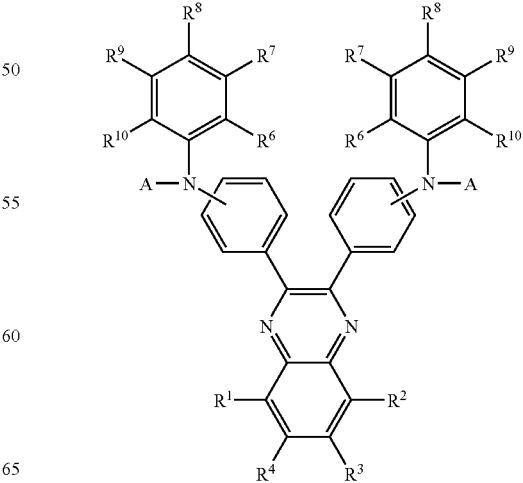
(9)

-continued (9-1)
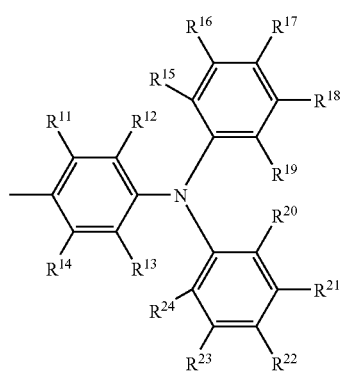

(9-2)
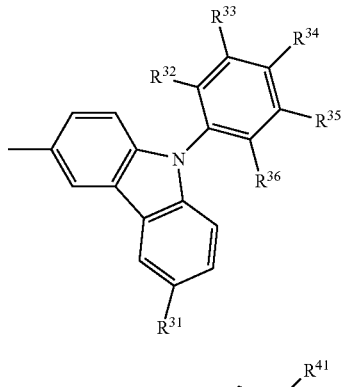

(9-3)
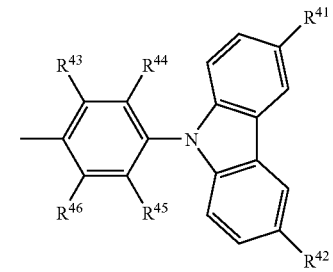

wherein $R^1$ to $R^4$ each represent any of a hydrogen atom, an alkyl group having 1 to 4 carbon atoms, or an aryl group having 6 to 25 carbon atoms; and $R^6$ to $R^{10}$ each represent any of a hydrogen atom, an alkyl group having 1 to 4 carbon atoms, or an aryl group having 6 to 15 carbon atoms. A represents a substituent represented by any of general formulas (9-1) to (9-3). In the general formulas (9-1) to (9-3), $R^{11}$ to $R^{24}$ each represent any of a hydrogen atom, an alkyl group having 1 to 4 carbon atoms, or an aryl group having 6 to 15 carbon atoms; $R^{31}$ represents any of a hydrogen atom, an alkyl group having 1 to 4 carbon atoms, or an aryl group having 6 to 25 carbon atoms; $R^{32}$ to $R^{36}$ each represent any of a hydrogen atom, an alkyl group having 1 to 4 carbon atoms, or an aryl group having 6 to 15 carbon atoms; $R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

Furthermore, among the quinoxaline derivatives represented by the general formula (6), a quinoxaline derivative represented by a general formula (10) is more preferable.

formula [20]

(10)
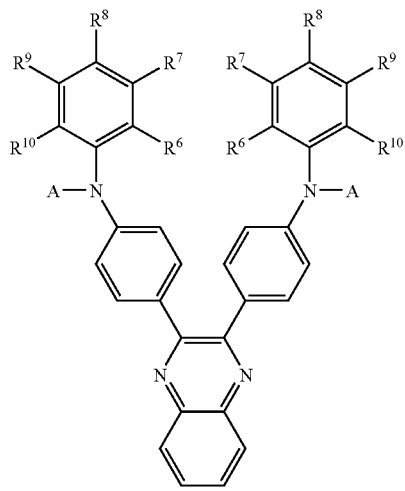

(10-1)
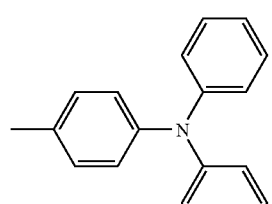

(10-2)
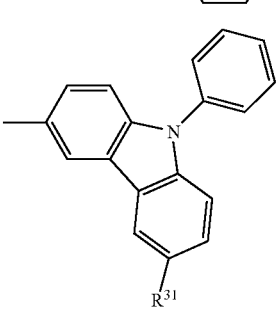

(10-3)
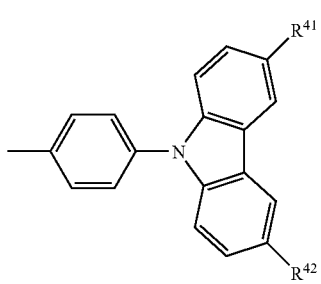

wherein $R^6$ to $R^{10}$ each represent any of a hydrogen atom, an alkyl group having 1 to 4 carbon atoms, or an aryl group having 6 to 15 carbon atoms. A represents a substituent represented by any of general formulas (10-1) to (10-3). In the general formulas (10-1) to (10-3), $R^{31}$ represents any of a hydrogen atom, an alkyl group having 1 to 4 carbon atoms, or an aryl group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

In the general formulas (1) to (3) and the general formulas (6) to (8), $Ar^1$, $Ar^3$, $Ar^4$, and $Ar^5$ each represent an aryl group having 6 to 25 carbon atoms. Specifically, substituents represented by structural formulas (11-1) to (11-6) are exemplified.

formula [21]

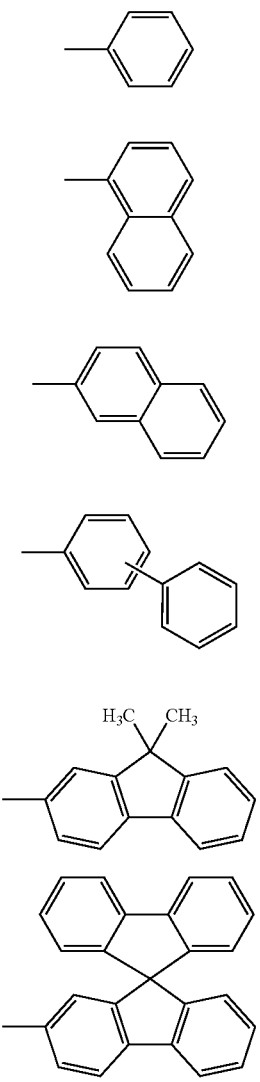

(11-1)

(11-2)

(11-3)

(11-4)

(11-5)

(11-6)

In the general formulas (1) and (2) and the general formulas (6) and (7), α, β, and γ each represent an arylene group having 6 to 25 carbon atoms. Specifically, substituents represented by structural formulas (12-1) to (12-6) are exemplified.

formula [22]

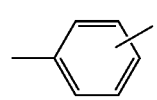

(12-1)

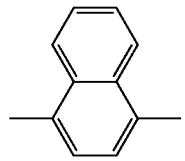

(12-2)

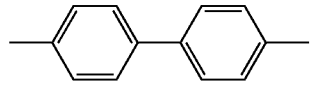

(12-3)

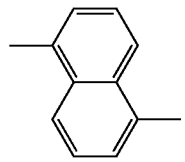

(12-4)

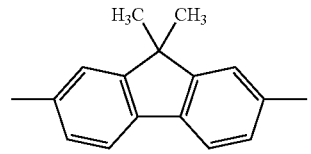

(12-5)

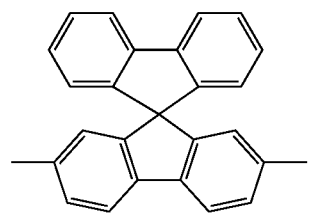

(12-6)

In the general formulas (1) to (10) described above, $R^1$ to $R^5$, $R^{31}$, $R^{41}$, and $R^{42}$ each represent any of a hydrogen atom, an alkyl group having 1 to 4 carbon atoms, or an aryl group having 6 to 25 carbon atoms. Specifically, substituents represented by structural formulas (13-1) to (13-10) are exemplified.

formula [23]

—H  (13-1)

—CH₃  (13-2)

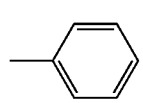

(13-3)

—CH₂—CH₃  (13-4)

-continued (13-5) 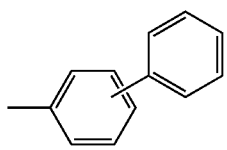

(13-6) 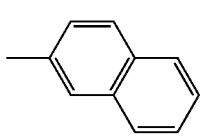

(13-7) 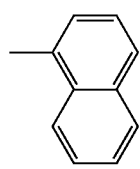

(13-8) 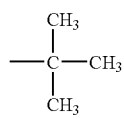

(13-9) 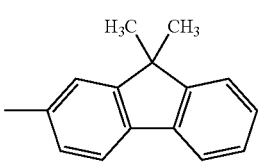

(13-10) 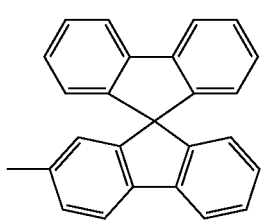

formula [24]

(14-1) 

(14-2) 

(14-3) 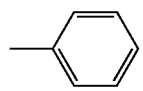

(14-4) 

(14-5) 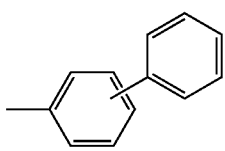

(14-6) 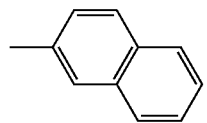

(14-7) 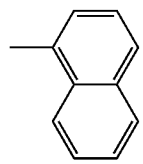

(14-8) 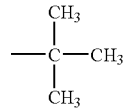

(14-9) 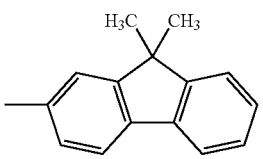

In the general formulas (2) to (5) and the general formulas (7) to (10), $R^6$ to $R^{10}$, $R^{11}$ to $R^{24}$, $R^{32}$ to $R^{36}$, and $R^{43}$ to $R^{46}$ each represent any of a hydrogen atom, an alkyl group having 1 to 4 carbon atoms, or an aryl group having 6 to 15 carbon atoms. Specifically, substituents represented by structural formulas (14-1) to (14-9) are exemplified.

As a specific example of a quinoxaline derivative represented by the general formulas (1) to (5), quinoxaline derivatives represented by structural formulas (21) to (366) can be given. However, the present invention is not limited thereto.

formula [25]
(21)
(22)
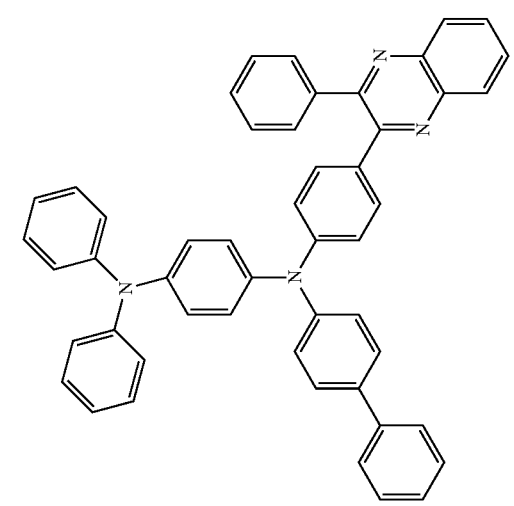
(23)
(24)
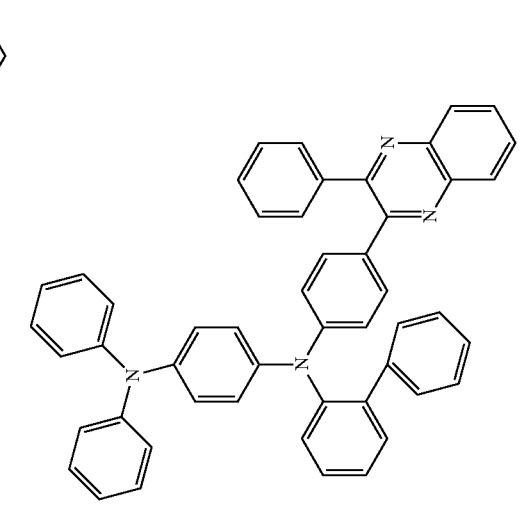
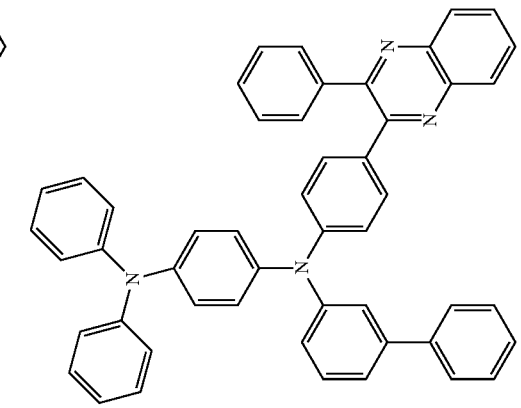

-continued
(26)
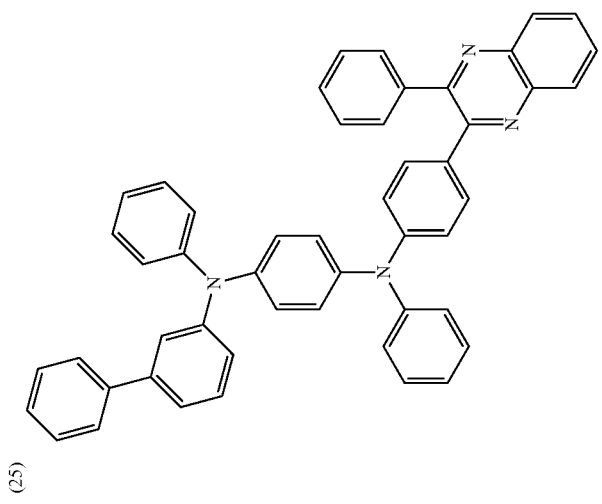
(25)
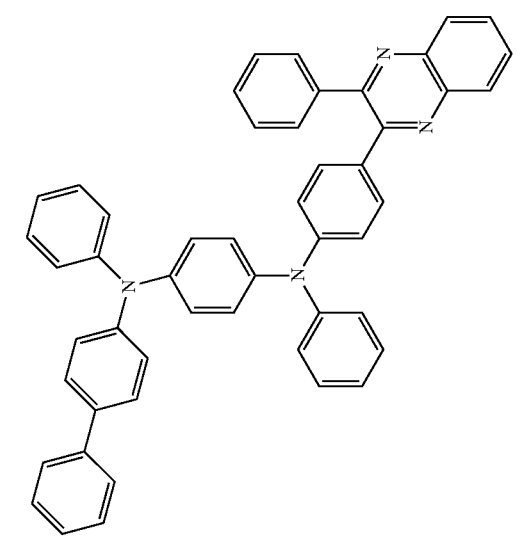
formula [26]

-continued
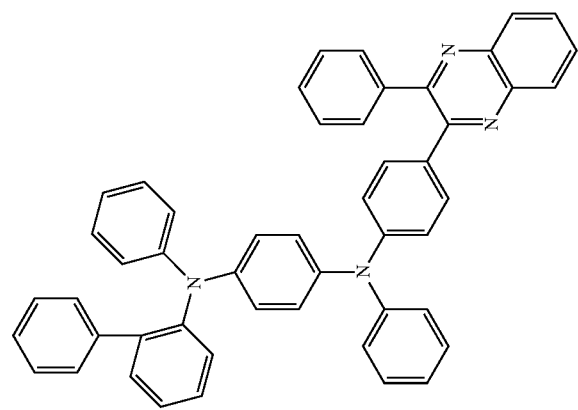
(27)

formula [27]
(28)
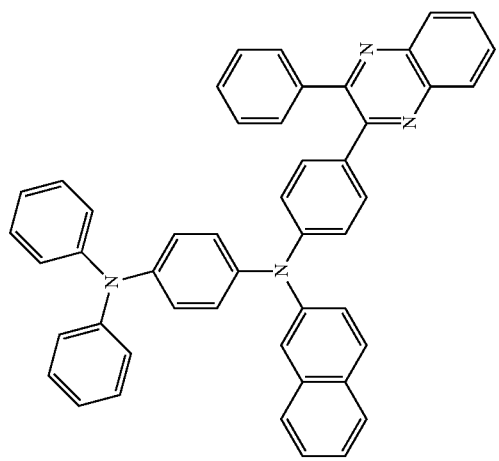
(29)
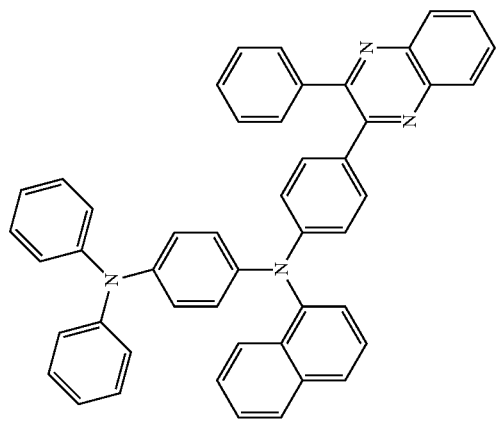
(30)
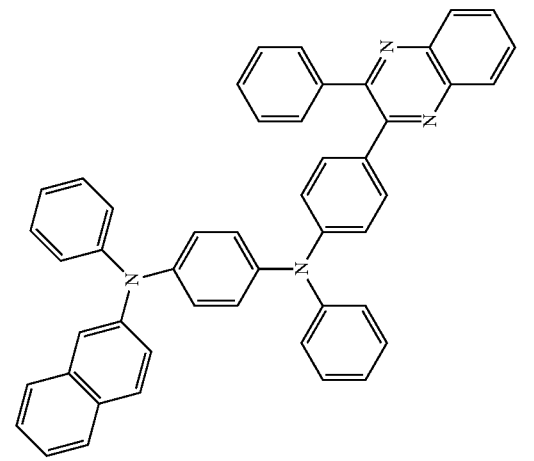
(31)
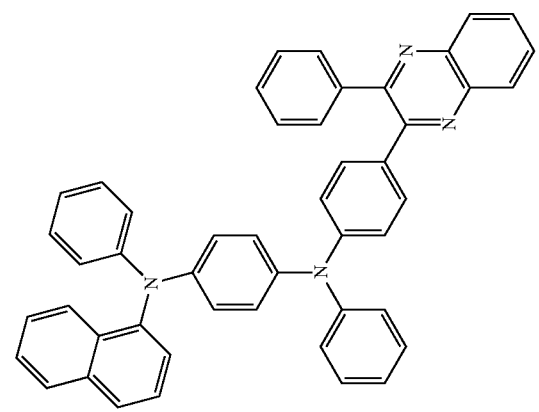

-continued
(32)
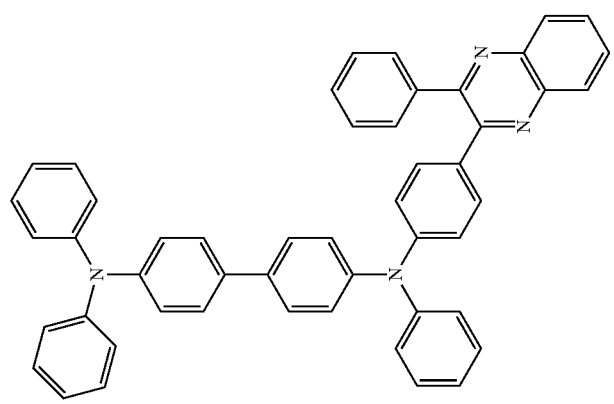
(33)
formula [28]
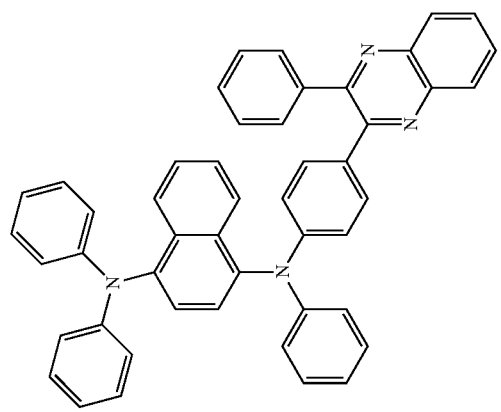

(34)
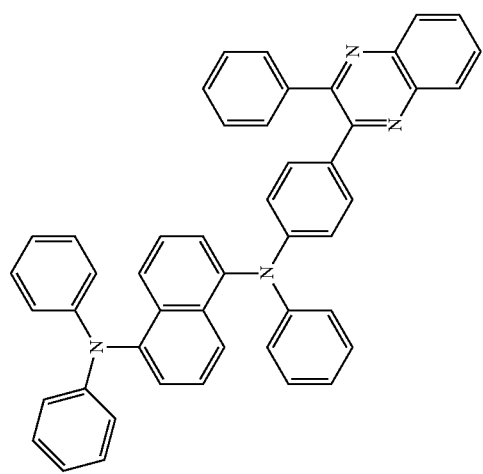

-continued
(35)
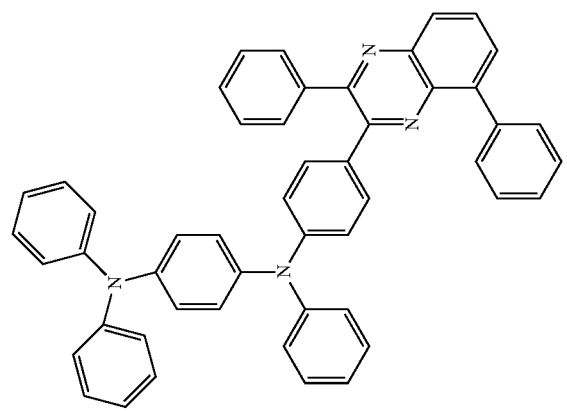
(36)
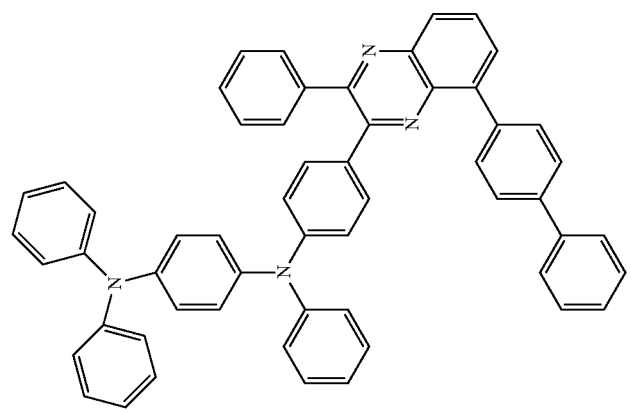

(38)
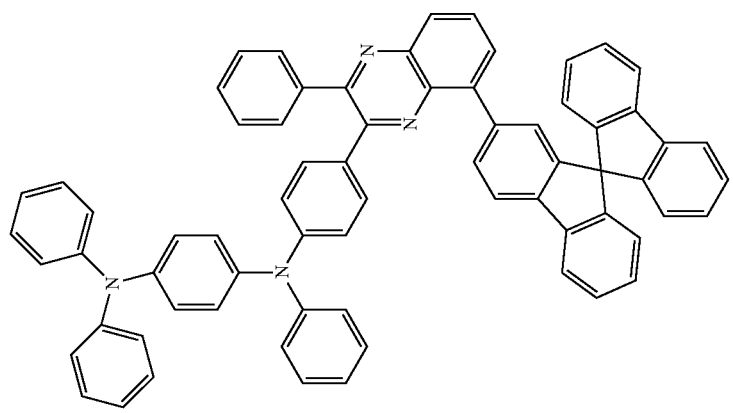
(37)
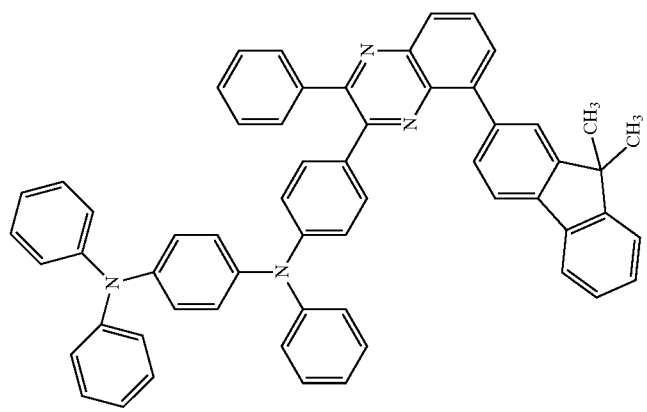

-continued
(40)
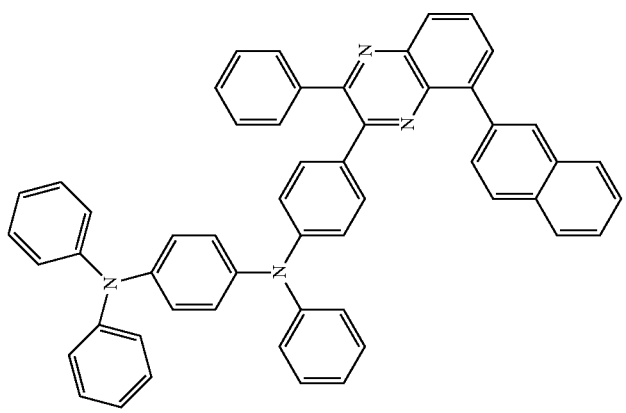
(39)
formula [30]
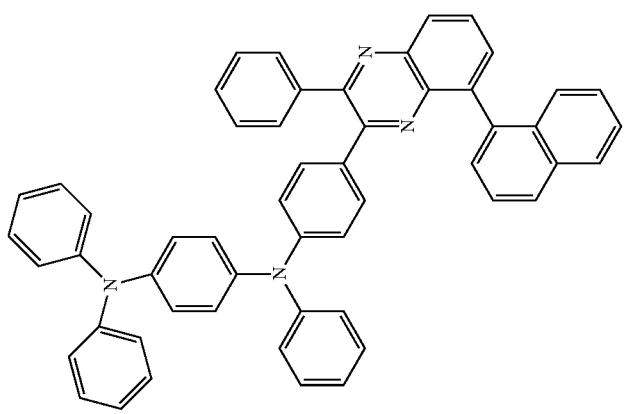

-continued
(42)
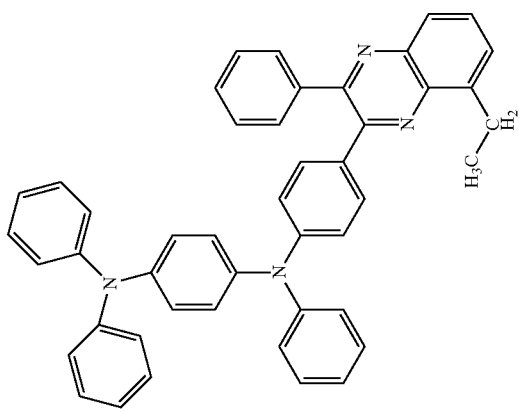
(41)
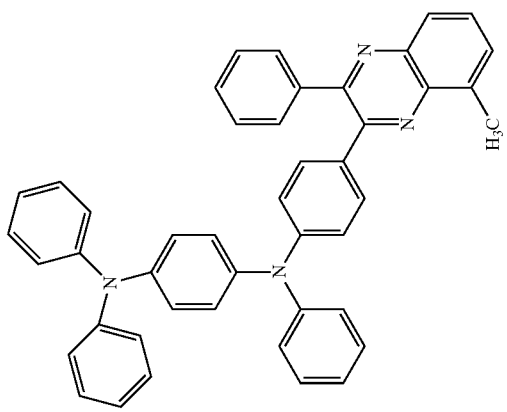

-continued
(44)
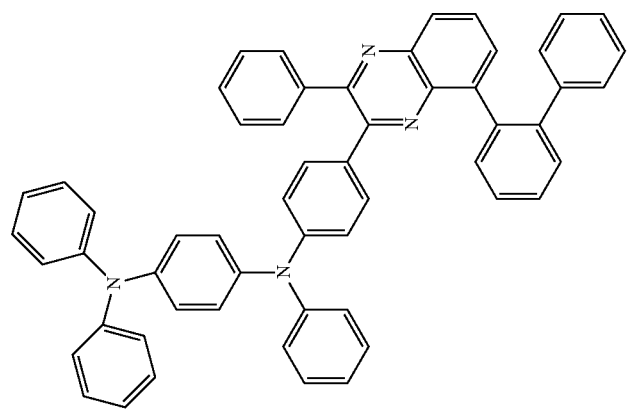
(43)
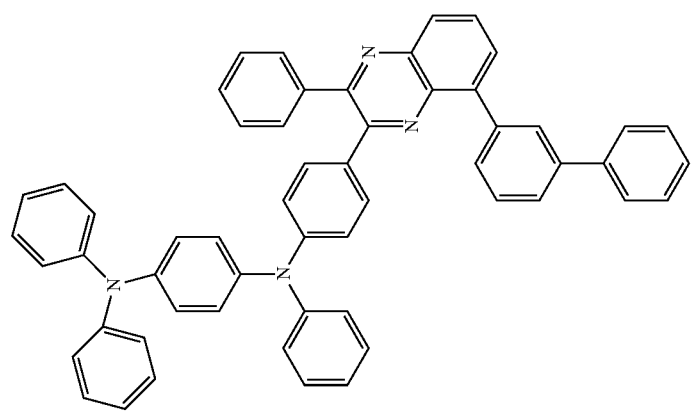

-continued
(45)
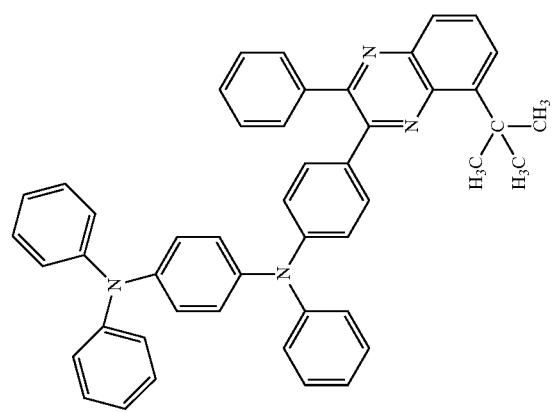

-continued
(47)
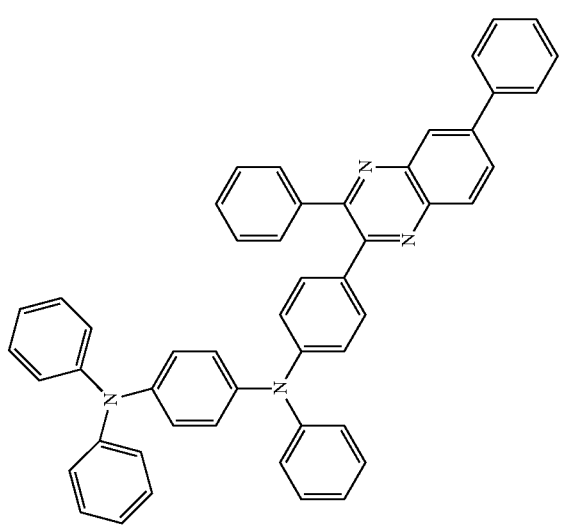
(46)
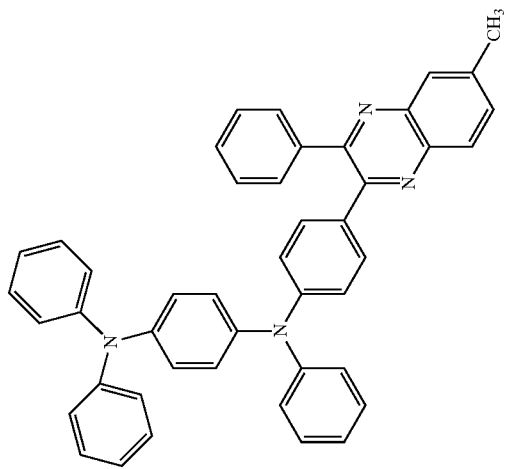
formula [32]

(49)
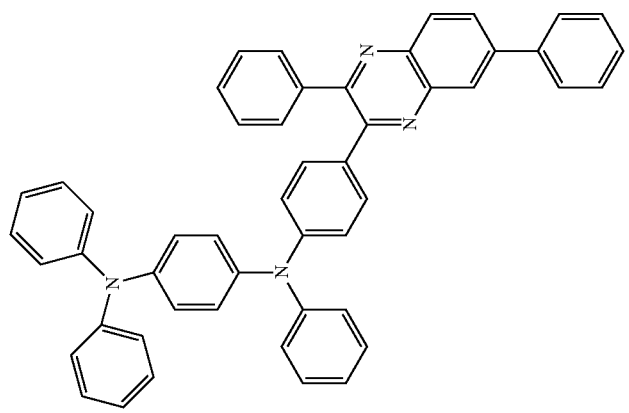
(48)
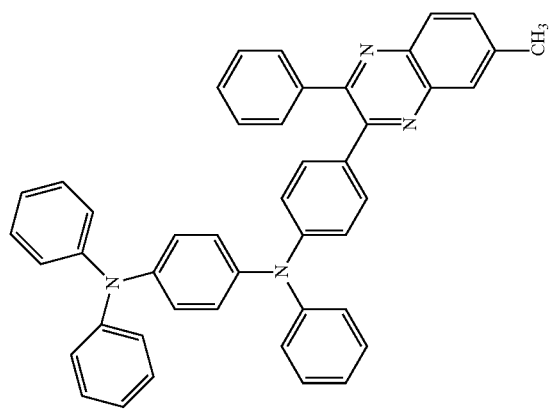

-continued
formula [33]
(50)
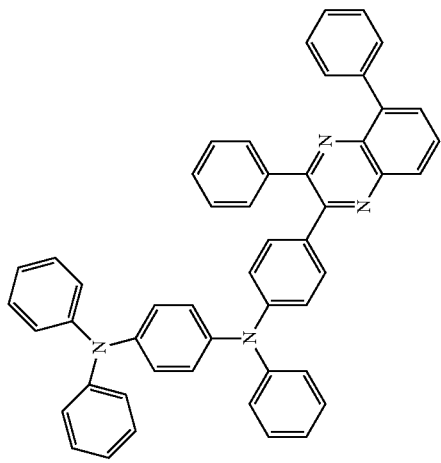
(51)
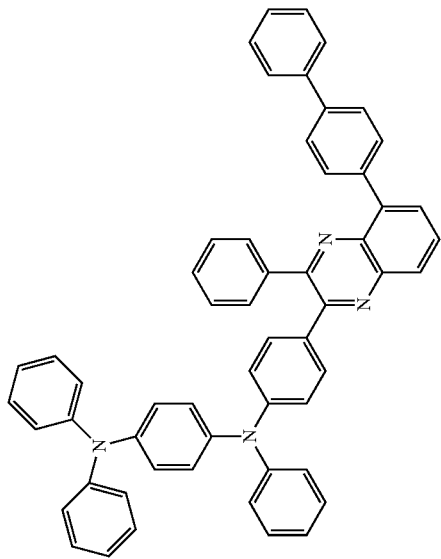
(52)
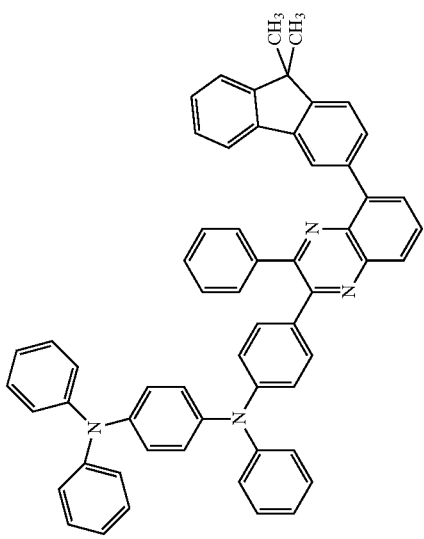
(53)
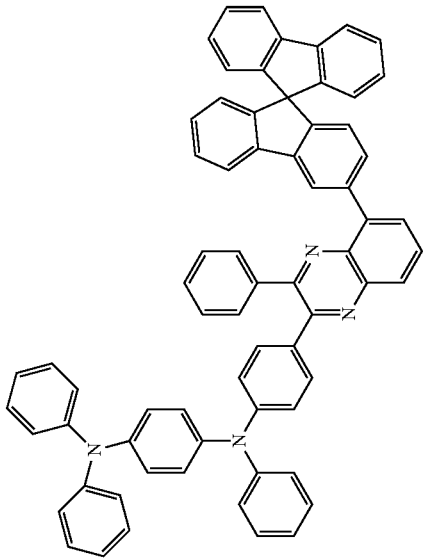

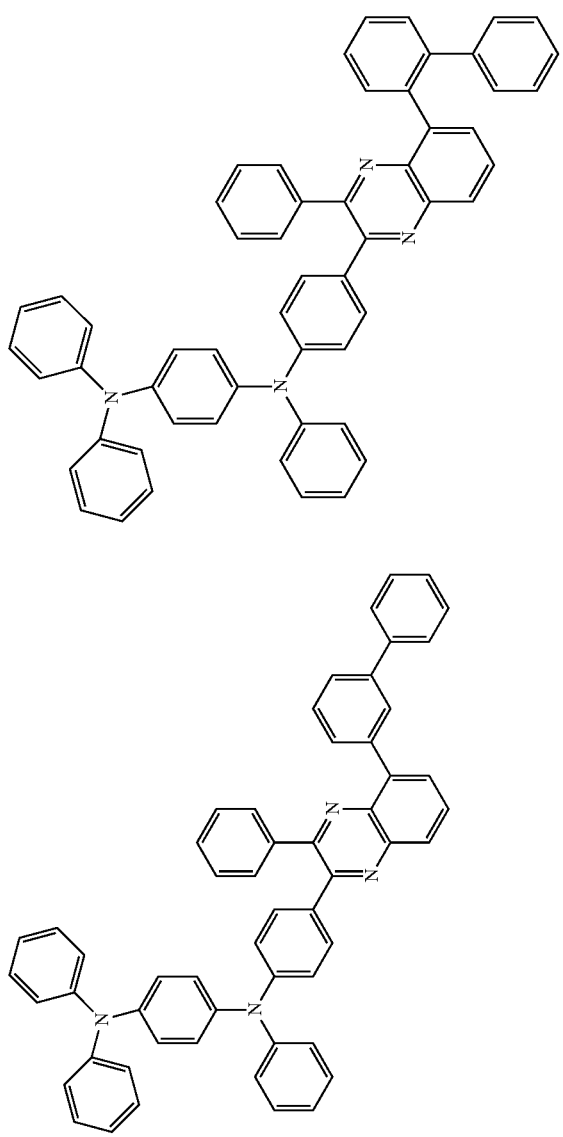

-continued
(56)
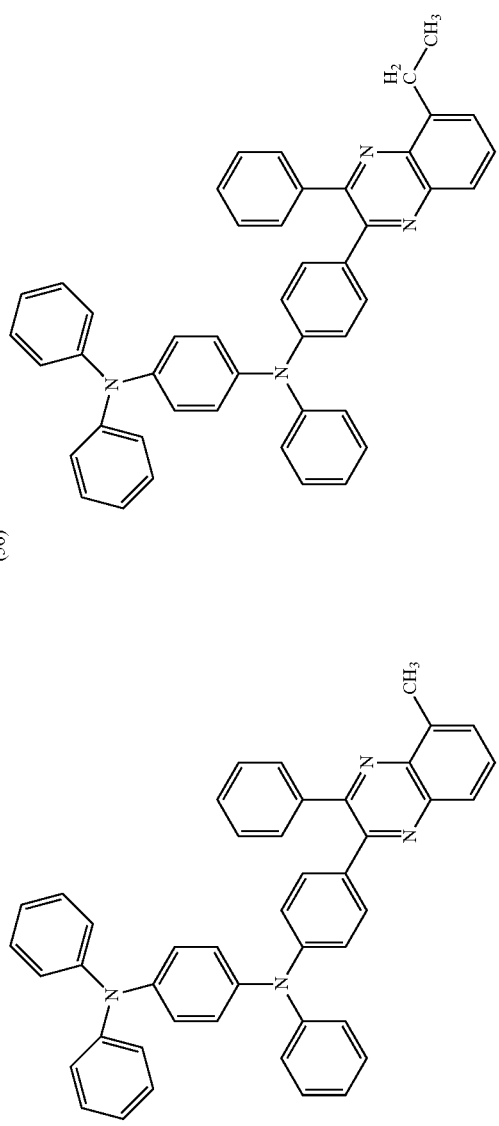
(57)
(58)
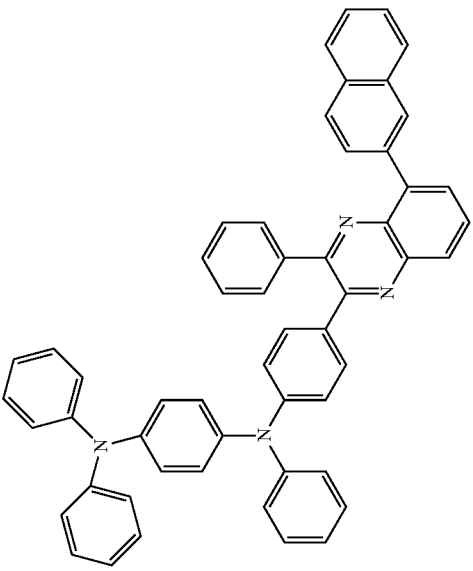
formula [35]
(59)
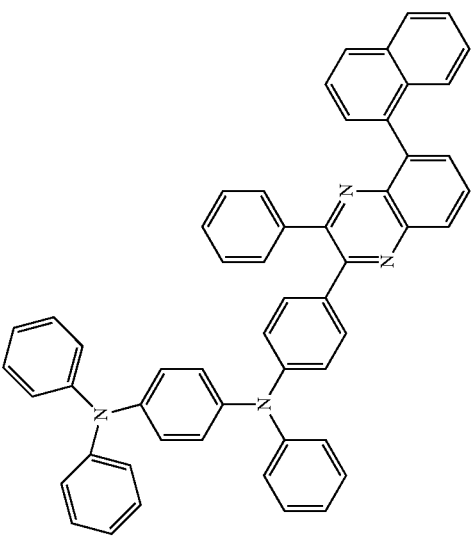

(60)
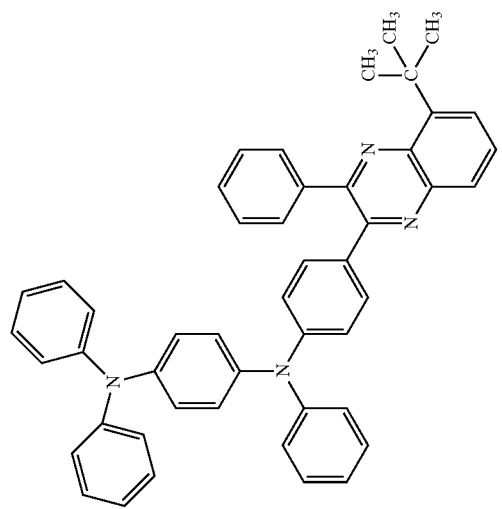

-continued
formula [36] (61)
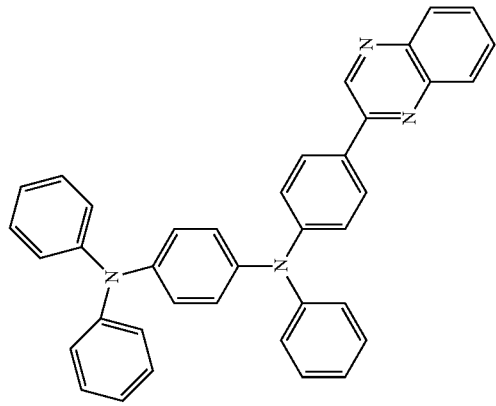
(62)
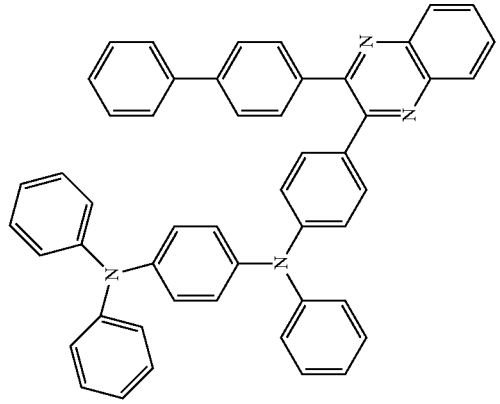
(63)
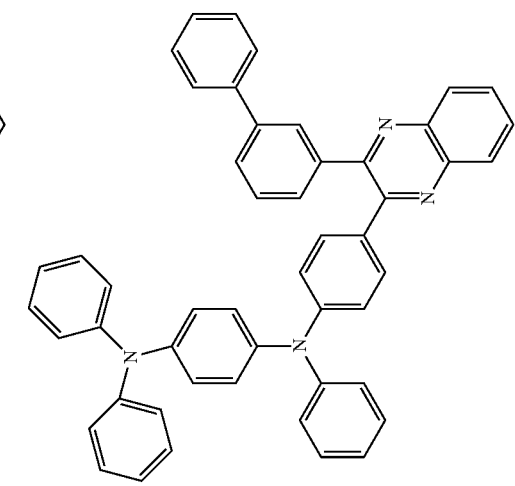
(64)
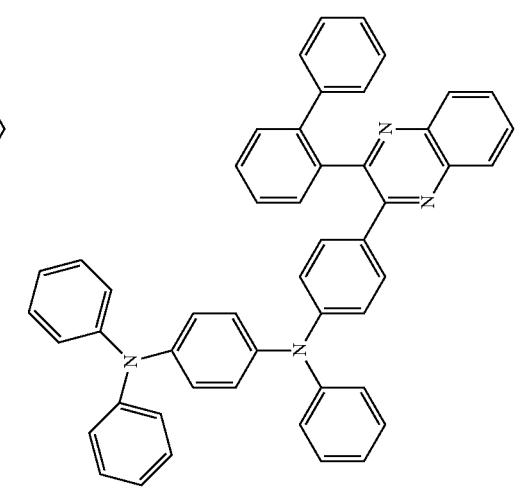

-continued
(65)
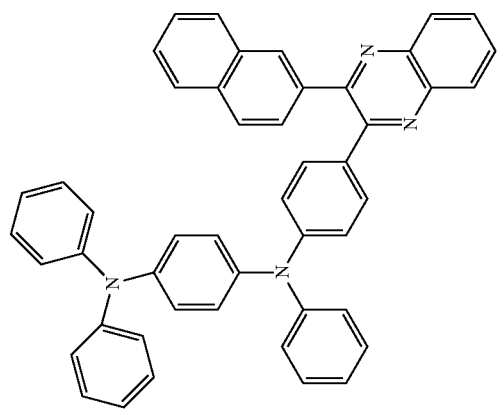
(66)
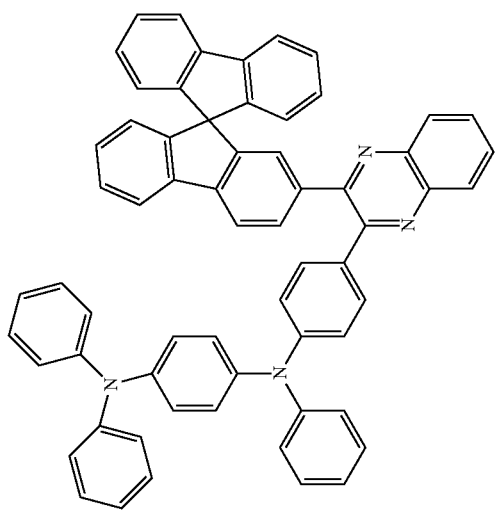
(68)
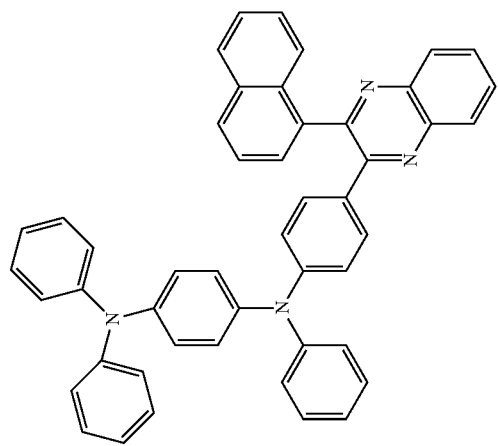
formula [37]
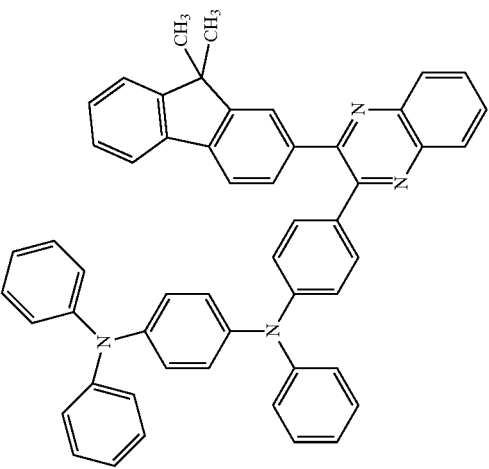
(67)

-continued
(69)
(70)
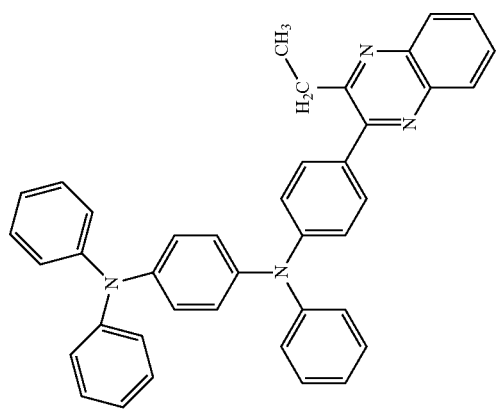
(71)
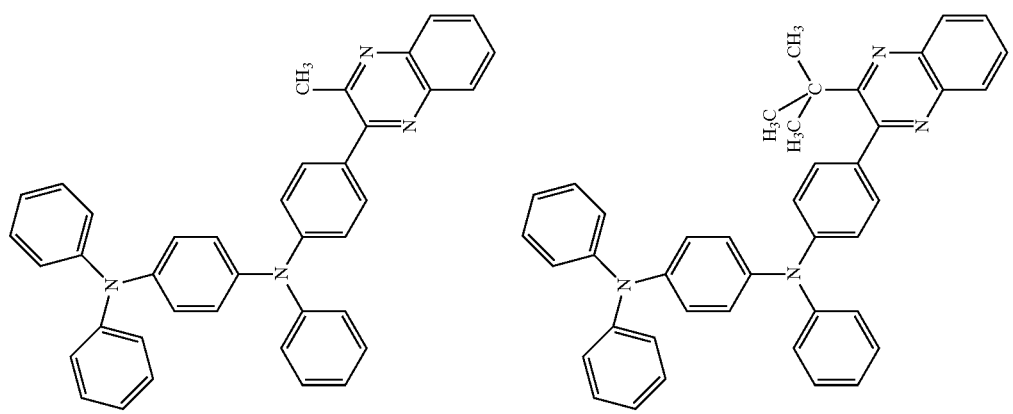

-continued
formula [38]
(72)
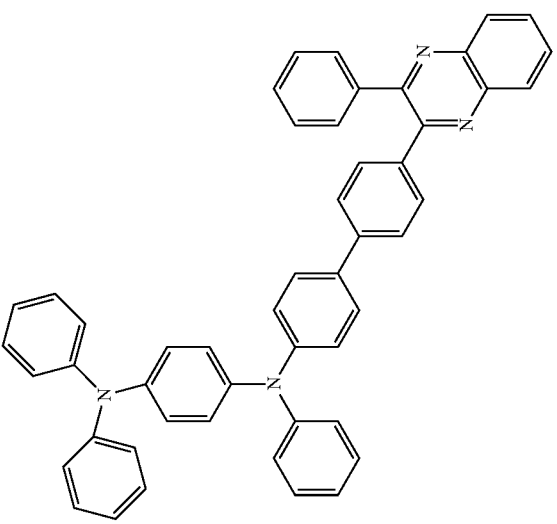
(73)
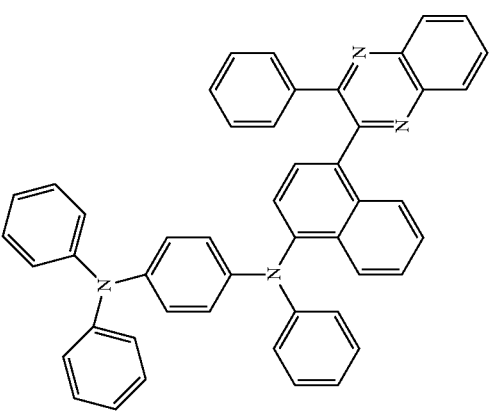
(74)
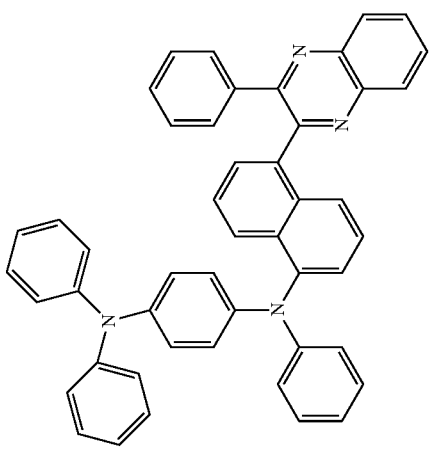

-continued
(76)
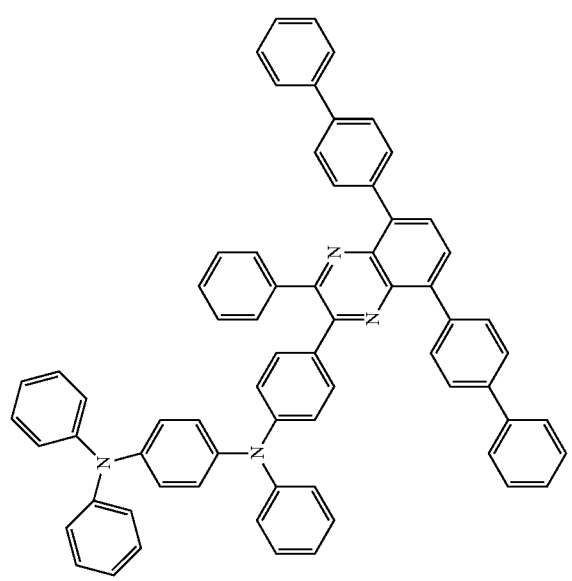
(75)
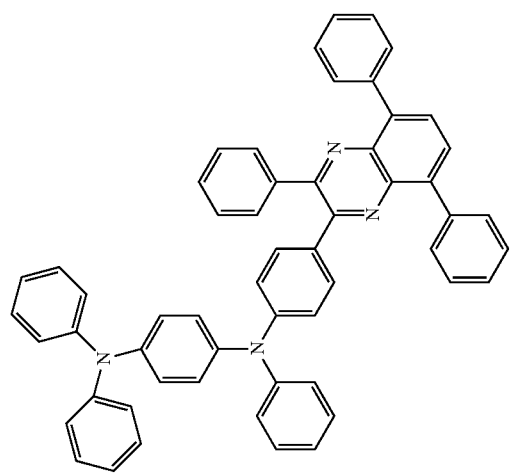
formula [39]

-continued
(78)
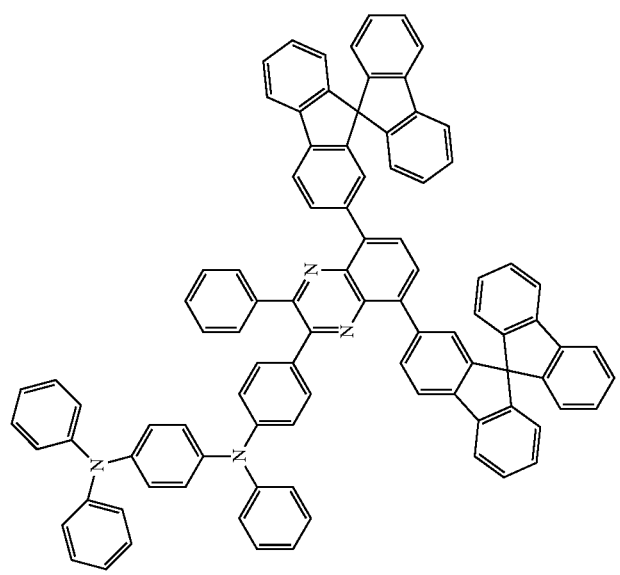
(77)
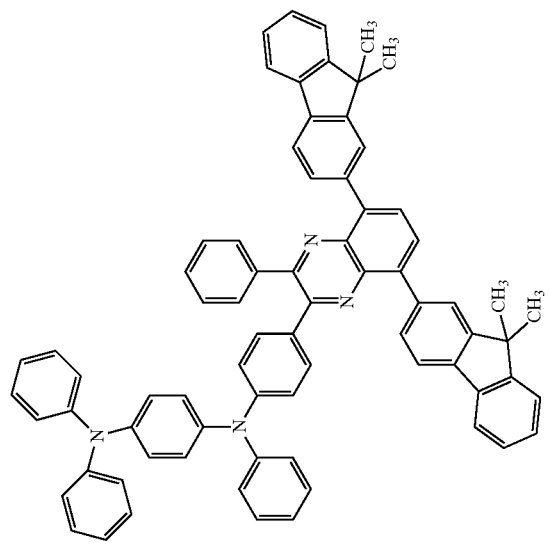

-continued
(79)
(80)
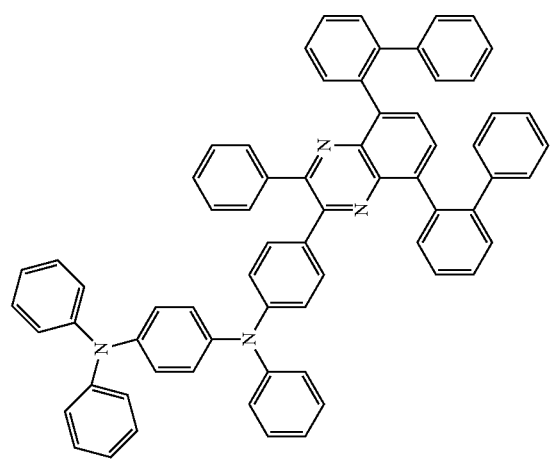
(84)
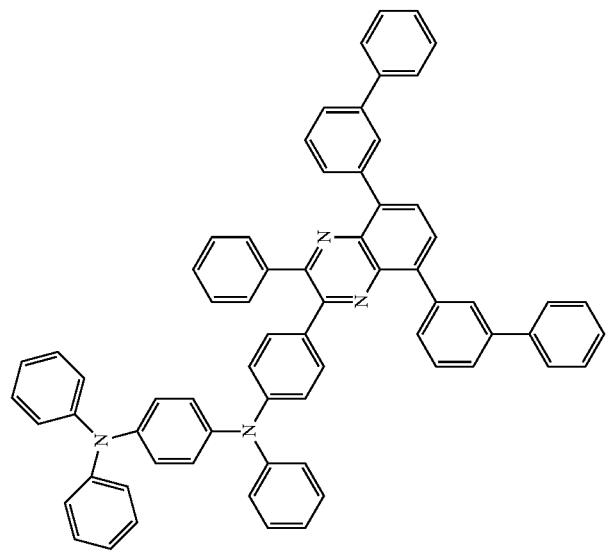
formula [40]

-continued
(82)
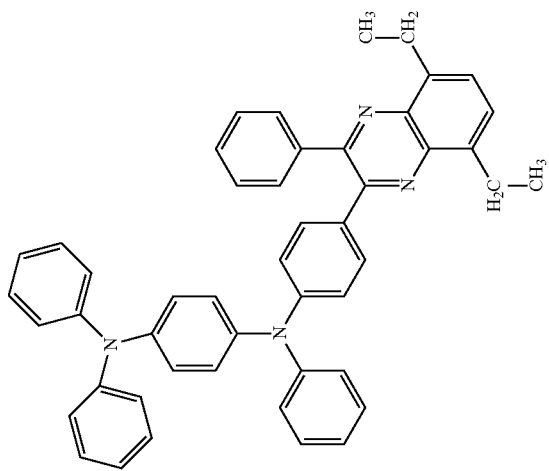
(81)
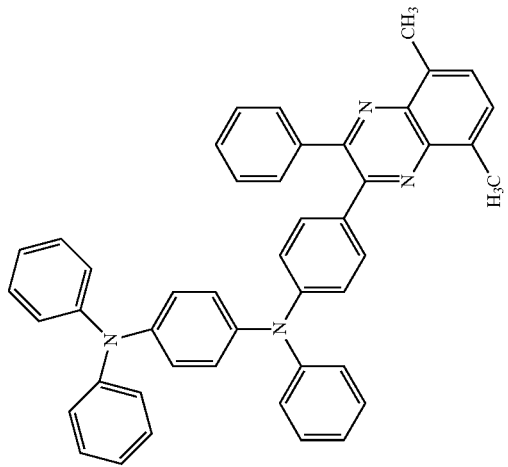

-continued
(84)
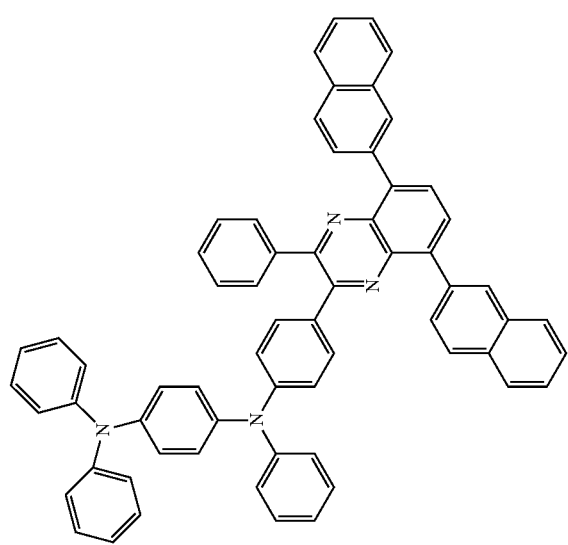
(83)
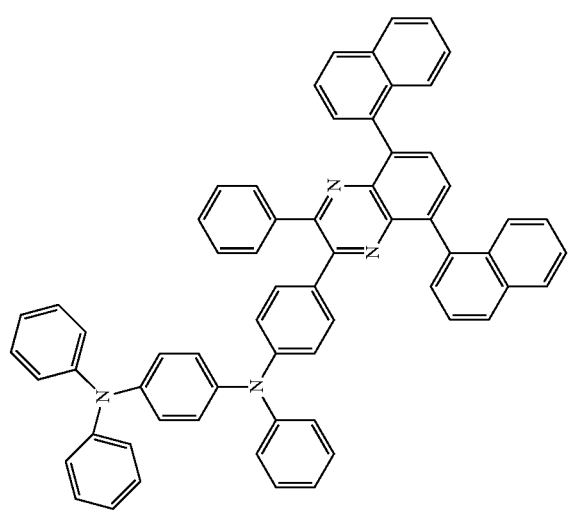
formula [41]

-continued
(85)
(87)
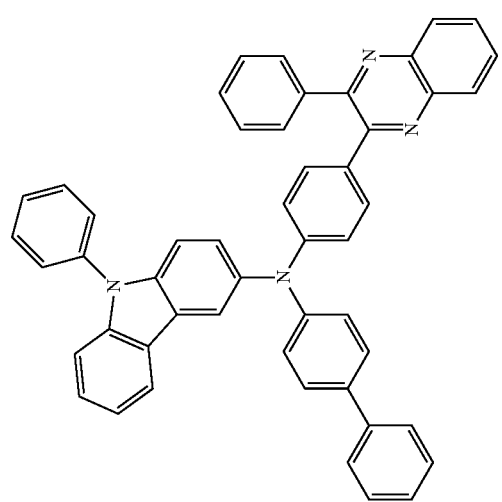
(86)
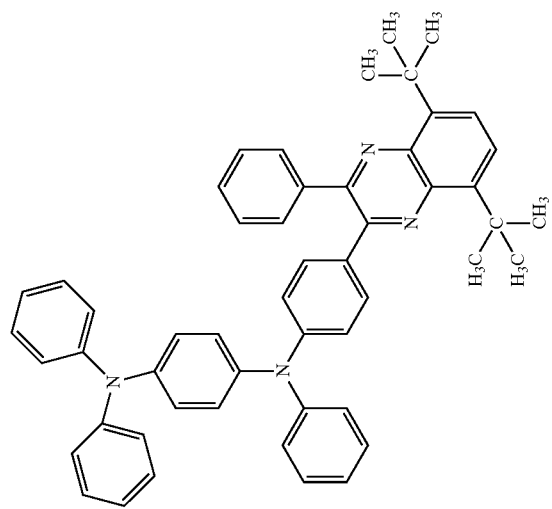
formula [42]
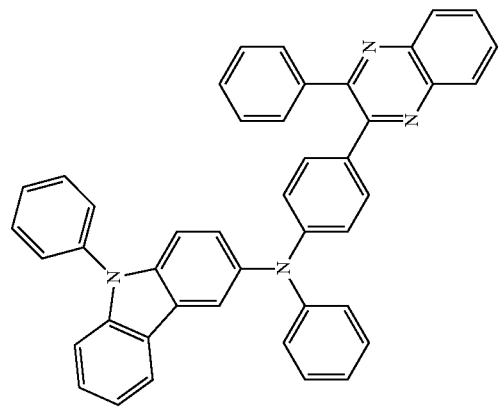

(89)
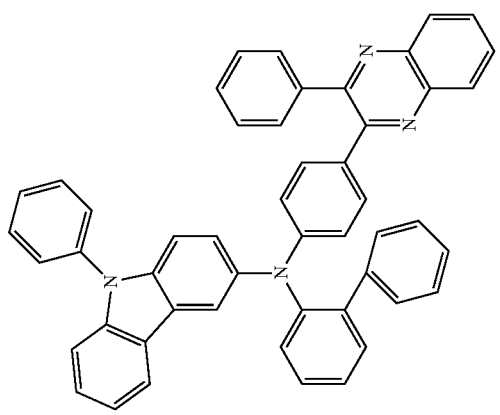
(88)
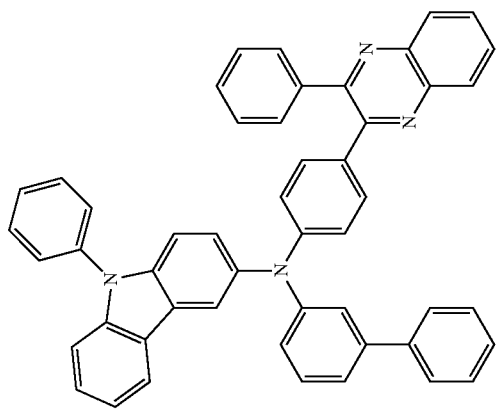

formula [43]
(90)
(91)
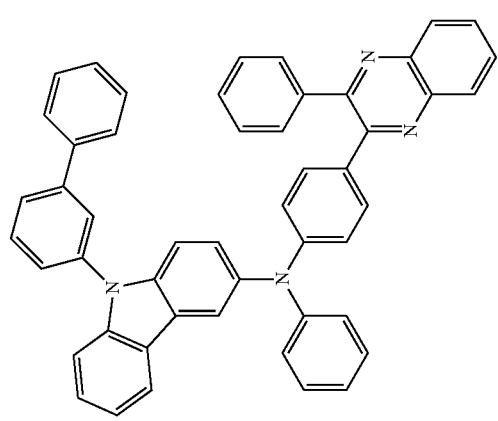

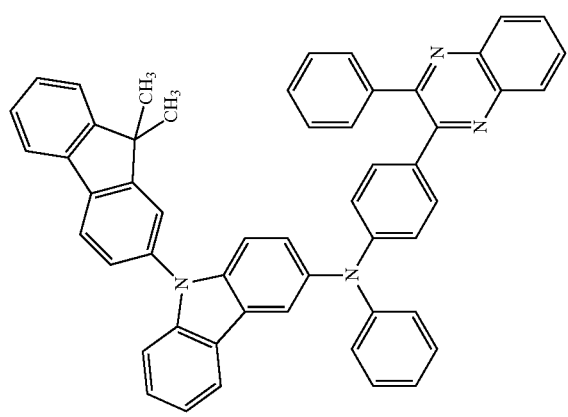
(93)
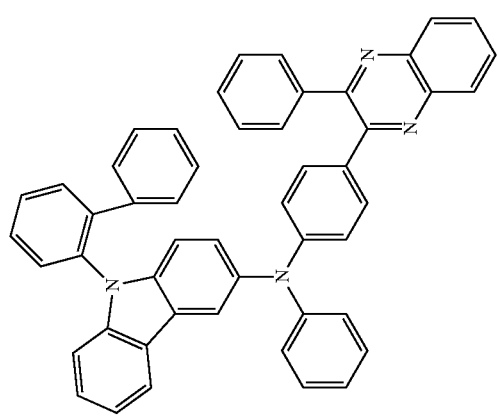
-continued
(92)

-continued
(94)
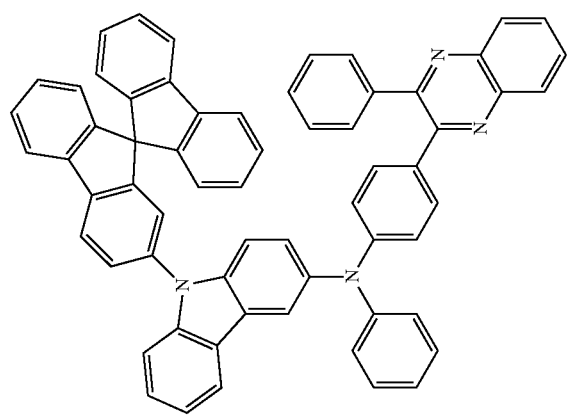
formula [44]
(95)
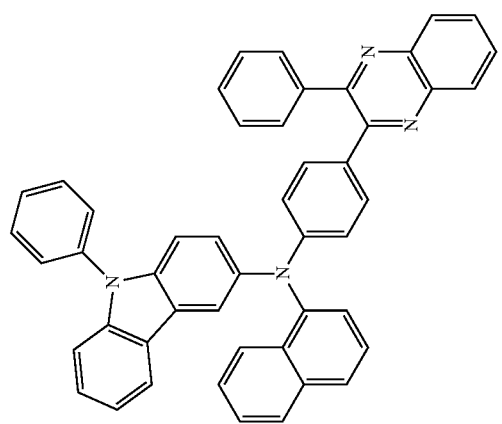
(96)
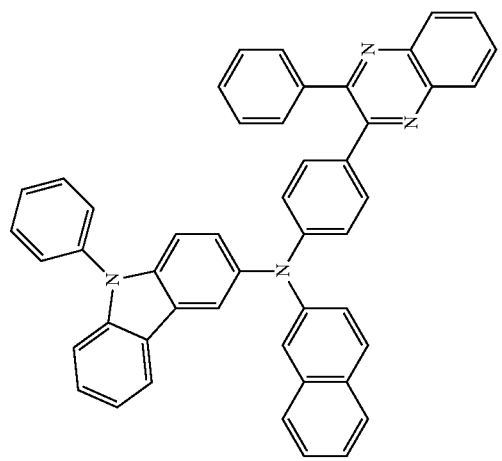

-continued
(97)
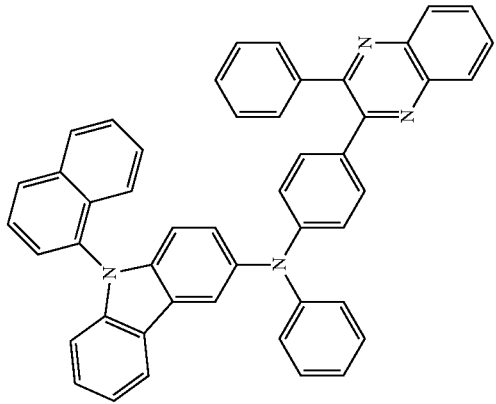
formula [45]
(98)
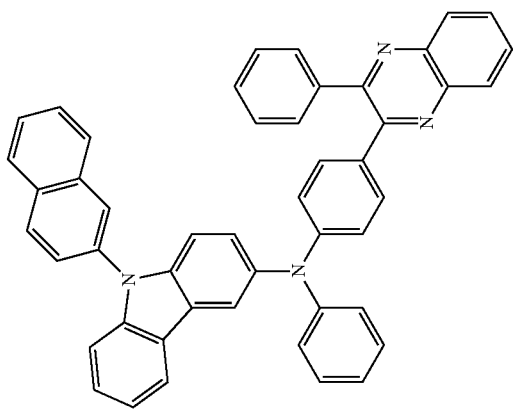
(99)
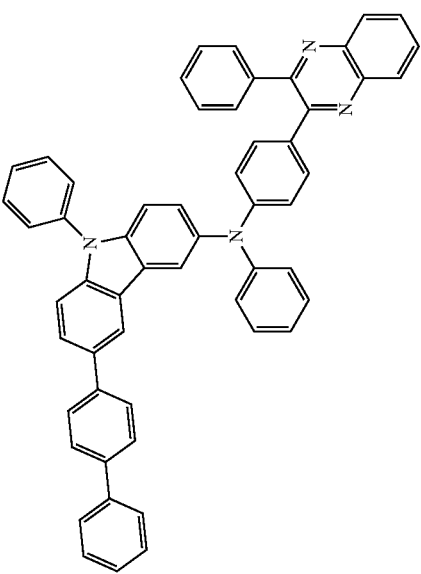
(100)

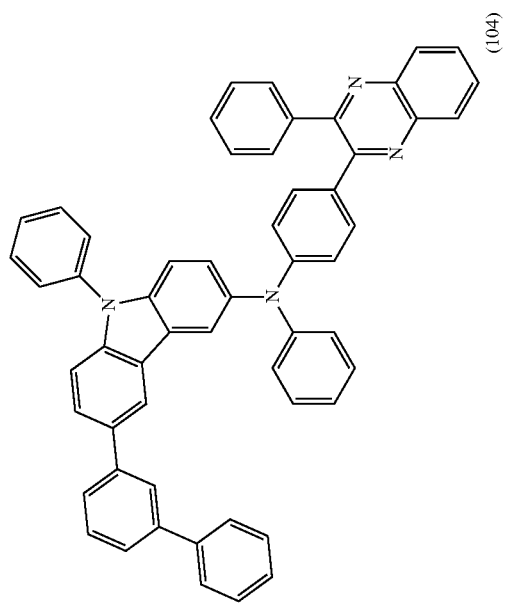
(102)
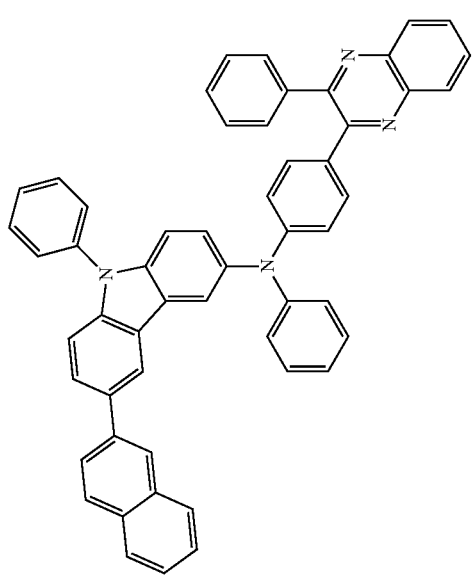
(104)
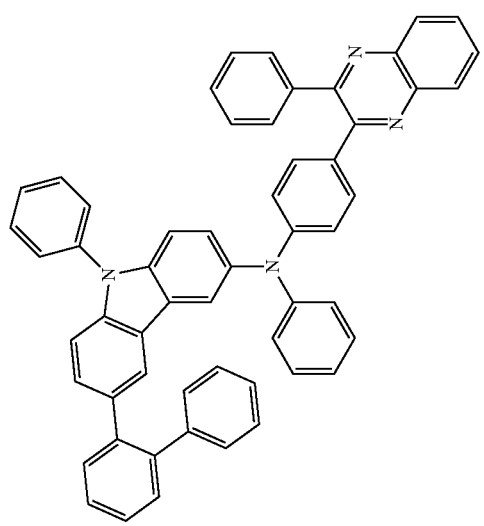
(103)
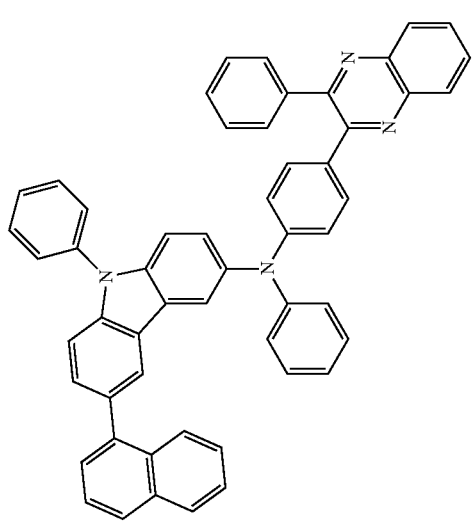
(101)

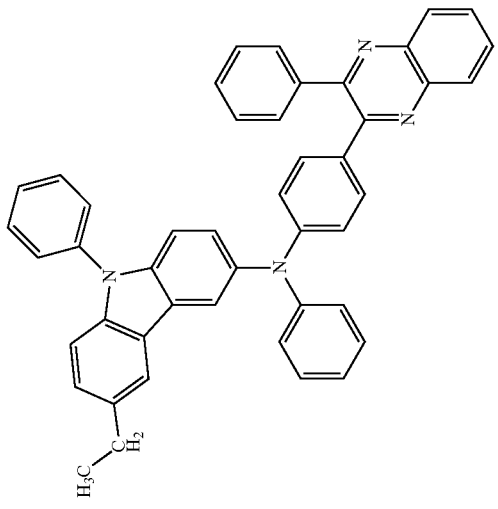

-continued
(109)
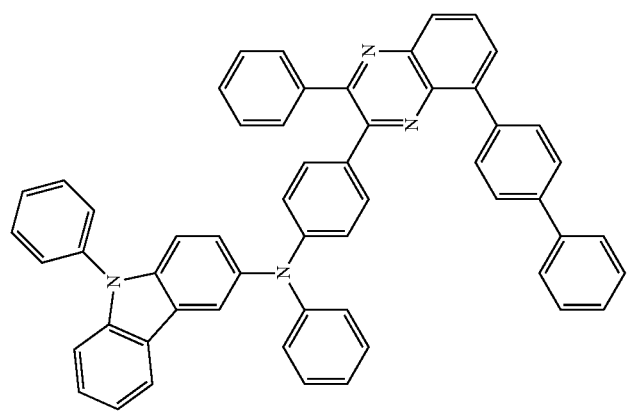
(108)
formula [47]
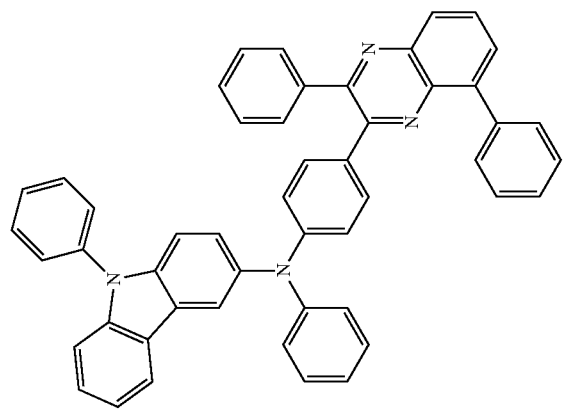

(111)
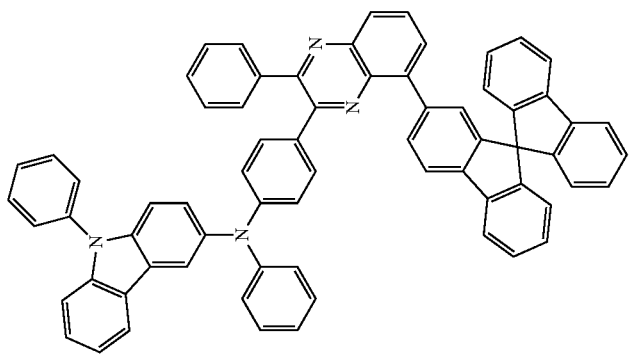
(110)
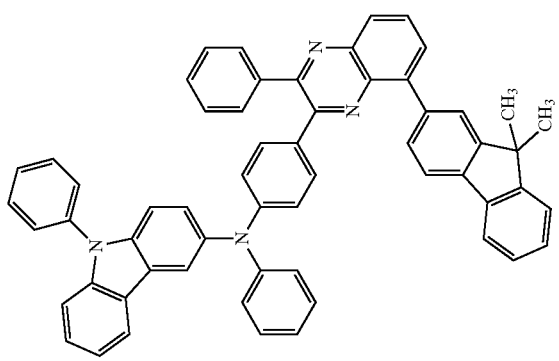

(113)
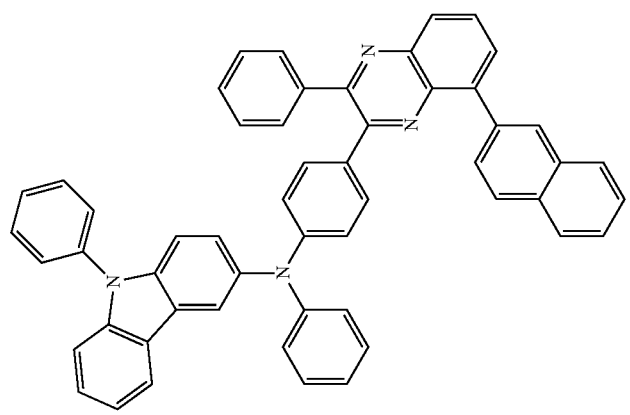
(112)
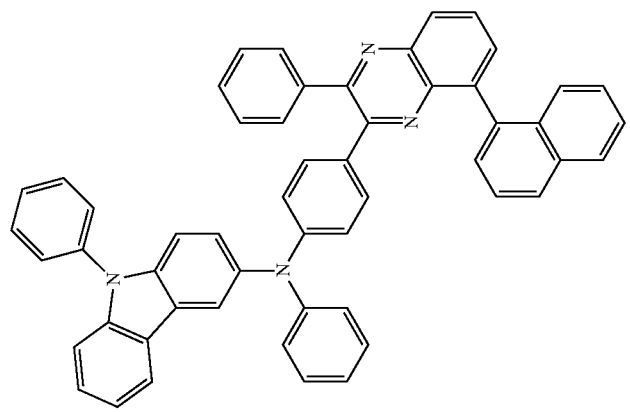
formula [48]

-continued
(115)
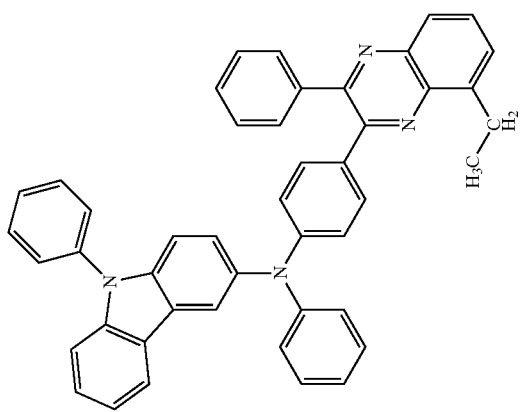
(114)
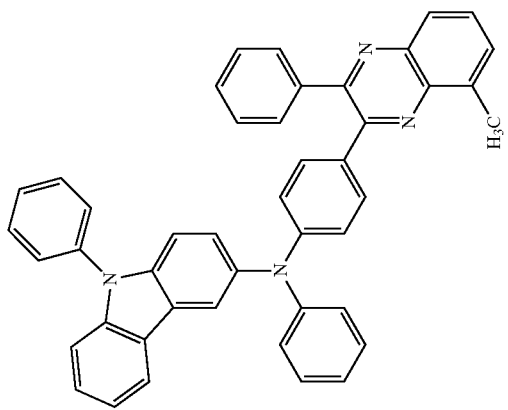

-continued
(117)
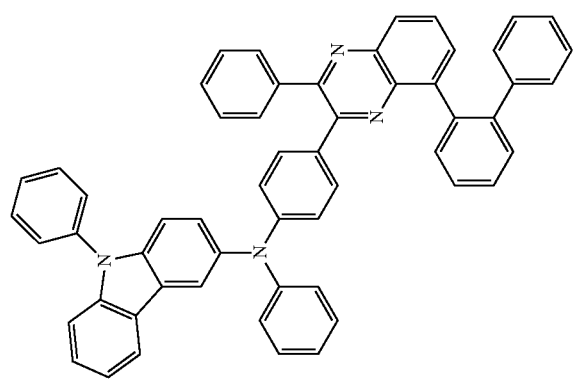
(116)
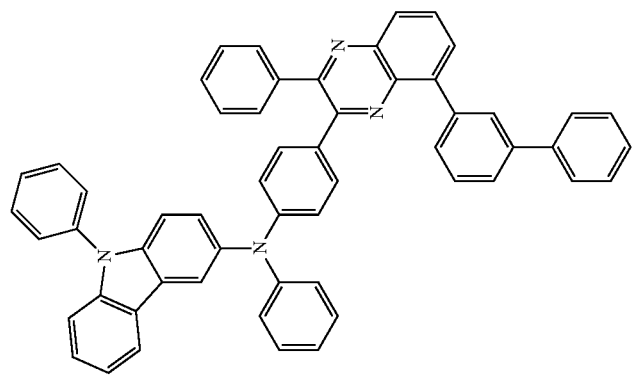
formula [49]

-continued
(118)
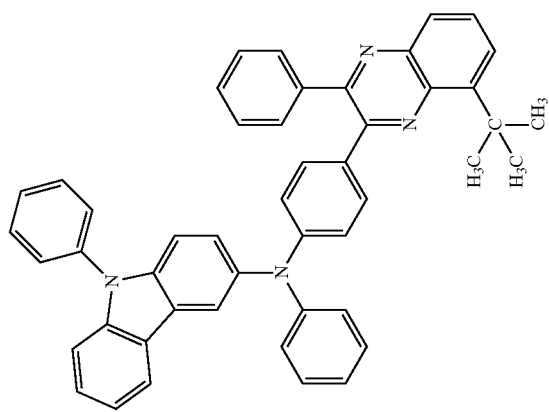

(120)
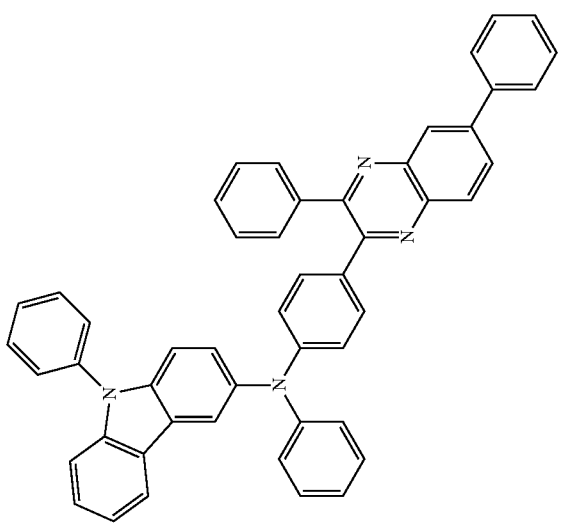
(119)
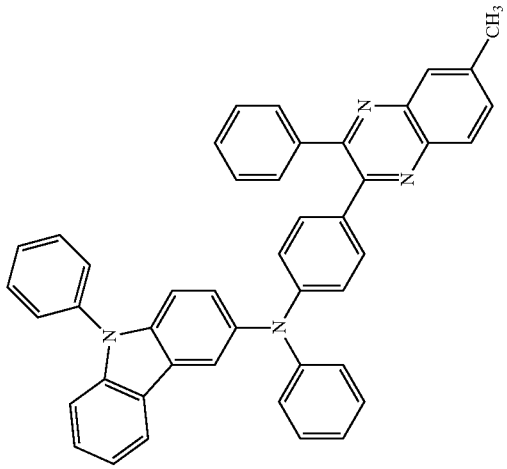
formula [50]

-continued
(122)
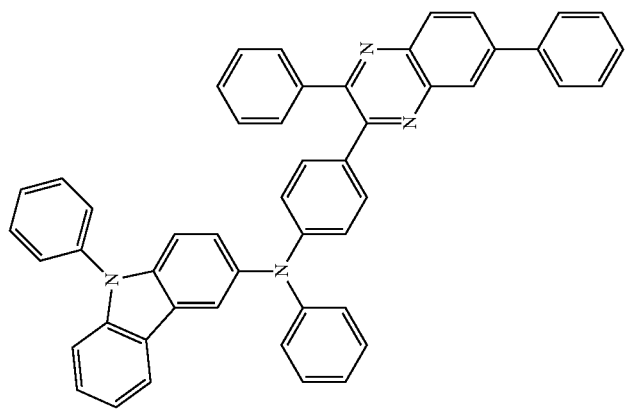
(121)
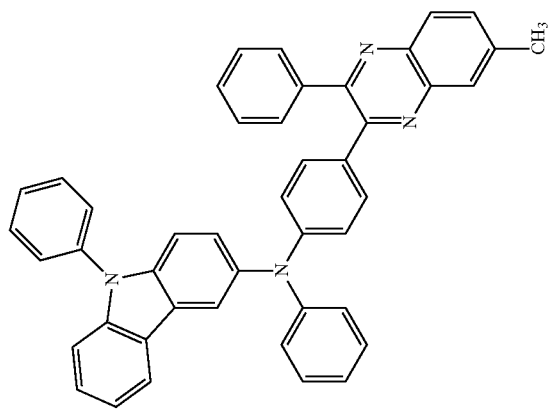

-continued
formula [51]
(123)
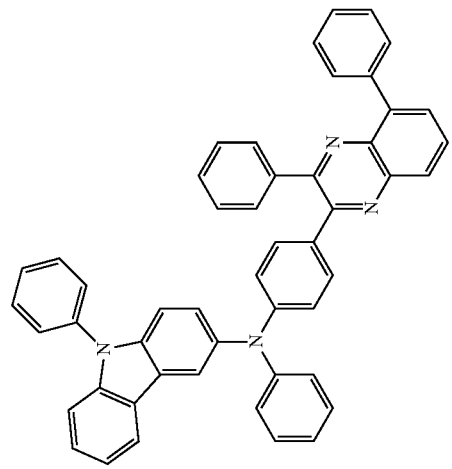
(124)
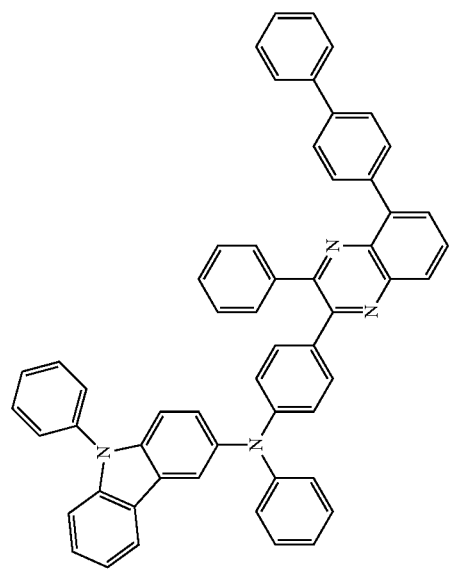
(125)
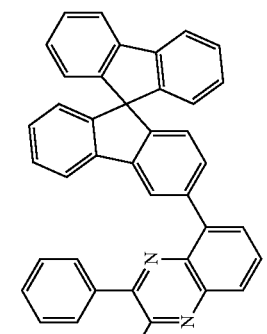
(126)
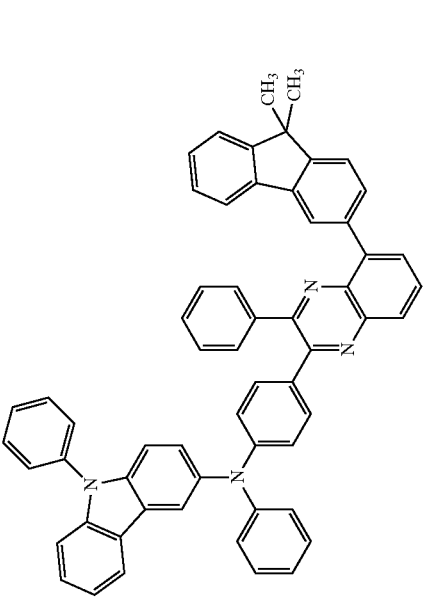

-continued
formula [52]
(127)
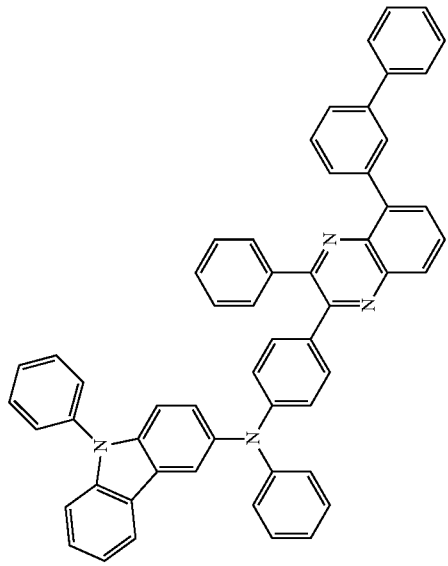
(128)
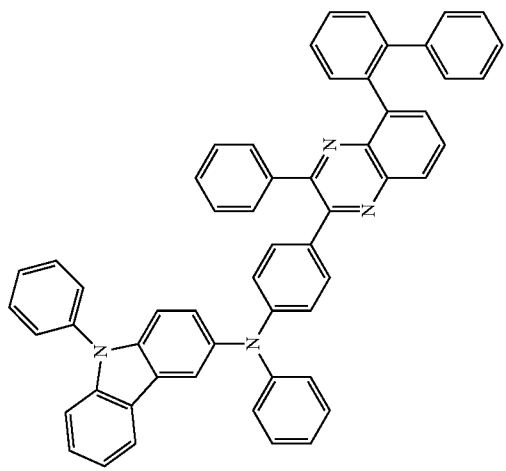
(129)
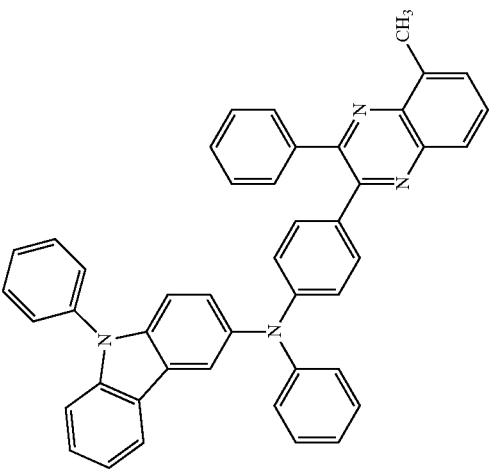
(130)
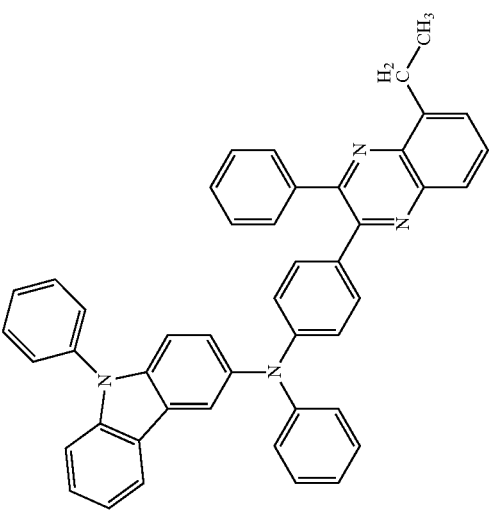

-continued
(132)
(133)
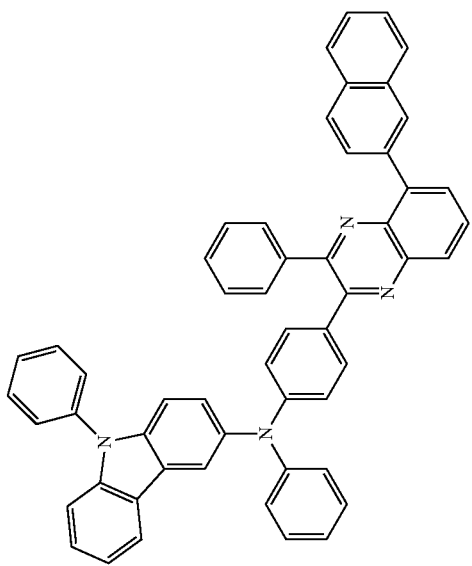
formula [53]
(131)
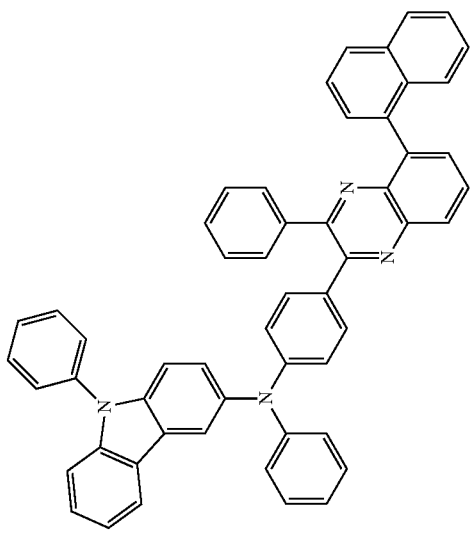
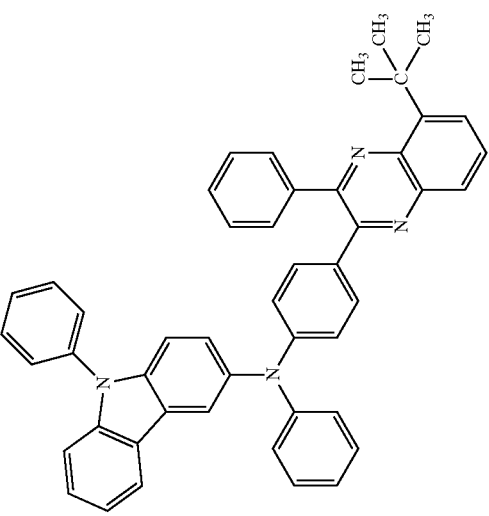

-continued
formula [54]
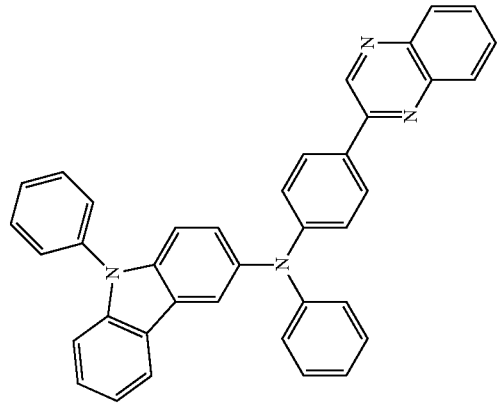
(134)
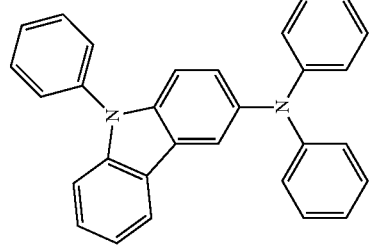
(135)
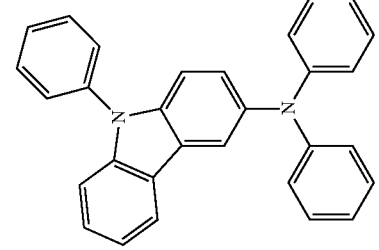
(136)
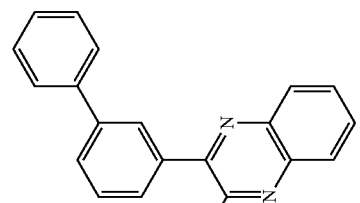
(137)

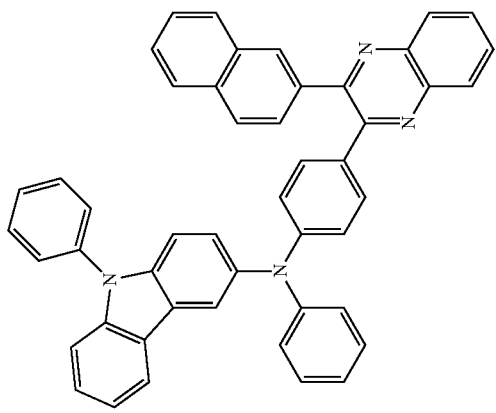
(138)
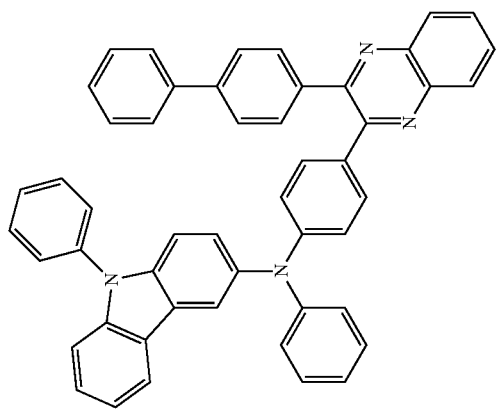
(134)
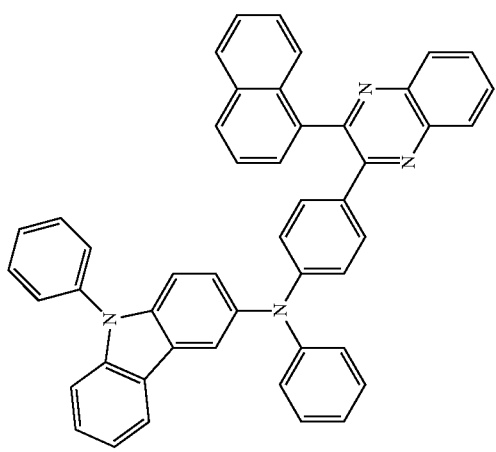
(139)
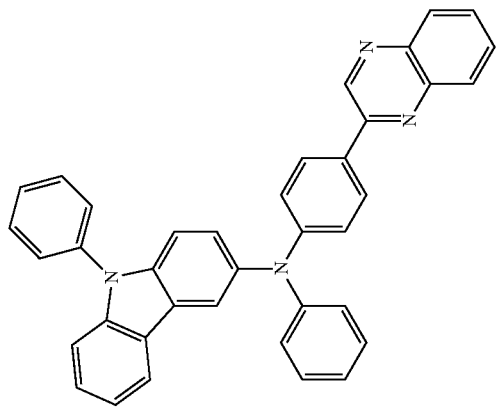
(135)

-continued
(137)
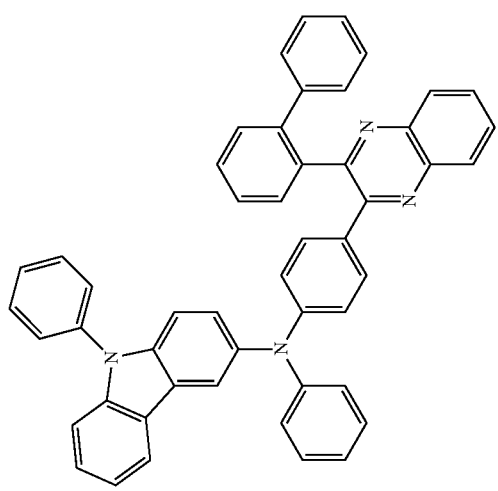
(139)
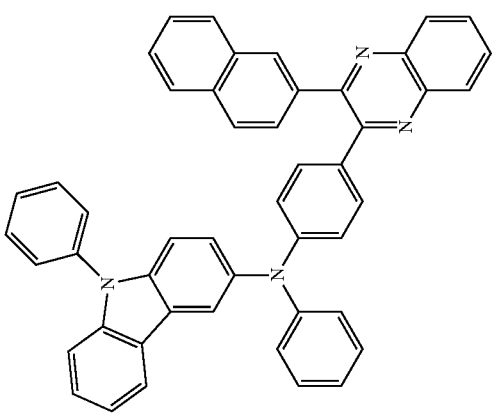
(136)
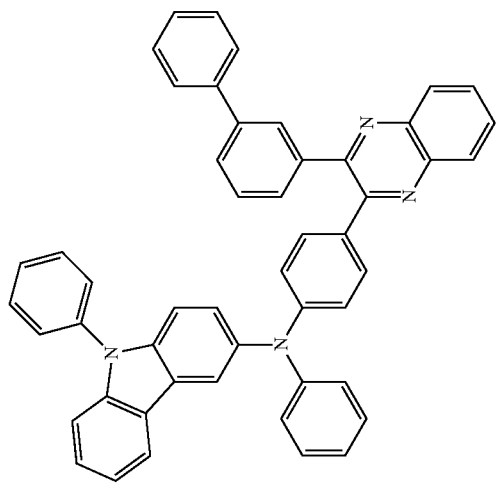
(138)
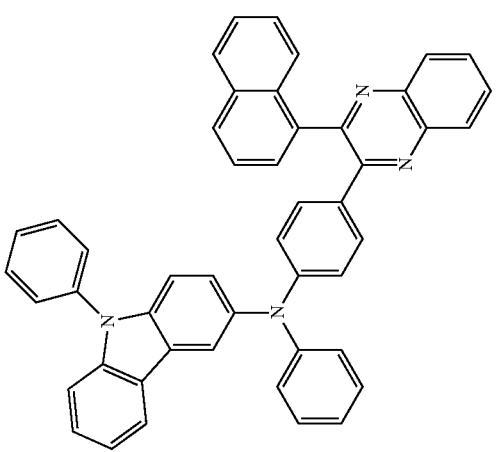

formula [56]
(145)
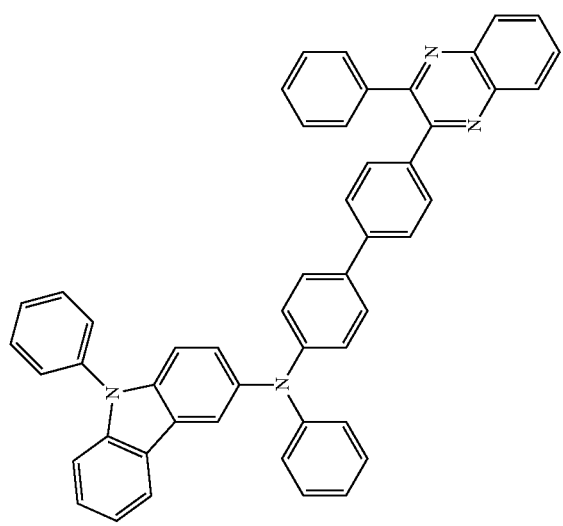
(146)
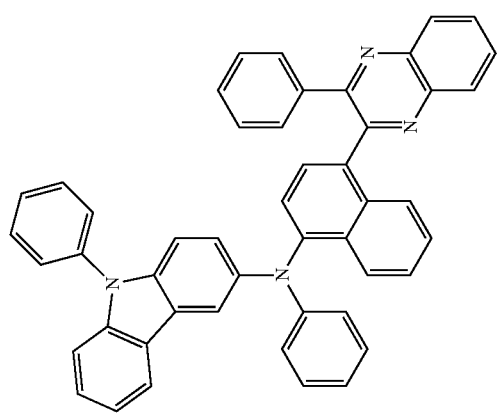
(147)
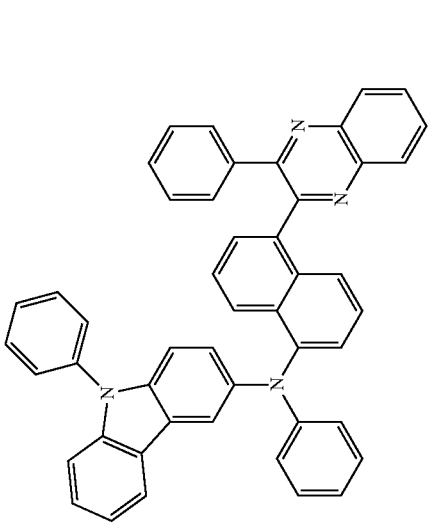

-continued
(149)
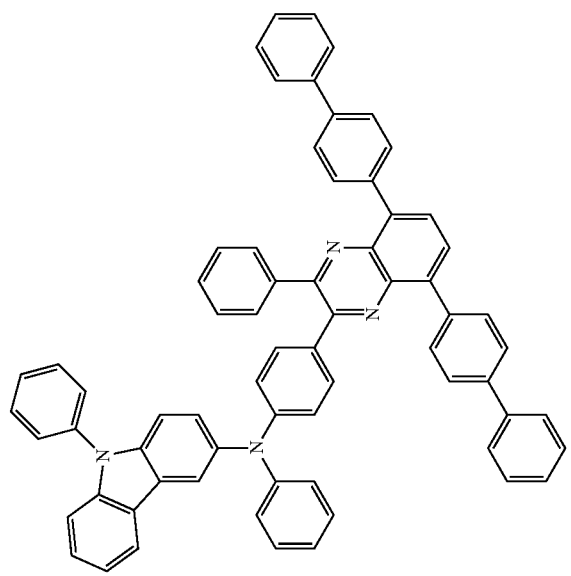
(148)
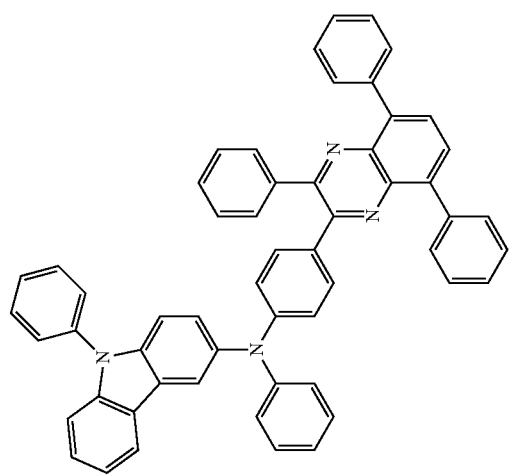

-continued
(151)
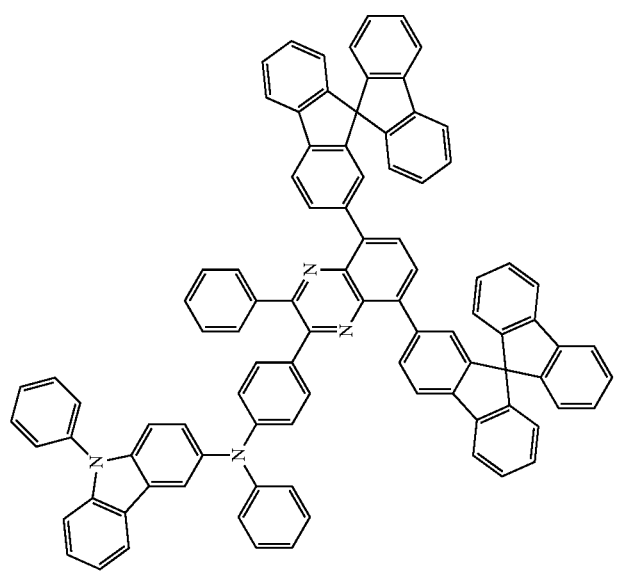
(150)
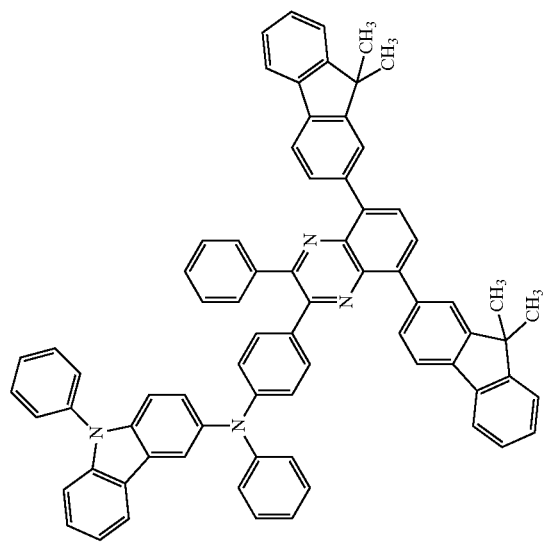

-continued
formula [58]
(153)
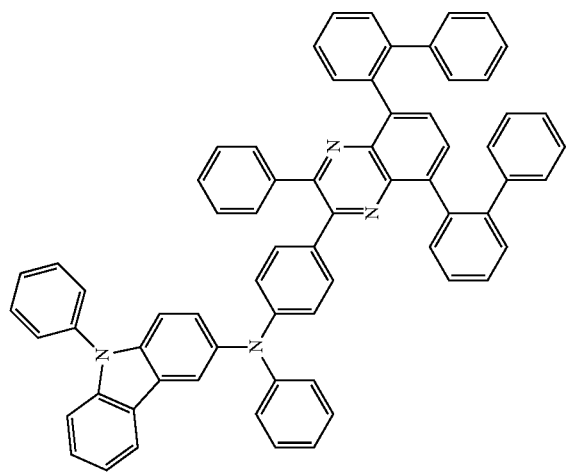
(152)
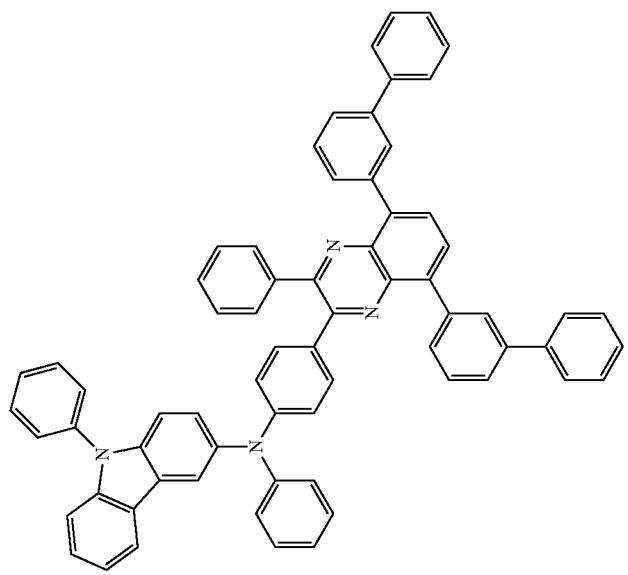

-continued
(155)
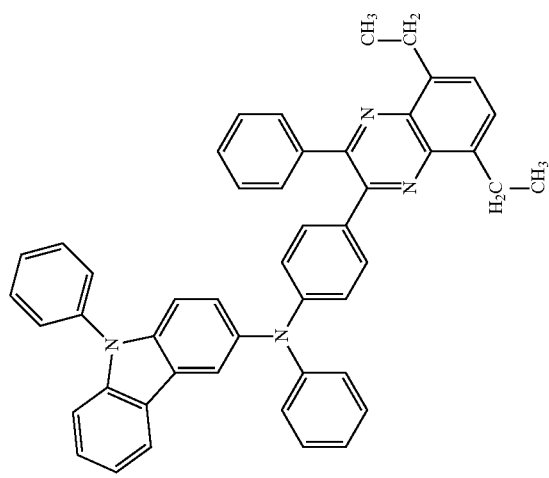
(154)
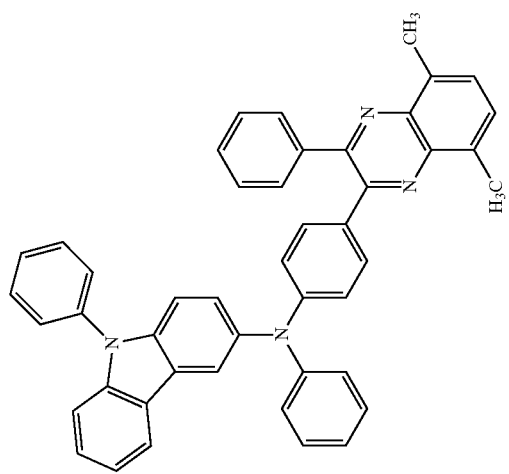

-continued
(156)
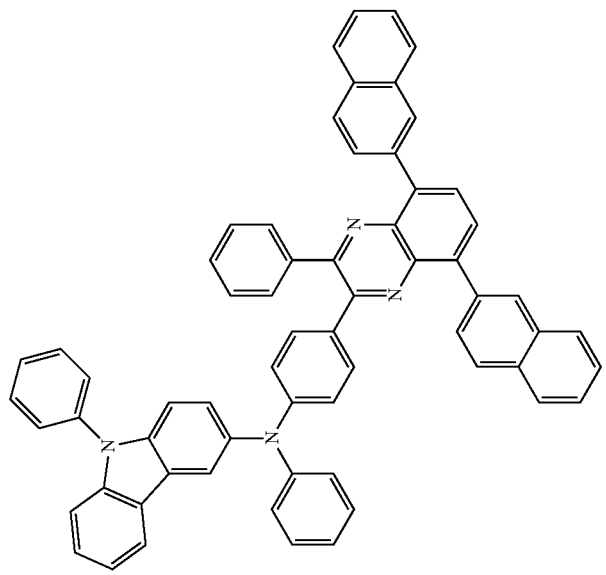
(167)
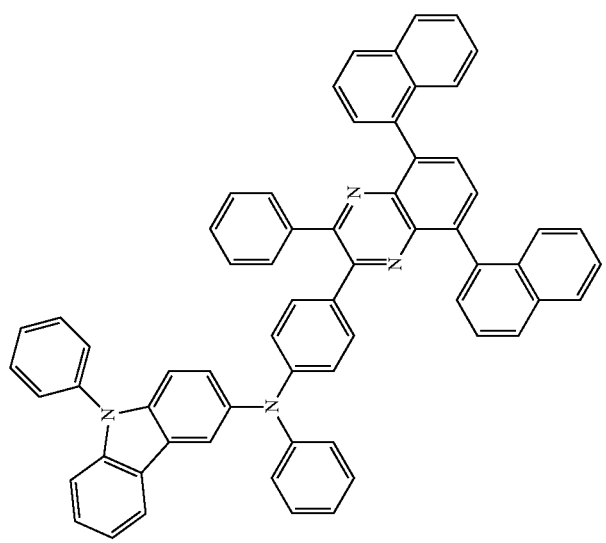

-continued
(158)
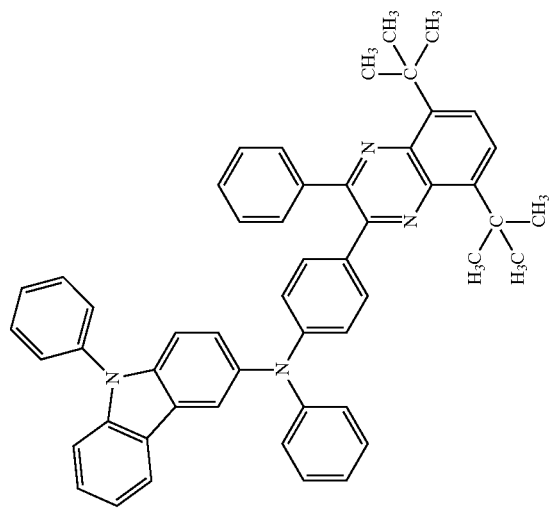
(159)
(160)
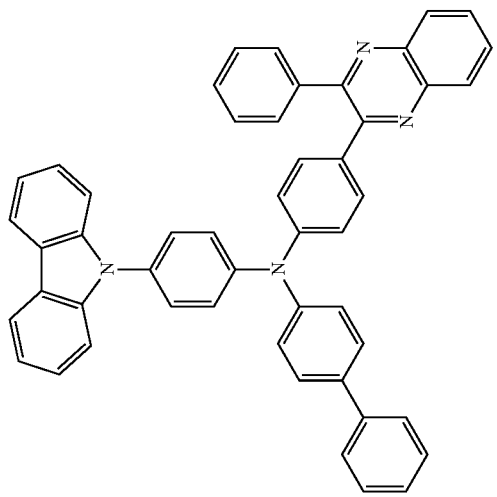
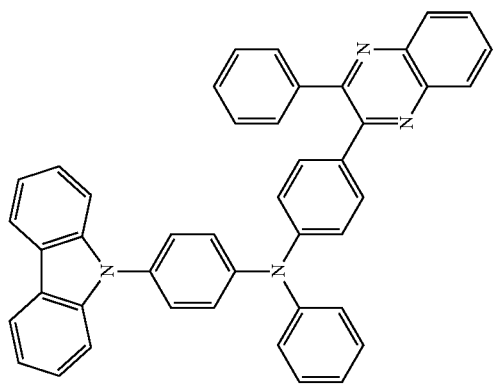
formula [60]

-continued
(162)
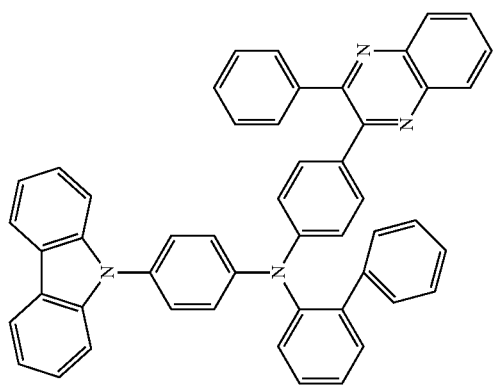
(161)
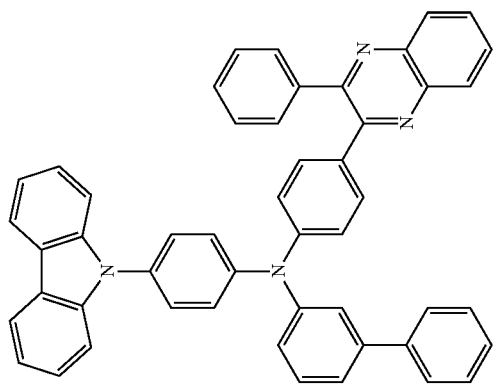

-continued
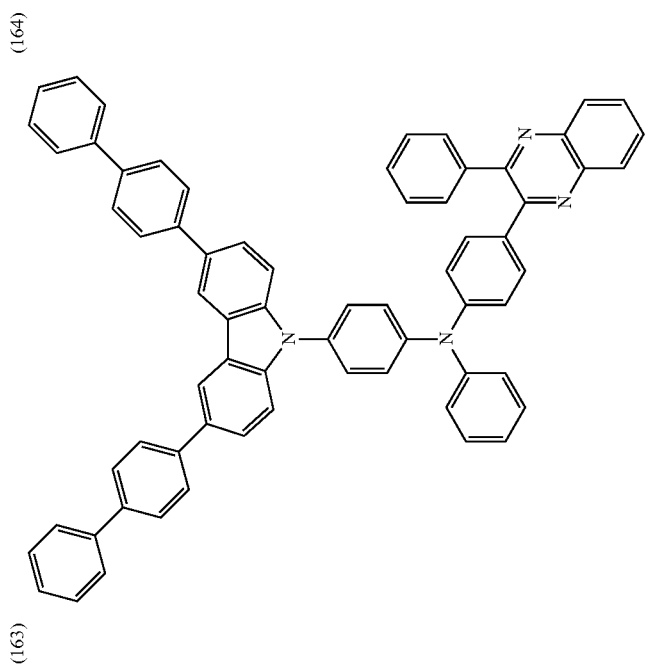
(164)
(163)
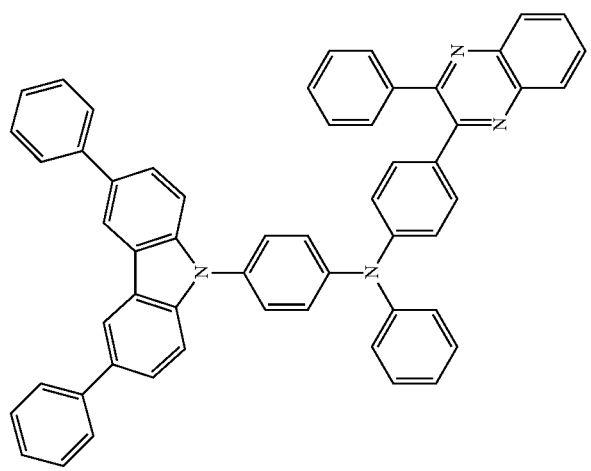
formula [61]

-continued
(166)
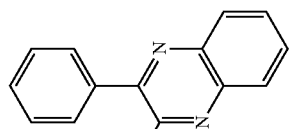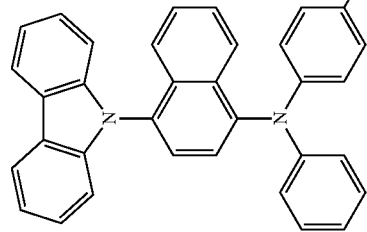
(165)
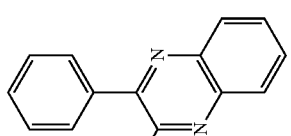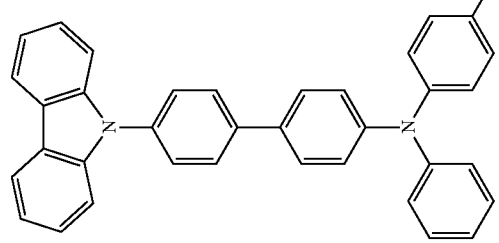

-continued
(167)
(169)
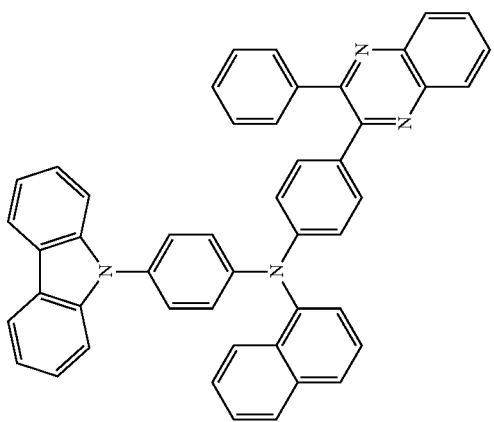
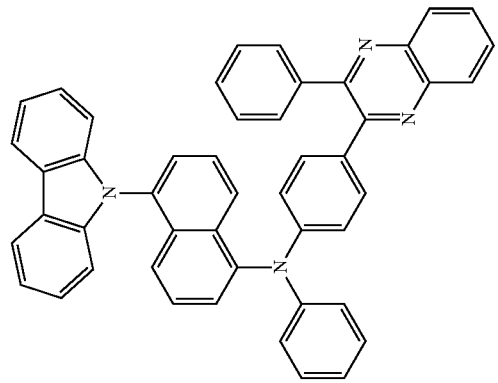
formula [62]
(168)
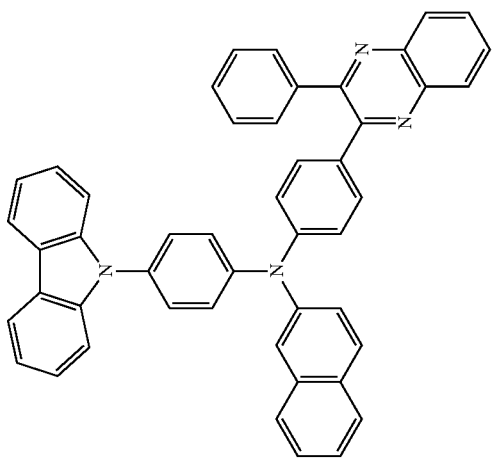

-continued
(171)
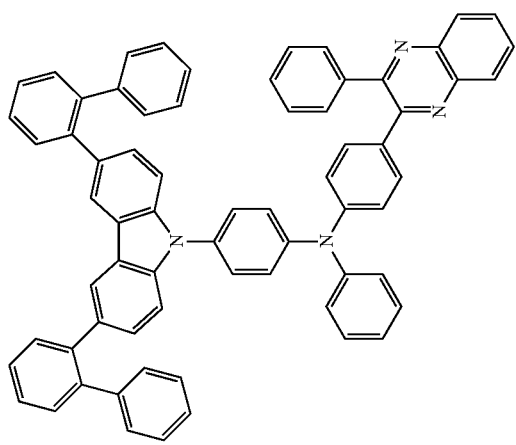
(170)
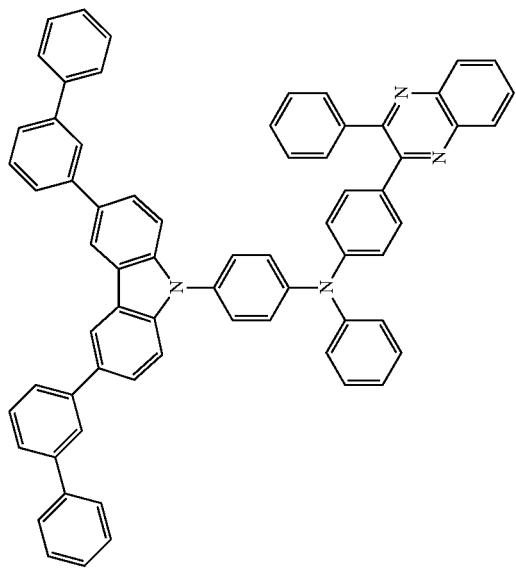

(173)
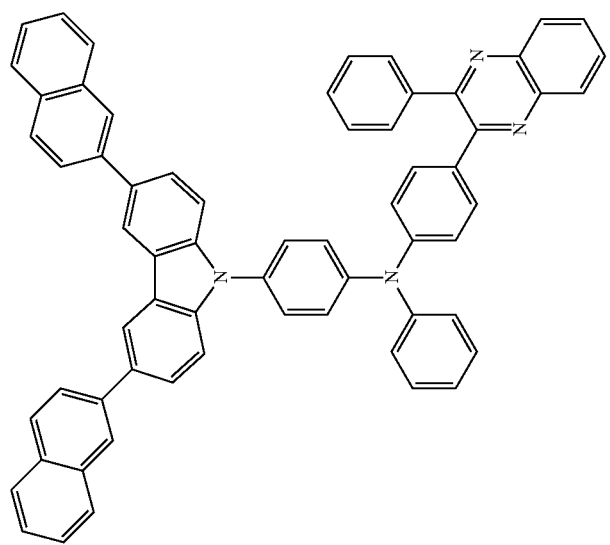
(172)
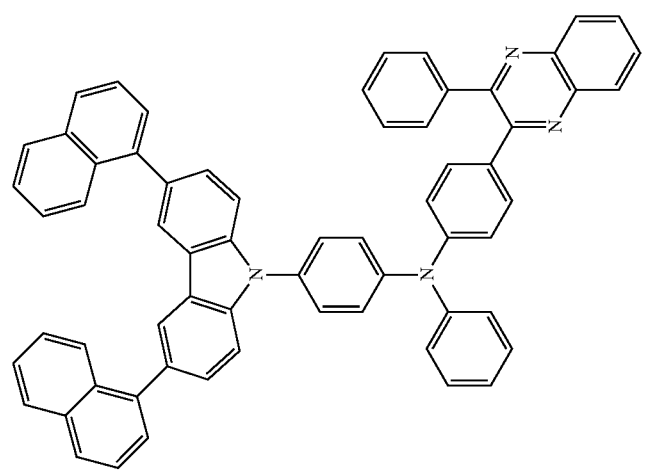

-continued
(175)
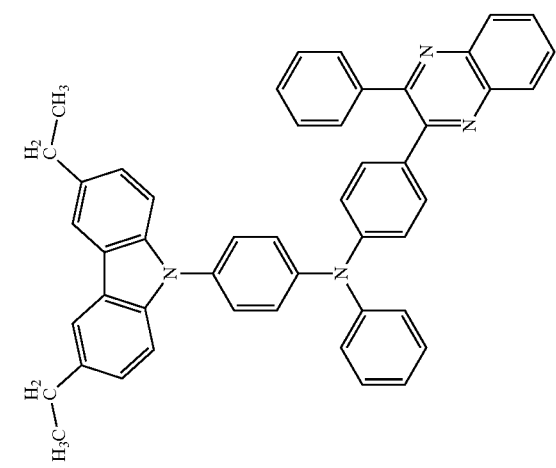
(174)
formula [63]
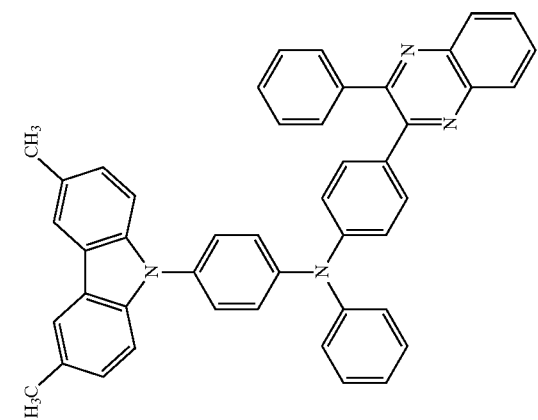

(177)
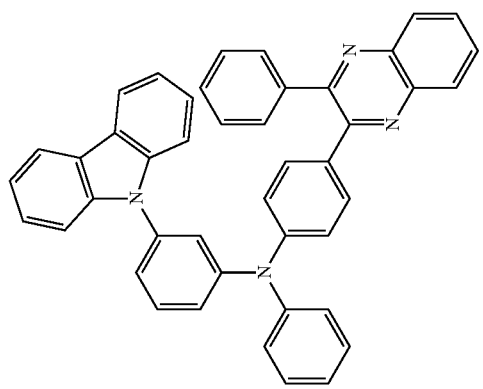
-continued
(176)
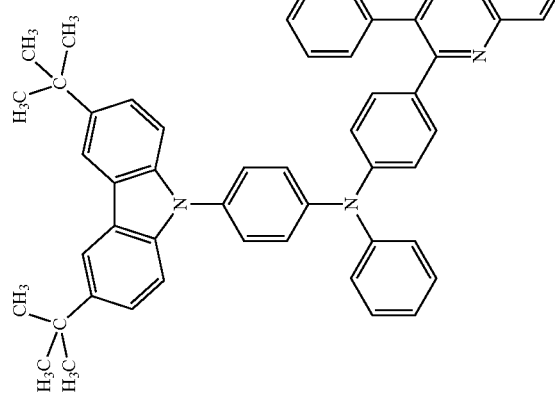
(178)
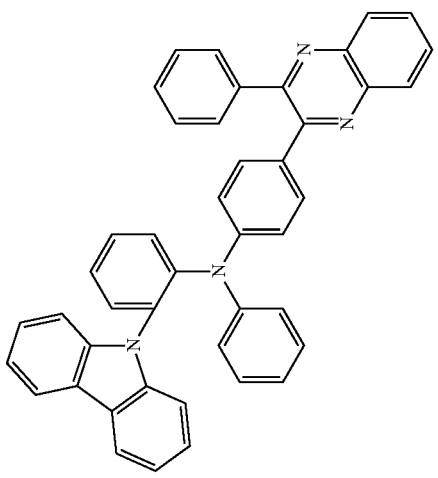

-continued
(180)
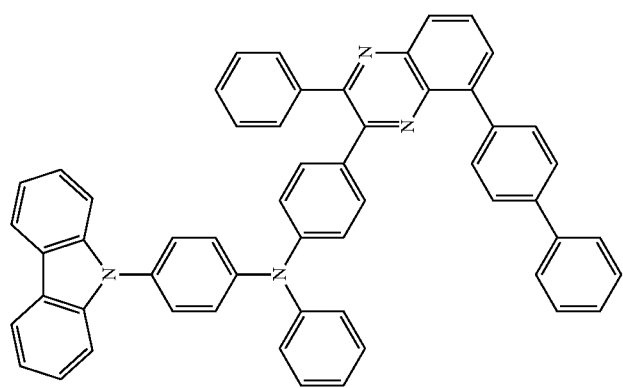
(179)
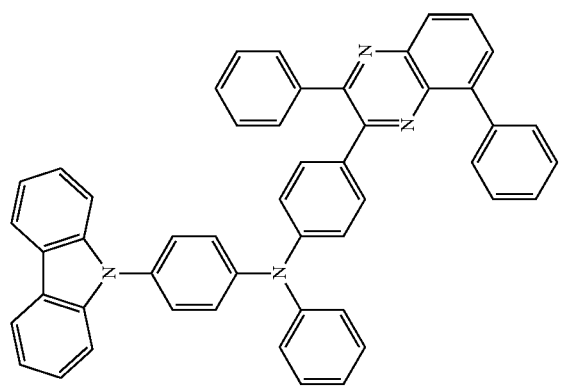
formula [64]

(182)
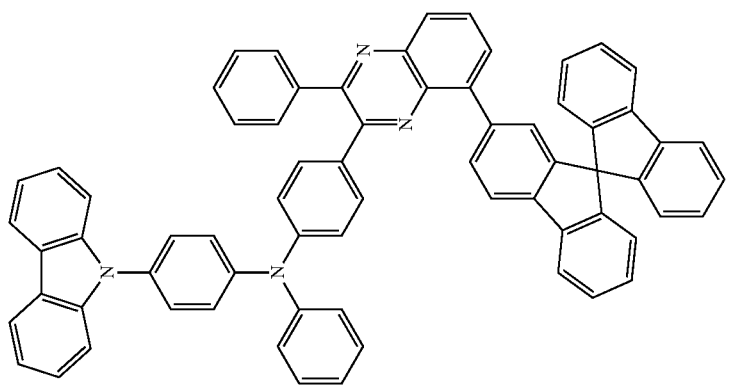
(181)
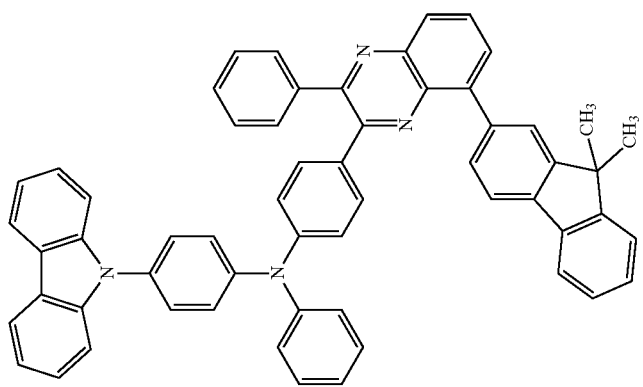

-continued
(184)
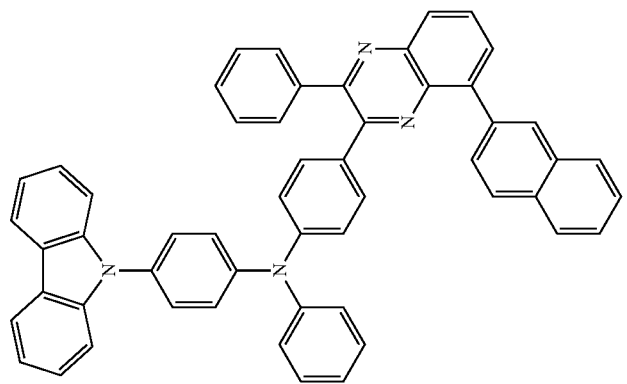
(183)
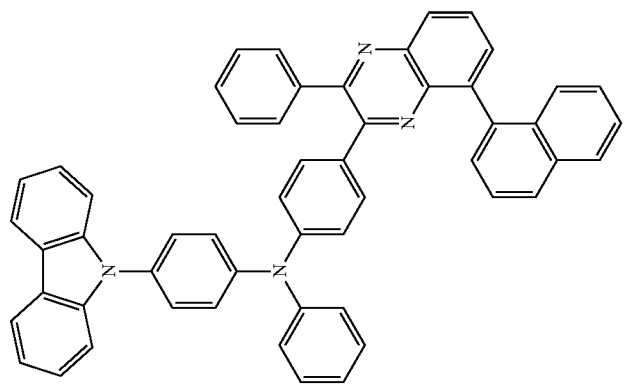
formula [65]

-continued
(185)
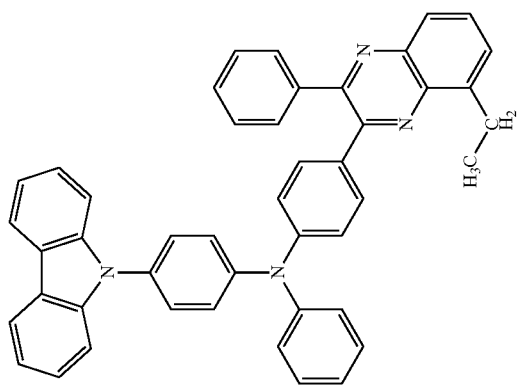
(186)
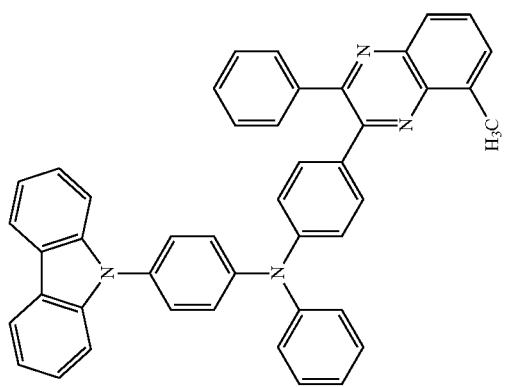

-continued
(188)
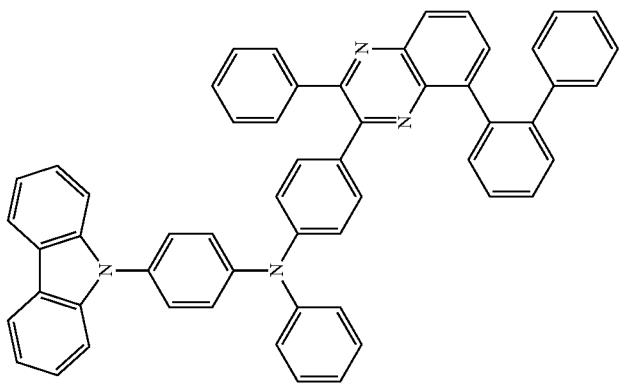
(187)
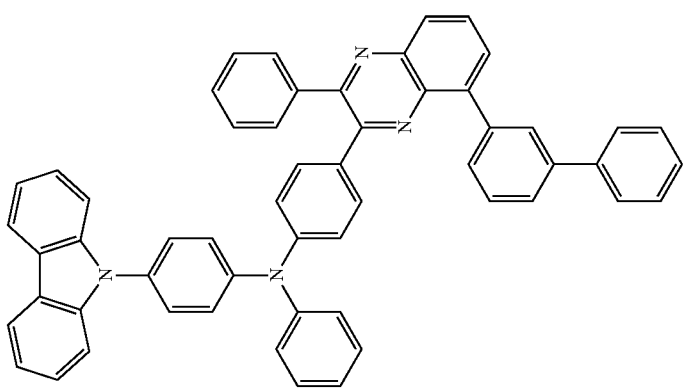
formula [66]

(189)
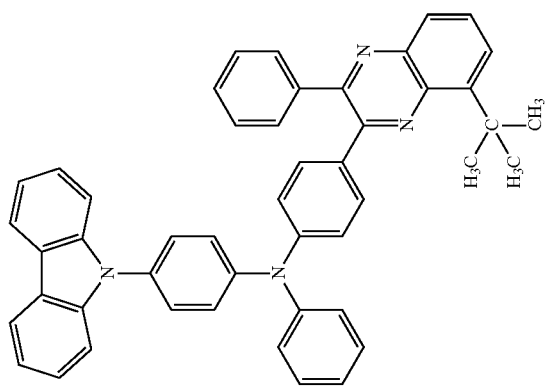

(191)
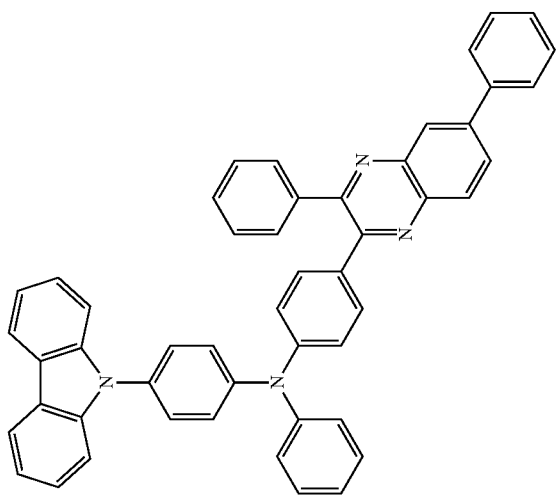
(190)
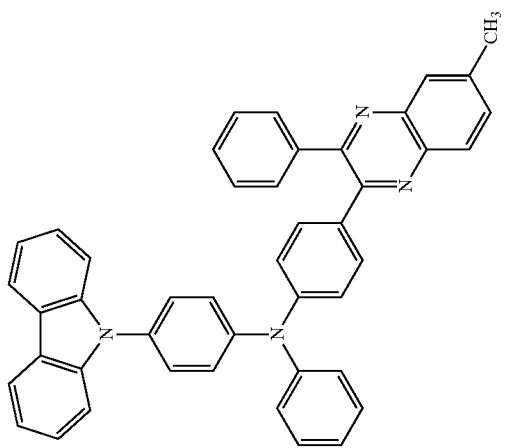
formula [67]

-continued
(193)
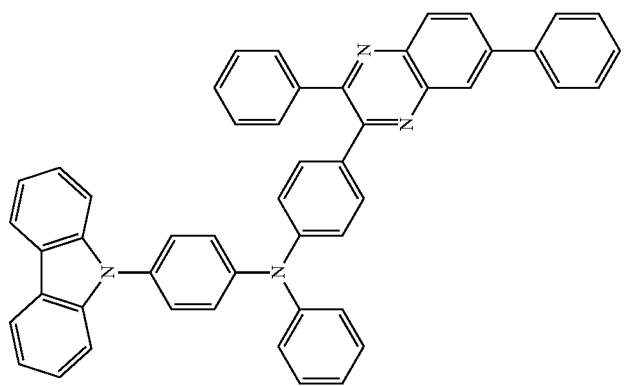
(192)
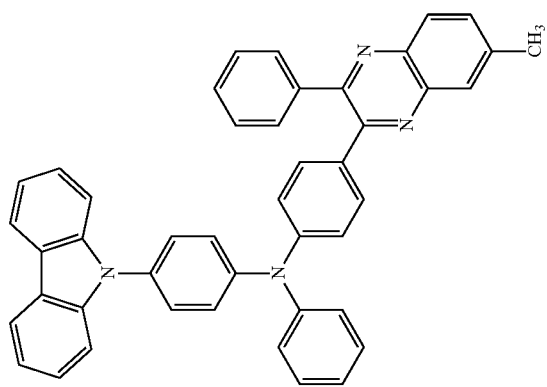

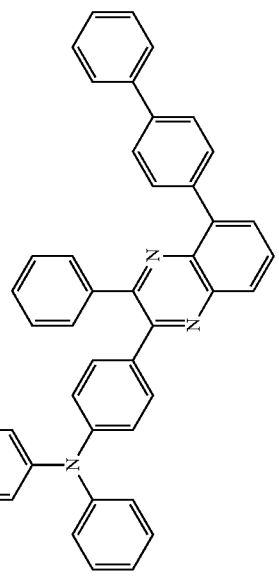
(194)
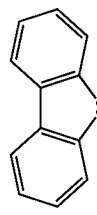
formula [68]
(195)
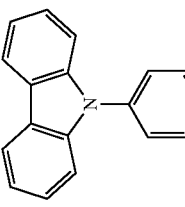
(196)
(197)
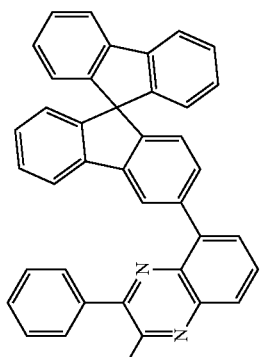

-continued
(198)
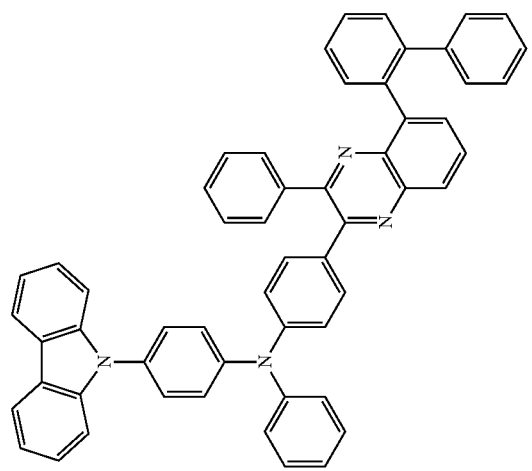
(199)
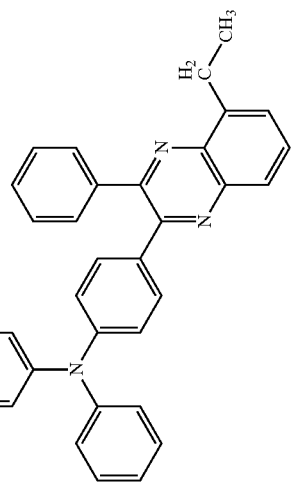
formula [69]
(200)
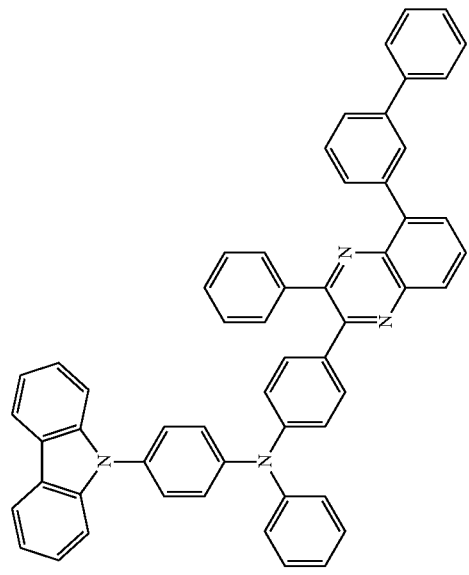
(201)
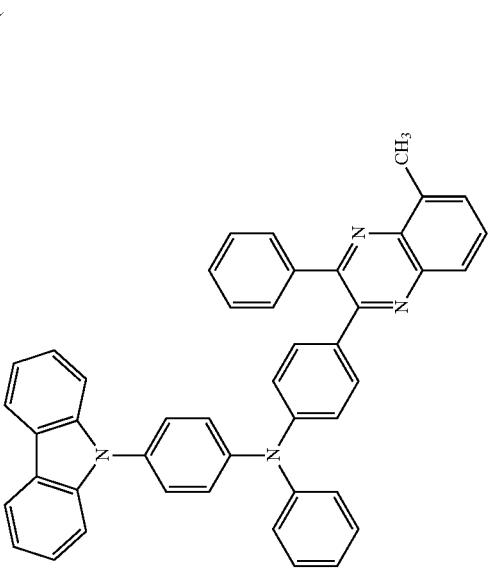

formula [70]
(202)
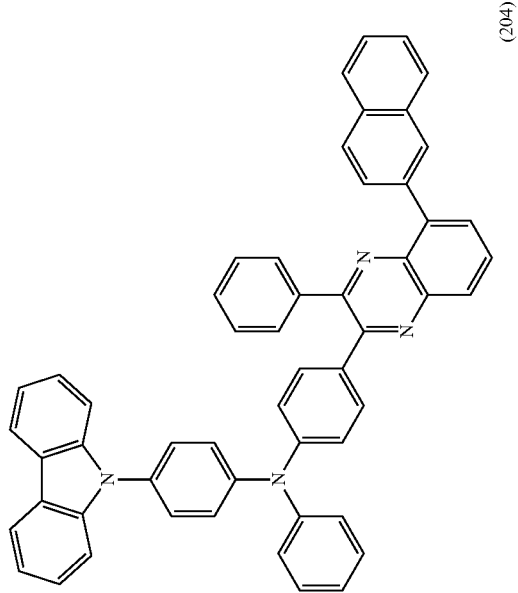
(203)
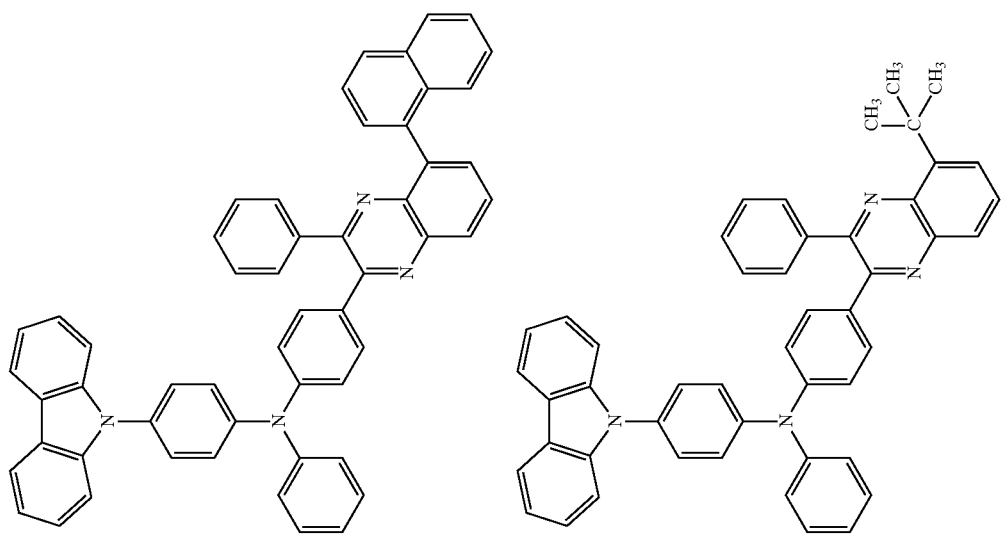
(204)
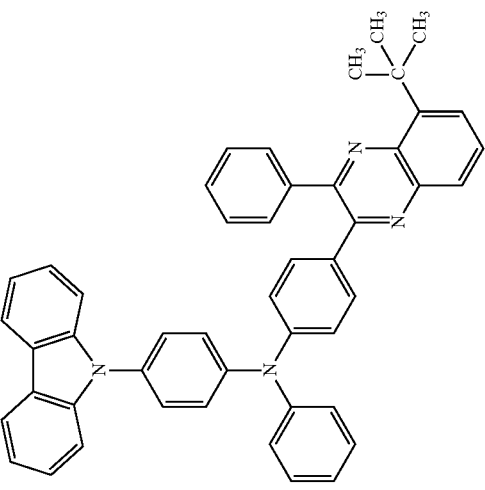

-continued
formula [71]
(202)
(203)
(204)
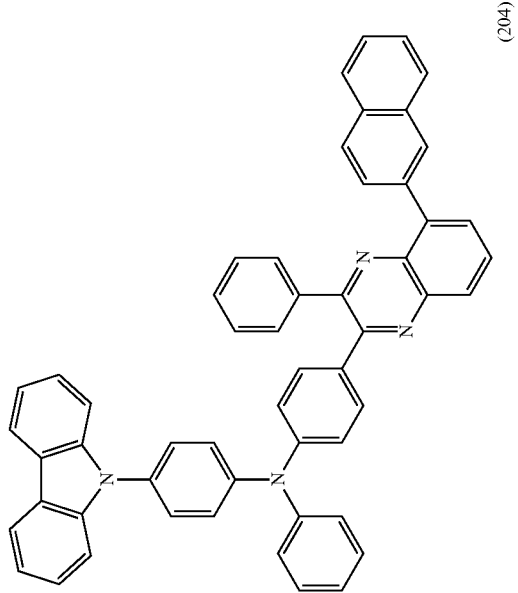
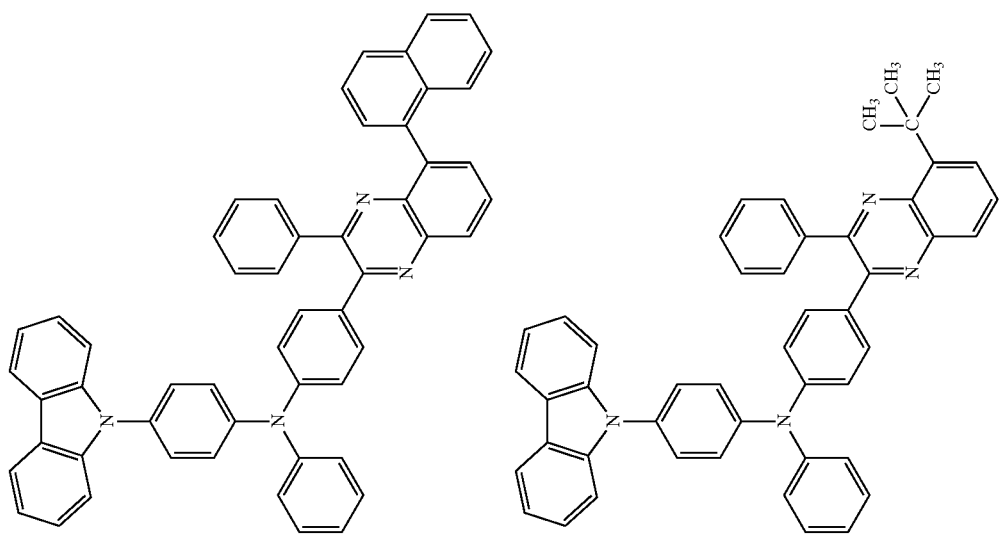

-continued
(211)
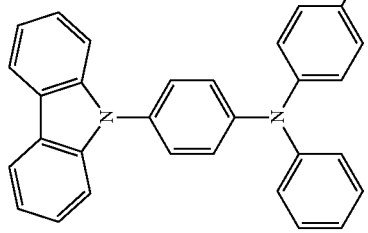
(212)
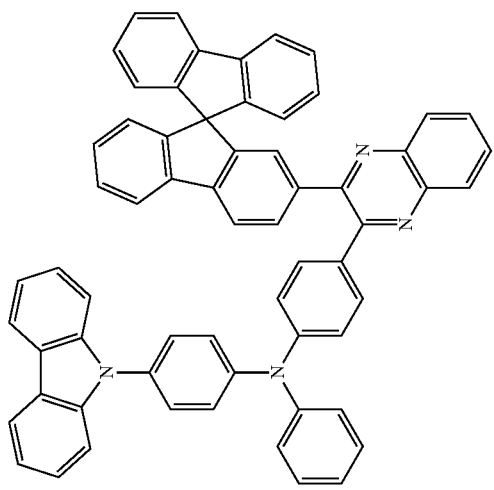
(213)
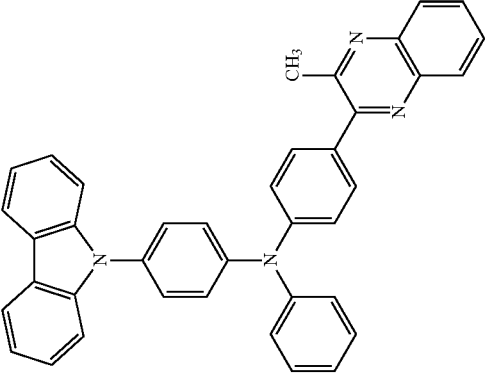
(214)
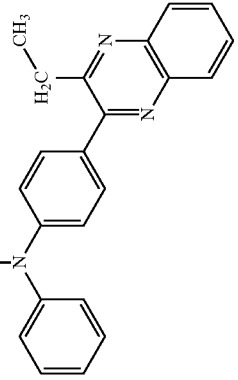
formula [72]
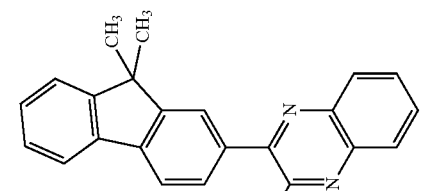

-continued
(215)
(216)
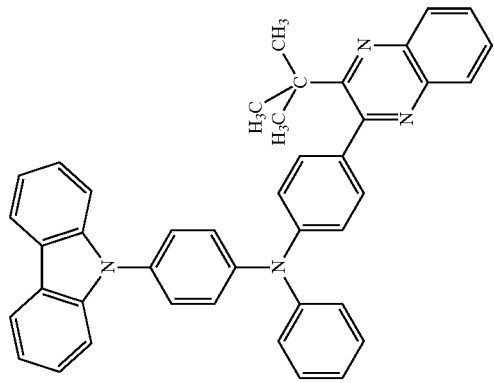
(217)
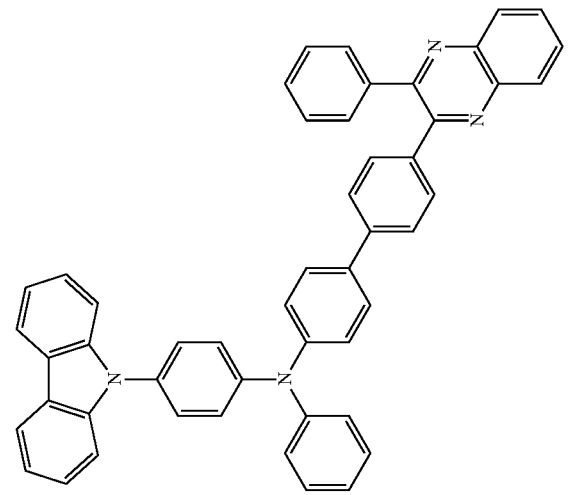
formula [73]
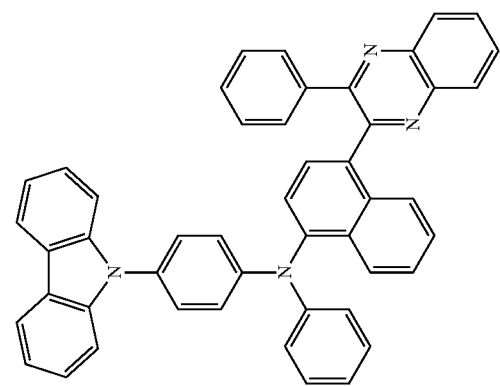

-continued
(218)
(220)
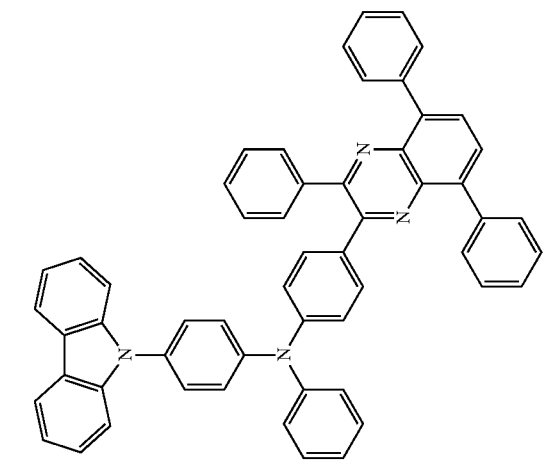
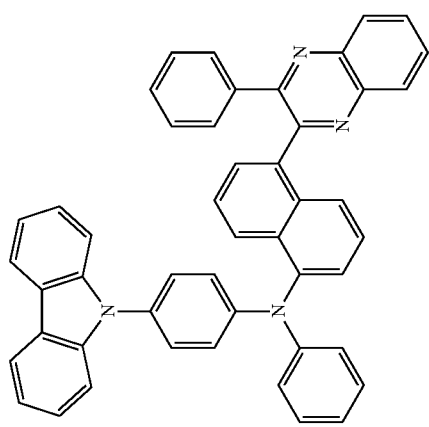
formula [74]
(219)
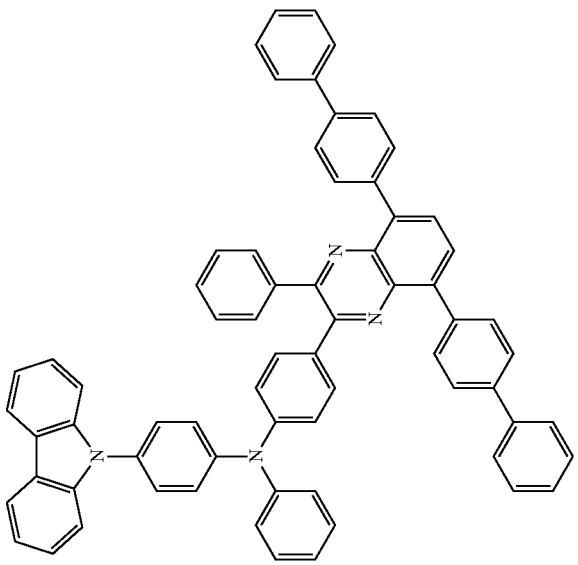

-continued
(222)
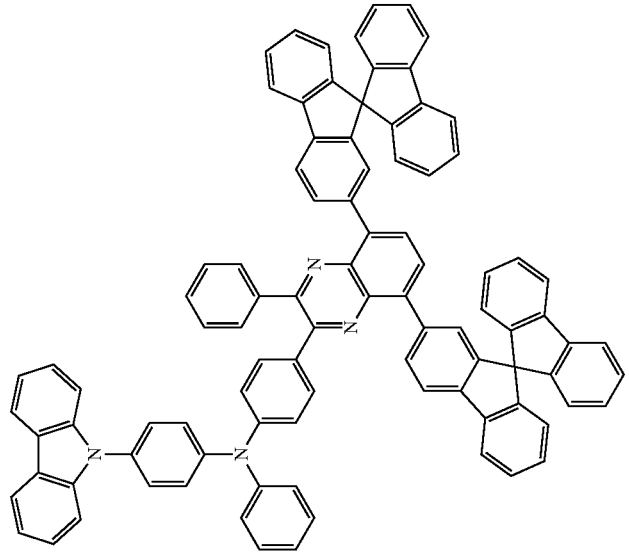
(221)
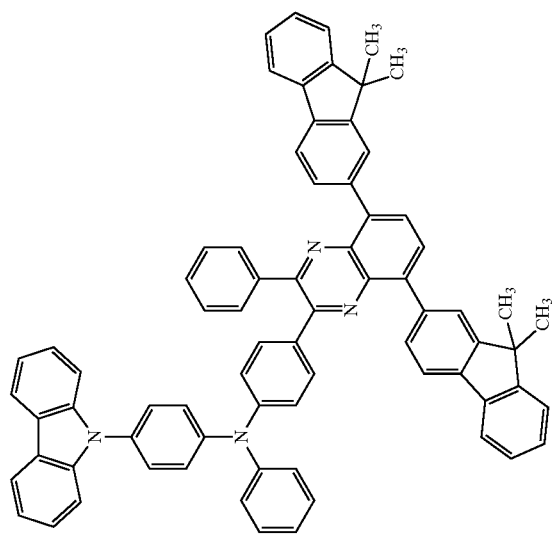

-continued
(224)
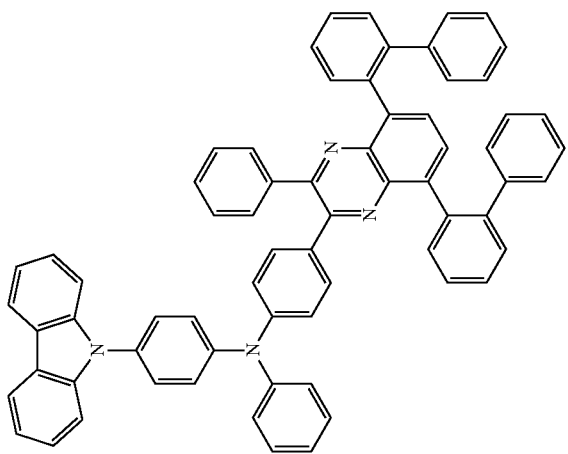
(223)
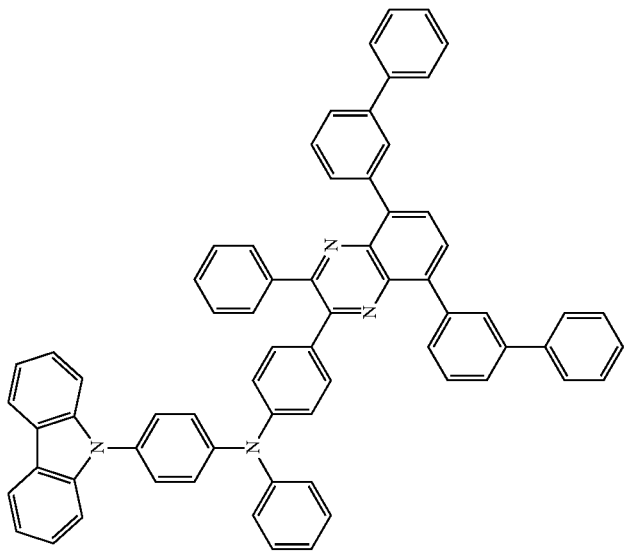
formula [75]

-continued
(225)
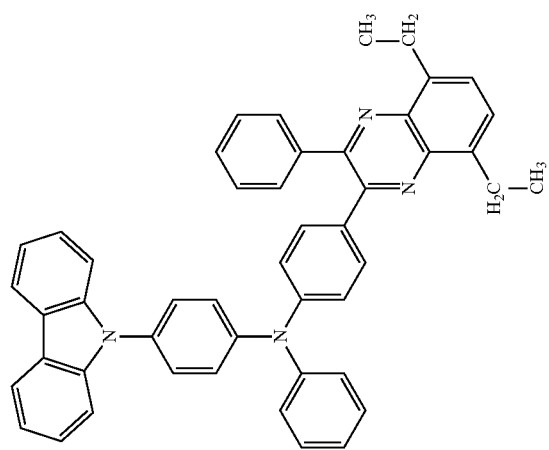
(226)
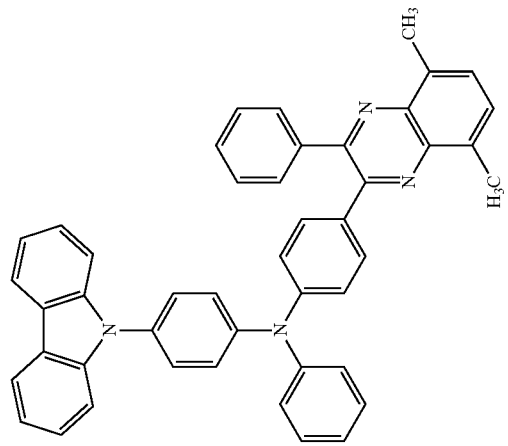
(227)
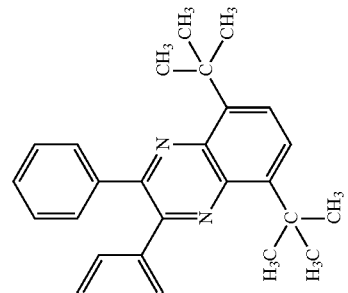
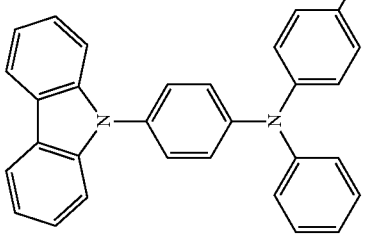

-continued
(224)
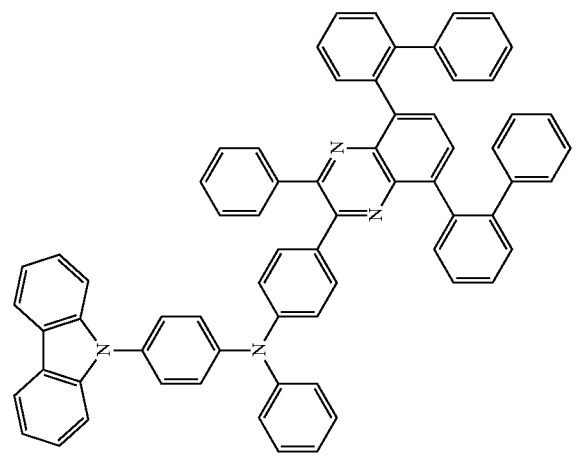
(223)
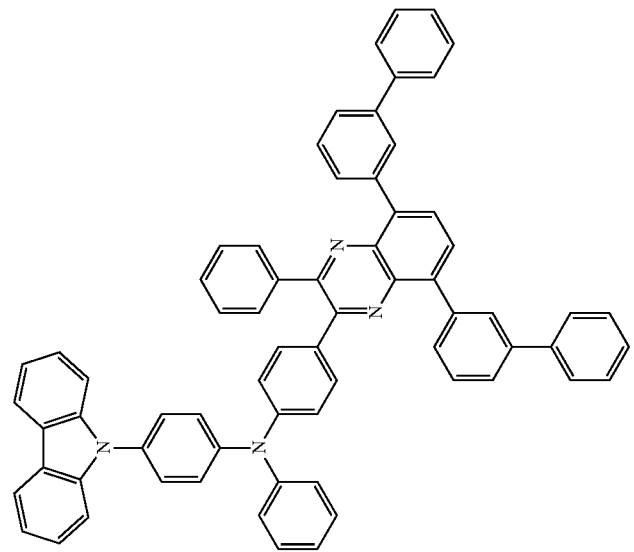
formula [76]

(225)
(226)
(227)
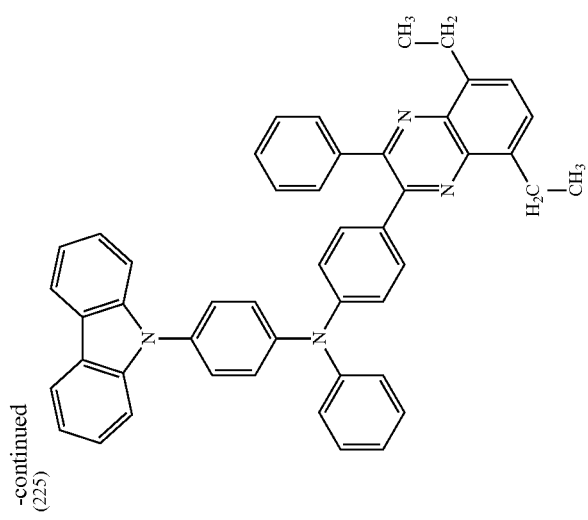
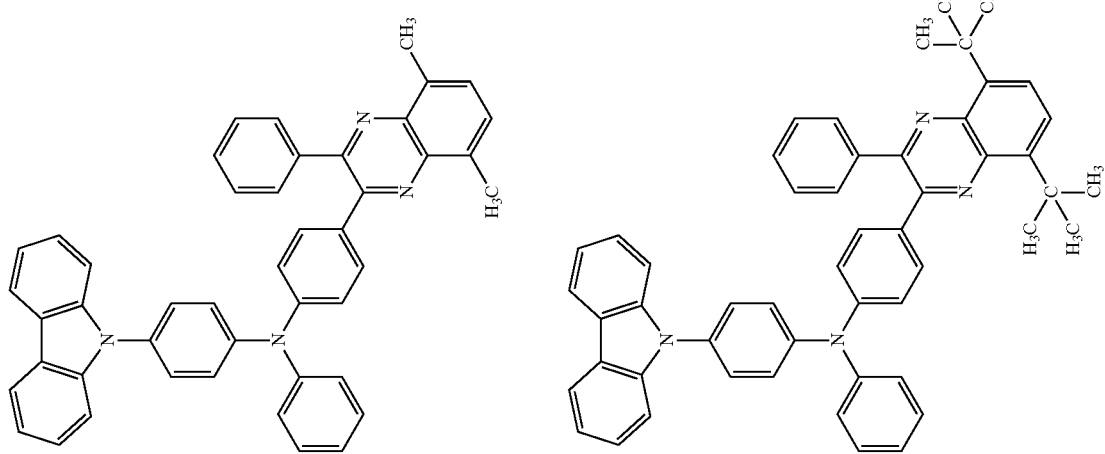

-continued
(231)
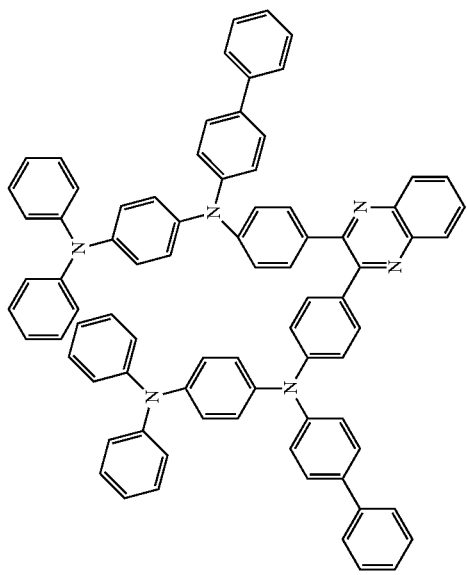
formula [77]
(230)
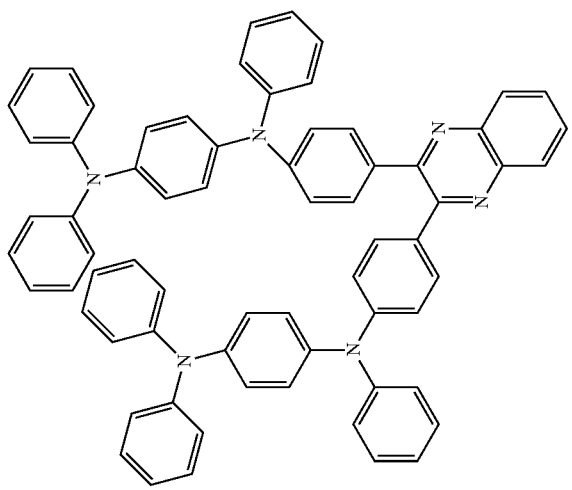

-continued
(233)
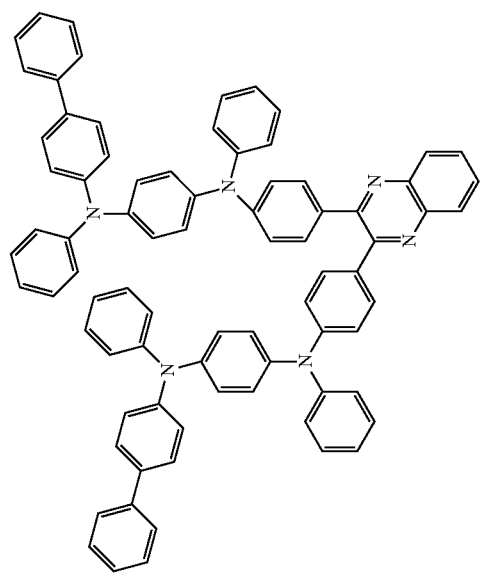
(232)
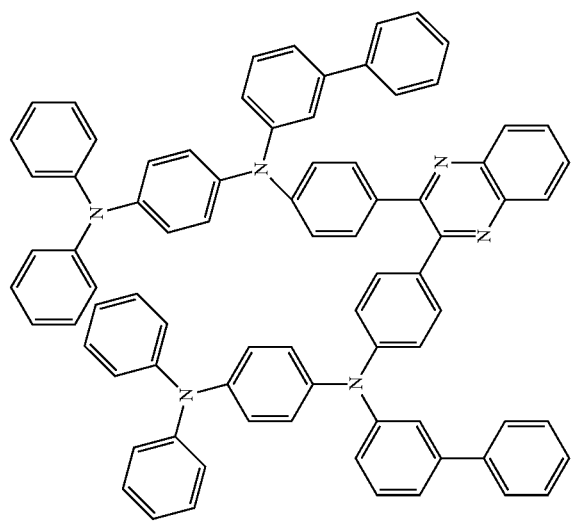

(234)
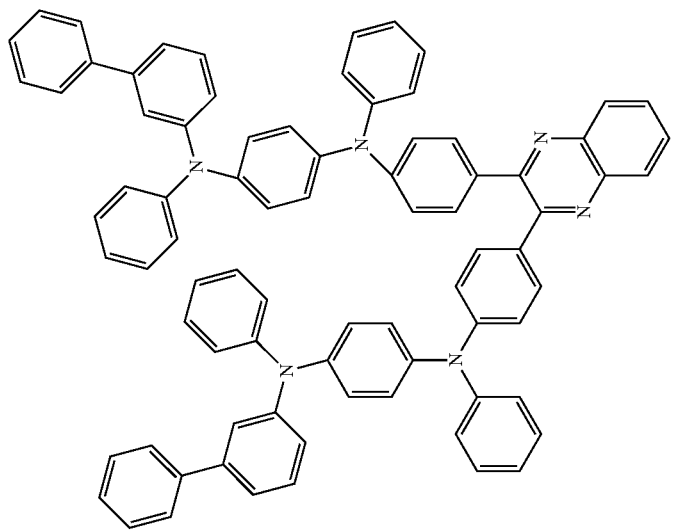

-continued
(236)
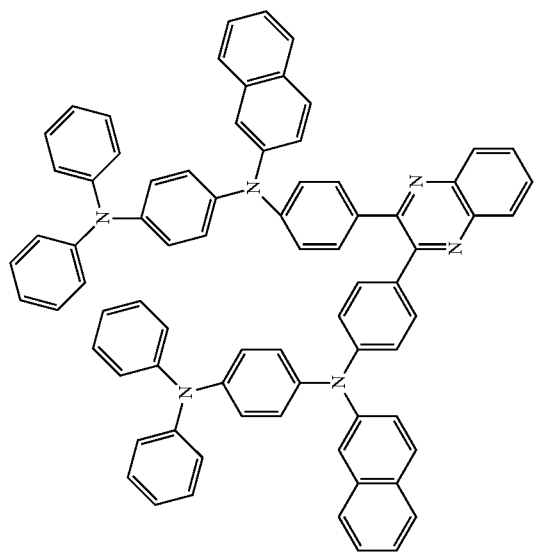
(235)
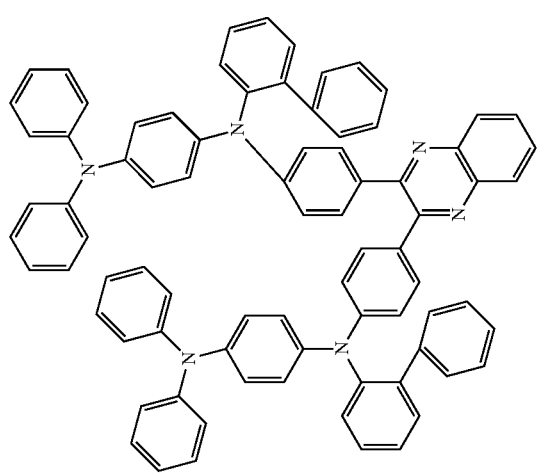
formula [78]

-continued
(238)
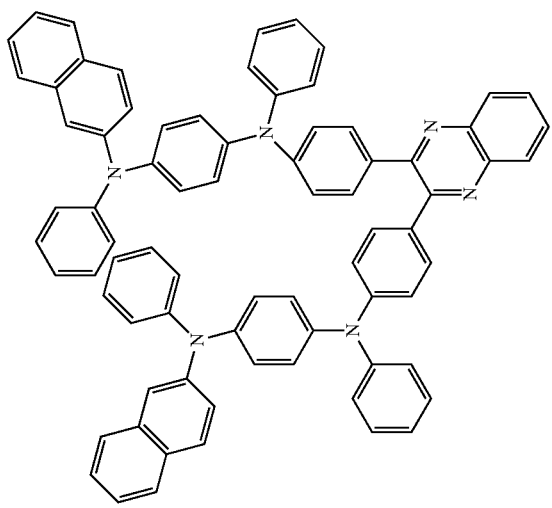
(237)
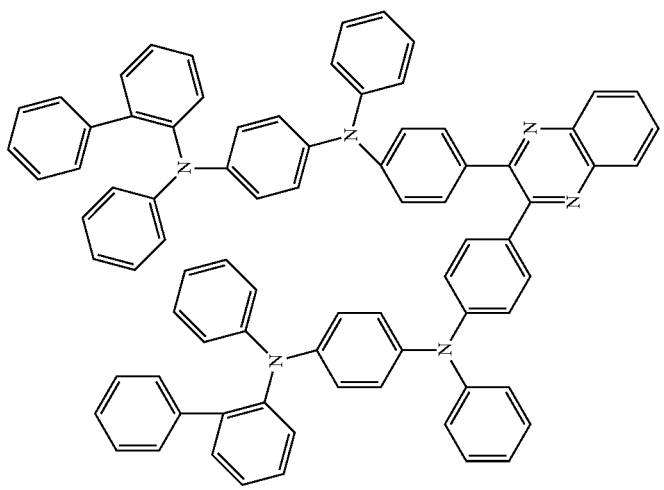

-continued
(240)
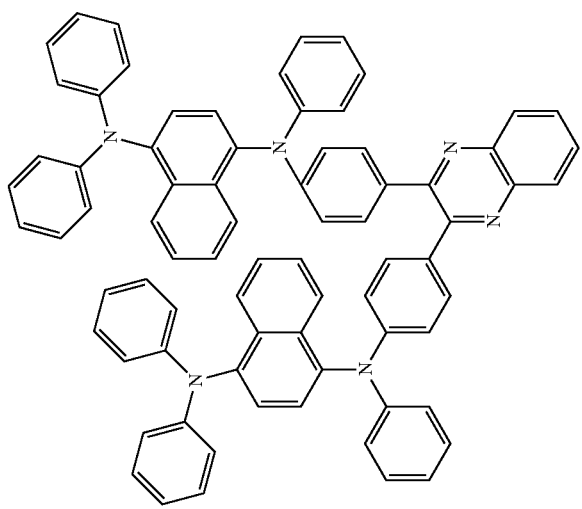
formula [79]
(239)
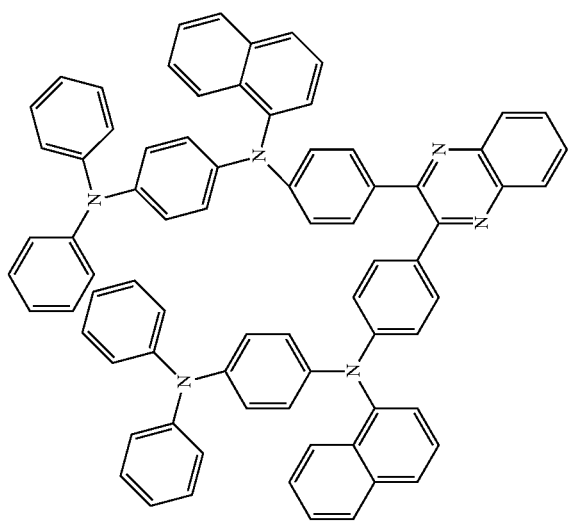

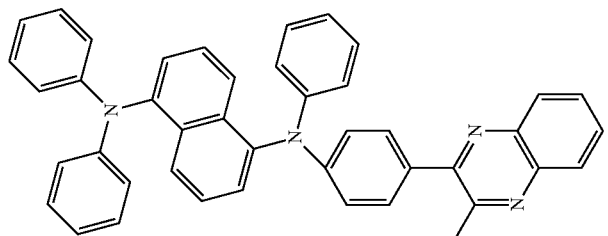
(242)
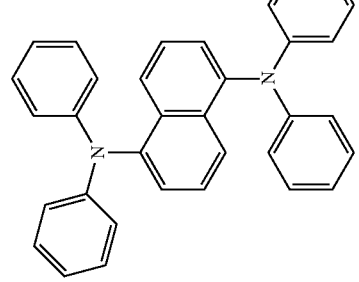
(241)
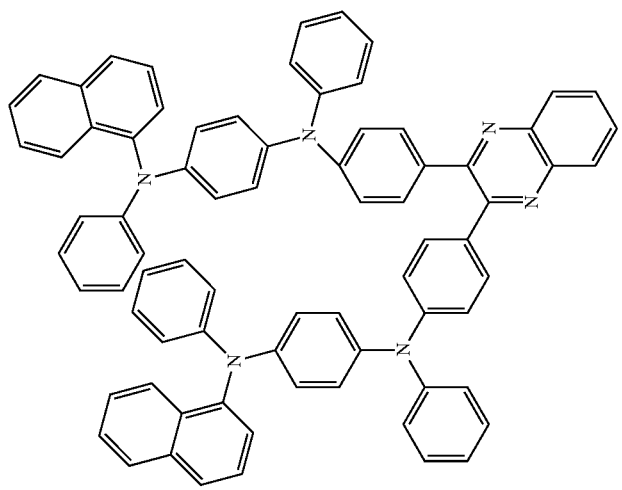

-continued
(244)
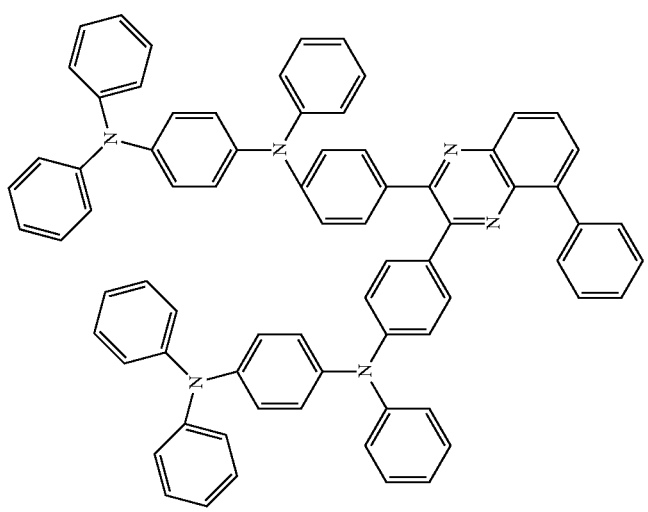
(243)
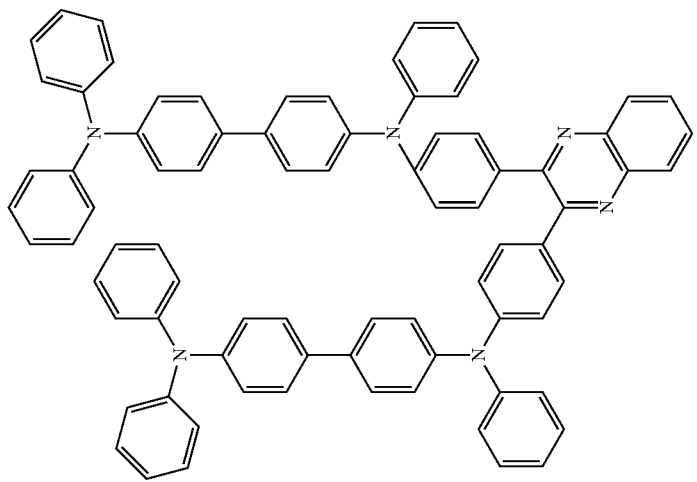
formula [80]

(245)
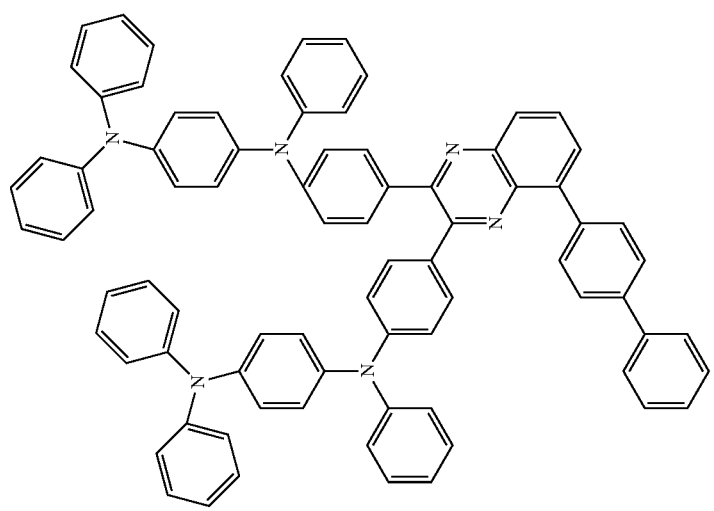

-continued
(247)
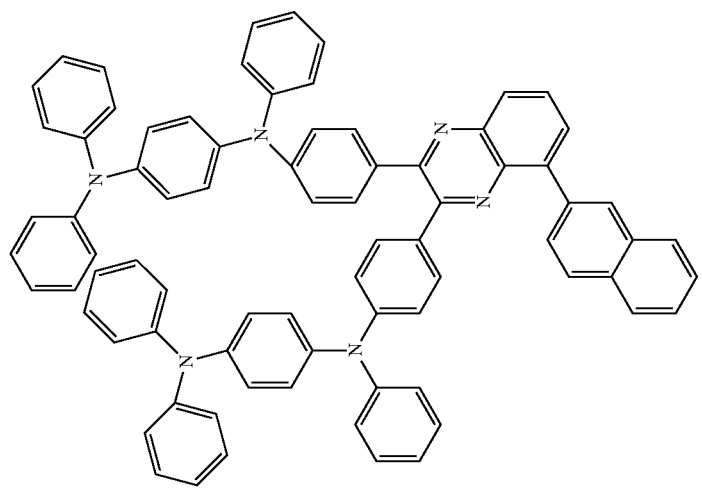
(246)
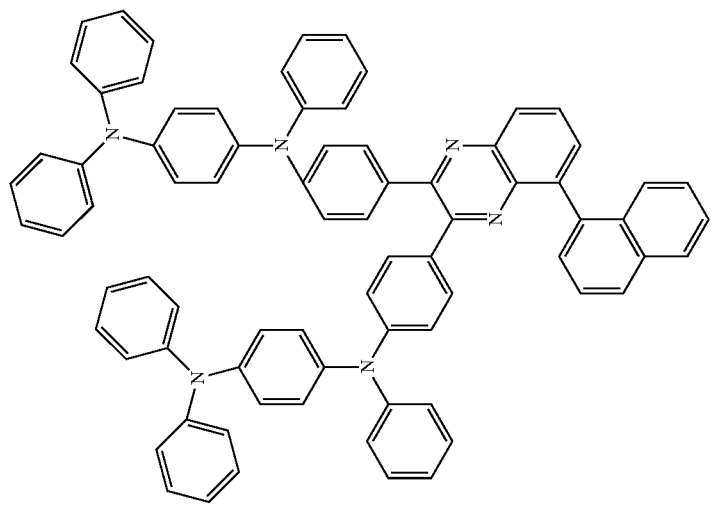
formula [81]

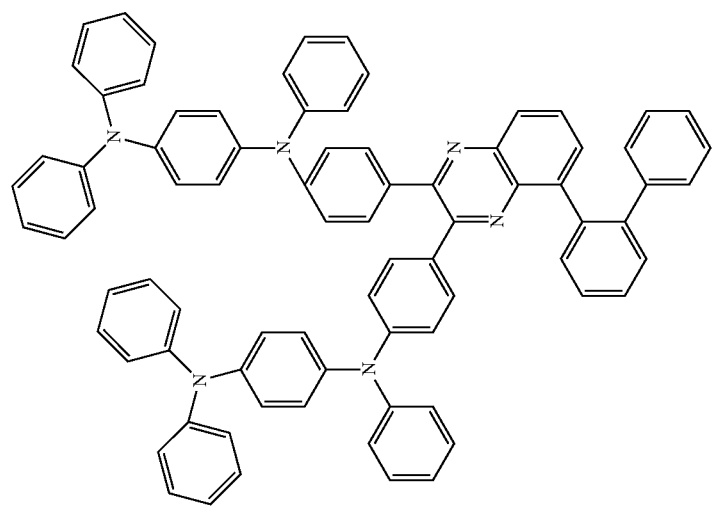
(249)
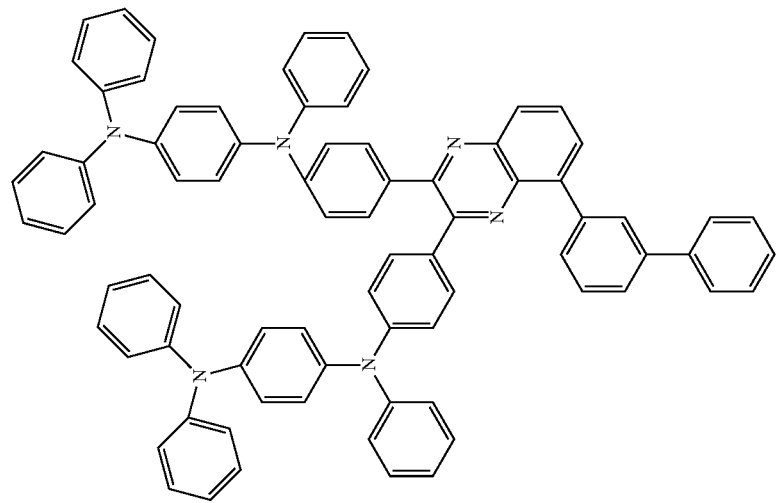
(248)

-continued
formula [82]
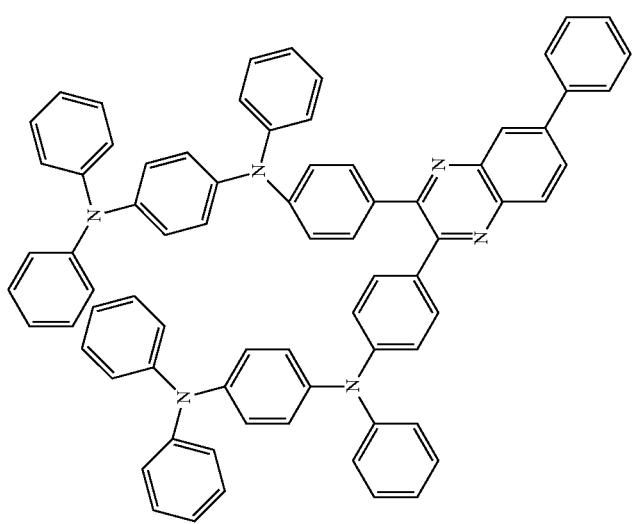
(251)
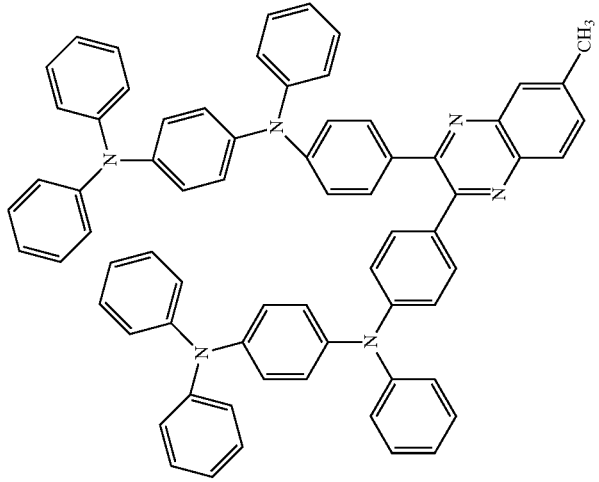
(250)

-continued
(253)
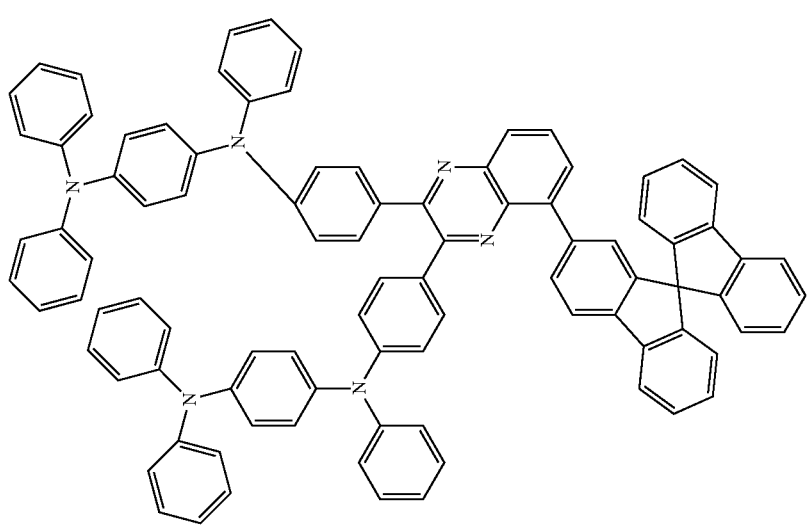
(252)
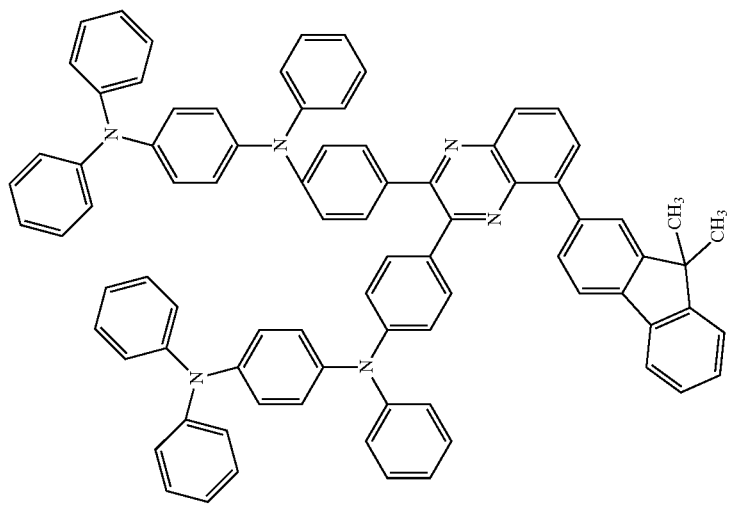

-continued
(254)
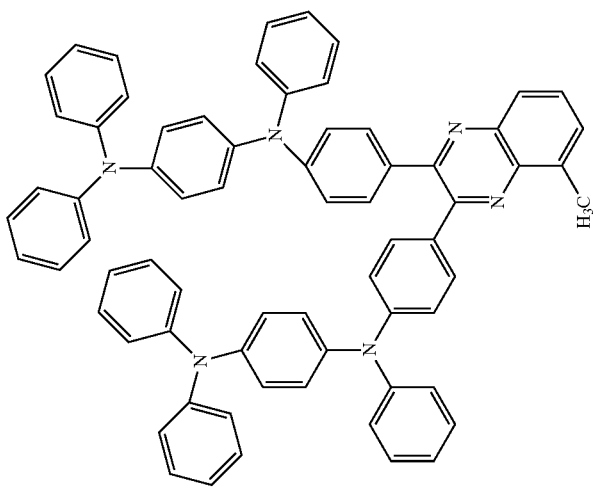
(255)
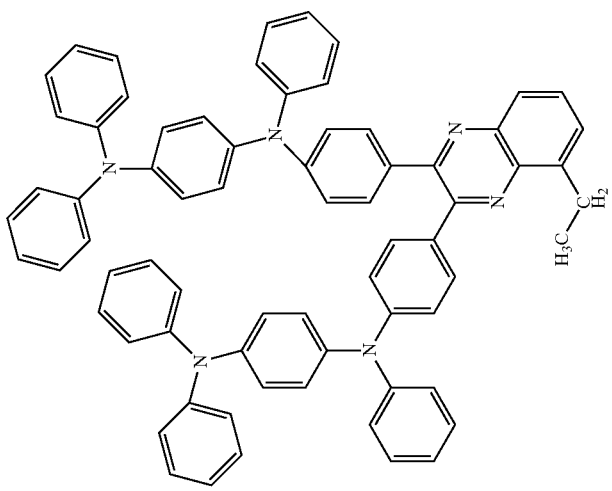
formula [83]

(256)
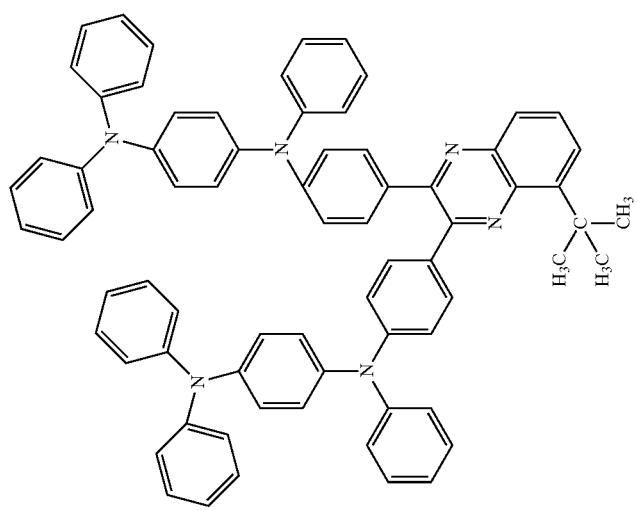

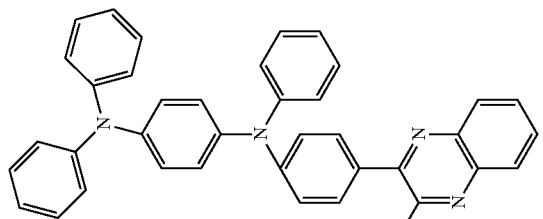
(258)
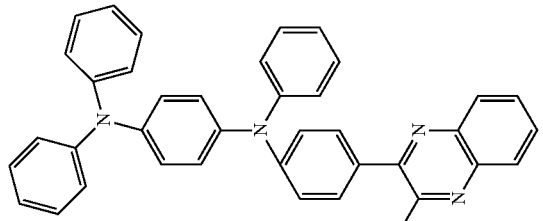
(257)
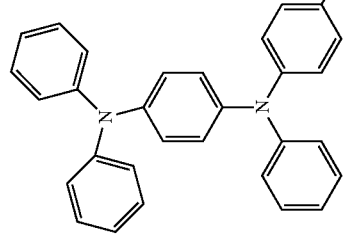
formula [84]

(259)
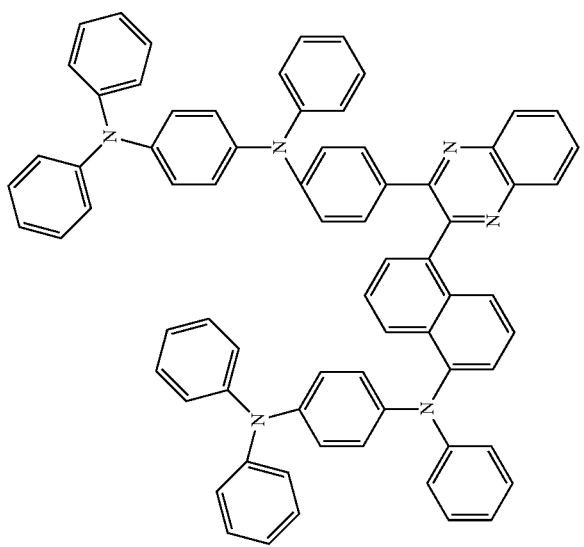

-continued
(261)
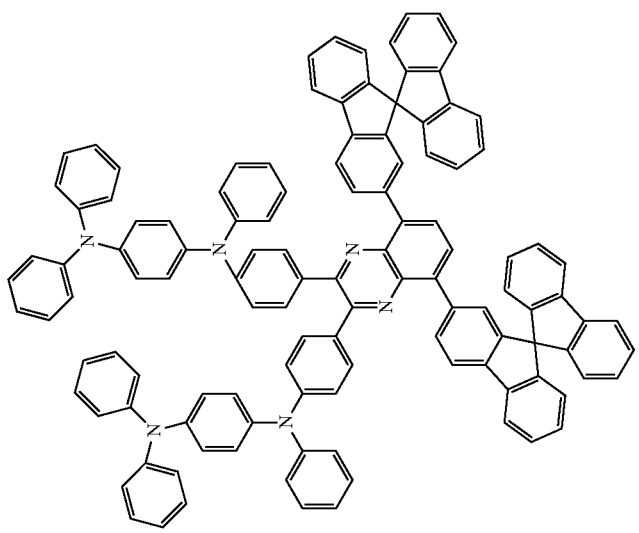
(260)
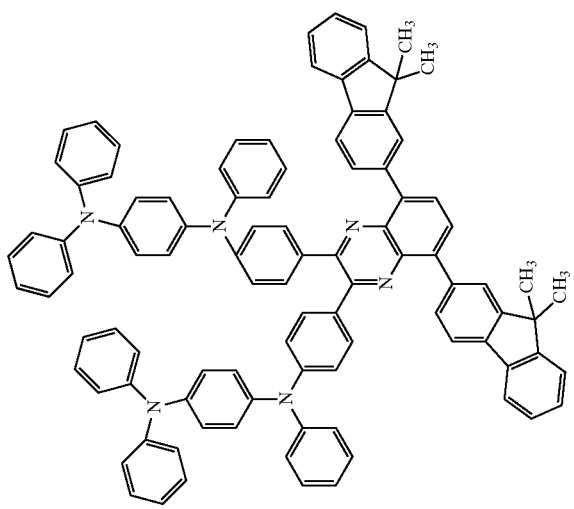
formula [85]

-continued
(263)
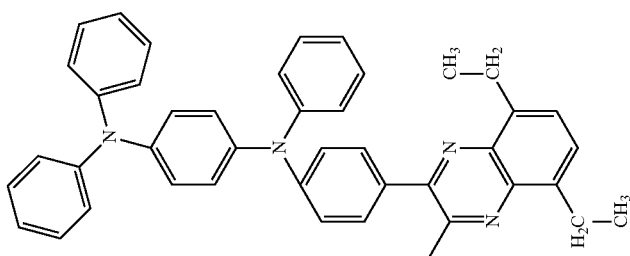
(262)
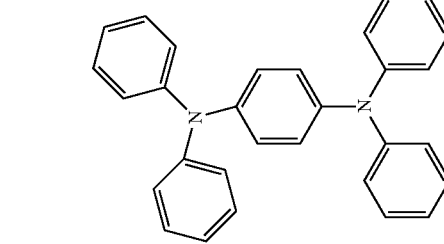
formula [86]

(264)
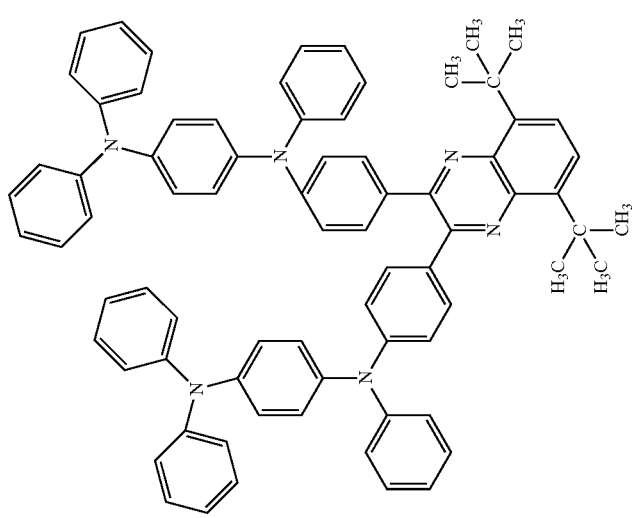

-continued
(266)
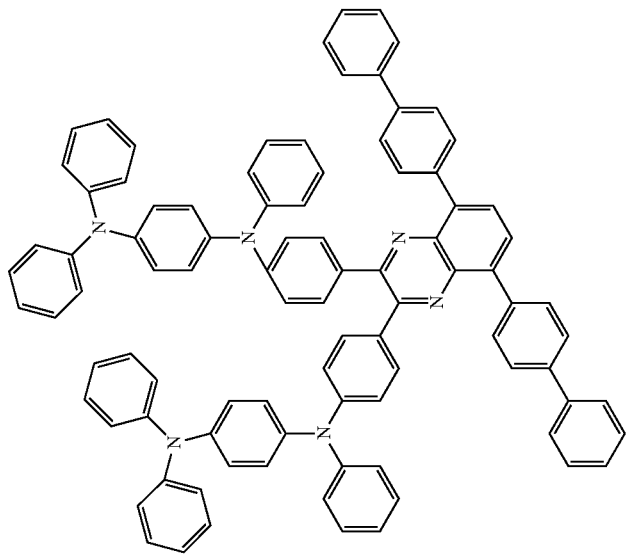
(265)
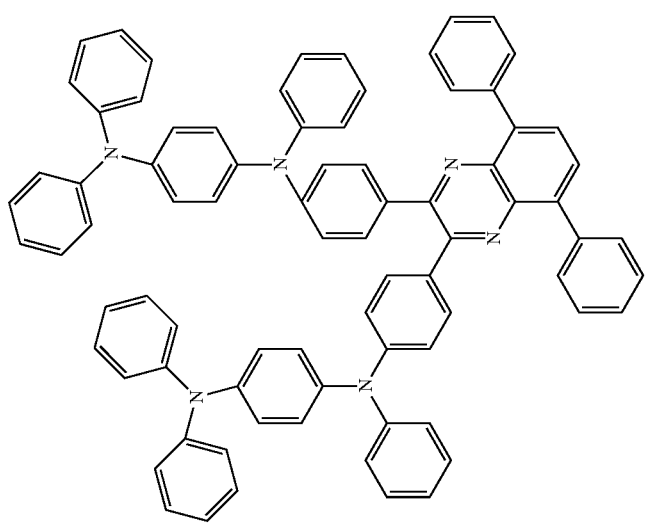
formula [87]

(268)
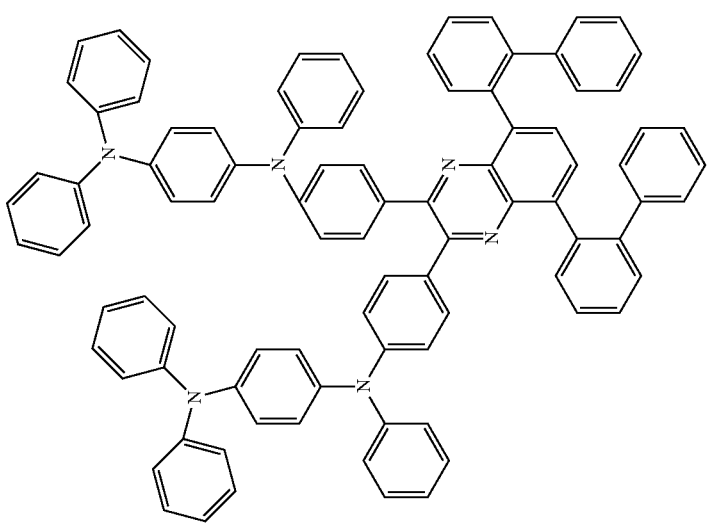
(267)
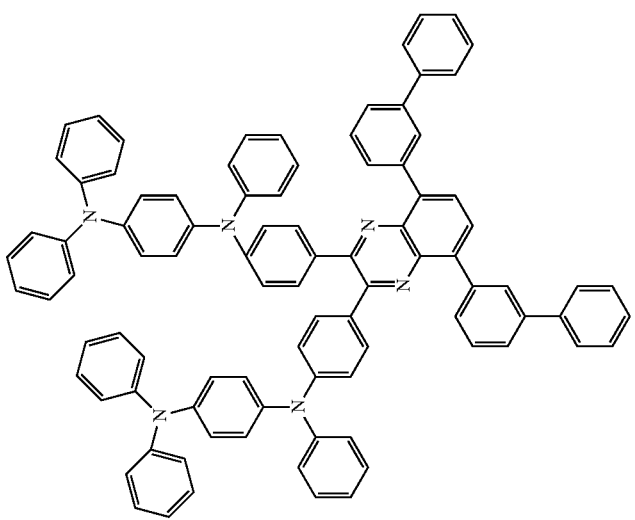

-continued
(270)
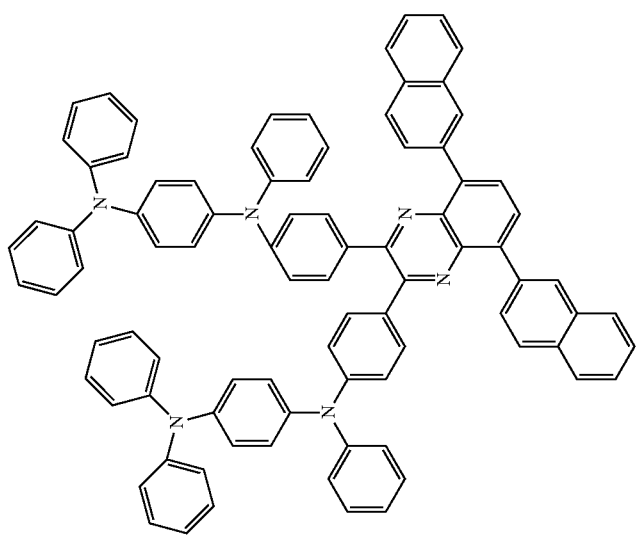
(269)
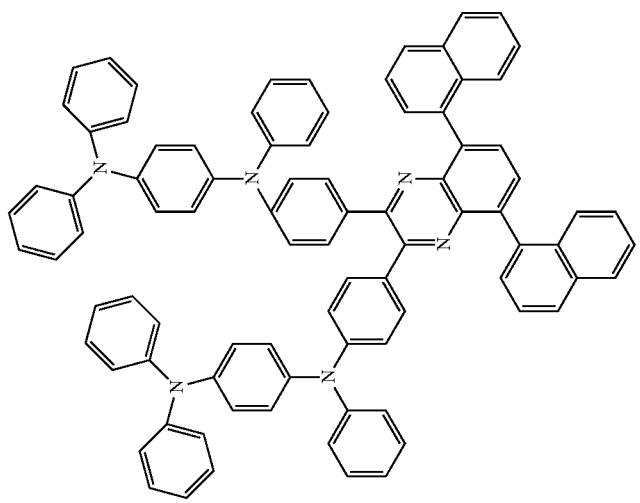
formula [88]

-continued
formula [89]
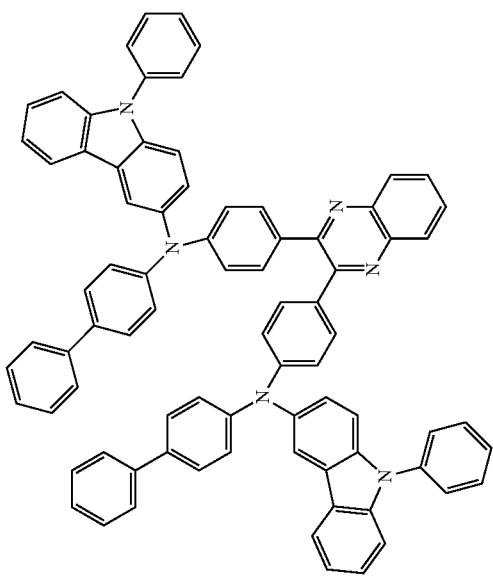
(272)
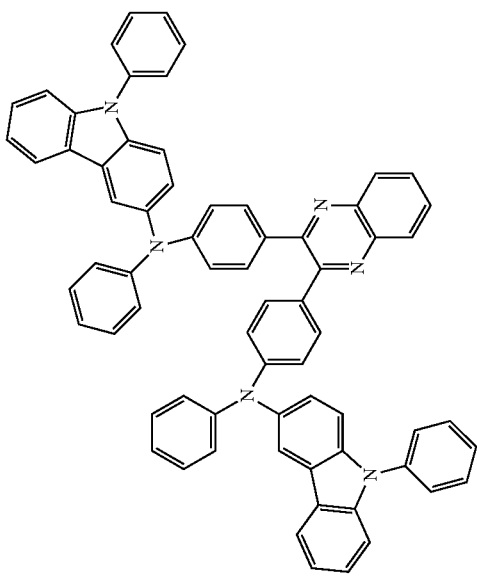
(271)

(273)
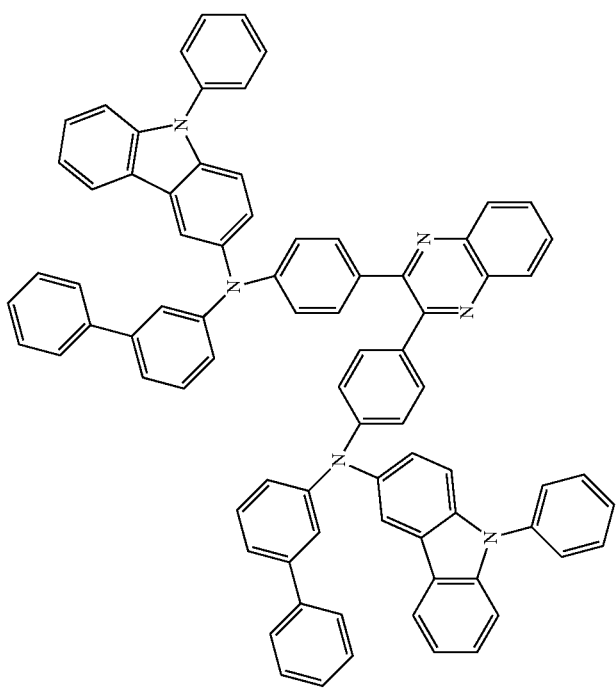

-continued
formula [90]
(274)
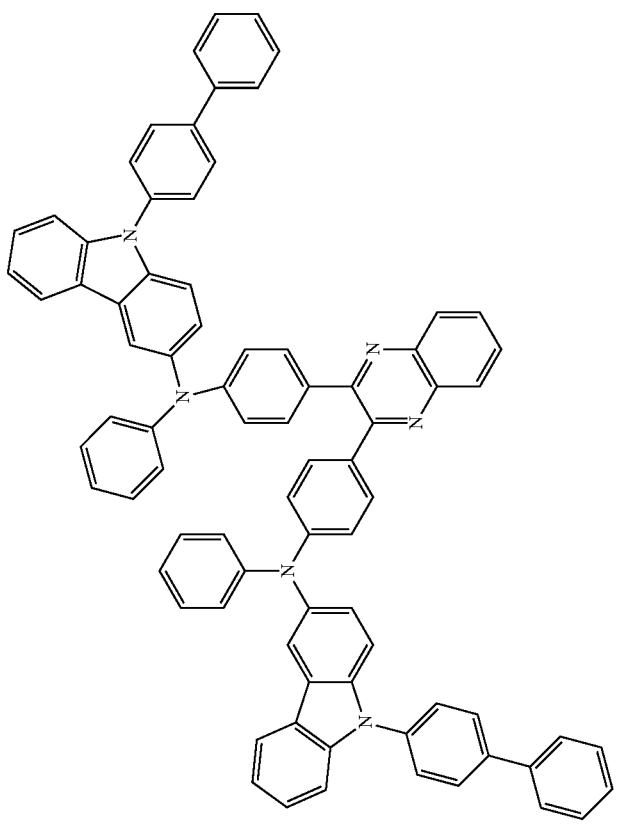

(276)
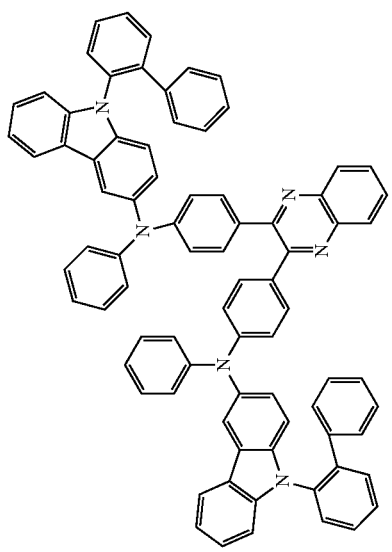
(275)
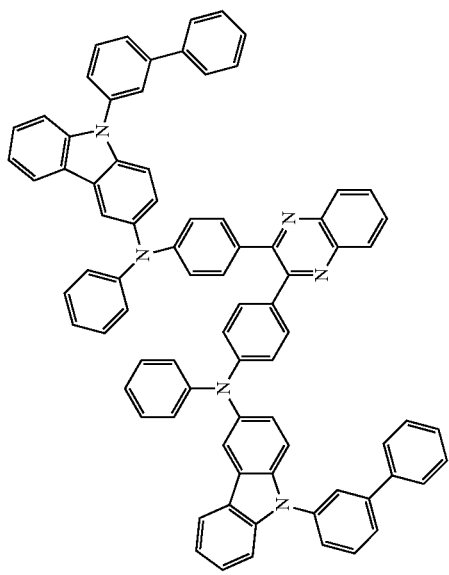

formula [91]
(277)
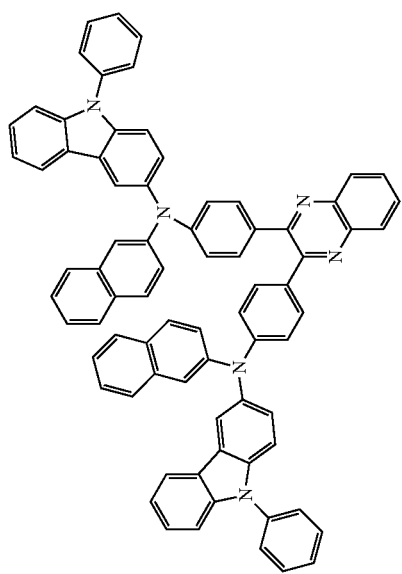
(278)
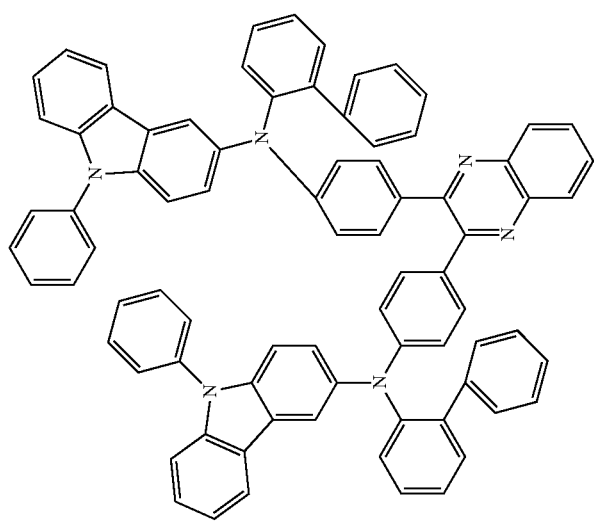

(279)
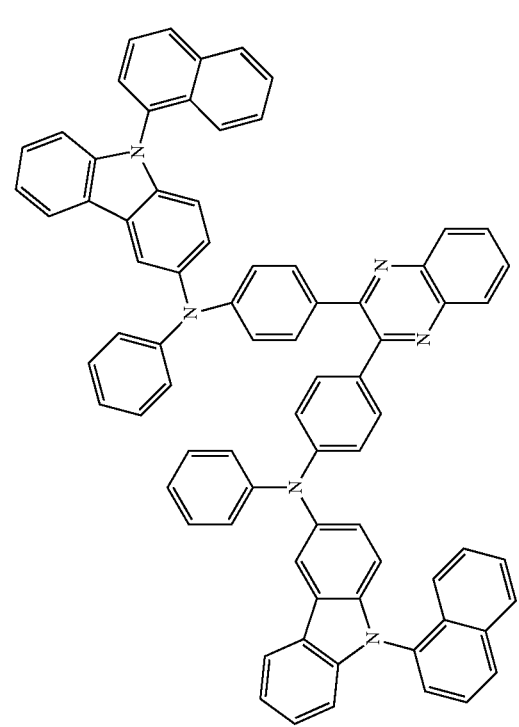
formula [92]
(281)
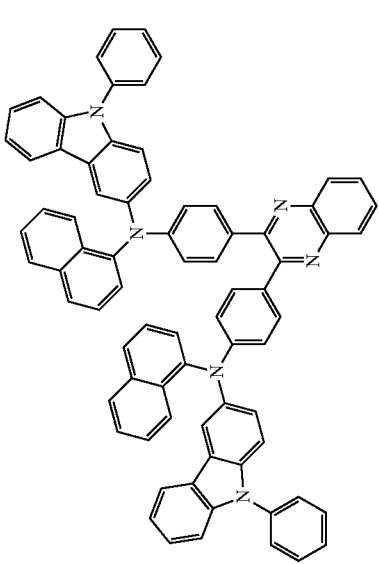
(280)
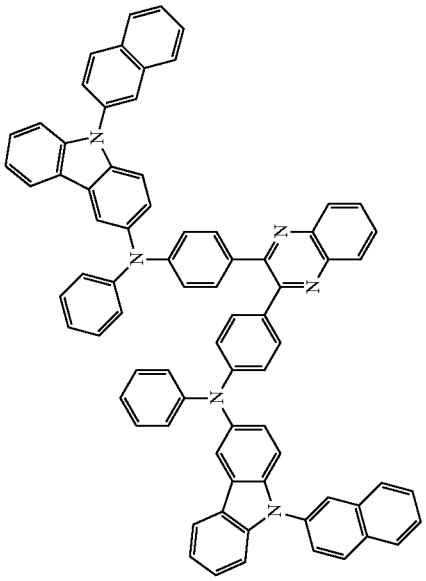

-continued
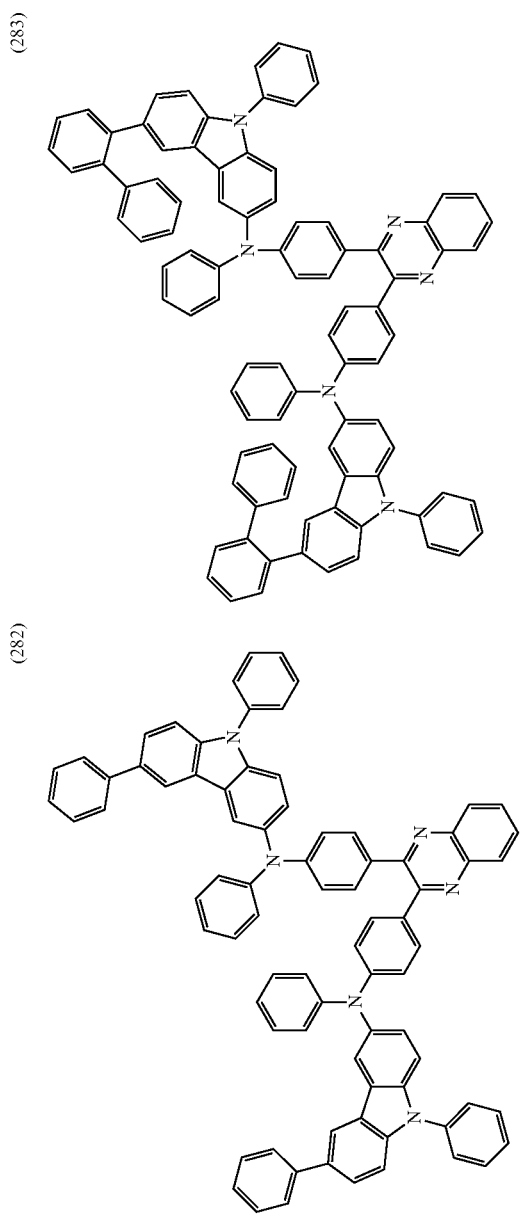

formula [94]
(284)
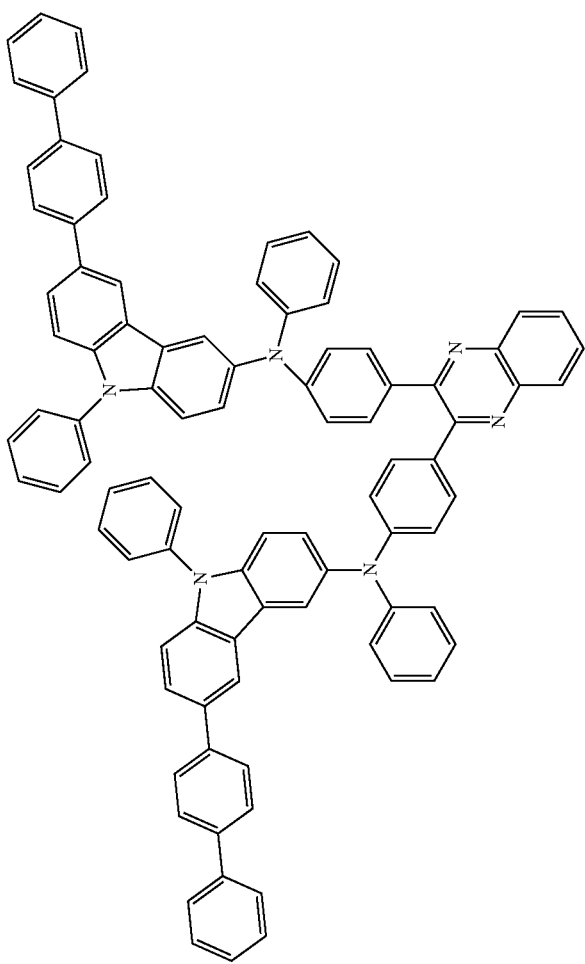

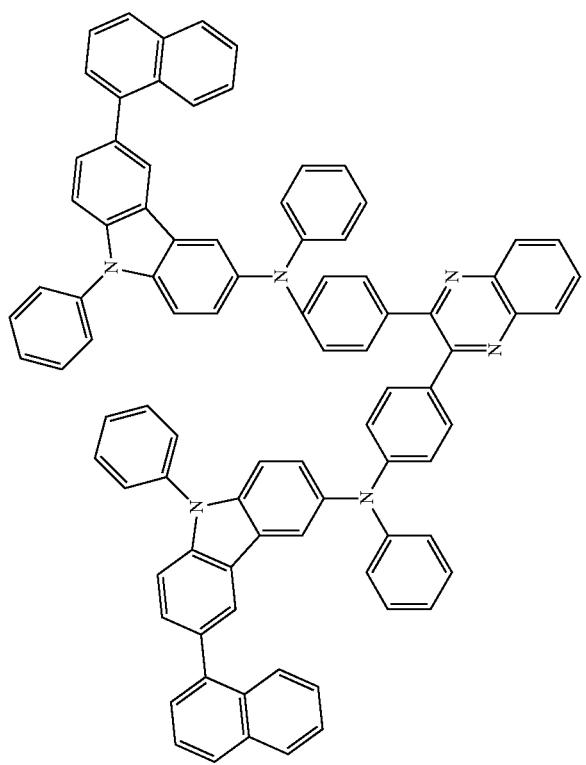
(285)

-continued
formula [95]
(286)
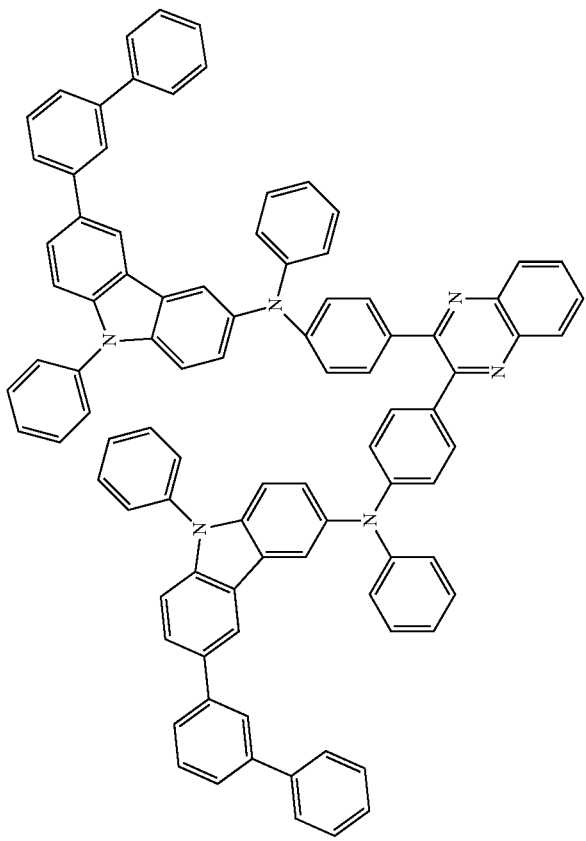

(287)
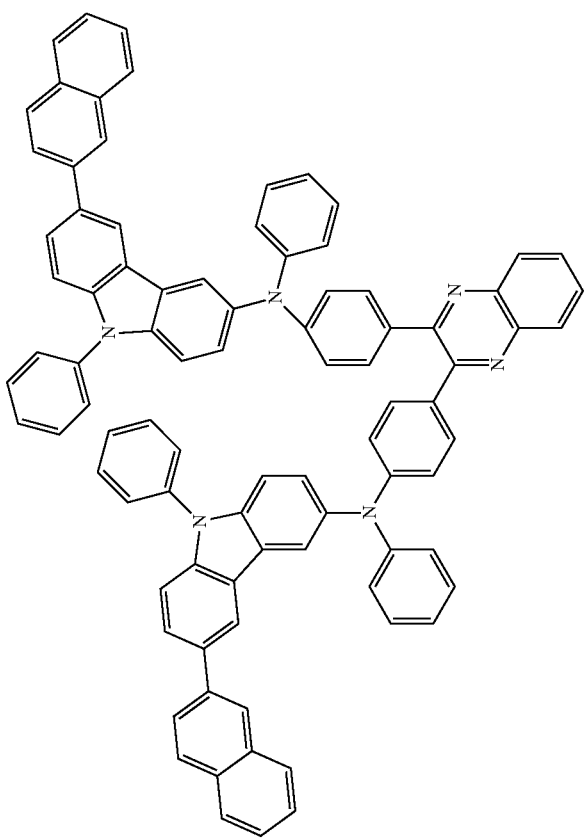

-continued
formula [96]
(288)
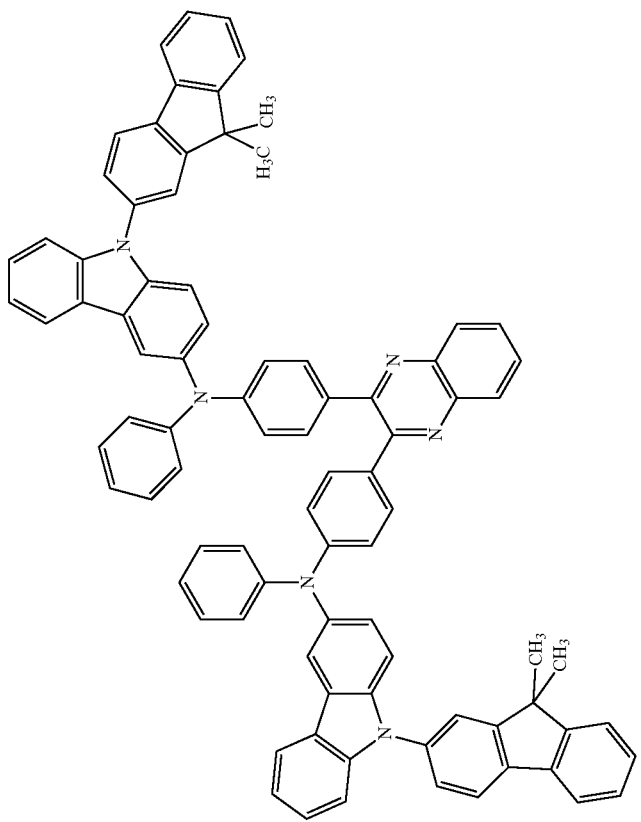

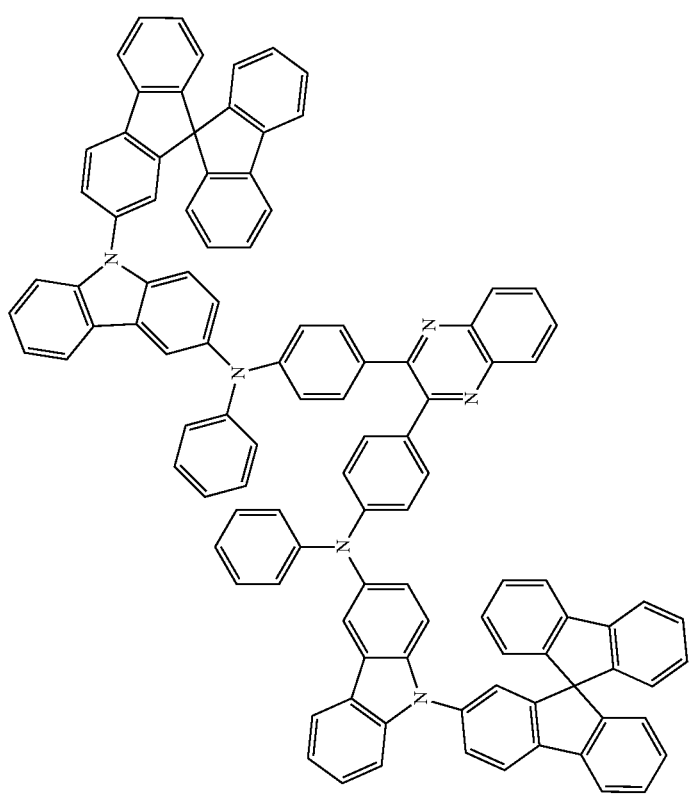
(289)

-continued
formula [97]
(291)
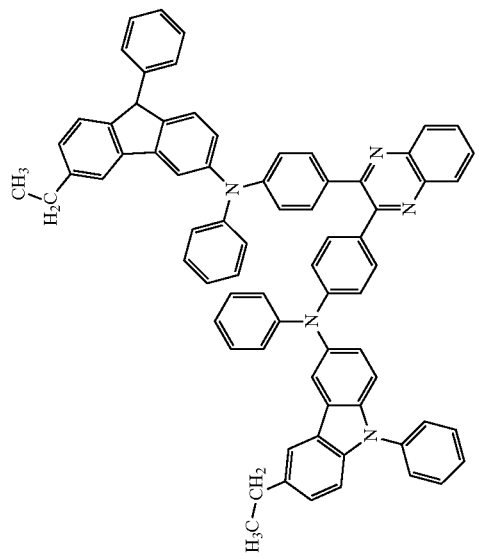
(290)
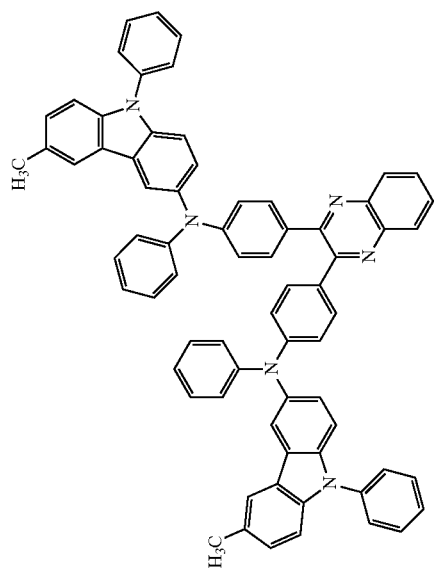

(292)
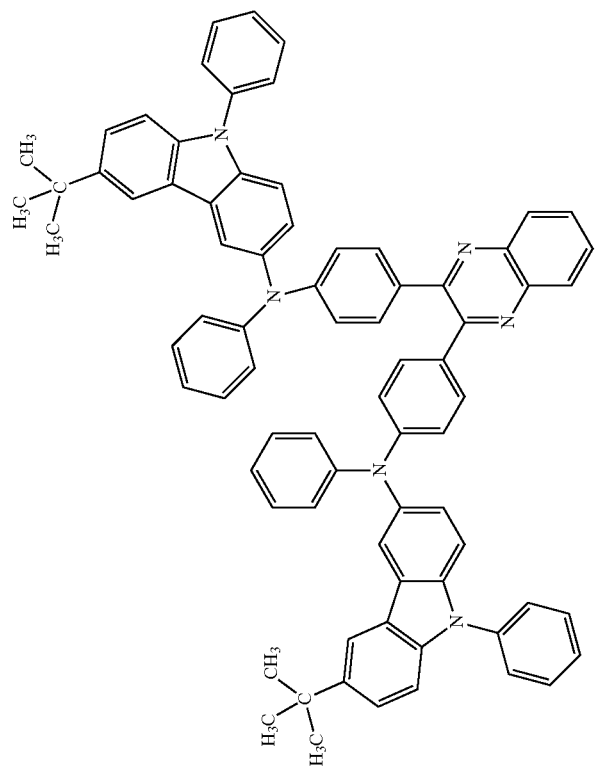

-continued
(294)
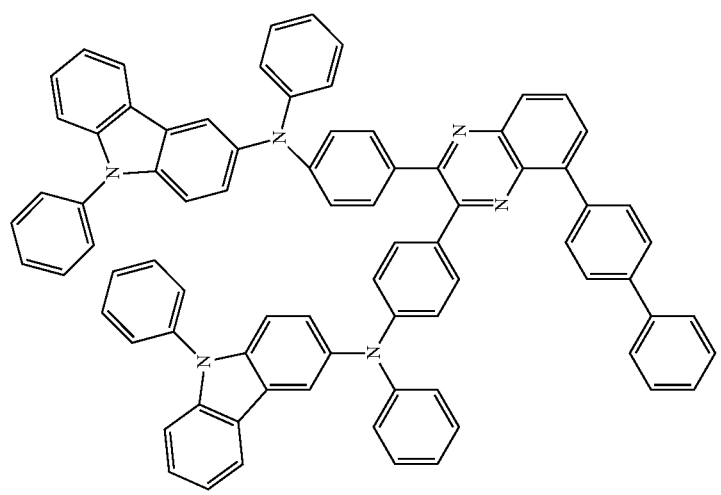
formula [98]
(293)
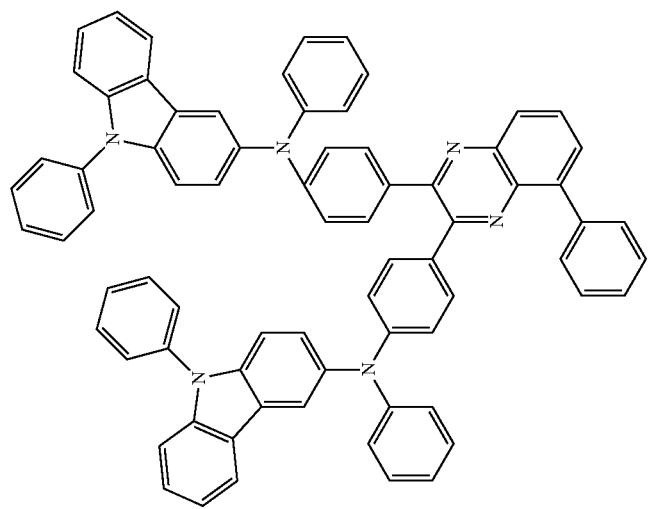

-continued
(296)
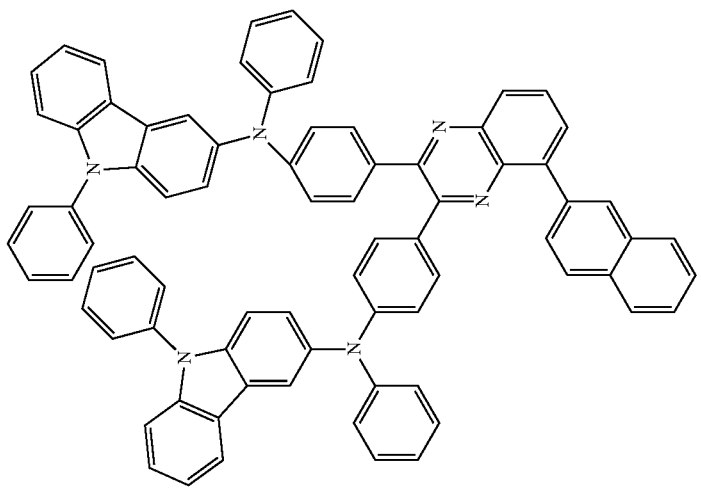
(295)
formula [99]
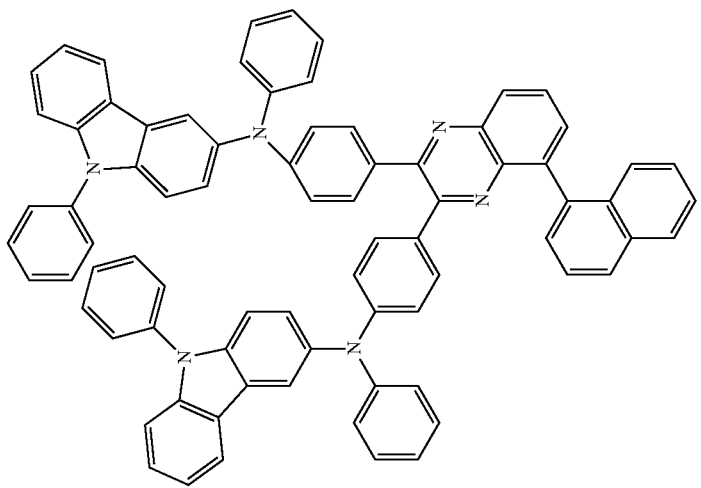

-continued
(298)
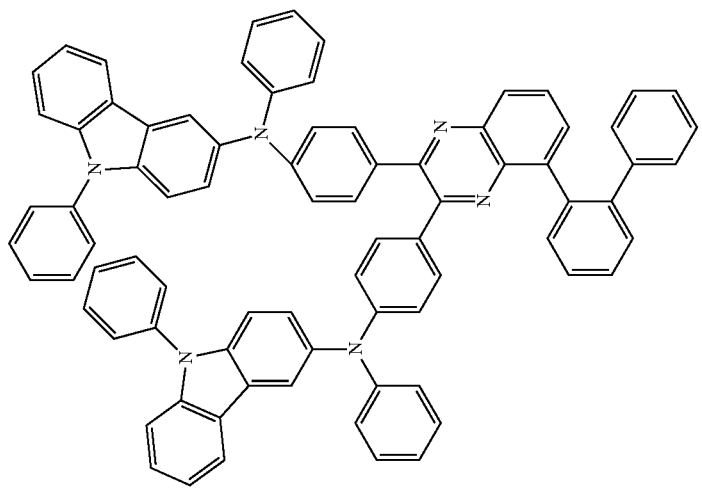
formula [100]
(297)
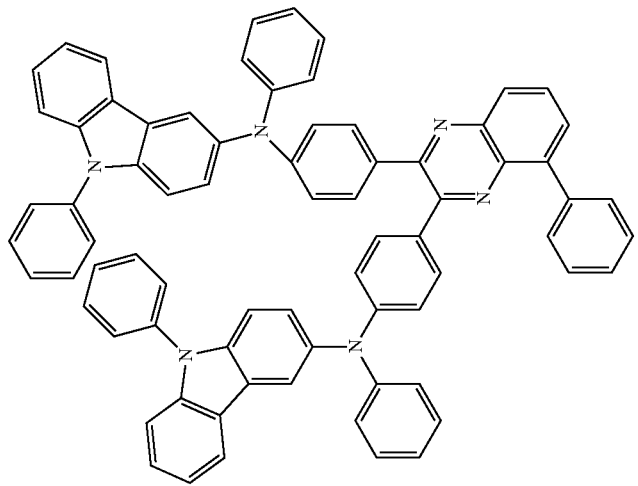

-continued
(300)
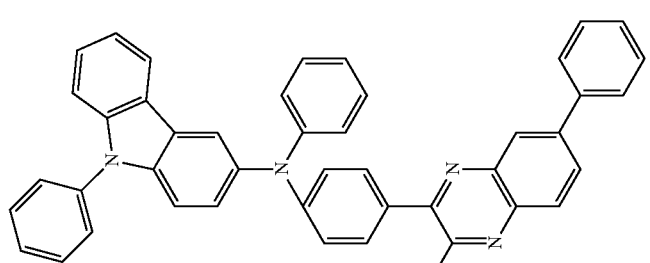
(299)
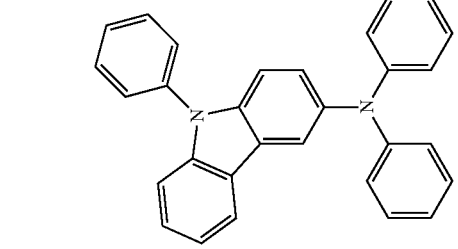
formula [101]
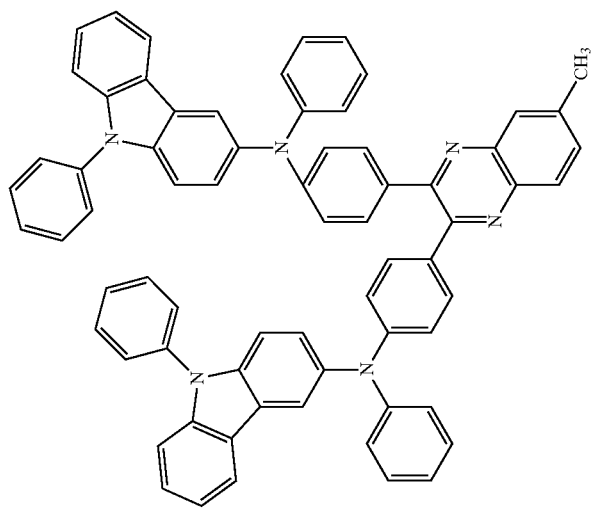

-continued
(302)
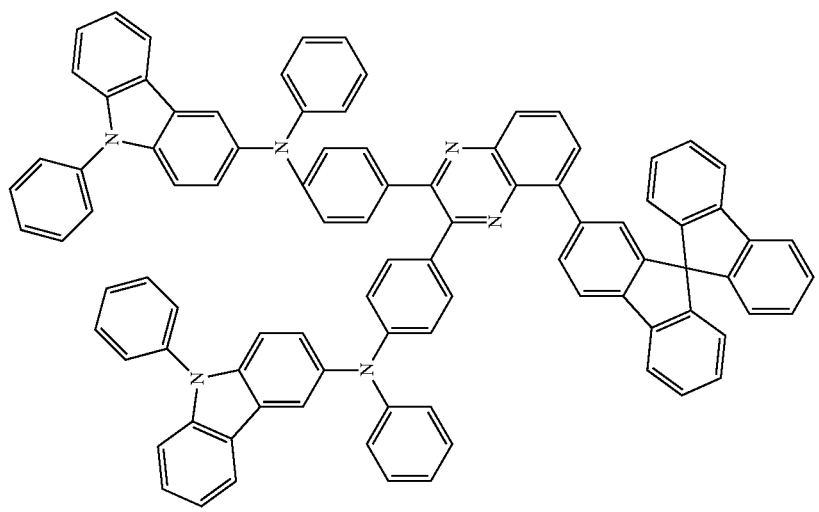
formula [102]
(301)
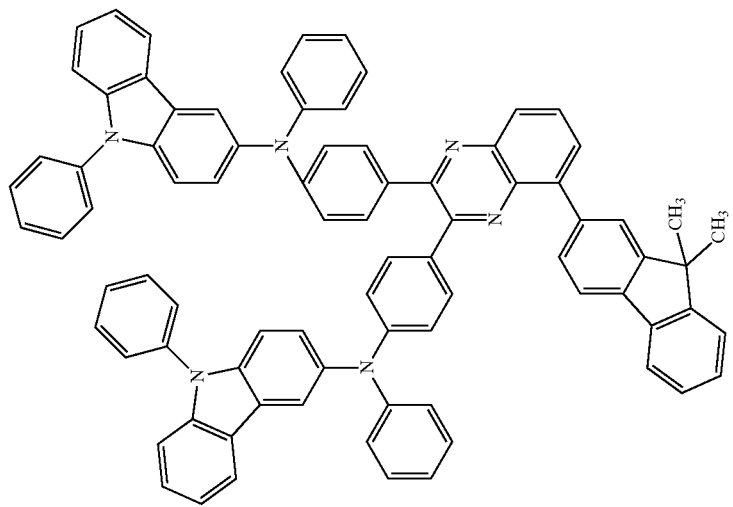

-continued
(304)
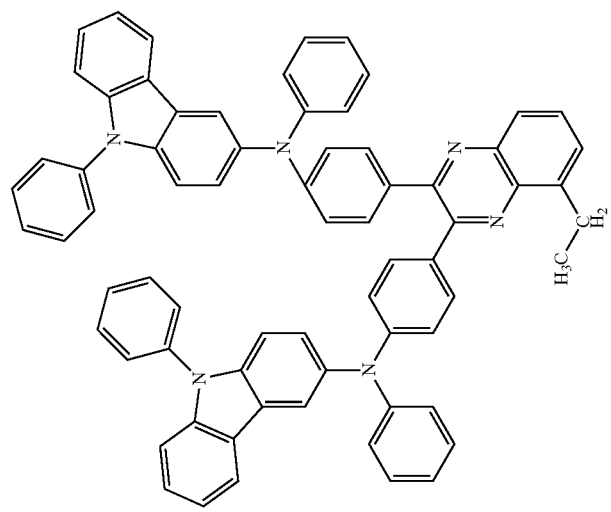
(303)
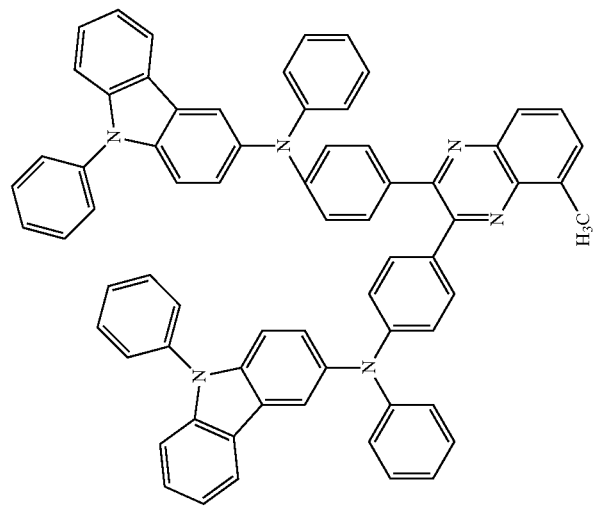
formula [103]

(305)
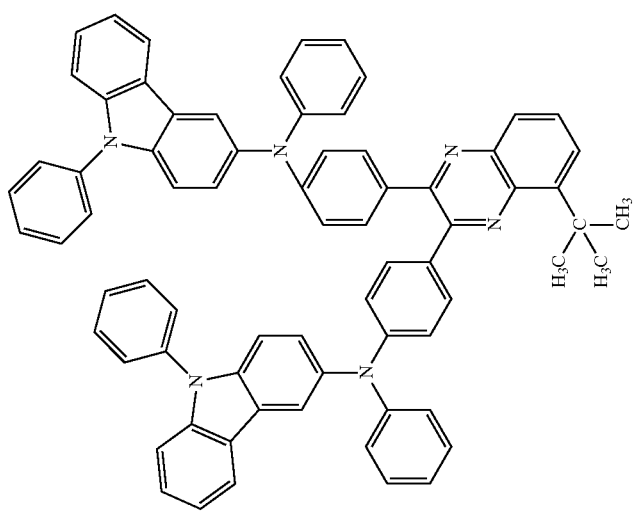

-continued
(306)
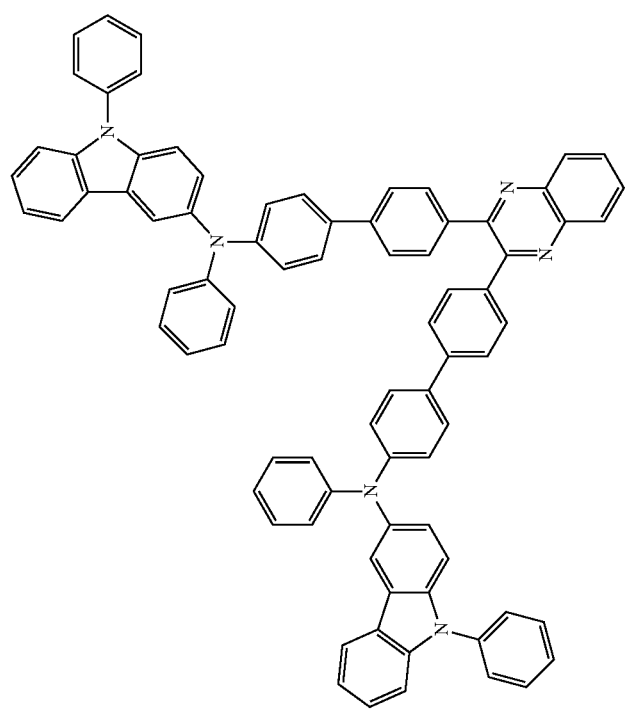
formula [104]

(307)
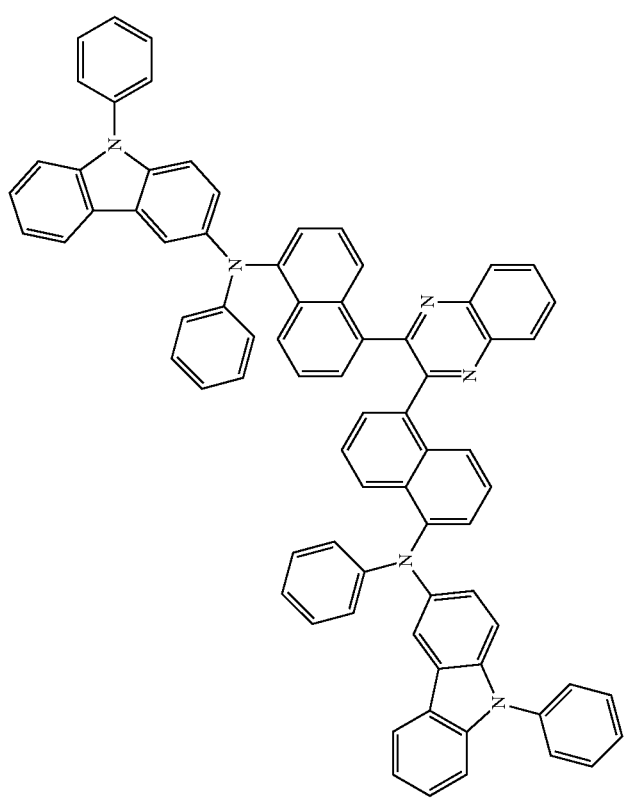

(308)
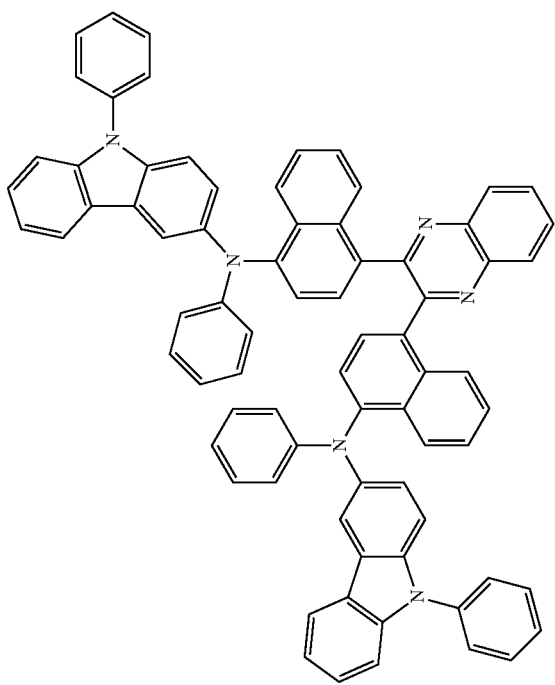

-continued
(309)
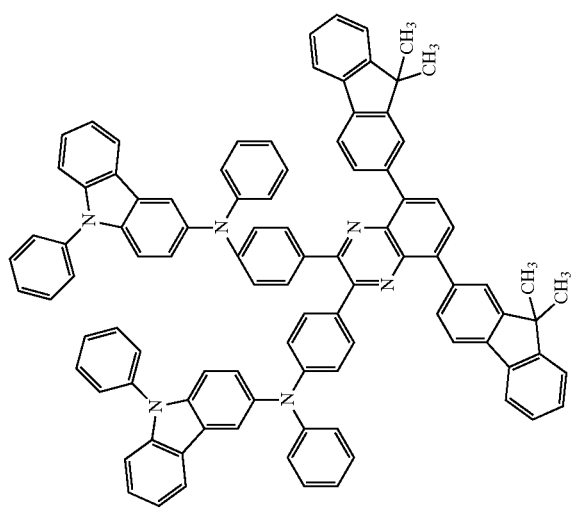
formula [105]
(310)
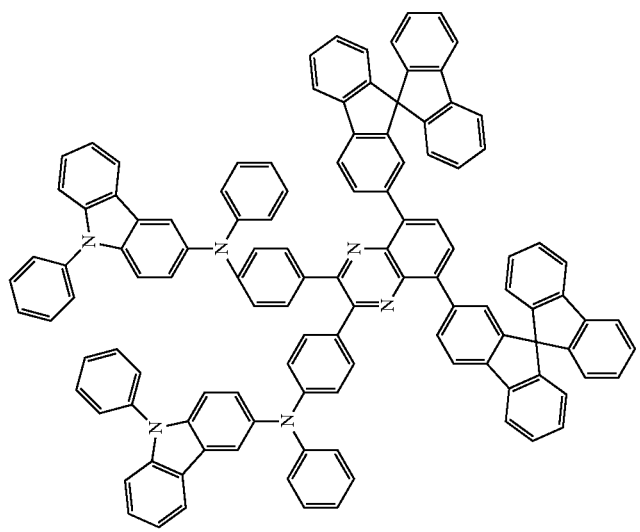

-continued
formula [106]
(312)
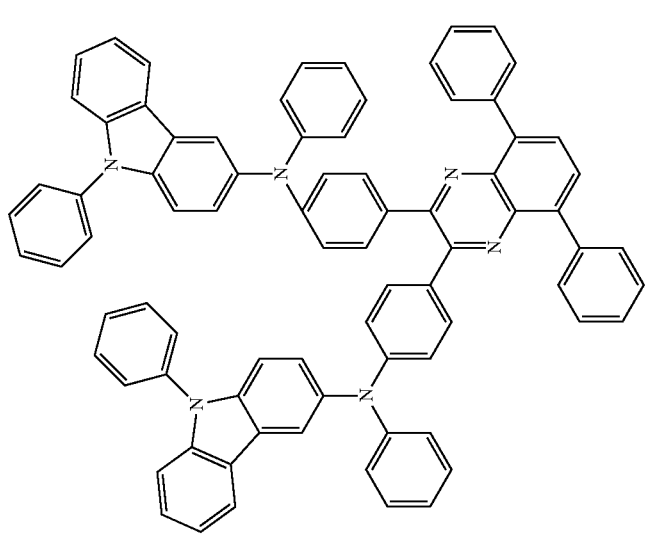
(311)
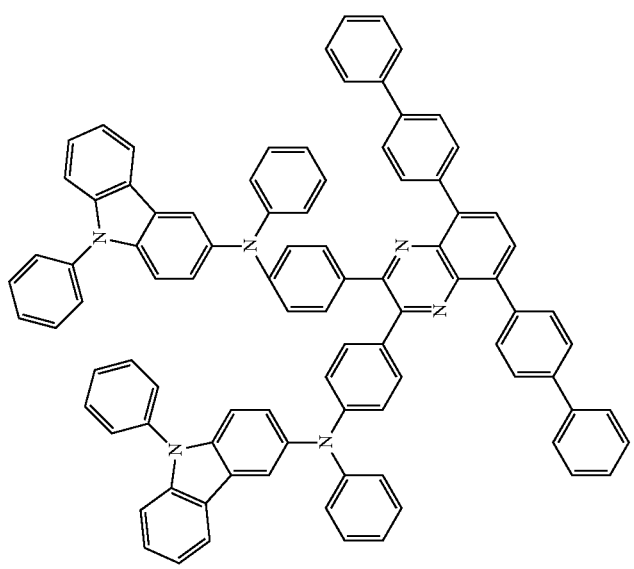

-continued
(314)
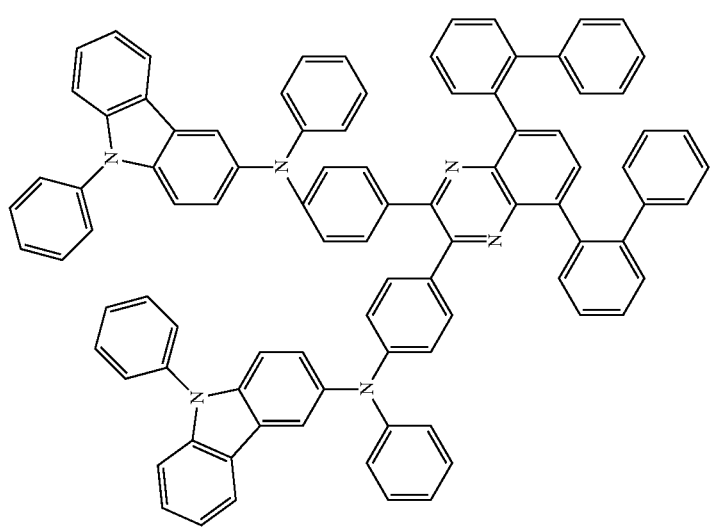
(313)
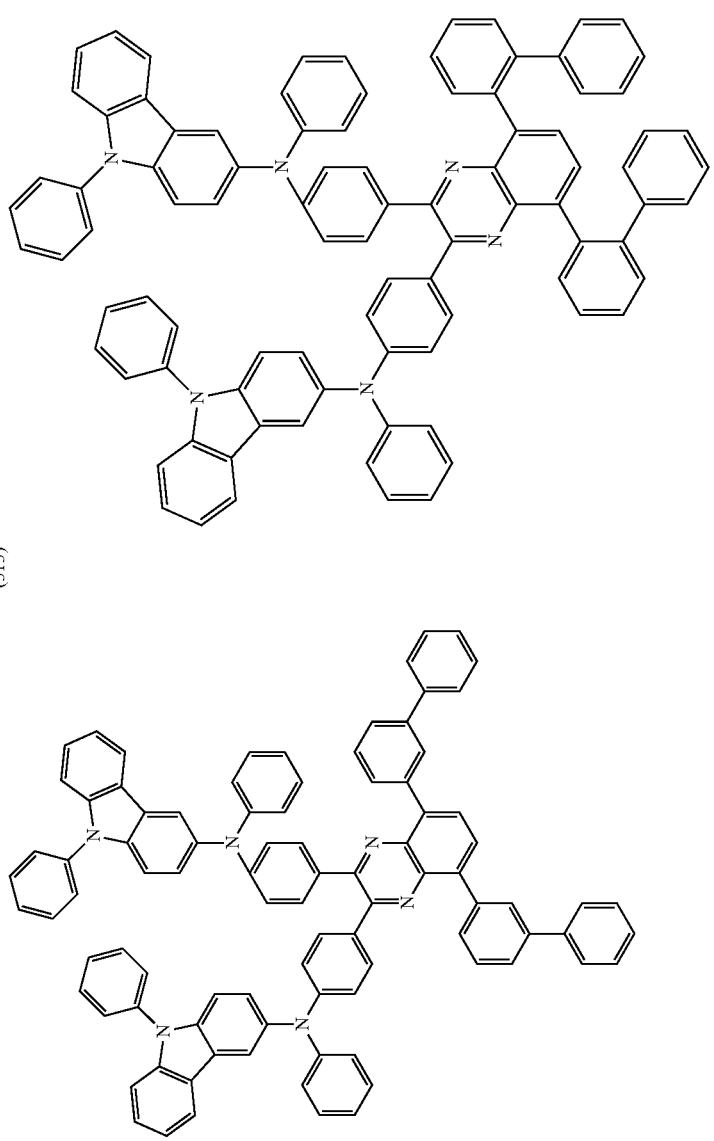
formula [107]

-continued
(316)
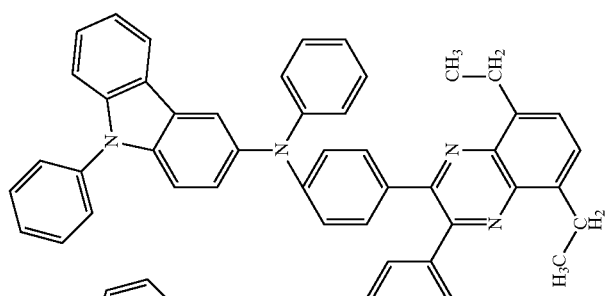
(315)
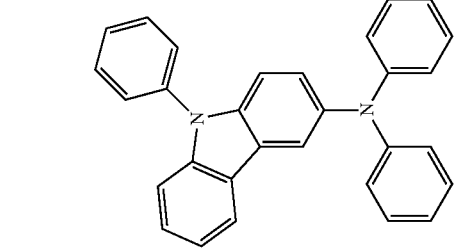
formula [108]
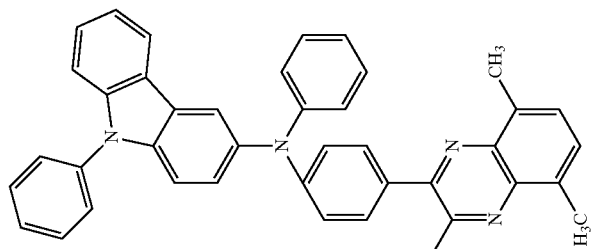
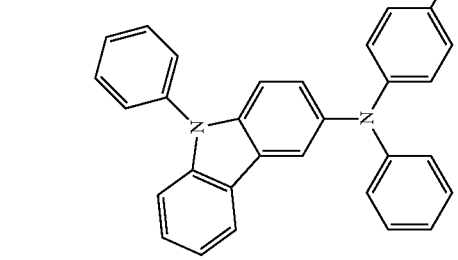

(317)
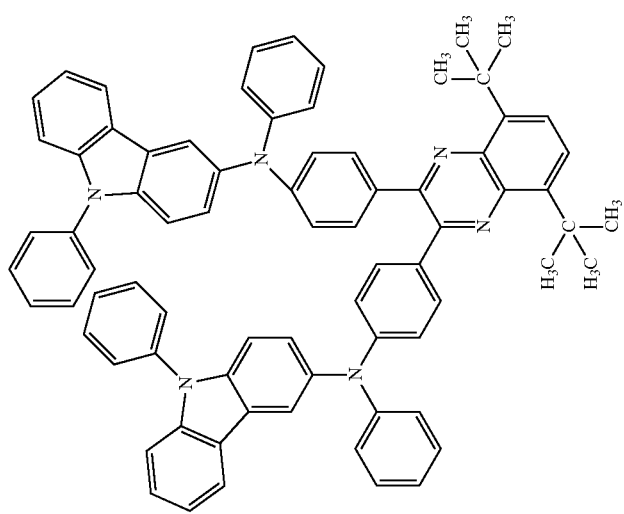

-continued
(319)
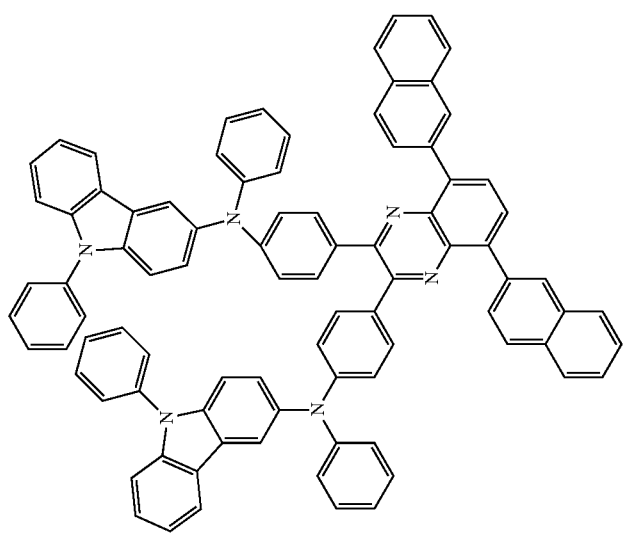
formula [109]
(318)
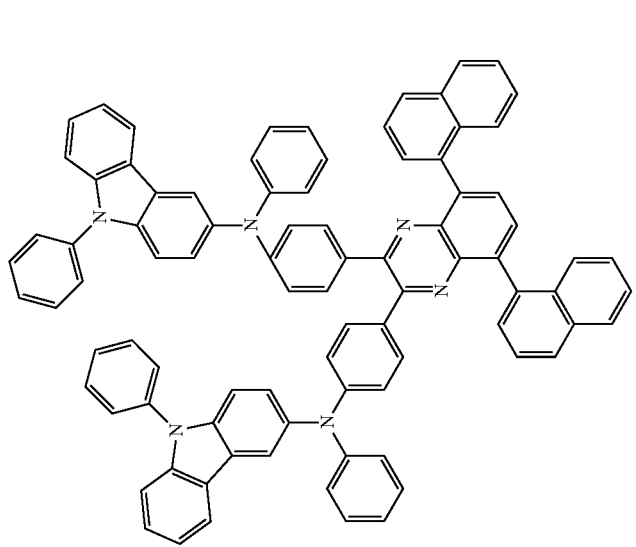

-continued
formula [110]
(320)
(321)
(322)
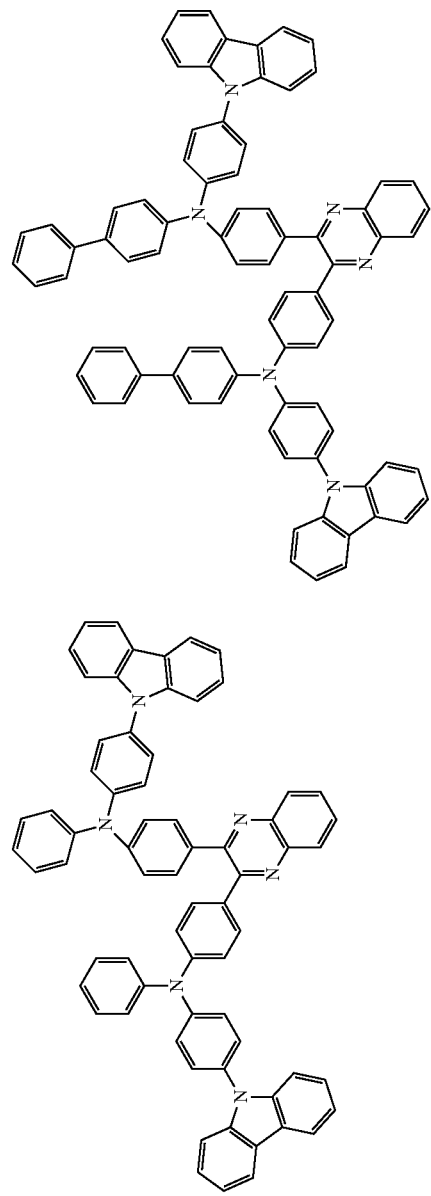
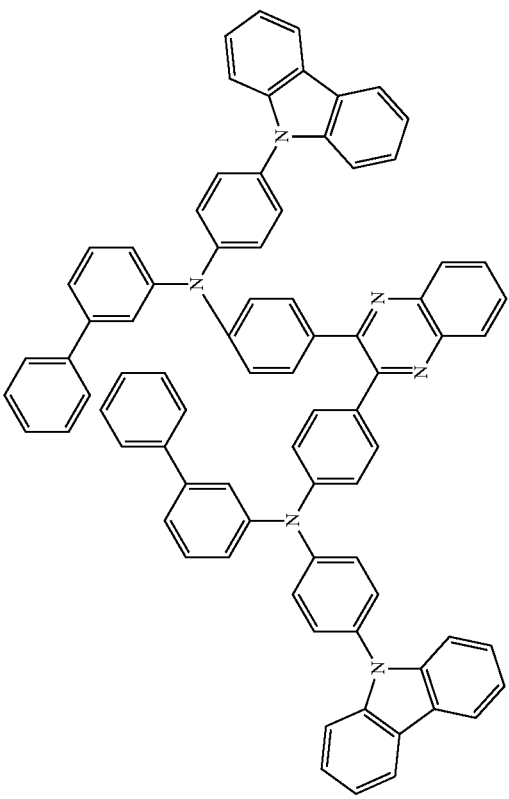

-continued
(324)
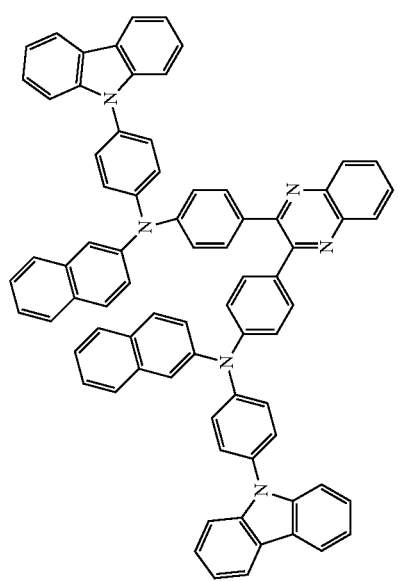
(323)
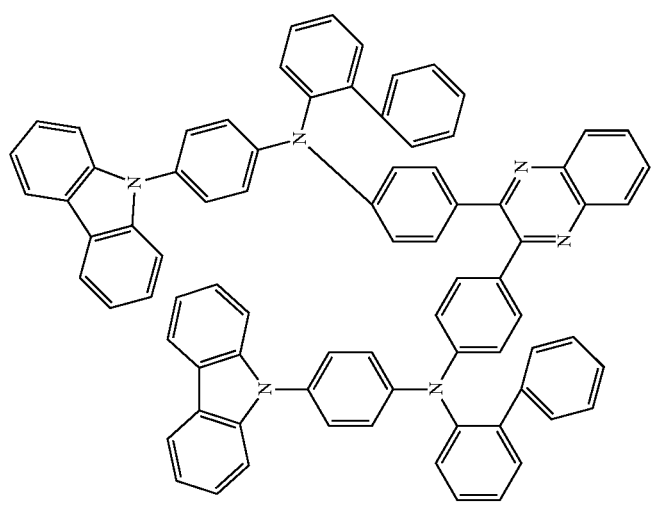
formula [111]

(325)
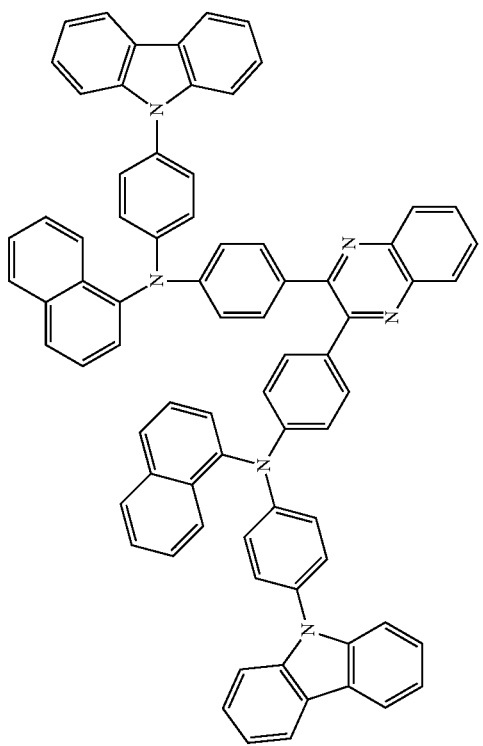

-continued
(326)
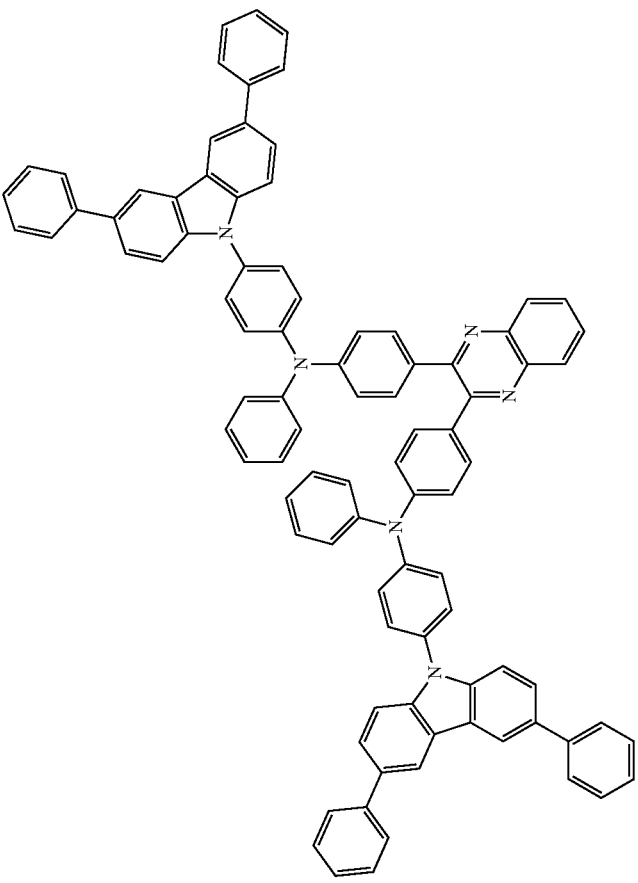
formula [112]
(327)
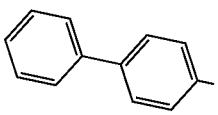

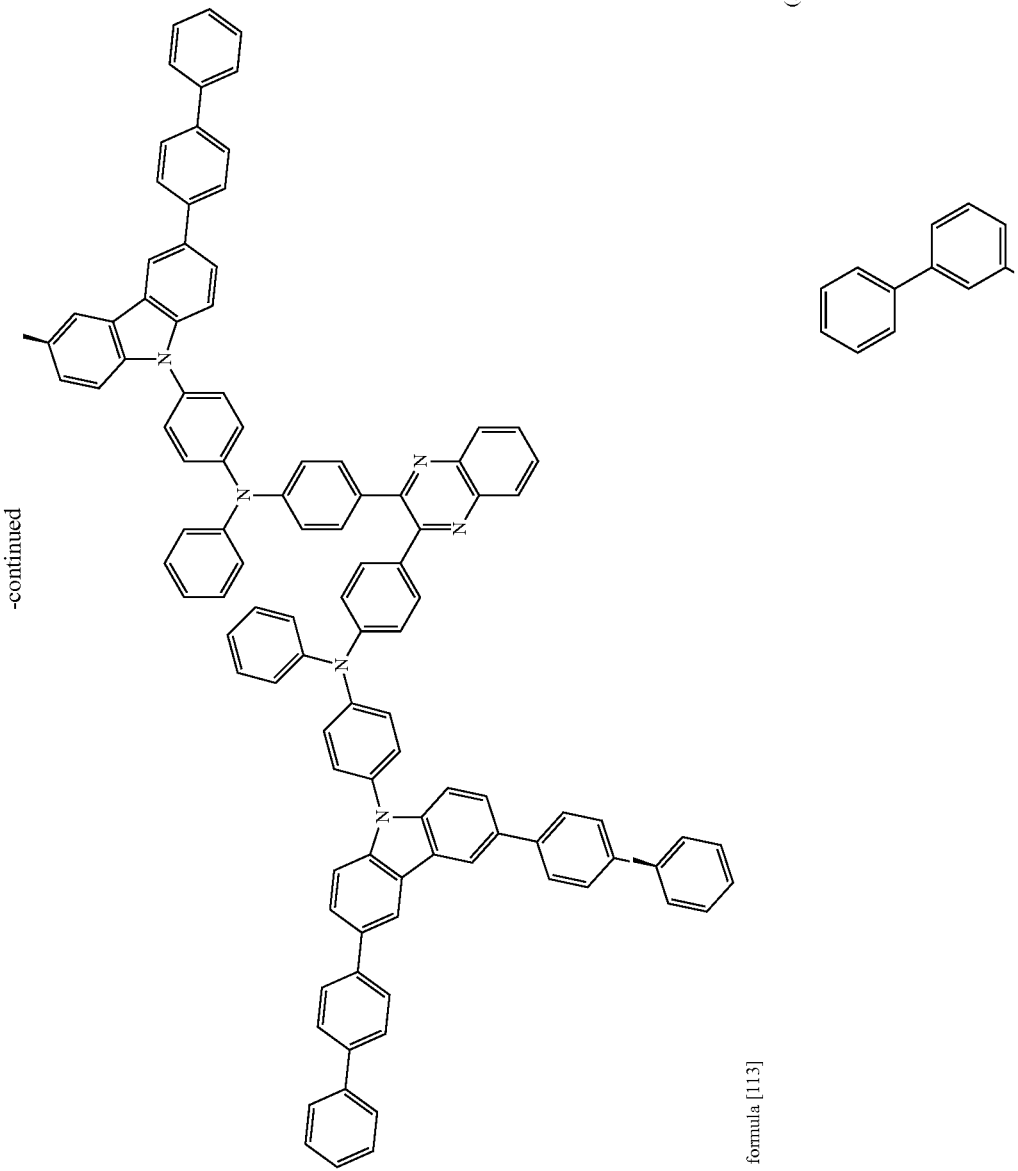
formula [113]

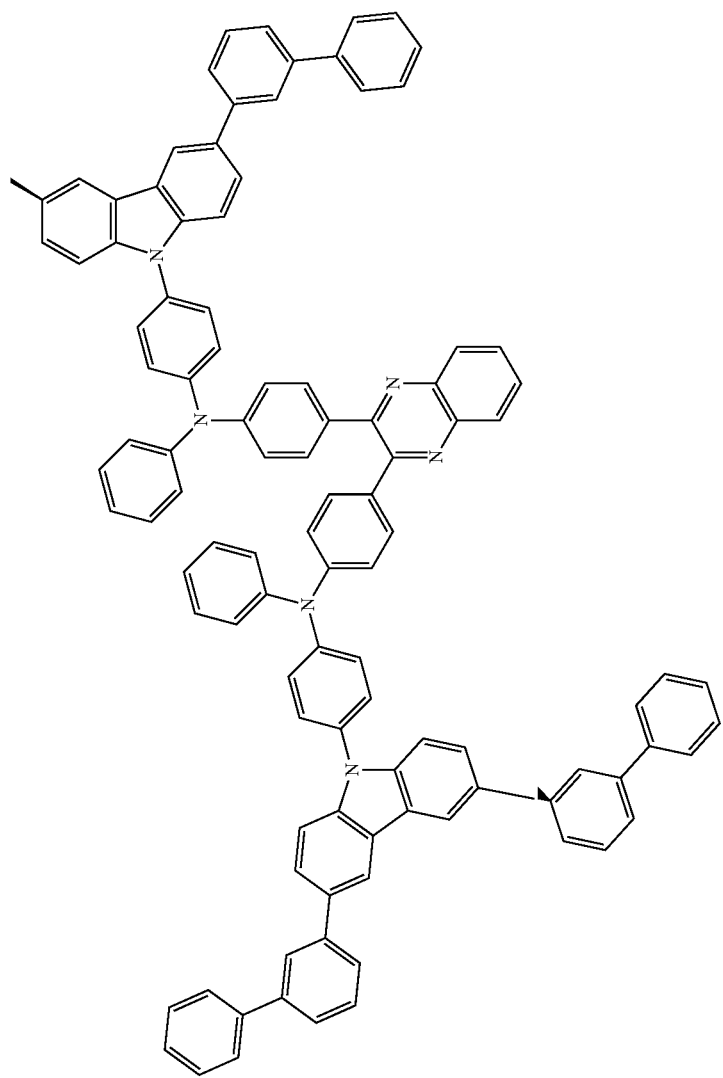

(329)
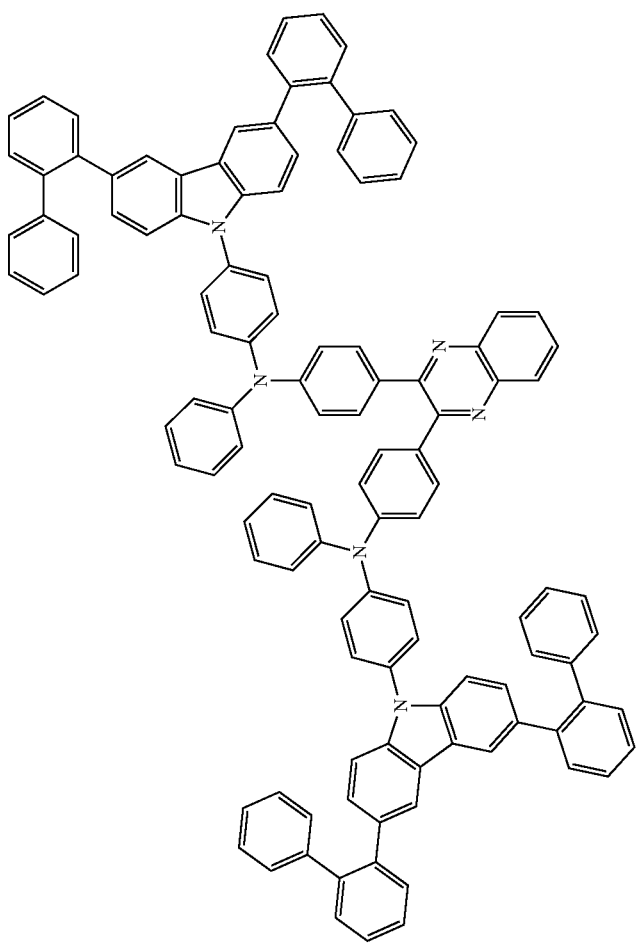

formula [114]
(330)
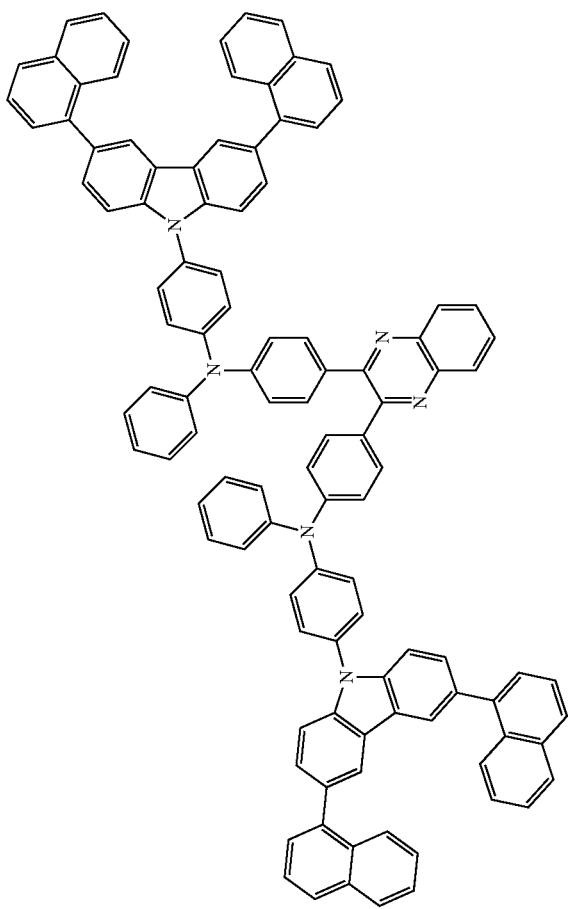

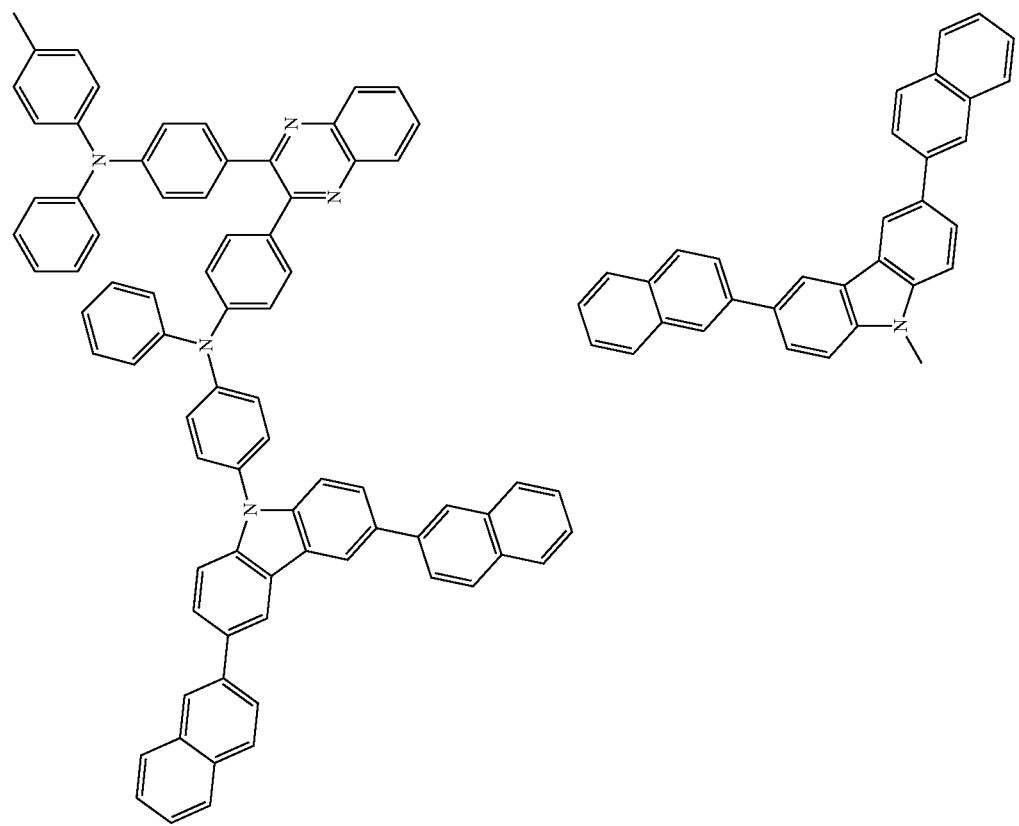

formula [115]
(332)
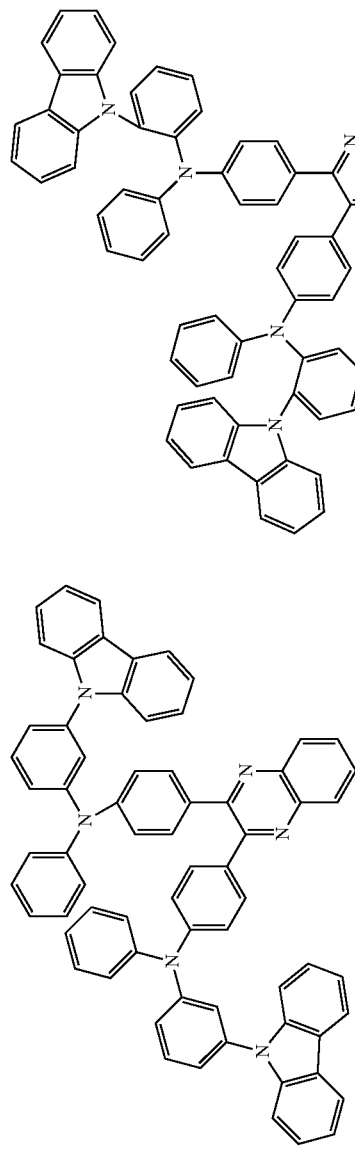
(333)
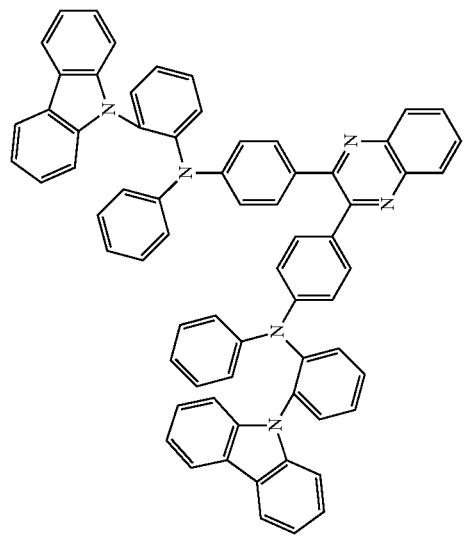
formula [116]
(334)
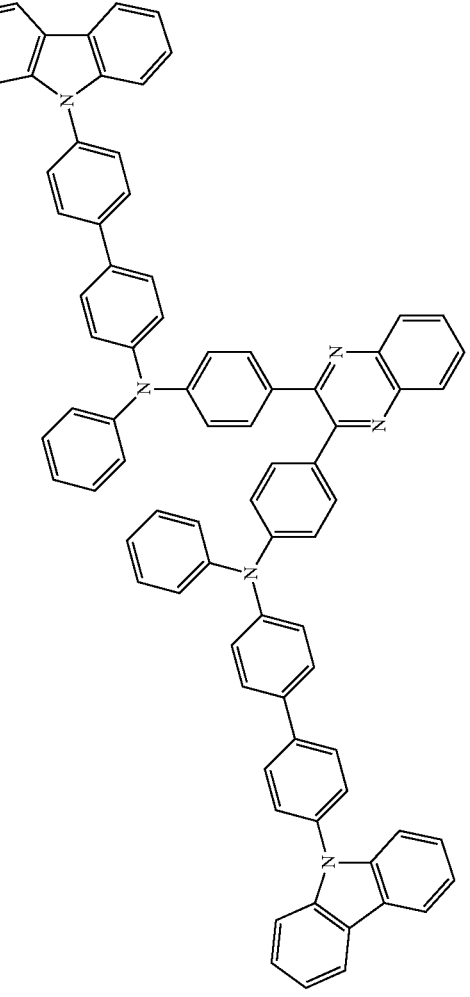

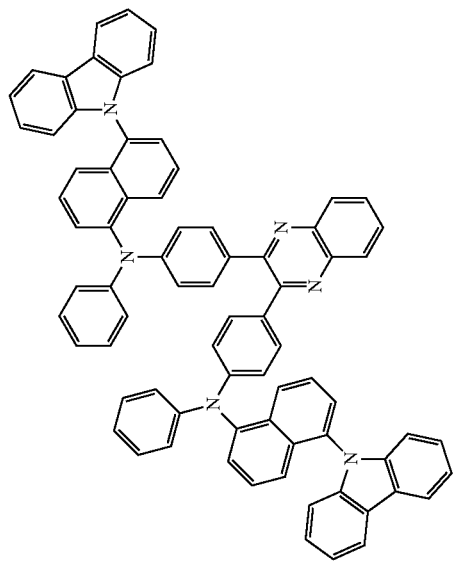
(336)
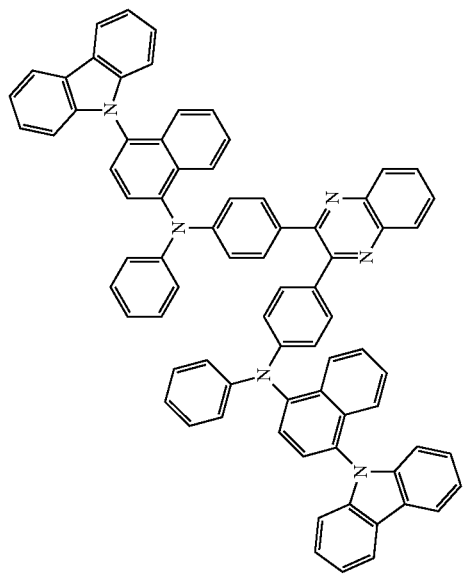
(335) formula [117]
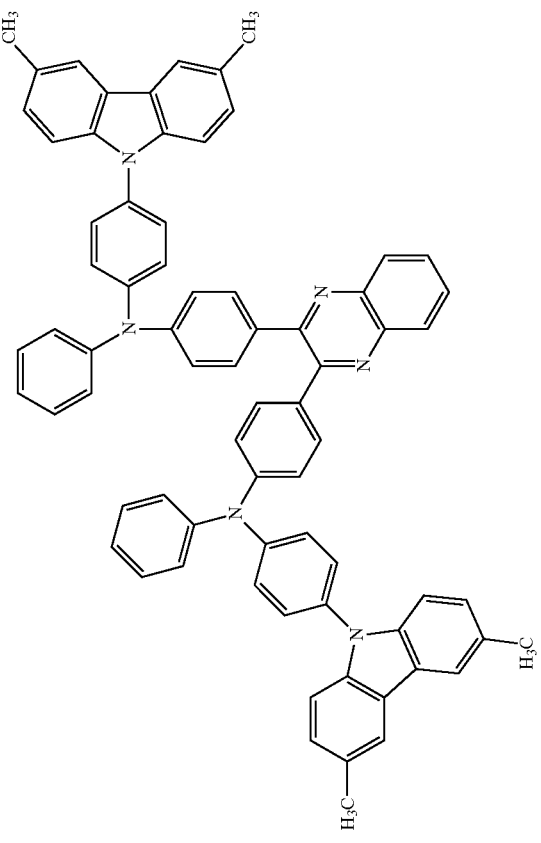
(337)

(338)
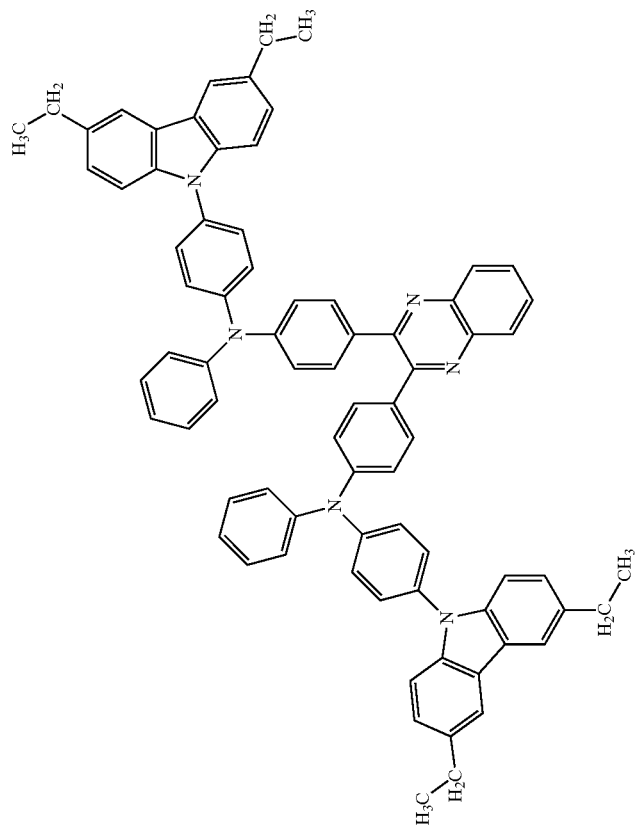

(339)
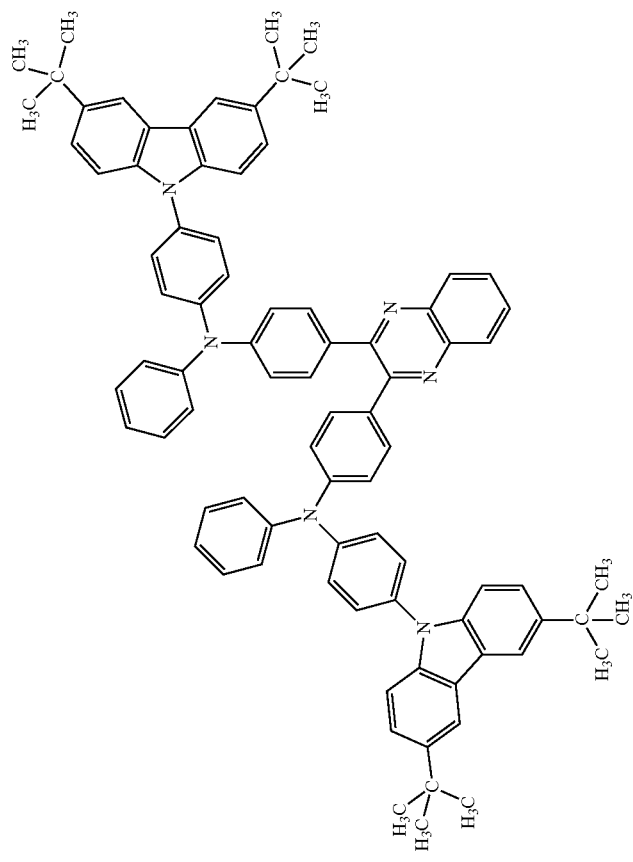

-continued
(341)
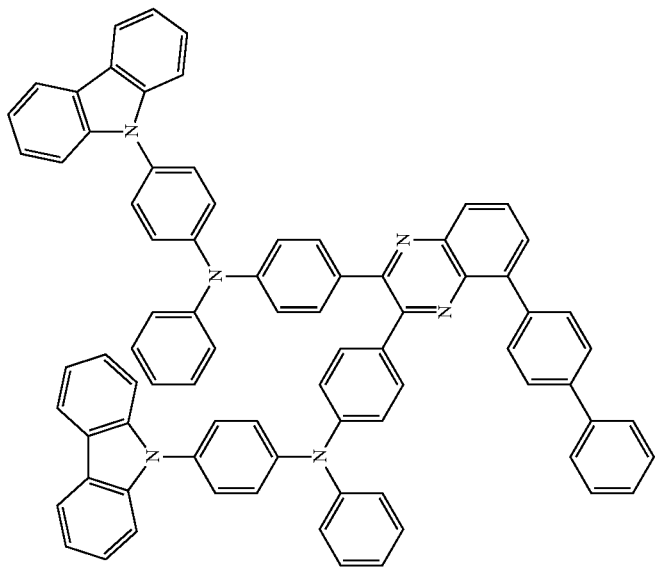
(340)
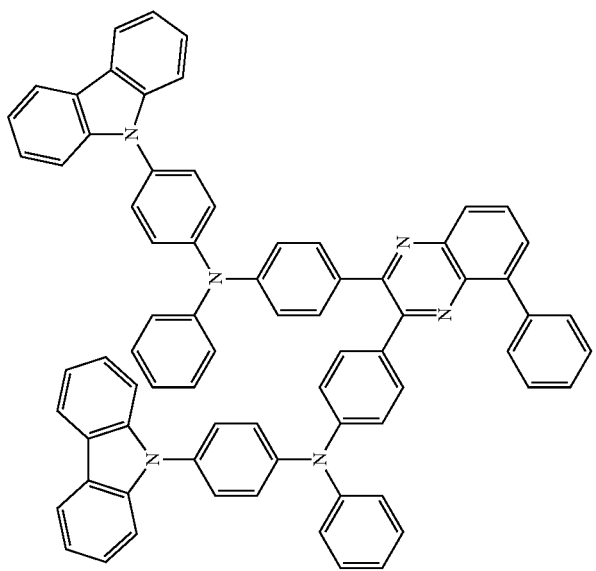
formula [118]

-continued
(343)
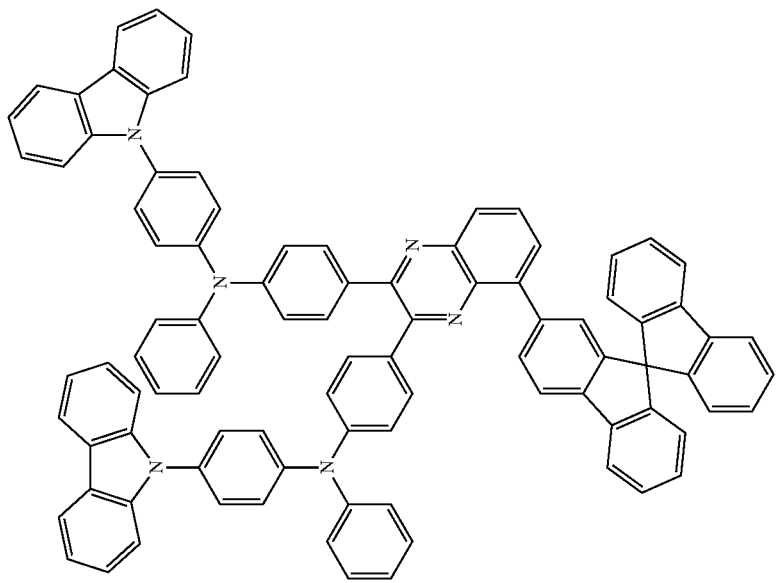
(342)
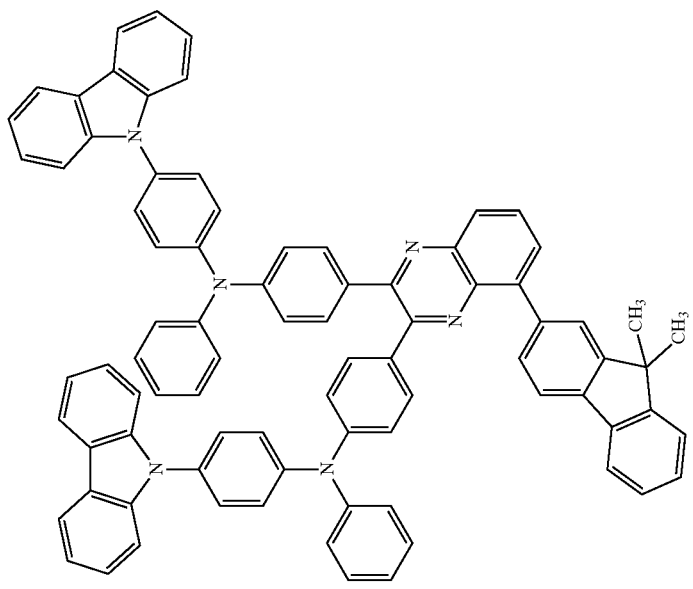

-continued
(345)
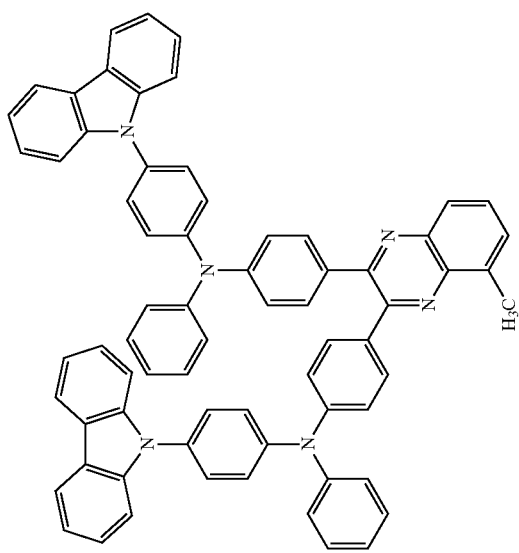
(344)
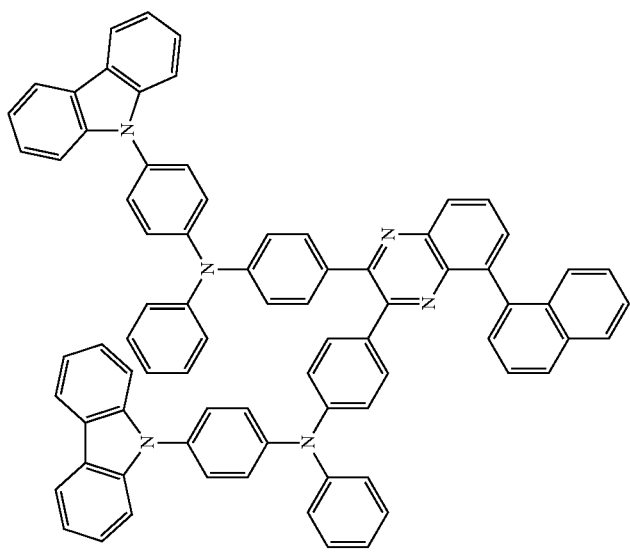

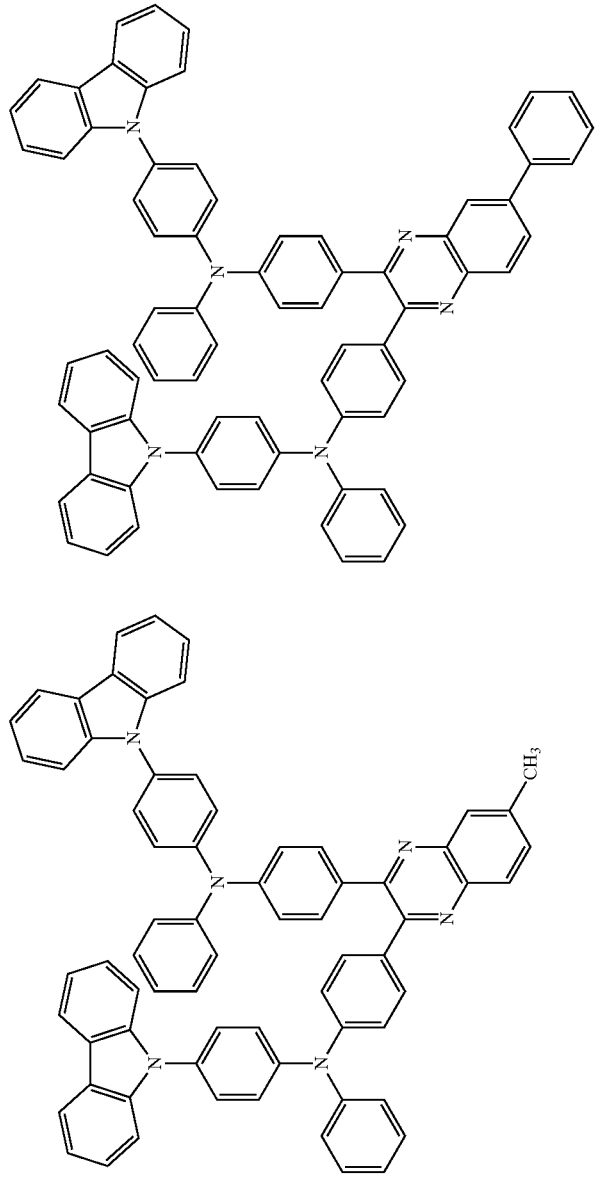

-continued
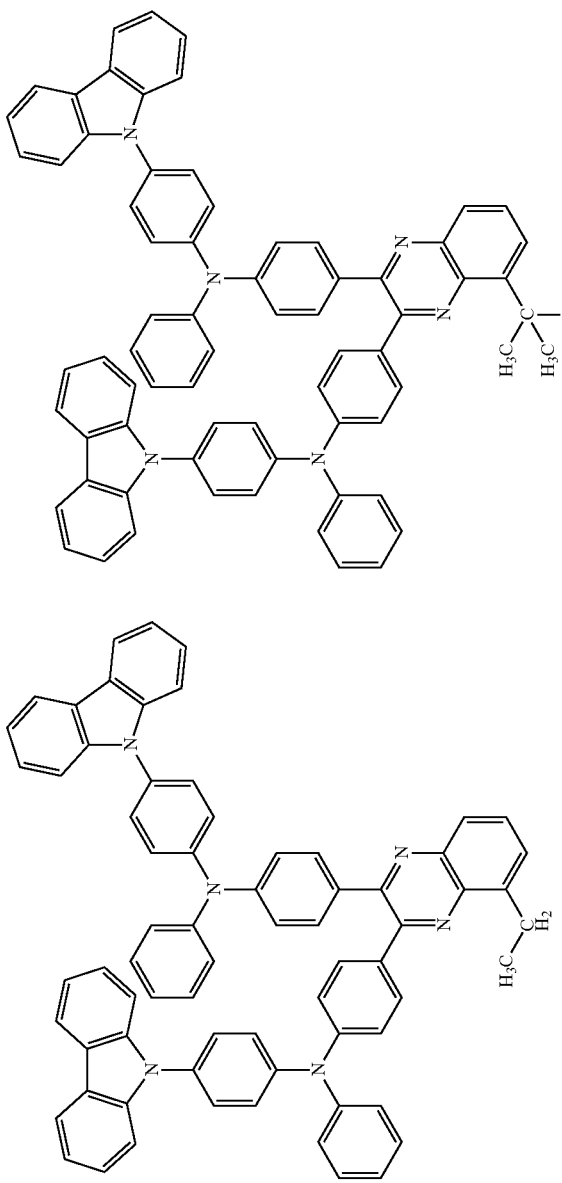
(349)
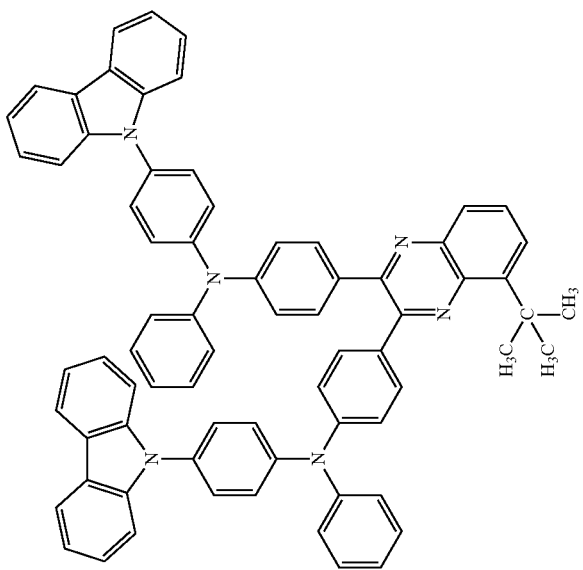
(348)
formula [122]

(350)
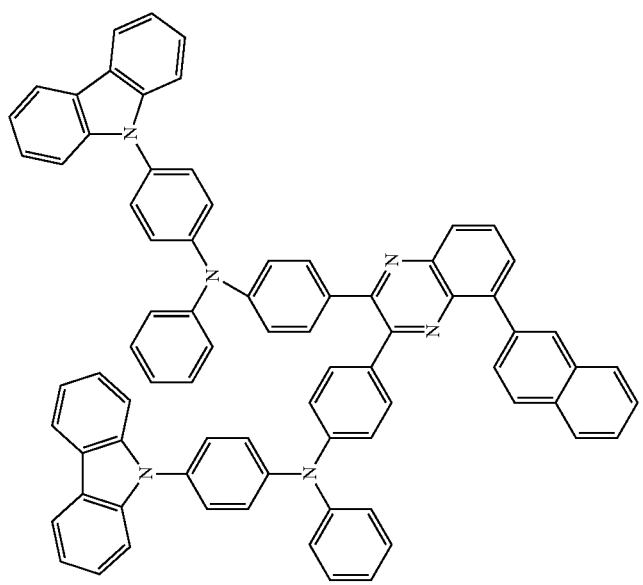

-continued
(352)
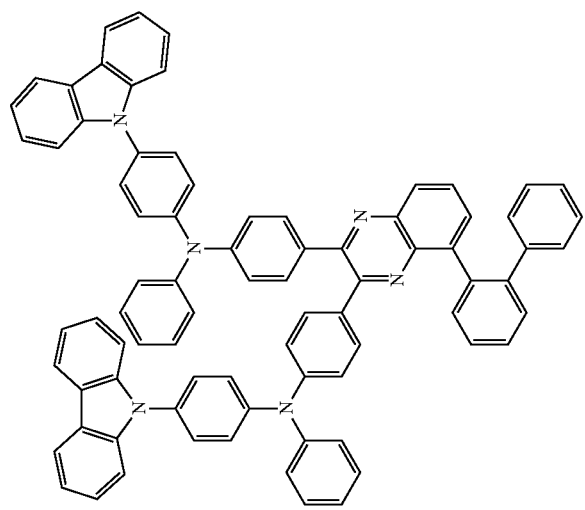
formula [123]
(351)
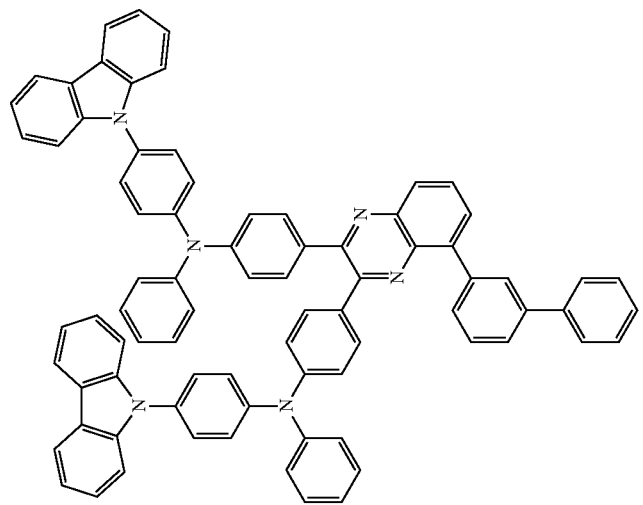

formula [124]
-continued
(353)
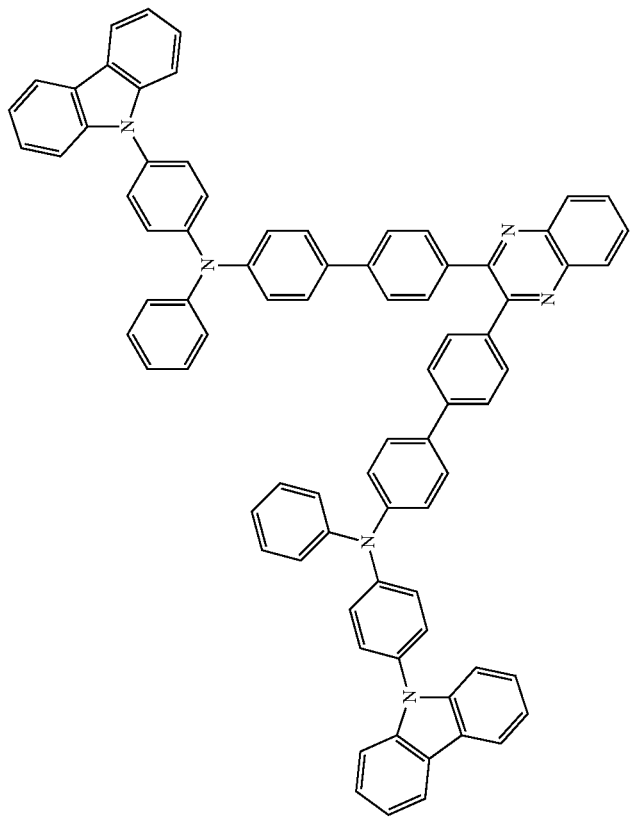

(354)
(355)
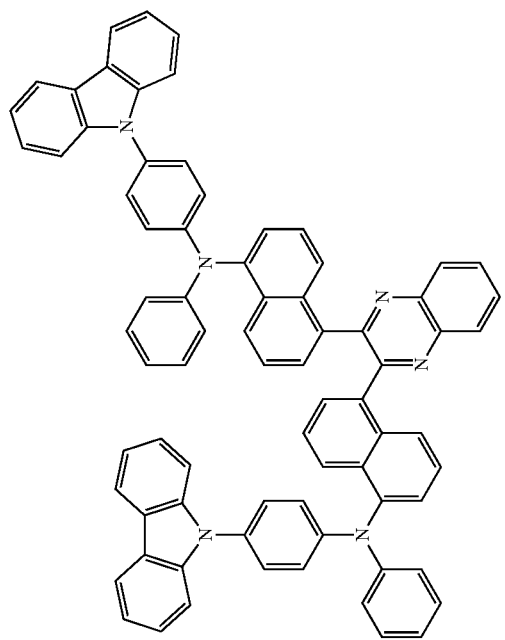
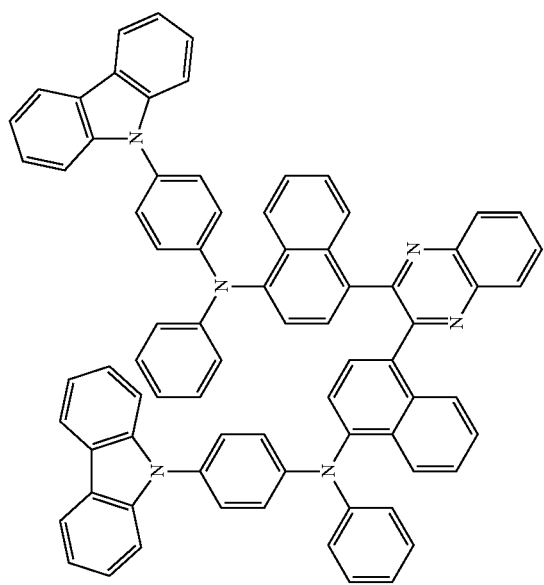

-continued
(357)
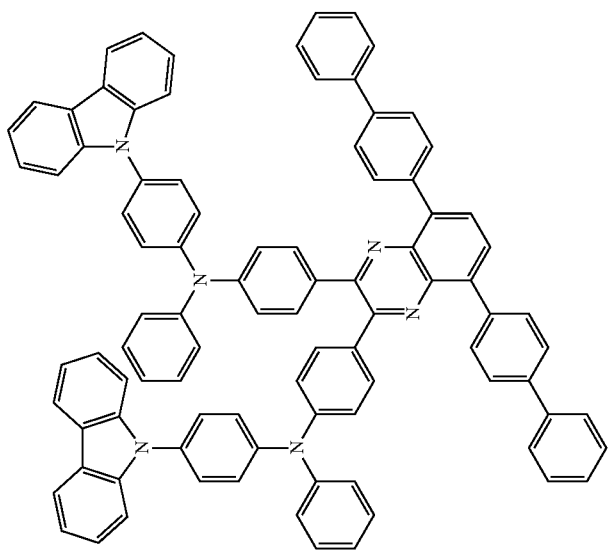
(356)
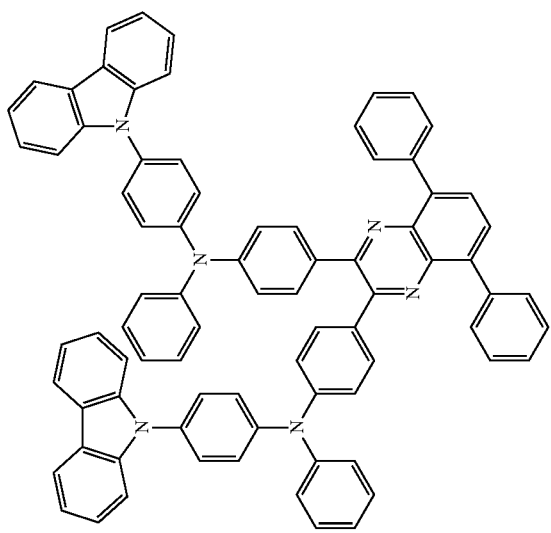
formula [125]

-continued
(359)
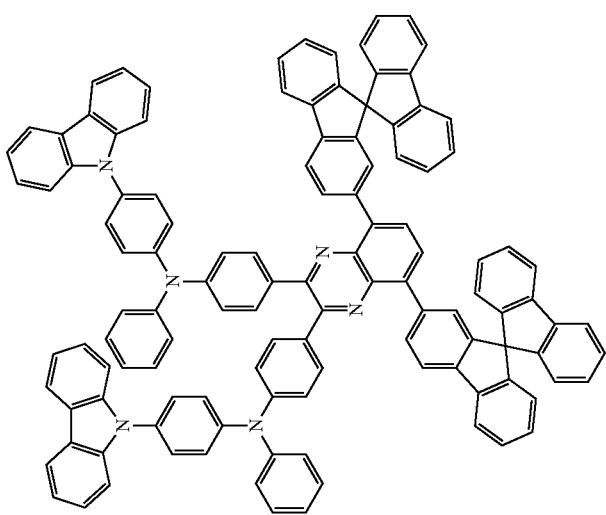
formula [126]
(358)
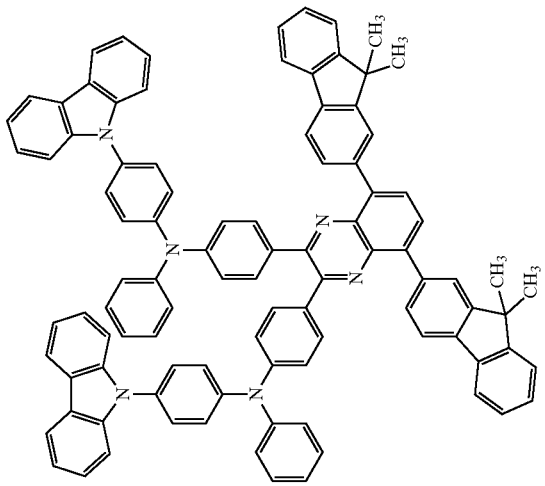

-continued
(361)
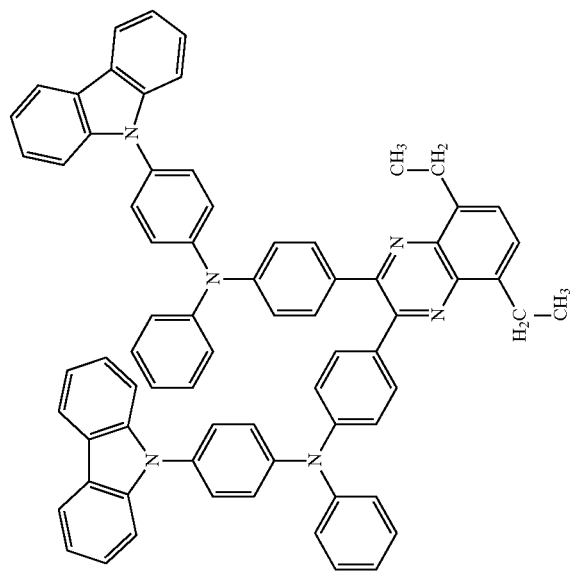
(360)
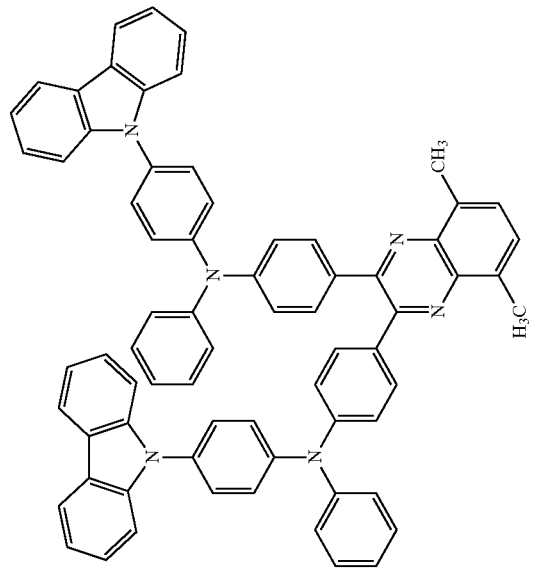
formula [127]

(362)
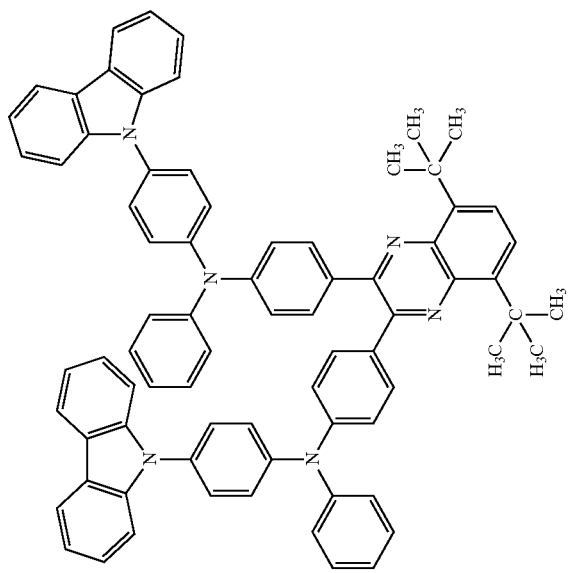

-continued
formula [128]
(364)
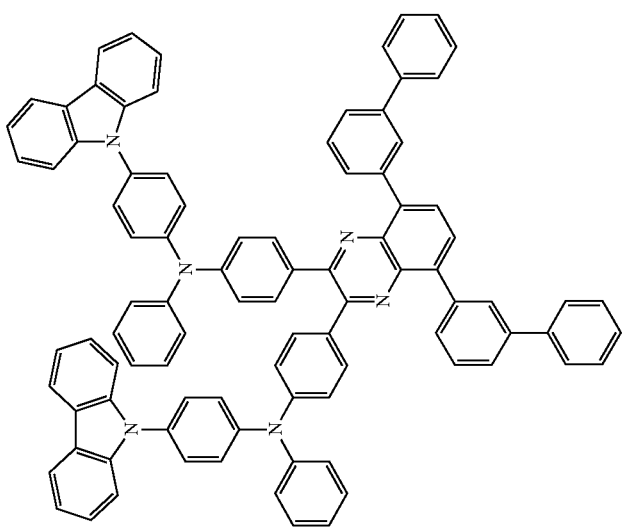
(363)
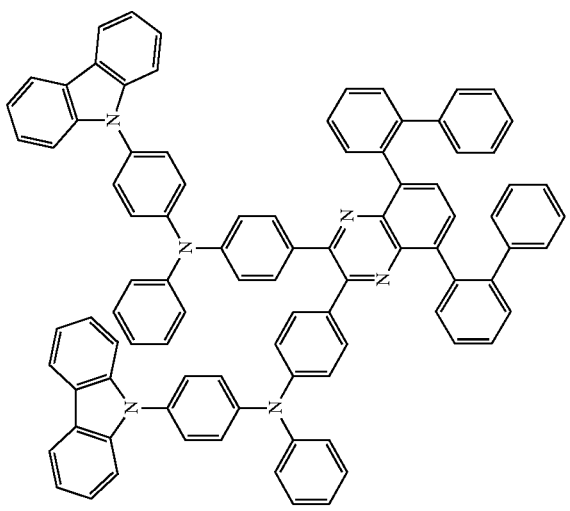

-continued
(365)
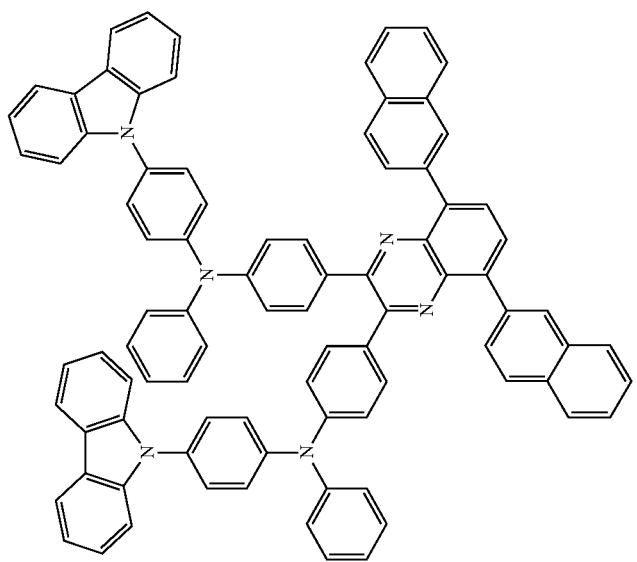
(366)
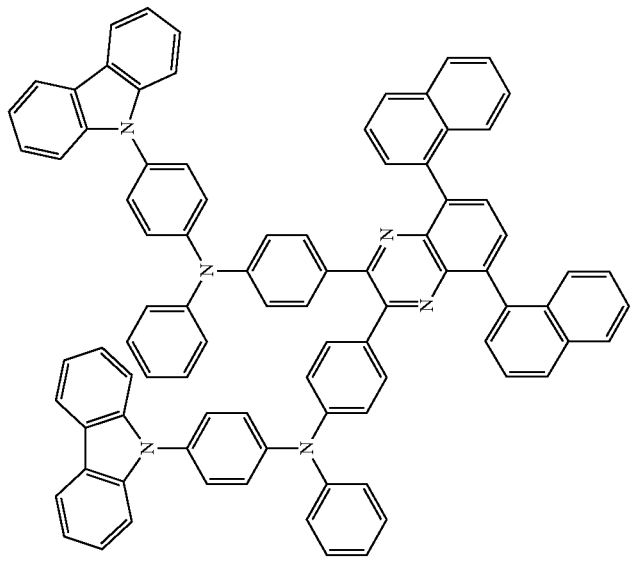

Various reactions can be applied to synthesize the quinoxaline derivatives of the present invention. For example, a quinoxaline derivative can be prepared by the reactions shown in the following reaction schemes (A-1), (A-2), and (B-1) to (B-6).

formula [130]

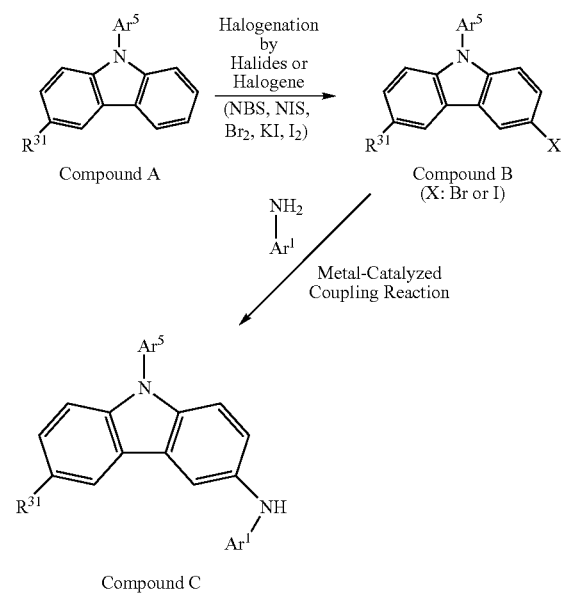

First, a compound including carbazole in a skeleton (compound A) is reacted with halogen or halides such as N-bromosuccinimide (NBS), N-iodosuccinimide (NIS), bromine ($Br_2$), potassium iodide (KI), or iodine ($I_2$) to synthesize a compound including 3-halogenated carbazole in a skeleton (compound B), which is followed by the coupling reaction with an arylamine using a metal catalyst such as a palladium catalyst (Pd catalyst) to give a compound C. In the synthetic scheme (A-1), a halogen element (X) is preferably iodine or bromine. $R^{31}$ represents any of a hydrogen atom, an alkyl group having 1 to 4 carbon atoms, or an aryl group having 6 to 25 carbon atoms. $Ar^5$ represents an aryl group having 6 to 25 carbon atoms. $Ar^1$ represents an aryl group having 6 to 25 carbon atoms.

formula [131]

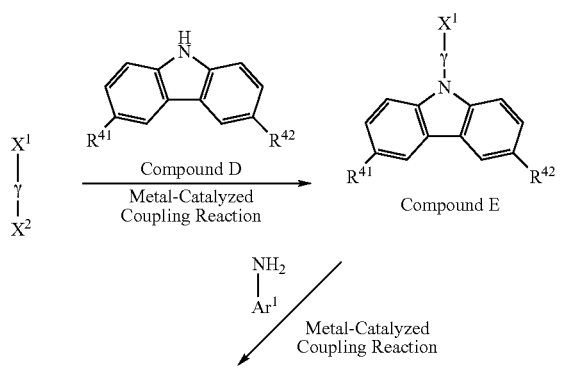

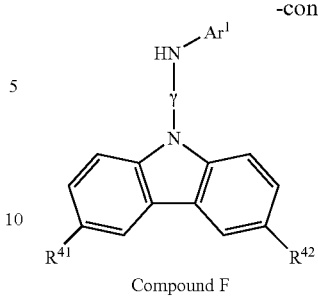

Compound F

First, a compound including carbazole in a skeleton (compound D) is reacted with dihalide of an aromatic compound to synthesize a compound including N-(halogenated aryl)carbazole in a skeleton (compound E), and then N-(halogenated aryl)carbazole is subjected to coupling reaction with arylamine using a metal catalyst such as palladium, giving a compound F. In the synthetic scheme (A-2), a halogen element ($X^1$ and $X^2$) of dihalide of an aromatic compound is preferably iodine or bromine. $X^1$ and $X^2$ may be the same or different from each other. $R^{41}$ and $R^{42}$ each represent any of a hydrogen atom, an alkyl group having 1 to 4 carbon atoms, or an aryl group having 6 to 25 carbon atoms. γ represents an arylene group having 6 to 25 carbon atoms. $Ar^1$ represents an aryl group having 6 to 25 carbon atoms.

formula [132]

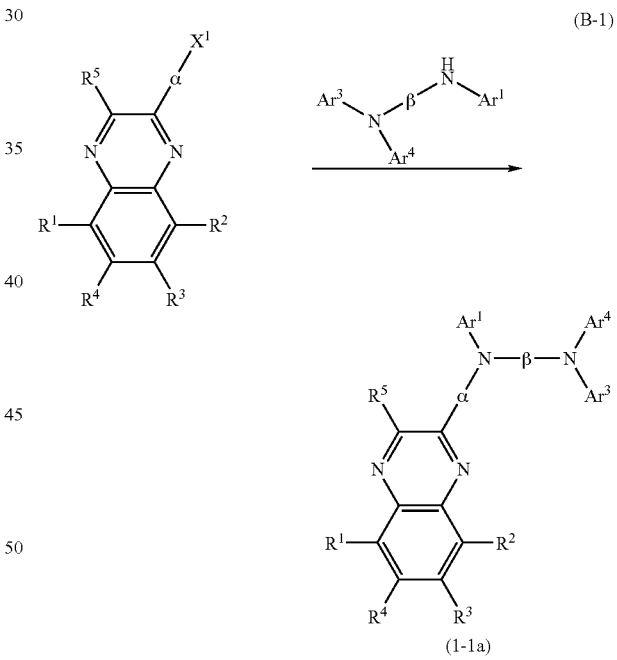

By the reaction shown in the synthetic scheme (B-1), the quinoxaline derivative of the present invention can be synthesized. In the synthetic scheme (B-1), $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. Further, β represents an arylene group having 6 to 25 carbon atoms, $Ar^3$ and $Ar^4$ each represent an aryl group having 6 to 26 carbon atoms. $X^1$ represents a halogen element. $X^1$ is preferably iodine or bromine.

formula [133]

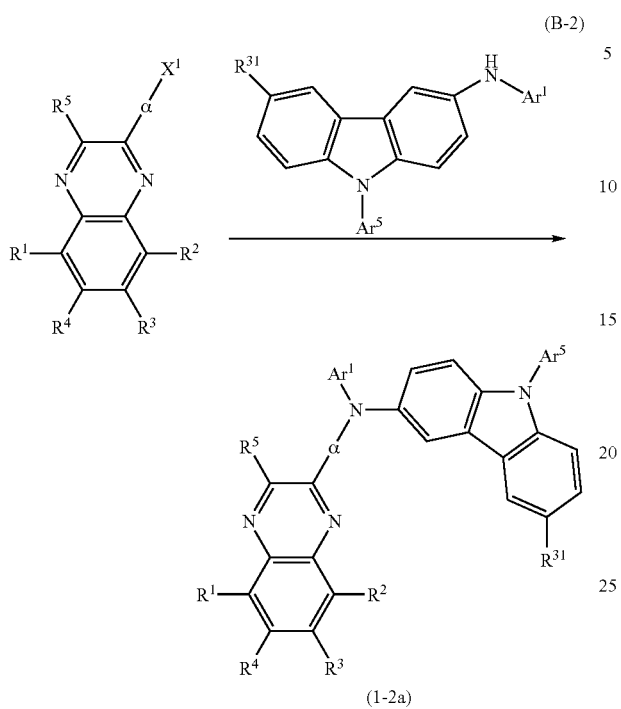

(B-2)

(1-2a)

By the reaction shown in the synthetic scheme (B-2), the quinoxaline derivative of the present invention can be synthesized from the compound C prepared by the reaction illustrated in the synthetic scheme (A-1). In the synthetic scheme (B-2), $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and a represents an arylene group having 6 to 25 carbon atoms. Further, $Ar^5$ represents an aryl group having 6 to 25 carbon atoms; and $R^{31}$ represents any of a hydrogen atom, an alkyl group having 1 to 4 carbon atoms, or an aryl group having 6 to 25 carbon atoms. $X^1$ represents a halogen element. $X^1$ is preferably iodine or bromine.

formula [134]

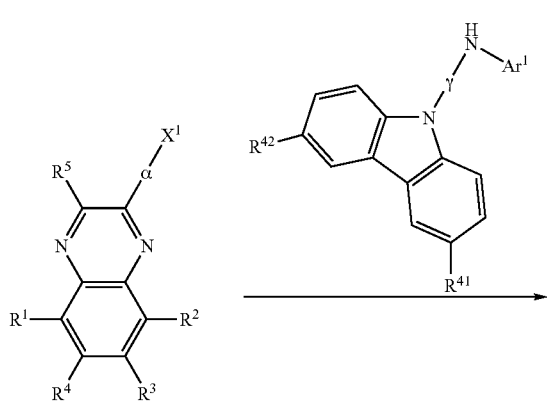

(B-3)

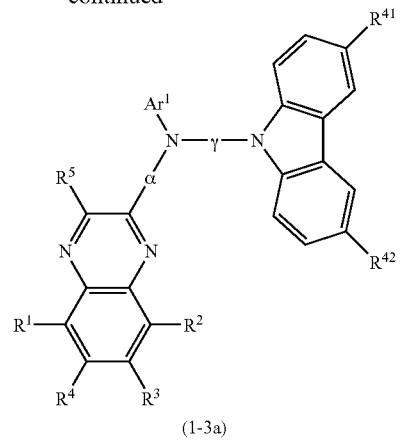

(1-3a)

By, the reaction shown in the synthetic scheme (B-3), the quinoxaline derivative of the present invention can be synthesized from the compound F prepared in the synthetic scheme (A-2). In the synthetic scheme (B-3), $R^1$ to $R^4$ each represent any of a hydrogen atom, an alkyl group having 1 to 4 carbon atoms, or an aryl group having 6 to 25 carbon atoms; $R^5$ represents any of a hydrogen atom, an alkyl group having 1 to 4 carbon atoms, or an aryl group having 6 to 25 carbon atoms; $Ar^1$ represents an aryl group having 6 to 25 carbon atoms; and a represents an arylene group having 6 to 25 carbon atoms. Further, γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms. $X^1$ represents a halogen element. $X^1$ is preferably iodine or bromine.

formula [135]

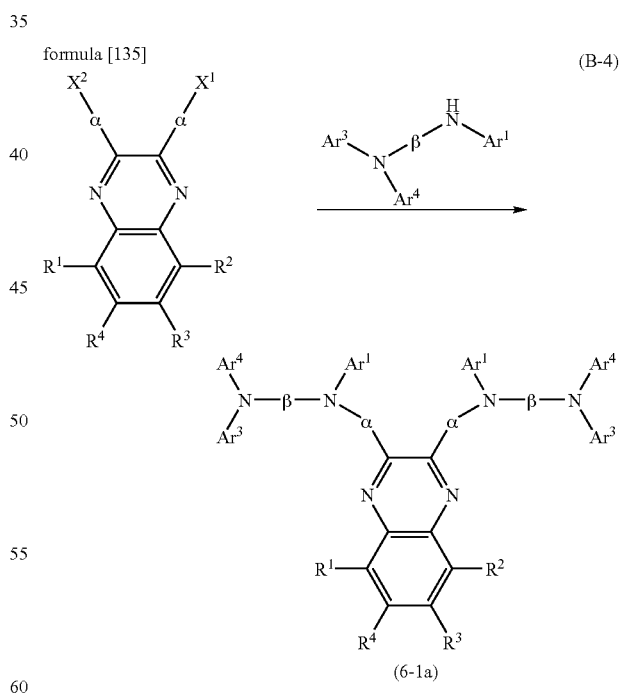

(B-4)

(6-1a)

By the reaction shown in the synthetic scheme (B-4), the quinoxaline derivative of the present invention can be synthesized. In the synthetic scheme (B-4), $R^1$ to $R^4$ each represent any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms.

Further, β represents an arylene group having 6 to 25 carbon atoms, and Ar³ and Ar⁴ each represent an aryl group having 6 to 26 carbon atoms. $X^1$ and $X^2$ each represent a halogen element. $X^1$ and $X^2$ are preferably iodine or bromine.

formula [136]

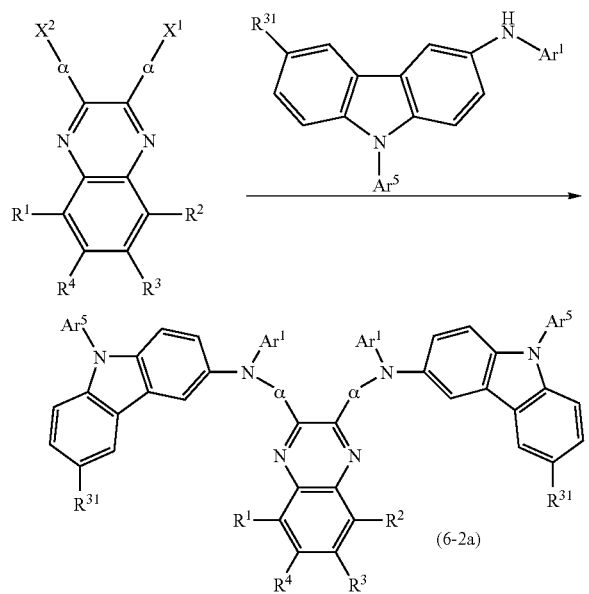

(B-5)

(6-2a)

By the reaction shown in the synthetic scheme (B-5), the quinoxaline derivative of the present invention can be synthesized from the compound C prepared in the synthesis scheme (A-1). In the synthetic scheme (B-5), $R^1$ to $R^4$ each represent any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. Further, $Ar^5$ represents an aryl group having 6 to 25 carbon atoms; and $R^{31}$ represents any of a hydrogen atom, an alkyl group having 1 to 4 carbon atoms, or an aryl group having 6 to 25 carbon atoms. $X^1$ and $X^2$ each represent a halogen element. $X^1$ and $X^2$ are preferably iodine or bromine.

formula [137]

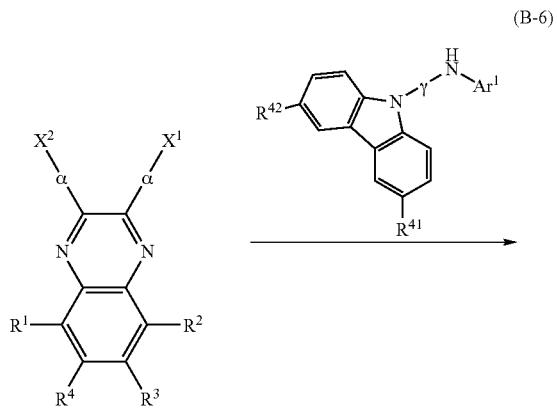

(B-6)

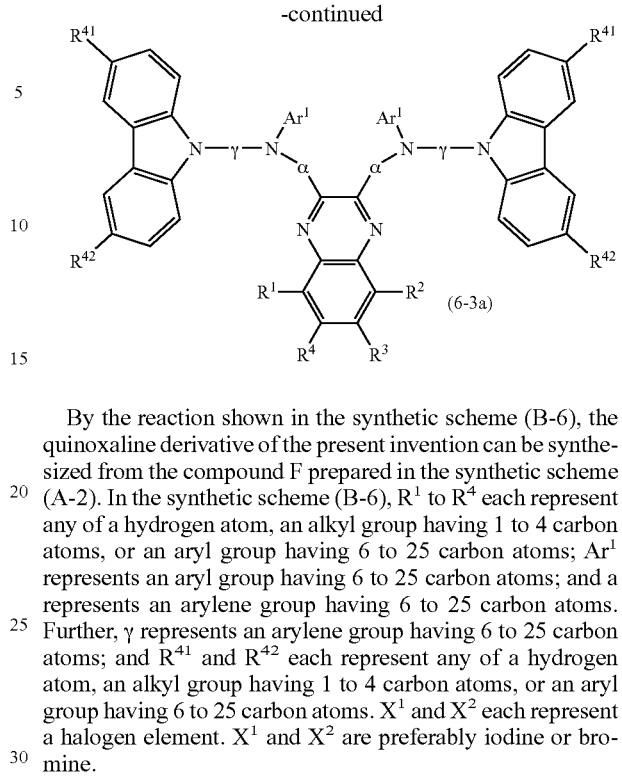

(6-3a)

By the reaction shown in the synthetic scheme (B-6), the quinoxaline derivative of the present invention can be synthesized from the compound F prepared in the synthetic scheme (A-2). In the synthetic scheme (B-6), $R^1$ to $R^4$ each represent any of a hydrogen atom, an alkyl group having 1 to 4 carbon atoms, or an aryl group having 6 to 25 carbon atoms; $Ar^1$ represents an aryl group having 6 to 25 carbon atoms; and α represents an arylene group having 6 to 25 carbon atoms. Further, γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms. $X^1$ and $X^2$ each represent a halogen element. $X^1$ and $X^2$ are preferably iodine or bromine.

In the synthetic schemes (B-1) to (B-6), a compound represented by the general formula (1-1a) corresponds to the case where A in the general formula (1) is the general formula (1-1); a compound represented by the general formula (1-2a) corresponds to the case where A in the general formula (1) is the general formula (1-2); and a compound represented by the general formula (1-3a) corresponds to the case where A in the general formula (1) is the general formula (1-3). A compound represented by the general formula (6-1a) corresponds to the case where A in the general formula (6) is the general formula (6-1); a compound represented by the general formula (6-2a) corresponds to the case where A in the general formula (6) is the general formula (6-2); and a compound represented by the general formula (6-3a) corresponds to the case where A in the general formula (6) is the general formula (6-3).

The quinoxaline derivatives of the present invention are bipolar and excellent in both an electron transporting property and a hole transporting property. Therefore, when the quinoxaline derivatives of the present invention are used for an electronics device, a good electric performance is attainable. Further, the quinoxaline derivative of the present invention has a high glass transition temperature and excellent in thermal stability; therefore, when the quinoxaline derivatives of the present invention are applied to an electronics device, an electronics device having excellent thermal stability can be obtained. Furthermore, the quinoxaline derivative of the present invention is stable with respect to repeated electrochemical oxidation-reduction cycles; therefore, when the quinoxaline derivative of the present invention is used for an electronics device, a long-life electronics device can be obtained.

Embodiment Mode 2

One mode of a light-emitting element using a quinoxaline derivative of the present invention will be explained below with reference to FIG. 1A.

A light-emitting element of the present invention has a plurality of layers between a pair of electrodes. The plurality of layers are fabricated by stacking layers comprising a substance having a high carrier injecting property and layers comprising substance having a high carrier transporting property. These layers are stacked so that a light-emitting region is located in a region away from the electrodes, that is, recombination of carriers is performed in an area away from the electrodes.

In this embodiment mode, a light-emitting element includes a first electrode 102, a first layer 103, a second layer 104, a third layer 105, and a fourth layer 106 which are sequentially stacked over the first electrode 102, and a second electrode 107 provided thereover. Following description will be provided regarding the first electrode 102 as an anode and the second electrode 107 as a cathode.

A substrate 101 is used as a support of the light-emitting element. For the substrate 101, glass, plastic, or the like can be used, for example. Note that another material may be used as long as it functions as a support in a manufacturing process of the light-emitting element.

As the first electrode 102, a metal, an alloy, a conductive compound, a mixture thereof, or the like having a high work function (specifically, 4.0 eV or more) is preferably used. Specifically, indium oxide-tin oxide (ITO: Indium Tin Oxide), indium oxide-tin oxide including silicon or silicon oxide, indium oxide-zinc oxide (IZO: Indium Zinc Oxide), indium oxide including tungsten oxide and zinc oxide (IWZO), or the like is given. Although these conductive metal oxide films are generally formed by sputtering, they may be formed by applying a sol-gel method or the like. For example, a layer of indium oxide-zinc oxide (IZO) can be formed by a sputtering method using a target in which 1 to 20 wt % of zinc oxide is added to indium oxide. A layer of indium oxide including tungsten oxide and zinc oxide (IWZO) can be formed by a sputtering method using a target in which 0.5 to 5 wt % of tungsten oxide and 0.1 to 1 wt % of zinc oxide are included in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal (such as titanium nitride: TiN), or the like can be employed.

The first layer 103 is a layer including a substance having a high hole injection property. Molybdenum oxide (MoOx), vanadium oxide (VOx), ruthenium oxide (RuOx), tungsten oxide (WOx), manganese oxide (MnOx), or the like can be used. Alternatively, the first layer 103 can be formed using phthalocyanine-based compound such as phthalocyanine (abbreviation: H$_2$Pc) or copper phthalocyanine (CuPc), or a high molecular compound such as poly(ethylene dioxythiophene)/poly(styrenesulfonic acid) (PEDOT/PSS), or the like.

Alternatively, a composite material formed by compositing an organic compound with an inorganic compound can be used for the first layer 103. In particular, a composite of an organic compound with an inorganic compound which has an electron accepting property with respect to the organic compound possesses an excellent hole injecting property and hole transporting property. This is because electron transfer between the organic compound and the inorganic compound occurs, increasing carrier density.

In a case of using a composite formed by compositing an organic compound with an inorganic compound for the first layer 103, the first layer 103 can perform an ohmic contact with the first electrode 102; therefore, a material of the first electrode can be selected regardless of work function.

As the inorganic compound used for the composite, transition metal oxide is preferred. Especially, an oxide of metals ranging from Groups 4 to 8 in the periodic table is preferred. Namely, it is preferable to use vanadium oxide, niobium oxide, tantalum oxide, chromium oxide, molybdenum oxide, tungsten oxide, manganese oxide, and rhenium oxide, because of their high electron accepting abilities. Above all, molybdenum oxide is particularly preferable because it is stable in air, has a low hygroscopicity and is easily treated.

As the organic compound of the composite, various compounds such as an aromatic amine compound, a carbazole derivative, an aromatic hydrocarbon, and a high molecular weight compound (such as oligomer, dendrimer, or polymer) can be used. The organic compound preferably used for the composite is an organic compound having a high hole transporting property. Specifically, a substance having a hole mobility of greater than or equal to 10$^{-6}$ cm$^2$/Vs is preferably used. However, other materials can also be used as long as the hole transporting property is higher than the electron transporting property. The organic compounds which can be used for the composite will be specifically shown below.

For example, the followings can be given as the aromatic amine compound: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivatives which can be used for the composite material, the followings can be given specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like can be used.

As the aromatic hydrocarbon which can be used for the composite, the followings can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. In particular, the aromatic hydrocarbon, which has a hole mobility of greater than or equal to 1×10$^{-6}$ cm$^2$/Vs and simultaneously has 14 to 42 carbon atoms, is more preferable.

The aromatic hydrocarbon which can be used for the composite may have a vinyl group. As the aromatic hydrocarbon having a vinyl group, the followings are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular weight compound such as poly(N-vinylcarbazole) (abbreviation: PVK) or poly(4-vinyltriphenylamine) (abbreviation: PVTPA) can also be used.

As a substance forming the second layer 104, a substance having a high hole transporting property, specifically, an aromatic amine compound (that is, a compound having a benzene ring-nitrogen bond) is preferable. A material that is widely used includes derivatives of 4,4'-bis[N-(3-methylphenyl)-N-phenylamino]biphenyl such as 4,4'-bis[N-(1-napthyl)-N-phenylamino]biphenyl (hereinafter referred to as NPB), and star burst aromatic amine compounds such as 4,4',4"-tris(N,N-diphenyl-amino)triphenylamine, and 4,4',4"-tris[N-(3-methylphenyl)-N-phenylamino]triphenylamine. These materials described here are substances each having a hole mobility of greater than or equal to $10^{-6}$ cm$^2$/Vs. However, other materials may also be used as long as the hole transporting property thereof are higher than the electron transporting property. The second layer 104 is not limited to a single layer, and two or more layers including the aforementioned compounds may be stacked.

The third layer 105 is a layer including a light-emitting substance. In this embodiment mode, the third layer 105 includes the quinoxaline derivative of the present invention described in Embodiment Mode 1. The quinoxaline derivative of the present invention can preferably be applied to a light-emitting element as a light-emitting substance since the quinoxaline derivative of the present invention exhibits emission of blue to blue green light.

As the fourth layer 106, a substance having a high electron transporting property can be used. For example, a layer including a metal complex or the like having a quinoline moiety or a benzoquinoline moiety such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The materials described here mainly are substances each having an electron mobility of greater than or equal to $10^{-6}$ cm$^2$/Vs. The electron transporting layer may be formed using other materials as long as the materials have higher electron transporting property than hole transporting property. Furthermore, the electron transporting layer is not limited to a single layer, and two or more layers comprising the aforementioned materials may be stacked.

As a substance forming the second electrode 107, a metal, an alloy, a conductive compound, a mixture thereof, or the like having a low work function (specifically, 3.8 eV or less) is preferably used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy including these metals (such as an Mg—Ag alloy or an Al—Li alloy), a rare earth metal such as europium (Eu) or ytterbium (Yb), an alloy including these rare earth metals, or the like is given. However, by introducing a layer, which has a function to promote electron injection, between the second electrode 107 and the fourth layer 106, various conductive materials such as Al, Ag, ITO, or ITO including silicon can be used as the second electrode 107 regardless of the magnitude of the work function.

As the layer having a function to promote electron injection, an alkali metal compound or an alkaline earth metal compound such as lithium fluoride (LiF), cesium fluoride (CsF), or calcium fluoride (CaF$_2$) can be used. Furthermore, a layer, in which a substance having an electron transporting property is combined with an alkali metal or an alkaline earth metal, can be employed. For instance, Alq including magnesium (Mg) can be used. It is more preferable to use the layer, in which a substance having an electron transporting property is combined with an alkali metal or an alkaline earth metal, since electron injection from the second electrode 107 efficiently proceeds.

Various methods can be applied for fabricating the first layer 103, the second layer 104, the third layer 105, and the fourth layer 106. For example, a vapor deposition method, an ink-jet method, a spin coating method, or the like may be used. Furthermore, each electrode or each layer may be formed by a different film formation method.

A current flows between the first electrode 102 and the second electrode 107 by applying voltage to the light-emitting element having the aforementioned device structure. Holes and electrons are recombined in the third layer 105 which includes a substance having a high light-emitting ability. That is, the light-emitting element of the present invention has a structure in which a light-emitting region is produced in the third layer 105.

Figure 1B:
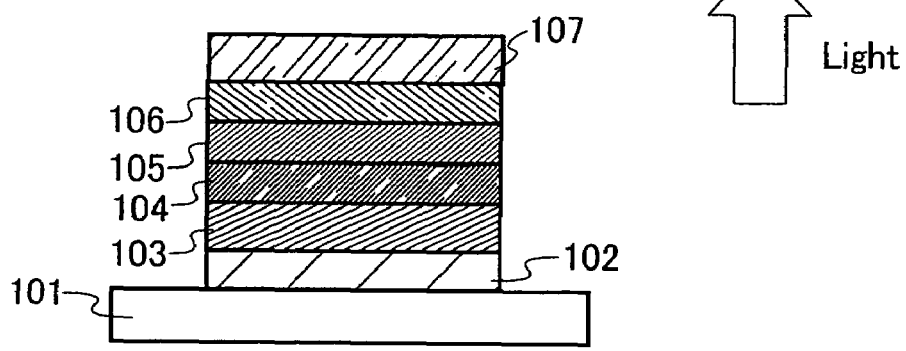
Figure 1C:
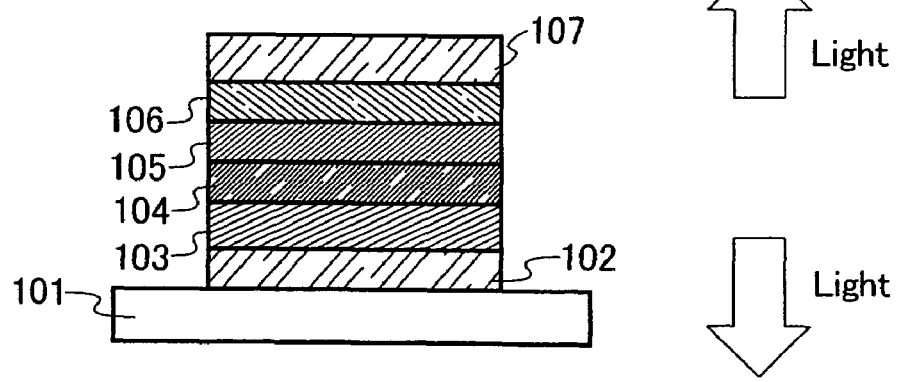

Light emission is extracted outside through one or both of the first electrode 102 and the second electrode 107. Therefore, one or both of the first electrode 102 and the second electrode 107 is/are formed using a substance having a light transmitting property. In a case where only the first electrode 102 is prepared using a substance having a light transmitting property, as shown in FIG. 1A, light is extracted from a substrate side through the first electrode 102. Alternatively, in a case where only the second electrode 107 is formed using a substance having a light transmitting property, as shown in FIG. 1B, light is extracted from the side opposite to the substrate through the second electrode 107. In a case where each of the first electrode 102 and the second electrode 107 are formed using a substance having a light transmitting property, as shown in FIG. 1C, light is extracted from both of the substrate side and the side opposite to the substrate through the first electrode 102 and the second electrode 107, respectively.

A structure of a layer provided between the first electrode 102 and the second electrode 107 is not limited to the above-described structure. Another structure may be used as long as the light-emitting region, in which holes and electrons are recombined, is located away from the first electrode 102 and the second electrode 107. By using such a device structure, quenching of the emission can be effectively suppressed since the quenching phenomenon readily occurs when the light-emitting region is close to an electrode.

In other words, a stacked structure of the layer is not strictly limited. A substance having a high electron transporting property, a substance having a high hole transporting property, a substance having a high electron injecting property, a substance having a high hole injecting property, a bipolar substance (substance having both a high electron transporting property and high hole transporting property), a hole blocking material, or the like may be freely combined with the quinoxaline derivative which is disclosed in the present invention.

Figure 2:
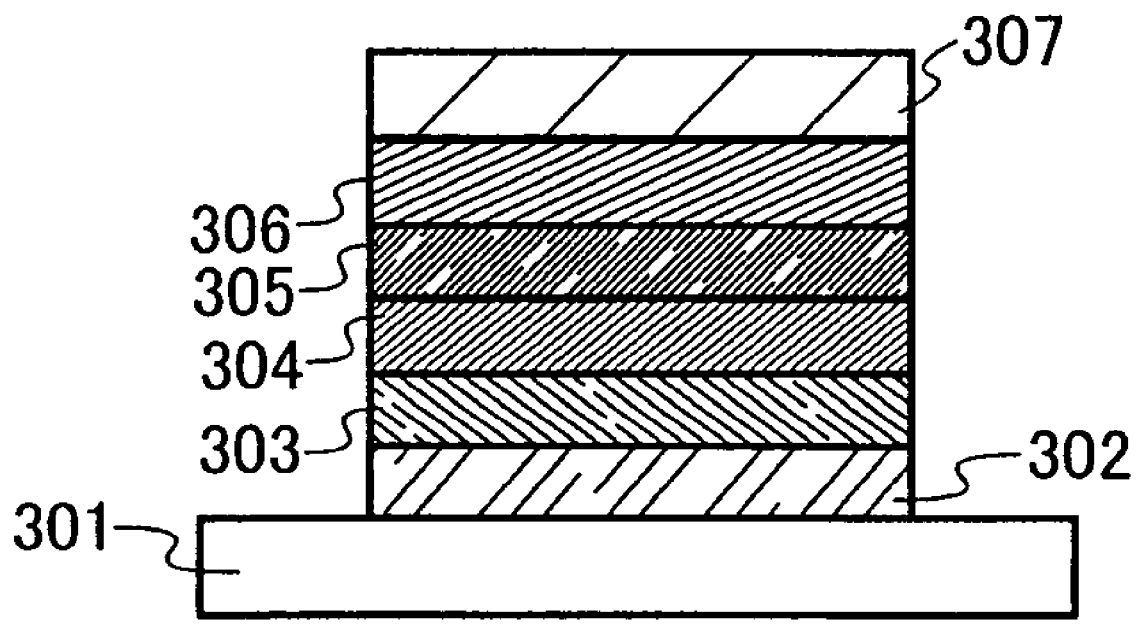
FIG. 2 is an explanatory view of a light-emitting element of the present invention.

A light-emitting element shown in FIG. 2 has a structure in which a first layer 303 comprising a substance with a high electron transporting property, a second layer 304 including a light emitting substance, a third layer 305 comprising a substance with a high hole transporting property, a fourth layer 306 comprising a substance with a high hole injecting property, and a second electrode 307 serving as an anode are sequentially stacked over a first electrode 302 which works as a cathode. Reference numeral 301 denotes a substrate.

In this embodiment mode, the light-emitting element is fabricated over a substrate made of glass, plastic, or the like. By fabricating a plurality of light-emitting elements over one substrate, a passive type light-emitting device can be manufactured. Alternatively, for example, a thin film transistor (TFT) may be formed over a substrate made of glass, plastic, or the like, and the light-emitting elements may be fabricated over an electrode electrically connected to the TFT. By this process, an active matrix light-emitting device can be manufactured, in which driving of the light-emitting element is controlled by a TFT. A structure of the TFT is not strictly limited, and may be a staggered TFT or an inverted staggered TFT. Crystallinity of a semiconductor used for the TFT is also not limited, and an amorphous semiconductor or a crystalline semiconductor may be used. In addition, a circuit for driving formed over a TFT substrate may be constructed using an N-type TFT and a P-type TFT, or may be constructed using any one of an N-type TFT and a P-type TFT.

Since the quinoxaline derivative of the present invention is bipolar and is a material having a light-emitting property. Therefore, as described in this embodiment mode, the quinoxaline derivative of the present invention can be used as a light emitting layer without including other light-emitting substances.

Further, since the quinoxaline derivative of the present invention is bipolar, the light-emitting region is not readily localized at an interface of the stacked layers. Hence, it is possible to provide a high-performance light-emitting element which shows almost no changes in emission spectrum and luminous efficiency, resulting from the exciplex formation, during operation. In addition, a light-emitting element with high luminous efficiency can be obtained.

Microcrystalline components are hardly generated in a layer formed using the quinoxaline derivatives of the present invention, which allows formation of a layer with a high quality. Therefore, a light-emitting element with few defects that result from the dielectric breakdown due to electric field concentration can be manufactured.

The quinoxaline derivative of the present invention is a material which is bipolar and excellent in a carrier transporting property (an electron transporting property and a hole transporting property); therefore, by using the quinoxaline derivative for a light-emitting element, a operation voltage of the light-emitting element can be reduced, leading to reduction in power consumption.

Further, the quinoxaline derivative of the present invention has a high glass transition temperature; therefore, by using the quinoxaline derivative of the present invention, a light-emitting element having high thermal stability can be obtained.

Further, the quinoxaline derivative of the present invention is stable with respect to repeated oxidation and reduction performed alternately. That is, the quinoxaline derivative is electrochemically stable. Therefore, by using the quinoxaline derivative of the present invention in a light-emitting element, a long-life light-emitting element can be obtained.

Embodiment Mode 3

In this embodiment mode, a light-emitting element having a different structure from that described in Embodiment Mode 2 will be explained.

The third layer 105, described in Embodiment Mode 2, can be formed by dispersing the quinoxaline derivative of the present invention in another substance, by which light emission can be obtained from the quinoxaline derivative of the present invention. Since the quinoxaline derivative of the present invention exhibits emission of blue to blue green light, a blue to blue green emissive light-emitting element can be obtained.

Here, various materials can be used as a substance in which the quinoxaline derivative of the present invention is dispersed. In addition to the substance having a high hole transporting property and the substance having a high electron transporting property, which are described in Embodiment Mode 2, 4,4'-bis(N-carbazolyl)-biphenyl (abbreviation: CBP), 2,2',2''-(1,3,5-benzenetri-yl)-tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA), and the like are given.

The quinoxaline derivative of the present invention is a material which is bipolar and excellent in a carrier transporting property (an electron transporting property and a hole transporting property); therefore, by using the quinoxaline derivative of the present invention for a light-emitting element, a driving voltage of the light-emitting element can be reduced, leading to reduction in power consumption.

Further, the quinoxaline derivative of the present invention has a high glass transition temperature; therefore, by using the quinoxaline derivative of the present invention, a light-emitting element having high thermal stability can be obtained.

Further, the quinoxaline derivative of the present invention is stable with respect to repeated oxidation and reduction performed alternately. That is, the quinoxaline derivative is electrochemically stable. Therefore, by using the quinoxaline derivative of the present invention to a light-emitting element, a long-life light-emitting element can be obtained.

It is to be noted that the structure described in Embodiment Mode 2 can be appropriately used for layers other than the third layer 105.

Embodiment Mode 4

In this embodiment mode, a light-emitting element having a different structure from those described in Embodiment Modes 2 and 3 will be explained.

The third layer 105, described in Embodiment Mode 2, can be formed by dispersing a light-emitting substance in the quinoxaline derivative of the present invention, whereby light emission from the light-emitting substance can be obtained.

The quinoxaline derivative of the present invention possesses bipolarity. Furthermore, microcrystalline components are hardly generated in a layer formed using the quinoxaline derivatives of the present invention, which allows formation of the layer with a high quality. Therefore, the quinoxaline derivative of the present invention can be preferably used as a material in which another light-emitting substance is dispersed.

In a case where the quinoxaline derivative of the present invention is used as a material in which another light-emitting substance is dispersed, an emission color originating from the light-emitting substance can be obtained. Further, it is also possible to obtain emission that which is mixed of the emission color originating from the quinoxaline derivative of the present invention and from the light-emitting substance dispersed in the quinoxaline derivative.

Here, various materials can be used as a light-emitting substance dispersed in the quinoxaline derivative of the present invention. Specifically, a substance emitting fluorescence such as 4-(dicyanomethylene)-2-methyl-6-(p-dimethylaminostyryl)-4H-pyran (abbreviation: DCM1), 4-(dicyanomethylene)-2-methyl-6-(julolidine-4-yl-vinyl)-4H-pyran (abbreviation: DCM2), N,N-dimethylquinacridone (abbreviation: DMQd), 9,10-diphenylanthracene (abbreviation: DPA); 5,12-diphenyltetracene (abbreviation: DPT), coumarin 6, perylene, or rubrene can be used. Further, a substance emitting phosphorescence such as bis(2-phenyl-benzothiazolato-N,$C^{2'}$)iridium(III)acetylacetonate (abbreviation: Ir(bt)$_2$(acac)), tris(2-phenylquinolinato-N,$C^{2'}$)iridium(III) (abbreviation: Ir(pq)$_3$), bis(2-phenylquinolinato-N,$C^{2'}$)iridium(III) acetylacetonate (abbreviation: Ir(pq)$_2$(acac)), bis[2-(2'-benzo[4,5-α]thienyl)pyridinato-N,$C^{3'}$)iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinplatinum(II) (abbreviation: PtOEP), or the like can be used.

Since the quinoxaline derivative of the present invention is a material which is bipolar and excellent in a carrier transporting property (an electron transporting property and a hole transporting property), by using the quinoxaline derivative of the present invention for a light-emitting element, a driving voltage of the light-emitting element can be reduced.

Further, since the quinoxaline derivative of the present invention is bipolar, the light-emitting region is not readily localized at an interface of the stacked layers. Hence, it is possible to provide a high-performance light-emitting element which shows almost no changes in emission spectrum and in luminous efficiency, resulting from the exciplex formation.

Further, since the quinoxaline derivative of the present invention is bipolar, a light-emitting region is not readily localized at an interface of stacked films. Therefore, in a case where a substance emitting phosphorescence is used, T-T annihilation can be prevented. Accordingly, a light-emitting element with high luminous efficiency can be obtained.

Further, the quinoxaline derivative of the present invention has a high glass transition temperature; therefore, by using the quinoxaline derivative of the present invention, a light-emitting element having high thermal stability can be obtained.

Further, the quinoxaline derivative of the present invention is stable with respect to repeated oxidation and reduction performed alternately. That is, the quinoxaline derivative is electrochemically stable. Therefore, by using the quinoxaline derivative of the present invention for a light-emitting element, a long-life light-emitting element can be obtained.

It is to be noted that the structure described in Embodiment Mode 2 can be appropriately used for layers other than the third layer 105.

Embodiment Mode 5

In this embodiment mode, a mode of a light-emitting element having a structure in which a plurality of light-emitting units according to the present invention is stacked (hereinafter, referred to as a stack type element) will be explained with reference to FIG. 3. This light-emitting element has a plurality of light-emitting units between a first electrode and a second electrode. A structure similar to that of the layer including a light-emitting substrate described in Embodiment Mode 2 can be used for the light-emitting unit. That is, the light-emitting element described in Embodiment Mode 2 is a light-emitting element having one light-emitting unit, while this embodiment demonstrates a light-emitting element having a plurality of light-emitting units.

Figure 3:
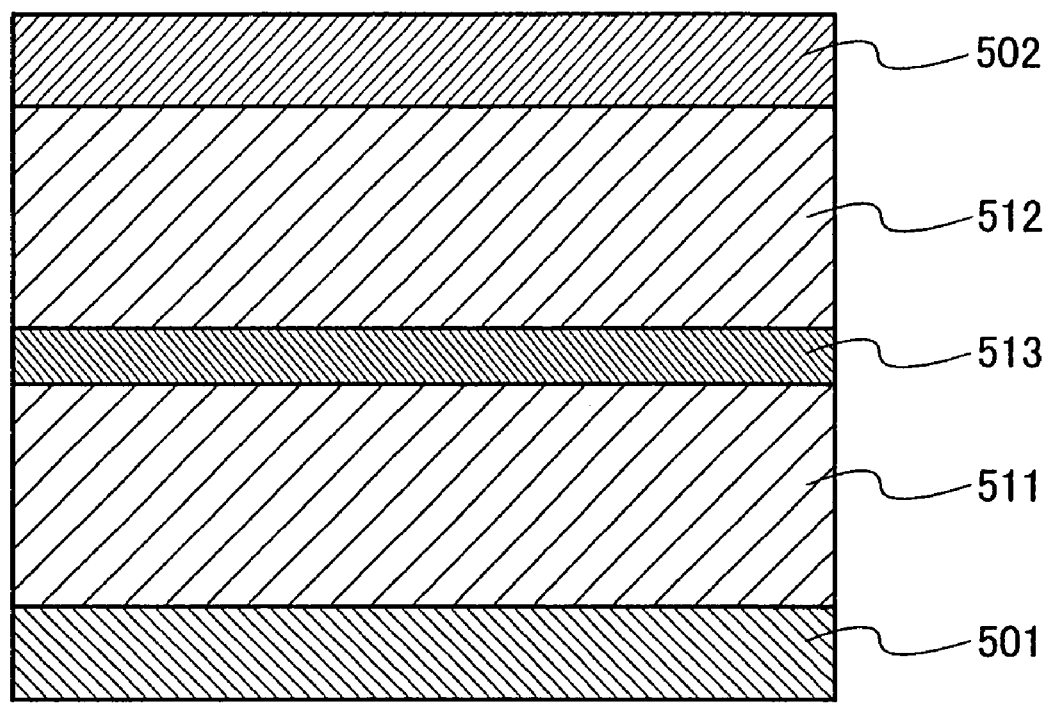
FIG. 3 is an explanatory view of a light-emitting element of the present invention.

In FIG. 3, a first light-emitting unit 511 and a second light-emitting unit 512 are stacked between a first electrode 501 and a second electrode 502. An electrode similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 4 can be applied.

A charge generation layer 513 includes a composite of an organic compound with metal oxide. The composite of an organic compound with metal oxide is the composite described in Embodiment Mode 2, and includes an organic compound and metal oxide such as vanadium oxide, molybdenum oxide, or tungsten oxide. As the organic compound, various compounds such as an aromatic amine compound, a carbazole derivative, aromatic hydrocarbon, and a high molecular weight compound (oligomer, dendrimer, polymer, or the like) can be used. The compound having hole mobility of greater than or equal to $1 \times 10^{-6}$ cm$^2$/Vs is preferably applied as an organic compound. However, other substances may also be used as long as the hole transporting property is higher than the electron transporting property. The composite of an organic compound with metal oxide is superior in a carrier injecting property and a carrier transporting property, and hence, low-voltage driving and low-current driving can be realized.

It is to be noted that the charge generation layer 513 may be formed with a combination of a composite of an organic compound with metal oxide and other materials. For example, the charge generation layer 513 may be formed with a combination of a layer including the composite of an organic compound with metal oxide and a layer including one compound selected from electron donating substances with a compound having a high electron transporting property. Further, the charge generation layer 513 may be formed by combining a layer including the composite of an organic compound with metal oxide and a transparent conductive film.

Any structure is acceptable as the charge generation layer 513 interposed between the first light-emitting unit 511 and the second light-emitting unit 512 as long as electrons can be injected to a light-emitting unit on one side and holes can be injected to a light-emitting unit on the other side when a voltage is applied between the first electrode 501 and the second electrode 502.

In this embodiment mode, the light-emitting element having two light-emitting units is explained; however, the present invention can be similarly applied to a light-emitting element in which three or more light-emitting units are stacked. By arranging a plurality of light-emitting units between a pair of electrodes in such a manner that the plurality of light-emitting units is partitioned with a charge generation layer, like the light-emitting element according to this embodiment mode, a long-life element which can emit light with a high luminance at low current density can be realized.

This embodiment mode can be appropriately combined with another embodiment mode.

Embodiment Mode 6

In this embodiment mode, a mode in which a quinoxaline derivative of the present invention is used for an active layer of a vertical transistor (SIT) which is one kind of an organic semiconductor element, will be exemplified.

Figure 4:
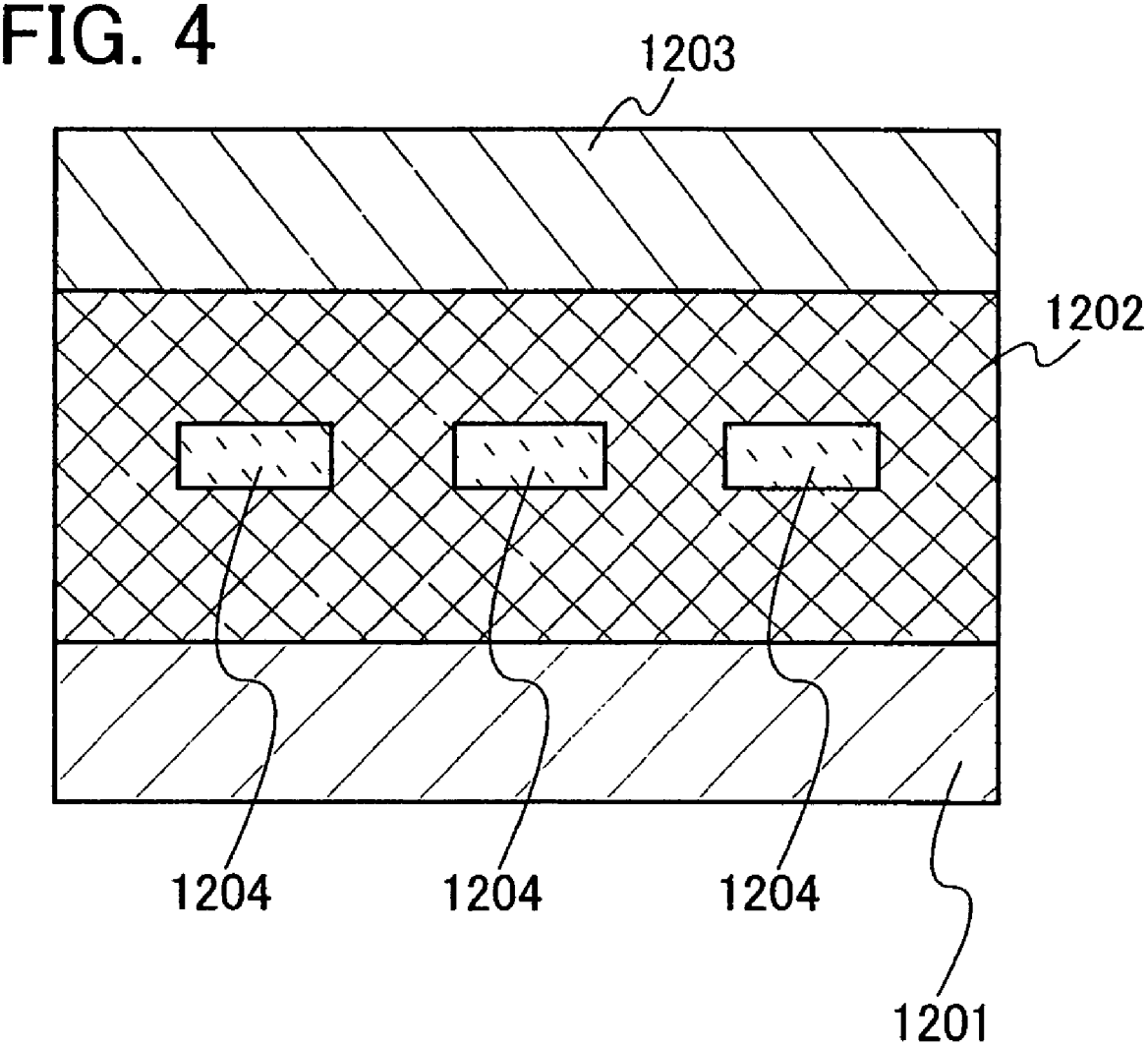
FIG. 4 is an explanatory view of an organic semiconductor element of the present invention.

The element has a structure in which a thin active layer 1202 including the quinoxaline derivative of the present invention is interposed between a source electrode 1201 and a drain electrode 1203, and a gate electrode 1204 is embedded in the active layer 1202, as shown in FIG. 4. The gate electrode 1204 is electrically connected to a means for applying a gate voltage, and the source electrode 1201 and the drain electrode 1203 are electrically connected to a means for controlling the voltage between the source and drain electrodes.

In such an element structure, when a voltage is applied between the source and the drain under the condition where a gate voltage is not applied, a current flows, as observed in a light-emitting element (an ON state). When a gate voltage is applied in this state, a depletion layer is generated in the periphery of the gate electrode 1204, whereby a current does not flow (an OFF state). With the aforementioned mechanism, the element operates as a transistor.

In a vertical transistor, a material which has both a carrier transporting property and an excellent film quality is required for an active layer similarly to a light-emitting element. The quinoxaline derivative of the present invention is useful since it sufficiently meets the requirement. Further, since the quinoxaline derivative of the present invention has a high glass transition temperature, an organic semiconductor element having high thermal stability can be obtained.

Embodiment Mode 7

In this embodiment mode, a light-emitting device manufactured using a quinoxaline derivative of the present invention will be explained.

In this embodiment mode, a light-emitting device manufactured using the quinoxaline derivative of the present invention will be explained with reference to FIGS. 5A and 5B. It is to be noted that FIG. 5A is a top view showing a light-emitting device and FIG. 5B is a cross-sectional view of FIG. 5A taken along lines A-A' and B-B'. This light-emitting device includes a driver circuit portion (source side driver circuit) denoted by reference numeral 601; a pixel portion denoted by reference numeral 602; and a driver circuit portion (gate side driver circuit) denoted by reference numeral 603, which are indicated by dotted lines. These portions control light emission of the light-emitting element. Reference numeral 604 denotes a sealing substrate; reference numeral 605 denotes a sealing material; and a portion surrounded by the sealing material 605 corresponds to a space 607.

A lead wiring 608 is a wiring for transmitting a signal to be inputted to the source side driver circuit 601 and the gate side driver circuit 603. The wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light-emitting device in this specification includes not only a light-emitting device itself but also a light-emitting device attached with an FPC or a PWB.

Subsequently, a cross-sectional structure will be explained with reference to FIG. 5B. The driver circuit portion and the pixel portion are formed over an element substrate 610. Here, the source side driver circuit 601, which is the driver circuit portion, and one pixel in the pixel portion 602 are shown.

A CMOS circuit, which is a combination of an n-channel TFT 623 and a p-channel TFT 624, is formed as the source side driver circuit 601. The driver circuit may be formed using various CMOS circuits, PMOS circuits, or NMOS circuits. Although a driver integration type in which a driver circuit is formed over a substrate is described in this embodiment mode, a driver circuit is not necessarily formed over a substrate and can be formed outside a substrate.

The pixel portion 602 has a plurality of pixels, each of which includes a switching TFT 611, a current control TFT 612, and a first electrode 613 which is electrically connected to a drain of the current control TFT 612. It is to be noted that an insulator 614 is formed to cover an end portion of the first electrode 613. Here, a positive photosensitive acrylic resin film is used for the insulator 614.

The insulator 614 is formed so as to have a curved surface having curvature at an upper end portion or a lower end portion thereof in order to make the coverage favorable. For example, in a case of using positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by light irradiation or a positive type resin which becomes soluble in an etchant by light irradiation can be used for the insulator 614.

A layer 616 including a light-emitting substance and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and another titanium nitride film; or the like as well as a single-layer film such as an ITO film, an indium tin oxide film including silicon, an indium oxide film including 2 to 20 wt % of zinc oxide, a titanium nitride film, a chromium film, a tungsten film, a Zn film, or a Pt film. When the first electrode 613 has a stacked structure, it can have low resistance as a wiring and form a favorable ohmic contact. Further, the first electrode 613 can function as an anode.

The layer 616 including a light-emitting substance is formed by various methods such as a vapor deposition method using a metal mask, an ink-jet method, and a spin coating method. The layer 616 including a light-emitting substance has the quinoxaline derivative of the present invention described in Embodiment Mode 1. Further, the layer 616 including a light-emitting substance may be formed using another material such as a high molecular weight compound (including an oligomer and a dendrimer).

As a material used for the second electrode 617 which is formed over the layer 616 including a light-emitting substance and serves as a cathode, a material having a low work function (Al, Mg, Li, Ca, or an alloy or a salt thereof such as MgAg, Mg—In, Al—Li, LiF, or $CaF_2$) is preferably used. In a case where light generated in the layer 616 including a light-emitting substance is transmitted through the second electrode 617, stacked layers of a metal thin film and a transparent conductive film (ITO, indium oxide including 2 to 20 wt % of zinc oxide, indium tin oxide including silicon, zinc oxide (ZnO), or the like) are preferably used as the second electrode 617.

By attaching the sealing substrate 604 to the element substrate 610 with the sealing material 605, a light-emitting element 618 is provided in the space 607 surrounded by the element substrate 610, the sealing substrate 604, and the sealing material 605. It is to be noted that the space 607 is filled with the sealing material 605 as well as an inert gas (nitrogen, argon, or the like).

It is to be noted that an epoxy-based resin is preferably used as the sealing material 605. It is preferred to use a material with low permeability of moisture and oxygen. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

By the method described above, a light-emitting device manufactured using the quinoxaline derivative of the present invention can be obtained.

Since the quinoxaline derivative described in Embodiment Mode 1 is used for the light-emitting device of the present invention, a high performance light-emitting device having can be obtained. Specifically, a light-emitting device having high thermal stability can be obtained.

Further, since the quinoxaline derivative of the present invention is electrochemically stable, a long-life light-emitting device can be obtained.

Furthermore, since the quinoxaline derivative of the present invention is a material which is bipolar and excellent in a carrier transporting property (an electron transporting property and a hole transporting property), by using the quinoxaline derivative of the present invention, a driving voltage of the light-emitting element can be reduced and power consumption of the light-emitting device can be reduced. In particular, in a case of using a phosphorescent substance as a light-emitting substance, a light-emitting device with high emission efficiency and low power consumption can be obtained.

Figure 6:
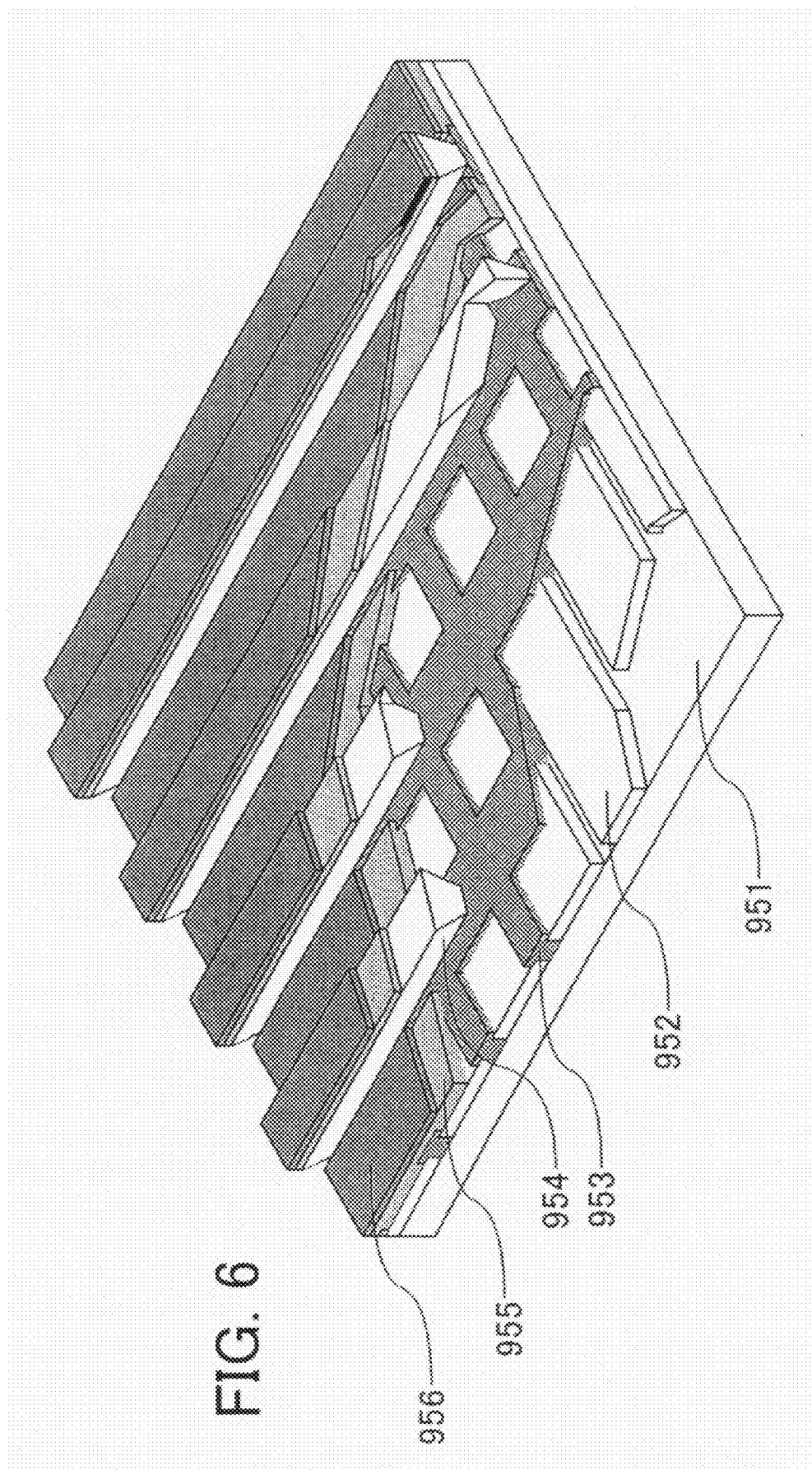
FIG. 6 is an explanatory view of a light-emitting device of the present invention.

As described above, in this embodiment mode, an active matrix light-emitting device in which operation of a light-emitting element is controlled by a transistor is explained. Alternatively, a passive type light-emitting device in which a light-emitting element is driven without providing an element for driving such as a transistor may also be used. FIG. 6 shows a perspective view of a passive type light-emitting device which is fabricated by applying the present invention. In FIG. 6, a layer 955 including a light-emitting substance is provided between an electrode 952 and an electrode 956 over a substrate 951. An edge portion of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side facing in the same direction as a plane direction of the insulating layer 953 and in contact with the insulating layer 953) is shorter than an upper side (a side facing in the same direction as the plane direction of the insulating layer 953 and not in contact with the insulating layer 953). Fabrication of the partition layer 954 in this manner allows patterning the electrode 956. The passive type light-emitting device can also be driven with low power consumption when it includes the light-emitting element of the present invention which operates at a low driving voltage.

Embodiment Mode 8

In this embodiment mode, an electronic device of the present invention including the light-emitting device described in Embodiment Mode 7 will be explained. The electronic device of the present invention including the quinoxaline derivative described in Embodiment Mode 1 has a display portion which shows high thermal stability, a long lifetime, and low power consumption.

As an electronic device including a light-emitting element manufactured using the quinoxaline derivative of the present invention, a video camera, a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic devices are shown in FIGS. 7A to 7D.

Figure 7A:
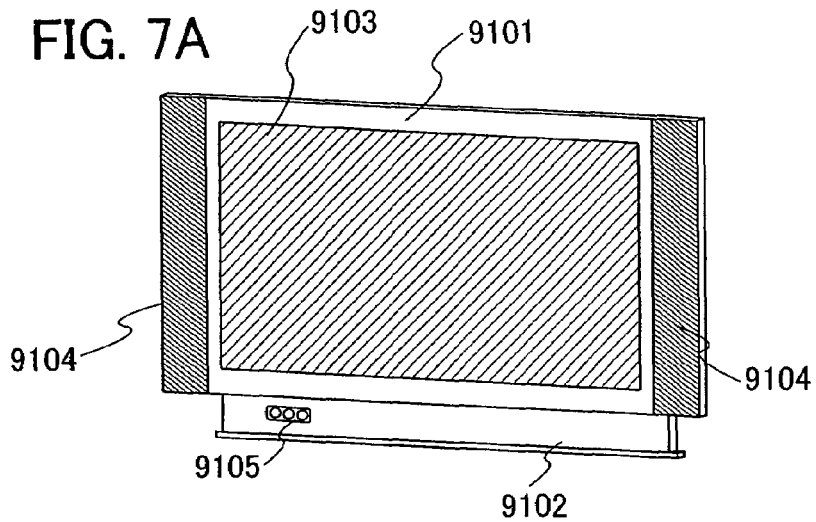
FIGS. 7A to 7D are explanatory views of electronic devices of the present invention.

FIG. 7A shows a television device according to the present invention, which includes a housing 9101, a supporting base 9102, a display portion 9103, a speaker portion 9104, a video input terminal 9105, and the like. In the television device, the display portion 9103 has light-emitting elements similar to those described in Embodiment Modes 2 to 5, which are arranged in matrix. One feature of the light-emitting element is that driving at a low voltage can be performed, the life is long, and the heat resistance is high. The display portion 9103 which includes the light-emitting elements has a similar feature. Therefore, in the television device, image quality is hardly deteriorated and low power consumption is achieved. With such a feature, deterioration compensation function circuits and power supply circuits can be significantly reduced or downsized in the television device; therefore, small sized and lightweight housing 9101 and supporting base 9102 can be achieved. In the television device according to the present invention, low power consumption, high image quality, and small size and lightweight are achieved; therefore, a product which is suitable for living environment can be provided.

Figure 7B:
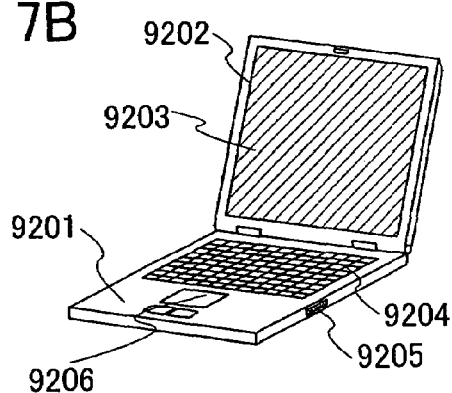

FIG. 7B shows a computer according to the present invention, which includes a main body 9201, a housing 9202, a display portion 9203, a keyboard 9204, an external connection port 9205, a pointing mouse 9206, and the like. In the computer, the display portion 9203 has light-emitting elements similar to those described in Embodiment Modes 2 to 5, which are arranged in matrix. One feature of the light-emitting element is that driving at a low voltage can be performed, the life is long, and the heat resistance is high. The display portion 9203 which includes the light-emitting elements has a similar feature. Therefore, in the computer, image quality is hardly deteriorated and lower power consumption is achieved. With such a feature, deterioration compensation function circuits and power supply circuits can be significantly reduced or downsized in the computer; therefore, small sized and lightweight main body 9201 and housing 9202 can be achieved. In the computer according to the present invention, low power consumption, high image quality, and small size and lightweight are achieved; therefore, a product which is suitable for environment can be provided.

Figure 7C:
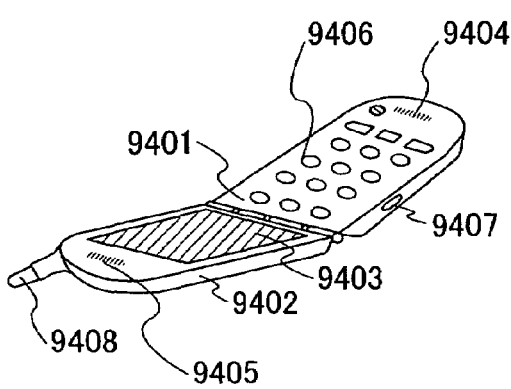

FIG. 7C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, a display portion 9403 has light-emitting elements similar to those described in Embodiment Modes 2 to 5, which are arranged in matrix. One feature of the light-emitting element is that driving at a low voltage can be performed, the life is long, and the heat resistance is high. The display portion 9403 which includes the light-emitting elements has a similar feature. Therefore, in the mobile phone, image quality is hardly deteriorated and lower power consumption is achieved. With such a feature, deterioration compensation function circuits and power supply circuits can be significantly reduced or downsized in the mobile phone; therefore, small sized and lightweight main body 9401 and housing 9402 can be achieved. In the mobile phone according to the present invention, low power consumption, high image quality, and a small size and lightweight are achieved; therefore, a production which is suitable for carrying can be provided.

Figure 7D:
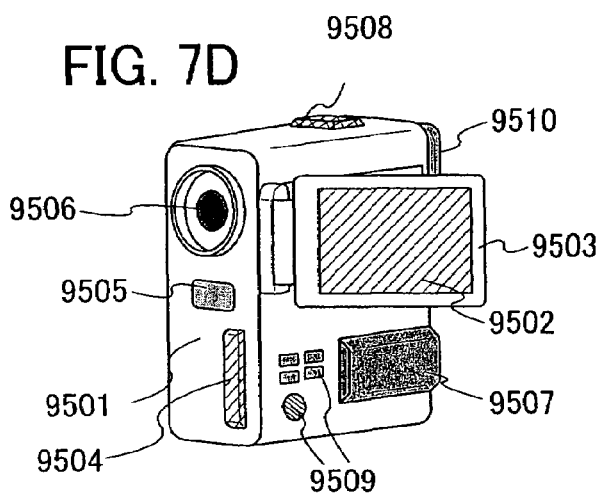

FIG. 7D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 2 to 5, which are arranged in matrix. One feature of the light-emitting element is that driving at a low voltage can be performed, the life is long, and the heat resistance is high. The display portion 9502 which includes the light-emitting elements has a similar feature. Therefore, in the camera, image quality is hardly deteriorated and lower power consumption can be achieved. With such a feature, deterioration compensation function circuits and power supply circuits can be significantly reduced or downsized in the camera; therefore, a small sized and lightweight main body 9501 can be achieved. In the camera according to the present invention, low power consumption, high image quality, and small size and lightweight are achieved; therefore, a product which is suitable for carrying can be provided.

As described above, the applicable range of the light-emitting device of the present invention is so wide that the light-emitting device can be applied to electronic devices in various fields. By using the quinoxaline derivative of the present invention, electronic devices having display portions that show low power consumption, long lifetime, and high thermal stability can be provided.

The light-emitting device of the present invention can also be used as a lighting device. One mode using the light-emitting element of the present invention as the lighting device will be explained with reference to FIG. 8.

Figure 8:
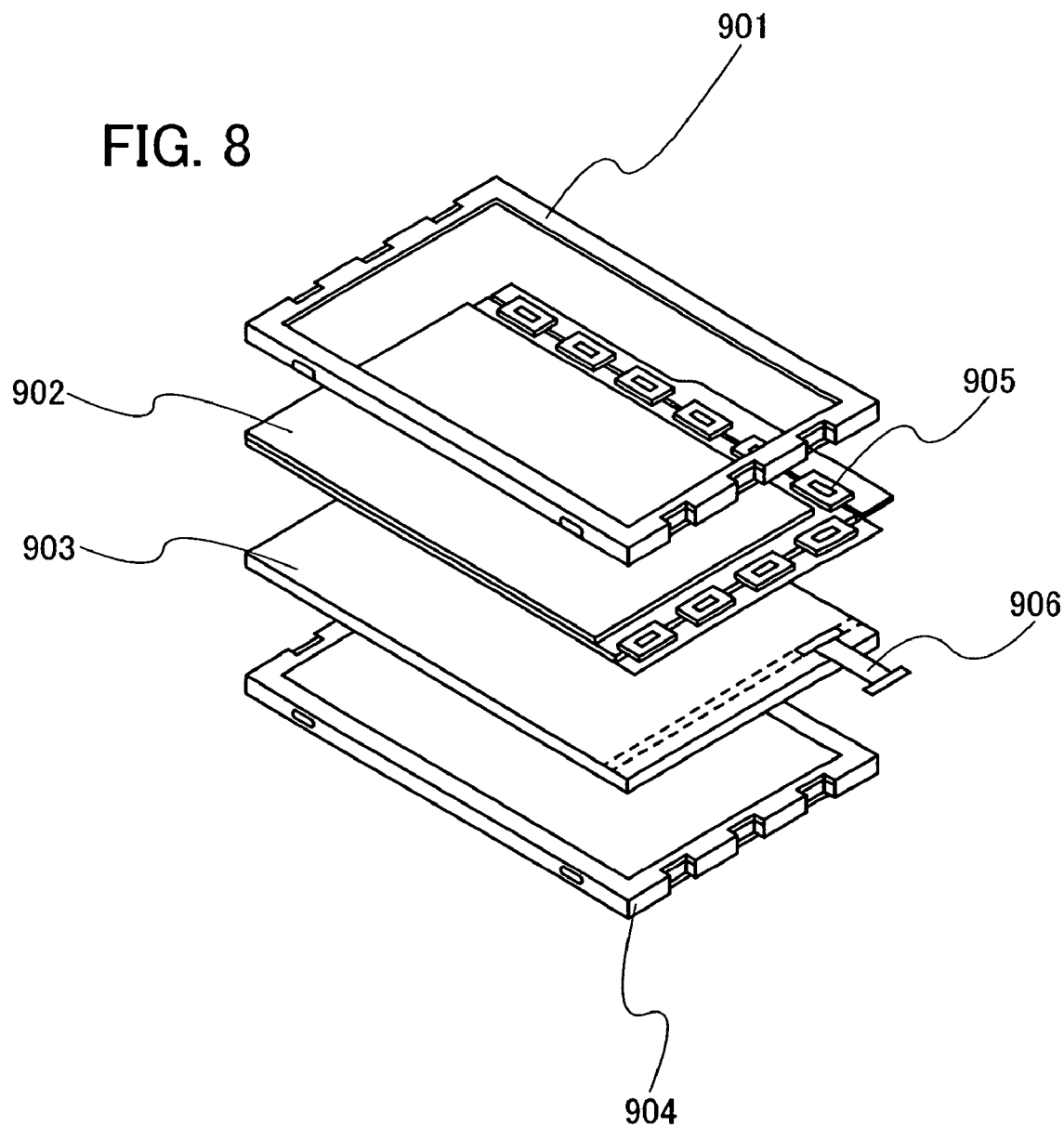
FIG. 8 is an explanatory view of an electronic device of the present invention.

FIG. 8 shows an example of a liquid crystal display device using the light-emitting device of the present invention as a backlight. The liquid crystal display device shown in FIG. 8 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with reduced power consumption can be obtained. The light-emitting device of the present invention is a lighting device with plane emission area, and enlargement of the emission area is readily performed, which allows enlargement of the backlight and, simultaneously, manufacturing a liquid crystal display device having a large display area. Furthermore, the light-emitting device of the present invention has a thin shape and consumes low power; therefore, reduction of the thickness and power consumption of a display device can also be achieved. Since the light-emitting device of the present invention has a long lifetime and excellent thermal stability, a liquid crystal display device using the light-emitting device of the present invention also has a long lifetime and an excellent thermal stability.

Figure 9:
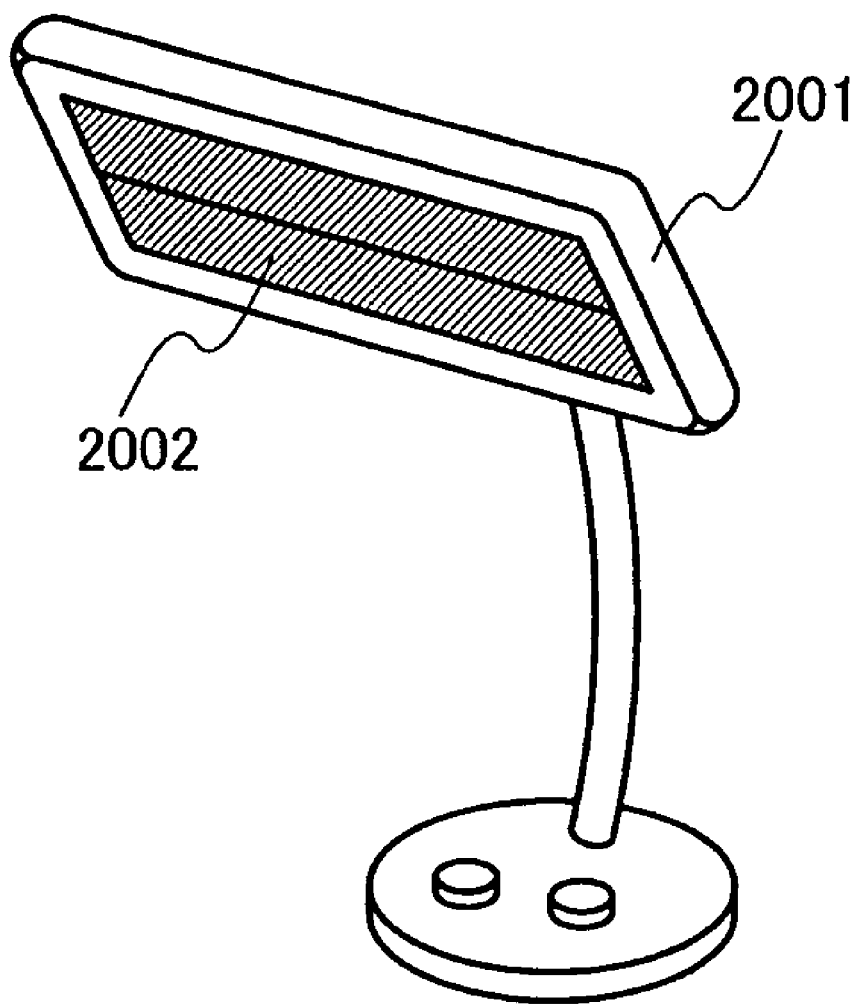
FIG. 9 is an explanatory view of a lighting device of the present invention.

FIG. 9 representatively demonstrates an application of the present invention into a table lamp as a lighting device. A table lamp shown in FIG. 9 has a chassis 2001 and a light source 2002, and the light-emitting device of the present invention is used as the light source 2002. The light-emitting device of the present invention can emit light with high luminance; therefore, when detailed work is being performed, the area at hand where the work is being performed can be brightly lighted up.

Figure 10:
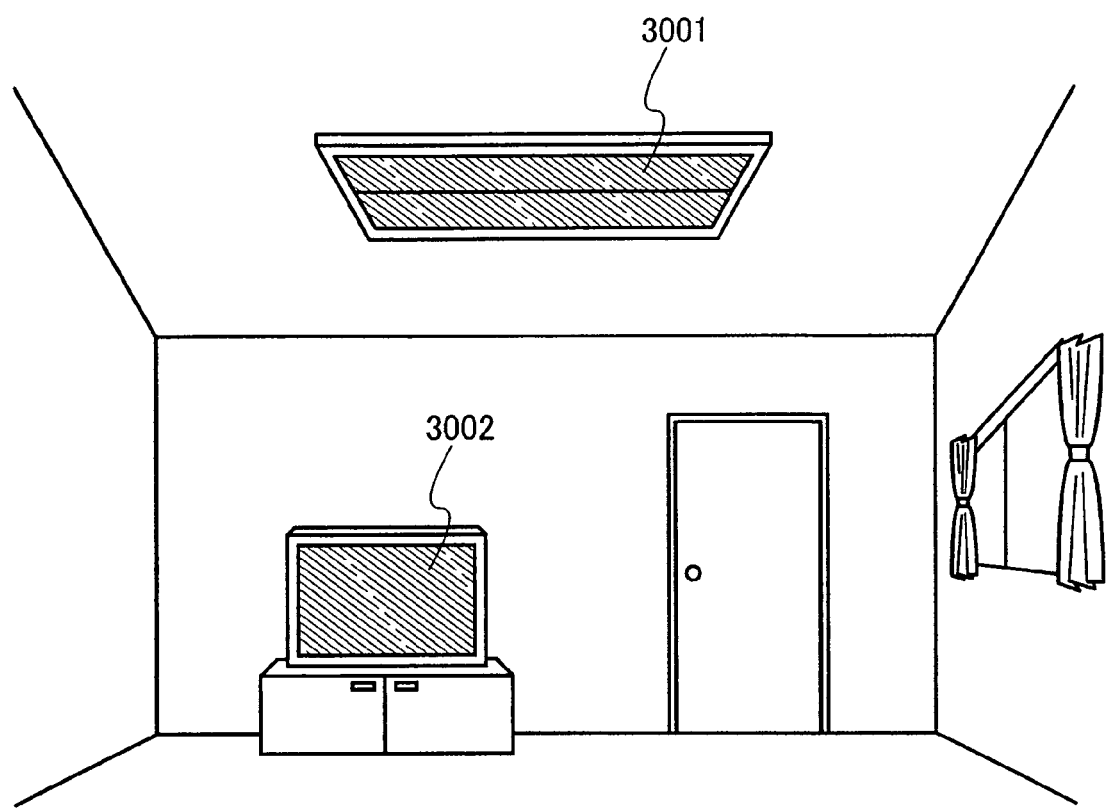
FIG. 10 is an explanatory view of a lighting device of the present invention.

FIG. 10 exemplifies an application of the present invention into an indoor lighting device 3001 as a light-emitting device. Since the light-emitting device of the present invention can possess a large emission area, the light-emitting device of the present invention can be used as a lighting device having a large emission area. Further, the light-emitting device of the present invention has a thin shape and consumes low power; therefore, the light-emitting device of the present invention can be used as a lighting device having a thin shape and consuming low power. A television device according to the present invention as explained in FIG. 7A is placed in a room in which the present invention is applied to the indoor lighting device 3001 as a light-emitting device. Thus, public broadcasting and movies can be watched. In such a case, since both of the devices consume low power, a powerful image can be watched in a bright room without concern about electricity charges.

EXAMPLE 1

In this example, a synthetic method of 4-(carbazol-9-yl)-4'-(3-phenylquinoxalin-2-yl)triphenylamine (abbreviation: YGA1PQ) that is a quinoxaline derivative of the present invention represented by a structural formula (159) will be specifically shown.

formula [138]

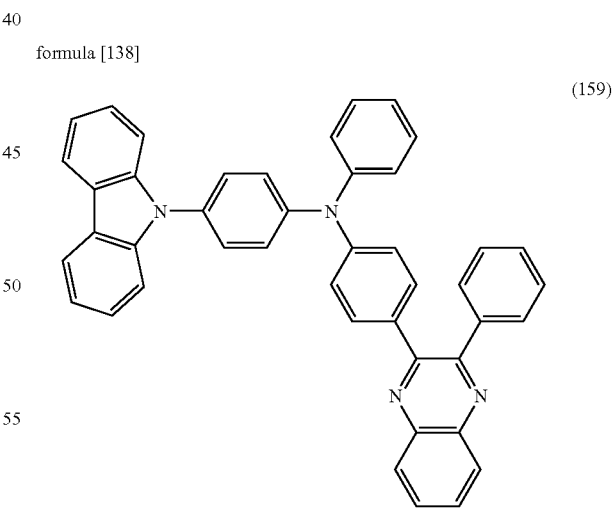

(159)

[Step 1]

A synthetic method of 2-(4-bromophenyl)-3-phenylquinoxaline will be explained.

(i) Synthesis of (4-bromophenyl)phenylacetylene

A synthetic scheme of (4-bromophenyl)phenylacetylene is shown in (C-1).

formula [139]

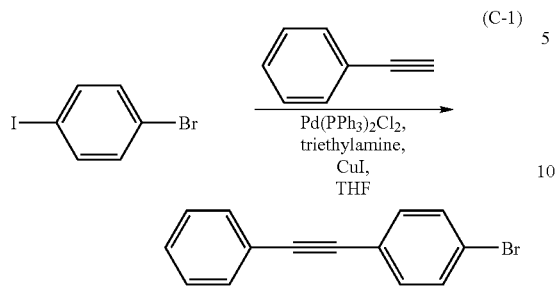

(C-1)

28.3 g (0.10 mol) of p-bromoiodobenzene, 10.2 g (0.10 mol) of phenylacetylene, 701 mg (1 mmol) of bis(triphenylphosphine)palladium(II)dichloride, and 190 mg (1 mmol) of copper (I) iodide were placed in a 1000-mL three-neck flask, and nitrogen substitution was carried out. Then, 350 mL of tetrahydrofuran and 18 mL of triethylamine were added thereto, and the mixture was stirred at room temperature for 12 hours. After the reaction, the reaction mixture washed with a 3% hydrochloric acid aqueous solution, and the aqueous phase was extracted with ethyl acetate. The extracted solution combined with the organic phase washed with brine and dried with magnesium sulfate. The mixture was filtered through celite, florisil, and alumina, and a solid obtained by the concentration of the filtrate was recrystallized with hexane to give 15 g of a solid that was the target substrate in the yield of 58%.

(ii) Synthesis of 1-(4-bromophenyl)-2-phenylethanedione

A synthetic scheme of 1-(4-bromophenyl)-2-phenylethanedione is shown in (C-2).

formula [140]

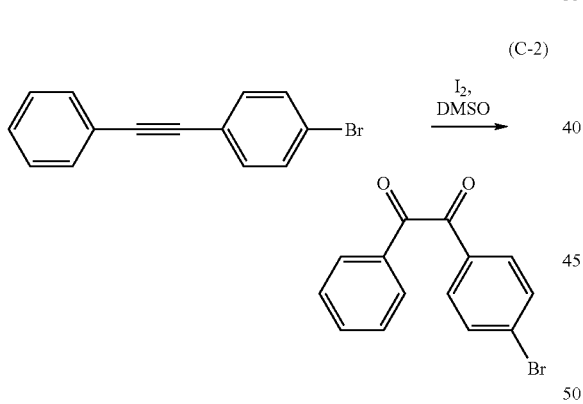

(C-2)

10.0 g (38.9 mmol) of (4-bromophenyl)phenylacetylene, 4.7 g (18.5 mmol) of iodine, and 100 mL of dimethyl sulfoxide were placed in a 300-mL three-neck flask, and the mixture was stirred at 155° C. for 4 hours. After the reaction, the reaction solution was cooled, then the reaction solution was put into a 1 wt % sodium sulfate aqueous solution. The precipitated solid was collected by suction filtration. The residue was dissolved into ethanol, and the insoluble part was filtered off through celite. The filtrate was concentrated, and the obtained solid was dissolved into ethyl acetate. The insoluble part was filtered off again by celite-filtration, and the filtrate was concentrated. A first recrystallization was performed on the obtained solid with ethyl acetate and hexane, giving 1.5 g of the target substrate as a solid. A second recrystallization was performed on the filtrate with acetone and hexane, giving 6.7 g of the target substrate as a solid. By the two-time recrystallization, 8.2 g of the product was obtained in the yield of 72%.

(iii) Synthetic of 2-(4-bromophenyl)-3-phenylquinoxaline

A synthesis scheme of 2-(4-bromophenyl)-3-phenylquinoxaline is shown in (C-3).

formula [141]

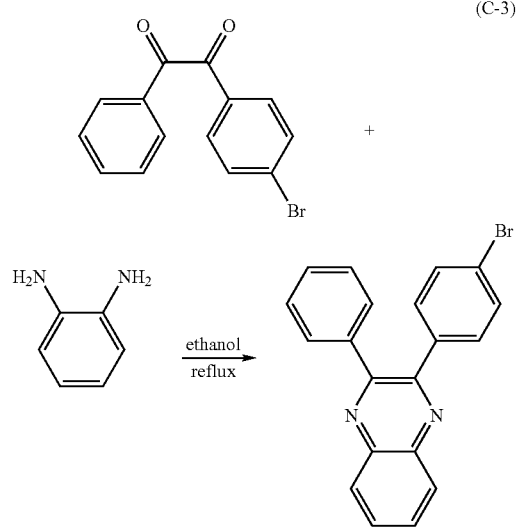

(C-3)

8.2 g (29 mmol) of 1-(4-bromophenyl)-2-phenylethanedione, 3.1 g (31 mmol) of o-phenylenediamine, and 100 mL of ethanol were placed into a 300-mL flask, and the mixture was refluxed for 2 hours. After the reaction, the precipitated solid was collected by suction filtration. The collected solid washed with ethanol and dried. 7.3 g of a light-yellow solid was obtained as the target substrate in 69% yield.

[Step 2]

A synthetic method of 4-(carbazol-9-yl)-diphenylamine (abbreviation: YGA) will be explained.

(i) Synthesis of N-(4-bromophenyl)carbazole

A synthetic scheme of N-(4-bromophenyl)carbazole is shown in (C-4).

formula [142]

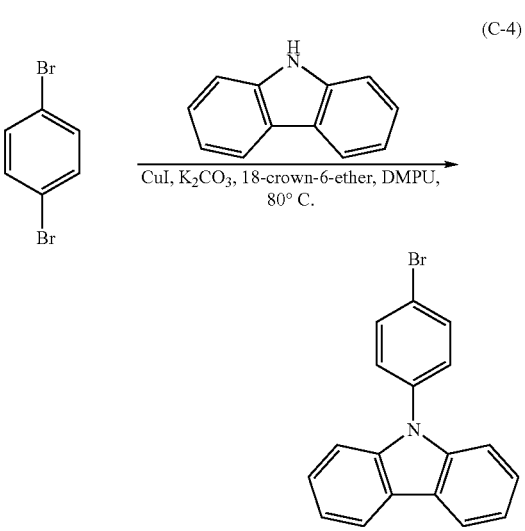

(C-4)

First, a synthesis of N-(4-bromophenyl)carbazole will be explained. 56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were placed into a 300-mL three-neck flask, and nitrogen substitution was carried out. Then, 8 mL of 1,3-dimethyl-3,4,5,6-tetrahydro-2(1H)-pyrimidinone (abbreviation: DMPU) was added thereto, and the mixture was stirred at 180° C. for 6 hours. After the reaction mixture was cooled to room temperature, the precipitate was removed by suction filtration. The filtrate washed with a diluted hydrochloric acid, a saturated sodium hydrogencarbonate aqueous solution and brine, and then dried with magnesium sulfate. After the drying, the reaction mixture was filtered and the filtrate was concentrated. The obtained oily residue was purified by silica gel column chromatography (hexane:ethyl acetate=9:1), and the obtained solid was recrystallized with chloroform/hexane to result in 20.7 g of a light-brown plate-like crystal of N-(4-bromophenyl)carbazole in the yield of 35%. This compound was confirmed by a nuclear magnetic resonance method (NMR) to be N-(4-bromophenyl)carbazole.

¹H NMR data of this compound is shown below.

¹H NMR (300 MHz, CDCl₃); δ=8.14 (d, J=7.8 Hz, 2H), δ=7.73 (d, J=8.7 Hz, 2H), δ=7.46 (d, J=8.4 Hz, 2H), δ=7.42-7.26 (m, 6H).

(ii) Synthesis of 4-(carbazol-9-yl)-diphenylamine (Abbreviation: YGA)

A synthetic scheme of YGA is shown in (C-5).

formula [143]

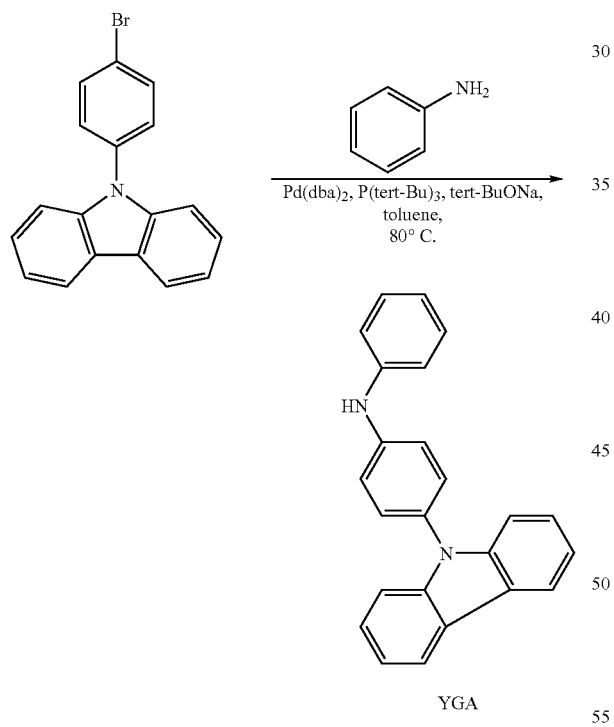

5.4 g (17.0 mmol) of N-(4-bromophenyl)carbazole obtained in the synthetic procedure (i), 1.8 mL (20.0 mmol) of aniline, 100 mg (0.17 mmol) of bis(dibenzylideneacetone)palladium(0), and 3.9 g (40 mmol) of sodium tert-butoxide were put into a 200-mL three-neck flask, and nitrogen substitution was carried out. Then, 0.1 mL of tri-tert-butylphosphine (10 wt % hexane solution) and 50 mL of toluene were added thereto, and the mixture was stirred at 80° C. for 6 hours. The reaction mixture was filtered through florisil, celite, and alumina. The filtrate was washed with water and brine, and then dried with magnesium sulfate. The reaction mixture was filtered, and the filtrate was concentrated to give oily substance. This substance was purified by silica gel column chromatography (hexane:ethyl acetate=9:1), leading to the formation of 4.1 g of 4-(carbazol-9-yl)-diphenylamine (abbreviation: YGA) in the yield of 73%. It was confirmed by a nuclear magnetic resonance method (NMR) that this compound was 4-(carbazol-9-yl)-diphenylamine (abbreviation: YGA).

¹H NMR data of this compound is shown below.

¹H NMR (300 MHz, DMSO-d₆); δ=8.47 (s, 1H), δ=8.22 (d, J=7.8 Hz, 2H), δ=7.44-7.16 (m, 14H), δ=6.92-6.87 (m, 1H).

Figure 52A:
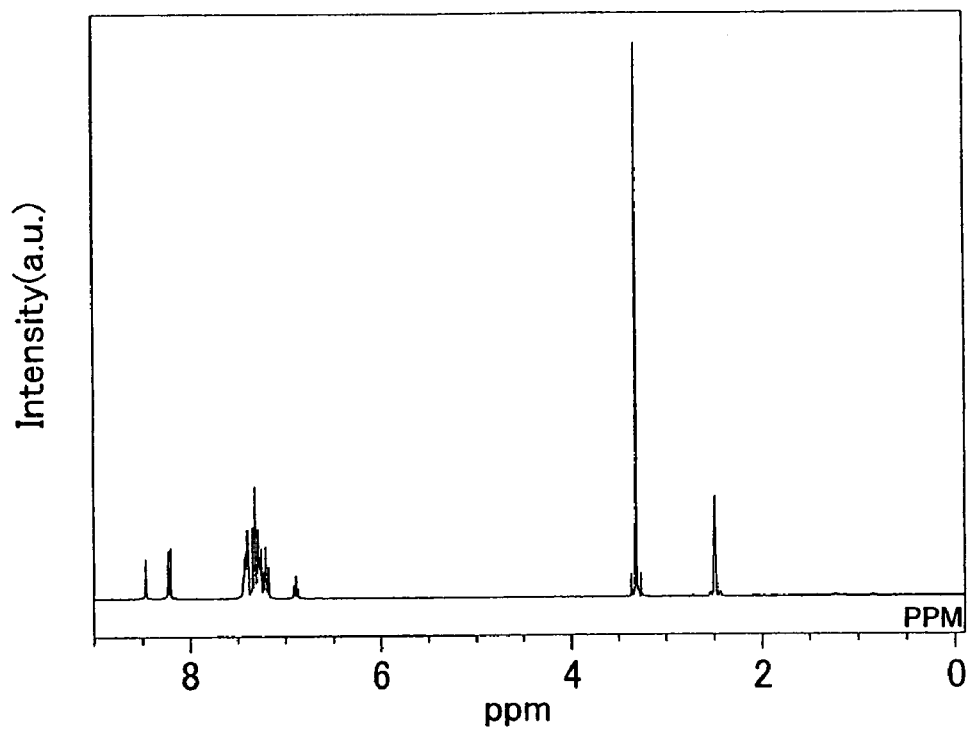
FIGS. 52A and 52B are graphs each showing a $^1$H NMR chart of 4-(carbazol-9-yl)-diphenylamine (abbreviation: YGA)
Figure 52B:
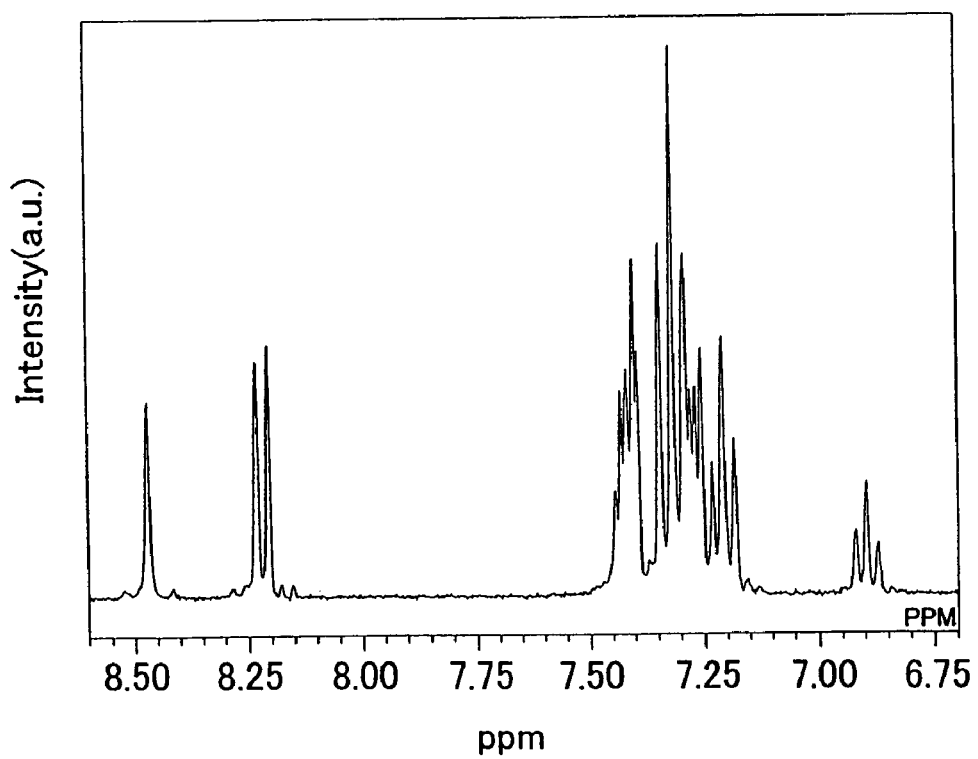

FIGS. 52A and 52B each show a ¹H NMR chart, and FIG. 52B shows an expanded chart of FIG. 52A in a range of 6.7 ppm to 8.6 ppm.

[Step 3]

Synthesis of 4-(carbazol-9-yl)-4'-(3-phenylquinoxalin-2-yl)triphenylamine (Abbreviation: YGA1PQ)

A scheme for the preparation of 4-(carbazol-9-yl)-4'-(3-phenylquinoxalin-2-yl)triphenylamine (abbreviation: YGA1PQ) is shown in (C-6).

formula [144]

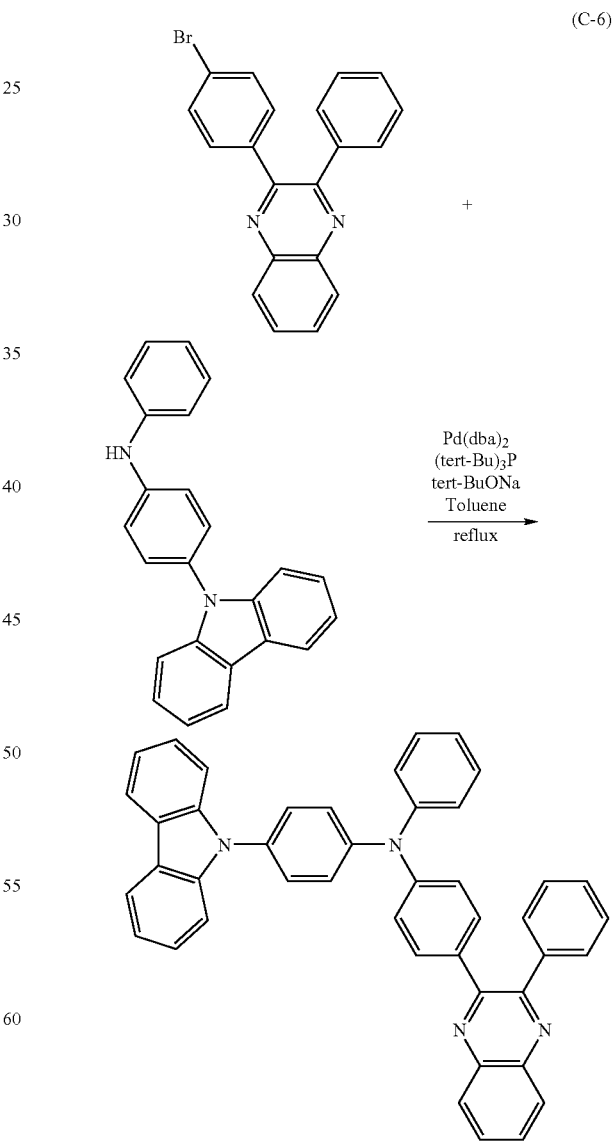

2.0 g (5.59 mmol) of 2-(4-bromophenyl)-3-phenylquinoxaline, 2.07 g (5.59 mmol) of 4-(carbazol-9-yl)-diphenylamine (abbreviation: YGA), 0.161 g (0.279 mmol) of bis(dibenzylideneacetone)palladium(0), and 2.68 g (27.93 mmol) of tert-butoxysodium were placed into a 100-mL three-neck flask, and nitrogen substitution was carried out. 30 mL of toluene and 0.57 g (0.279 mmol) of tri-tert-butylphosphine (10% hexane solution) were added thereto, and the mixture was stirred at 80° C. for 6 hours. After the reaction, the mixture washed with water, and the water phase was extracted with toluene. The organic phase was dried with magnesium sulfate. After the drying, the residue that was obtained by filtration followed by concentration was dissolved into toluene, and the solution was passed through celite, florisil, and alumina. The filtrate was concentrated, and the reside was recrystallized with chloroform, methanol, and hexane, giving 2.25 g of a yellow solid in the yield of 65%. It was confirmed by a nuclear magnetic resonance method (NMR) that this compound was 4-(carbazol-9-yl)-4'-(3-phenylquinoxalin-2-yl)triphenylamine (abbreviation: YGA1PQ).

$^1$H NMR data of this compound is shown below.

$^1$H NMR (CDCl$_3$, 300 MHz): δ=7.11-7.14 (m, 3H), 7.21-7.48 (m, 19H), 7.59-7.62 (m, 2H), 7.75-7.78 (m, 2H), 8.13-8.20 (m, 4H).

Figure 11A:
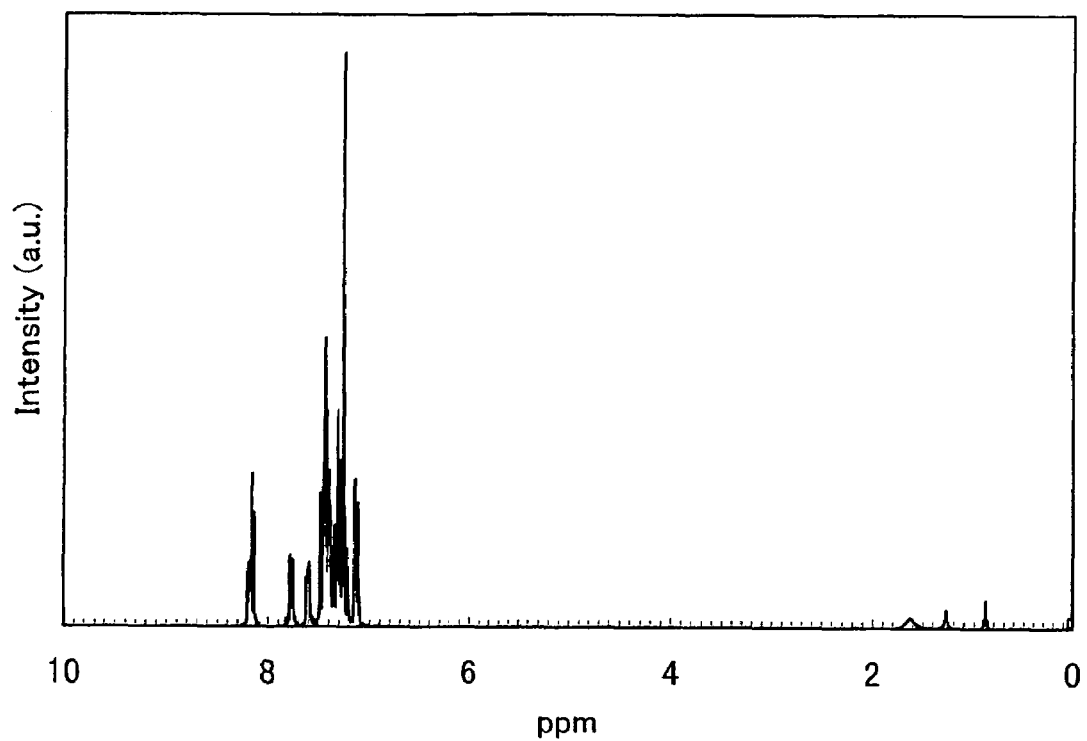
FIGS. 11A and 11B are graphs each showing a $^1$H NMR chart of 4-(carbazol-9-yl)-4'-(3-phenylquinoxalin-2-yl)triphenylamine (abbreviation: YGA1PQ)
Figure 11B:
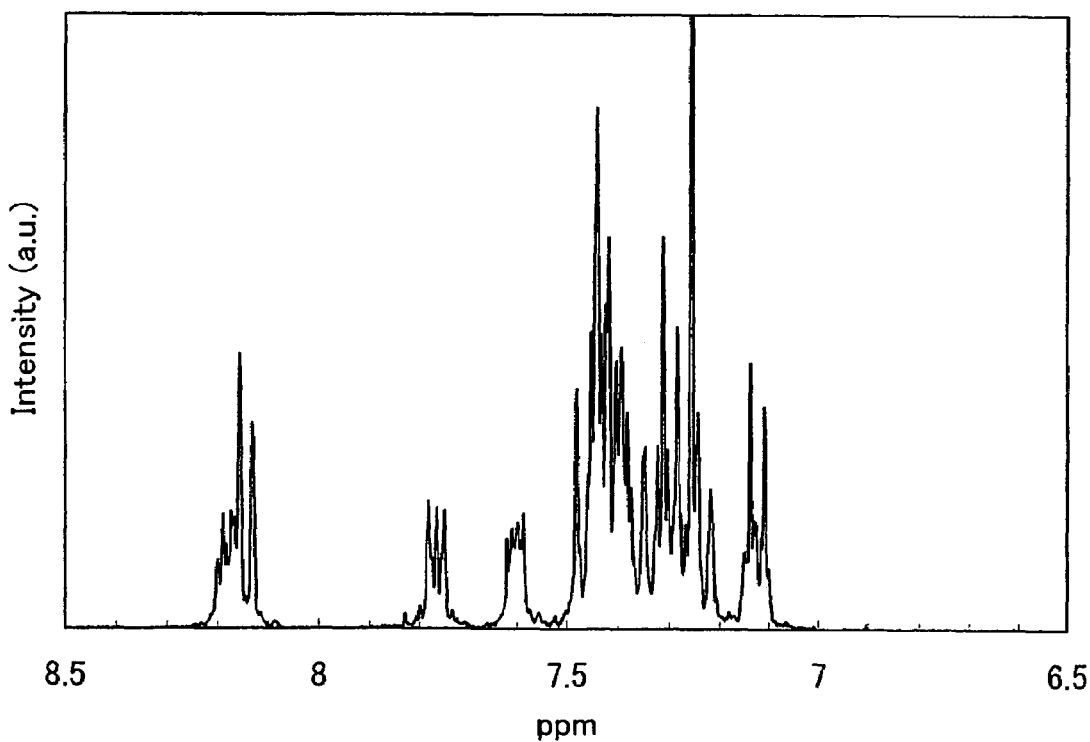

FIGS. 11A and 11B each show a $^1$H NMR chart, and FIG. 11B shows an expanded chart of FIG. 11A in a range of 6.5 ppm to 8.5 ppm.

The decomposition temperature (T$_d$) of YGA1PQ measured by a thermo-gravimetric/differential thermal analyzer (TG/DTA 320, manufactured by Seiko Instruments Inc.) was 424° C., which means that YGA1PQ shows high thermal stability.

Figure 12:
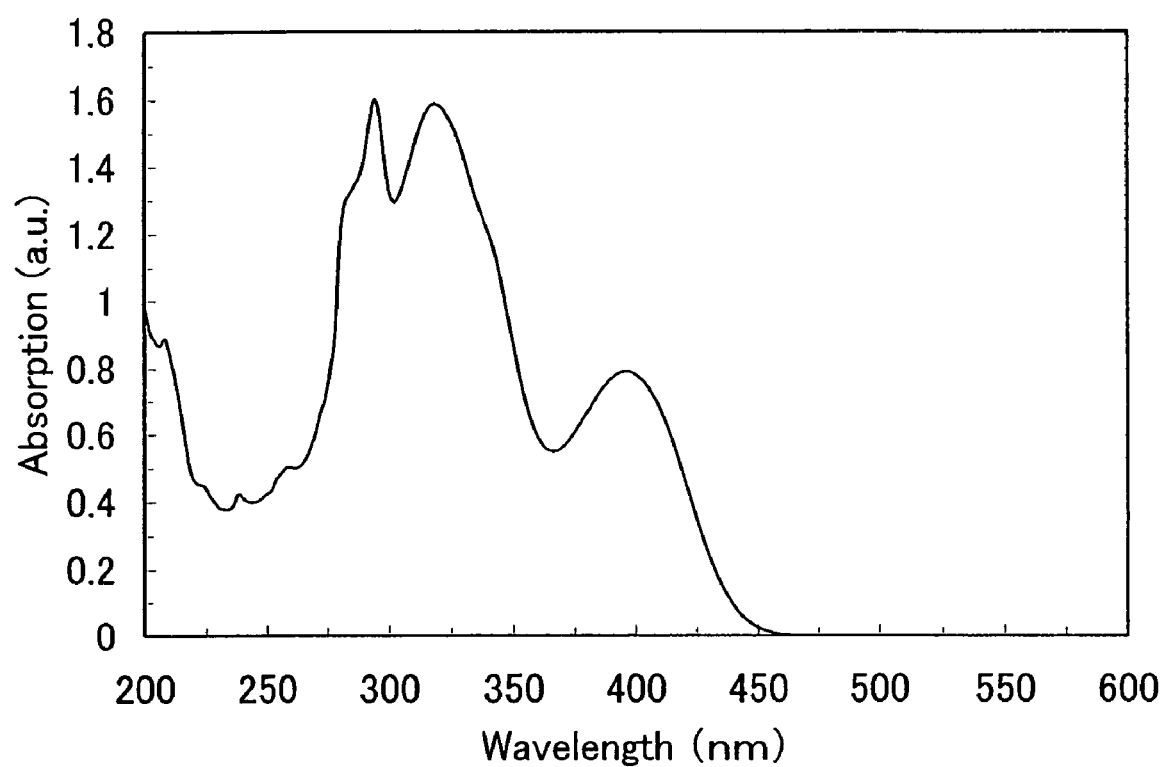
FIG. 12 is a graph showing an absorption spectrum of a toluene solution of 4-(carbazol-9-yl)-4'-(3-phenylquinoxalin-2-yl)triphenylamine (abbreviation: YGA1PQ)
Figure 13:
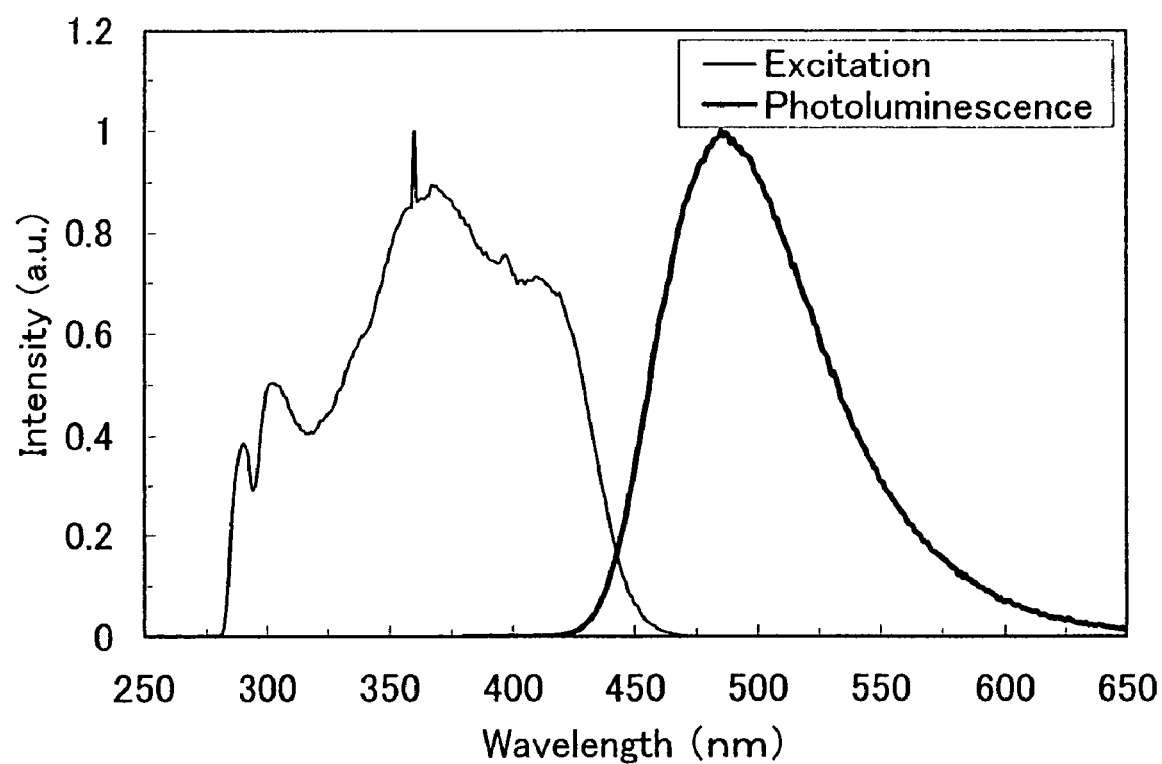
FIG. 13 is a graph showing an emission spectrum of a thin film of 4-(carbazol-9-yl)-4'-(3-phenylquinoxalin-2-yl)triphenylamine (abbreviation: YGA1PQ)

FIG. 12 shows an absorption spectrum of a toluene solution of YGA1PQ. An ultraviolet-visible spectrophotometer (V-550, manufactured by JASCO Corporation) was used for the measurement. The solution was put into a quartz cell, and the absorption spectrum thereof, from which the absorption spectrum of quartz was subtracted, is shown in FIG. 12. In FIG. 12, the horizontal axis indicates the wavelength (nm) and the vertical axis indicates the absorption intensity (arbitrary unit). The absorption was observed at around 396 nm in the case of the toluene solution. FIG. 13 shows the emission spectrum and the excitation spectrum of the toluene solution (the excitation wavelength: 368 nm) of YGA1PQ. In FIG. 13, the horizontal axis indicates the wavelength (nm) and the vertical axis indicates the emission intensity (arbitrary unit). The maximum emission wavelength was 486 nm (the excitation wavelength: 368 nm) in the case of the toluene solution.

Figure 71:
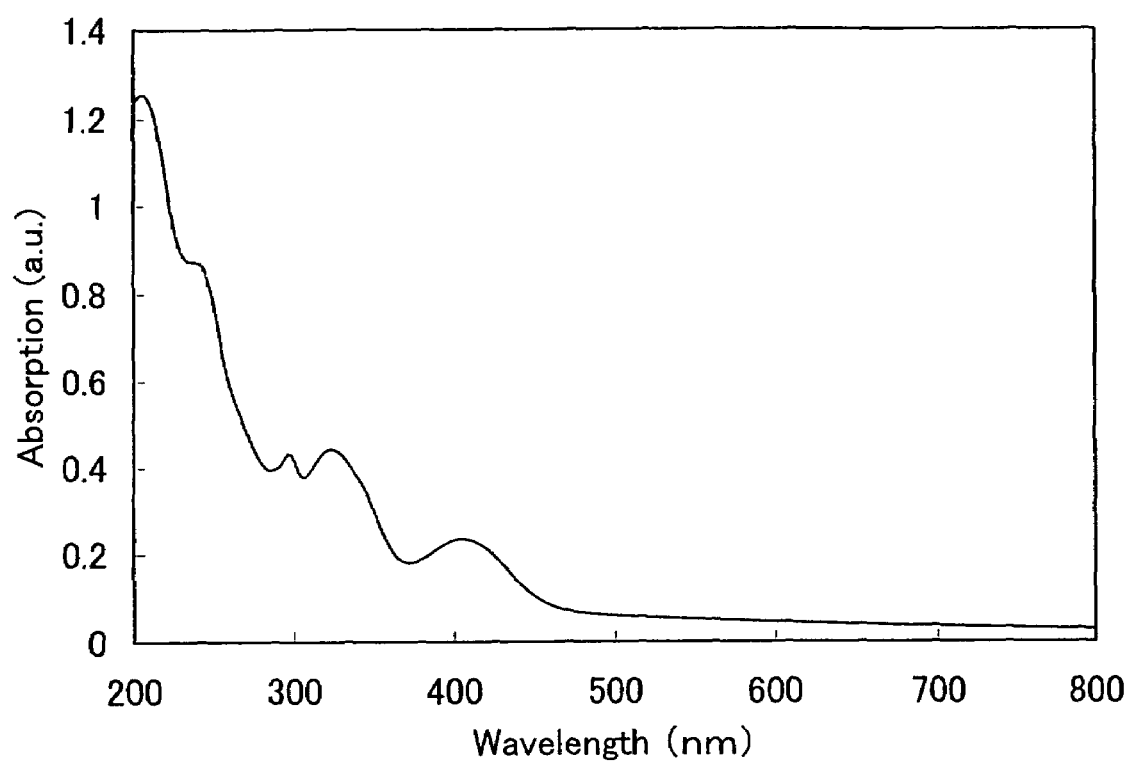
FIG. 71 is a graph showing an absorption spectrum of a thin film of 4-(carbazol-9-yl)-4'-(3-phenylquinoxalin-2-yl)triphenylamine (abbreviation: YGA1PQ)
Figure 72:
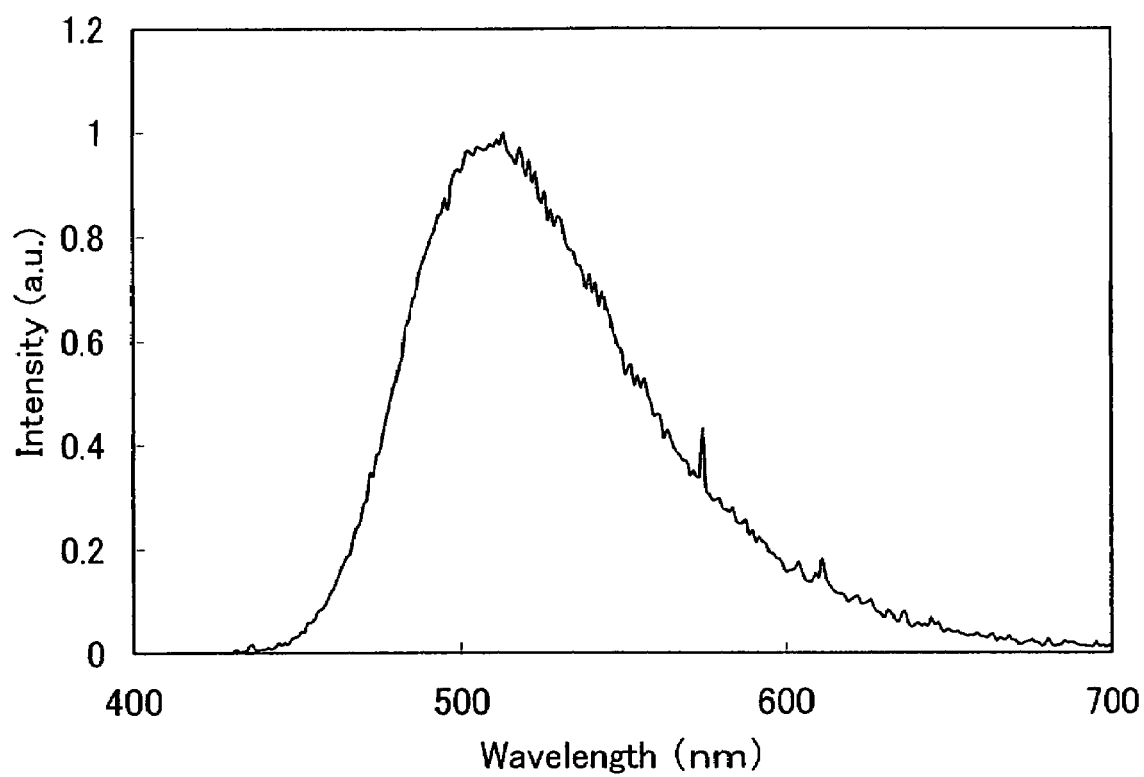
FIG. 72 is a graph showing an emission spectrum of a thin film of 4-(carbazol-9-yl)-4'-(3-phenylquinoxalin-2-yl)triphenylamine (abbreviation: YGA1PQ)

FIG. 71 shows an absorption spectrum of a thin film of YGA1PQ. An ultraviolet-visible spectrophotometer (V-550, manufactured by JASCO Corporation) was used for the measurement. The thin film sample was prepared by vapor deposition of substrate on a quartz substrate, and the absorption spectrum thereof, from which the absorption spectrum of a quartz substrate was subtracted, is shown in FIG. 71. In FIG. 71, the horizontal axis indicates the wavelength (nm) and the vertical axis indicates the absorption intensity (arbitrary unit). The absorption was observed at around 406 nm in the case of the thin film. FIG. 72 shows the emission spectrum of a thin film (the excitation wavelength: 406 nm) of YGA1PQ. In FIG. 72, the horizontal axis indicates the wavelength (nm) and the vertical axis indicates the emission intensity (arbitrary unit). The maximum emission wavelength was 513 nm (the excitation wavelength: 406 nm) in the case of the thin film.

The result of measuring the thin-film using a photoelectron spectrometer (AC-2, manufactured by Riken Keiki Co., Ltd.) under the atmosphere indicated that the HOMO level of YGA1PQ in the solid state is −5.45 eV. The Tauc plot of the absorption spectrum shown in FIG. 71 revealed that the absorption edge was 2.66 eV. Thus, the energy gap of YGA1PQ in the solid state was estimated to be 2.66 eV, which means that the LUMO level of YGA1PQ in the solid state is −2.79 eV.

An optimal molecular structure of YGA1PQ in the ground state was estimated using a density functional theory (DFT) at the B3LYP/6-311 (d, p) level. The accuracy of calculation of the DFT is higher than that of a Hartree-Fock (HF) method which neglects electron correlation. In addition, a calculation cost of the DFT is lower than that of a method of perturbation (MP) which has the same level of accuracy of calculation as that of the DFT. Therefore, the DFT was employed in this calculation. The calculation was performed using a high performance computer (HPC) (Altix3700 DX, manufactured by SGI Japan, Ltd.). The singlet excitation energy (energy gap) of YGA1PQ was calculated by applying a time-dependent density functional theory (TDDFT) at the B3LYP/6-311 (d, p) level to the molecular structure optimized by the DFT. The singlet excitation energy of YGA1PQ was calculated to be 2.77 eV. The triplet excitation energy of YGA1PQ was calculated to be 2.43 eV. From these results, it can be concluded that the quinoxaline derivative of the present invention has high excitation energy, in particular, high triplet excitation energy.

EXAMPLE 2

In this example, a synthetic method of 4,4'-(quinoxaline-2,3-diyl)bis{N-[4-(9-carbazolyl)phenyl]-N-phenylbenzeneamine} (abbreviation: YGAPQ) that is a quinoxaline derivative of the present invention represented by a structural formula (320) will be specifically shown.

formula [145]

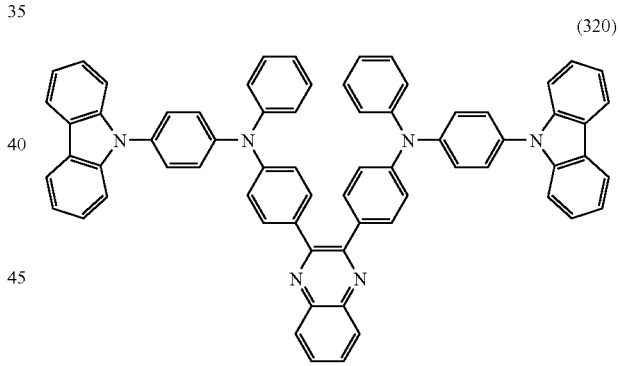

(320)

[Step 1]

Synthesis of 2,3-bis(4-bromophenyl)quinoxaline will be explained. A synthetic scheme of 2,3-bis(4-bromophenyl)quinoxaline is shown in (D-1).

formula [146]

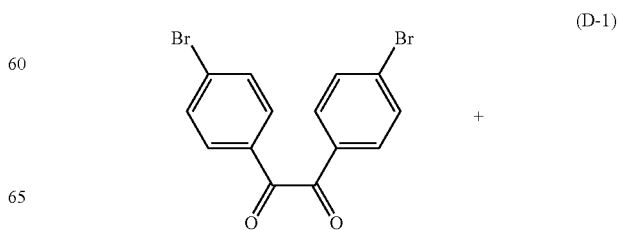

(D-1)

-continued

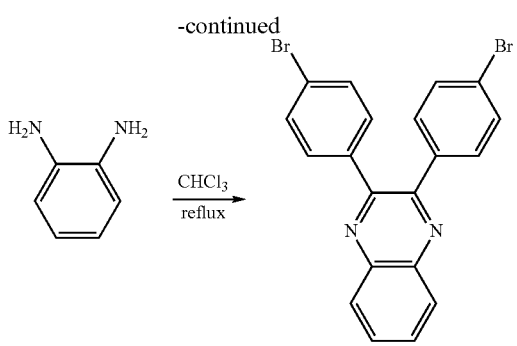

Under a nitrogen atmosphere, a chloroform solution (200 mL) of 30.0 g (81.5 mmol) of 4,4'-dibromobenzyl and 9.00 g (83.2 mmol) of o-phenylenediamine was heated and refluxed at 80° C. for 3 hours. After the reaction mixture was cooled to room temperature, the reaction solution washed with water. The organic phase was separated, and the water phase was extracted with chloroform. The chloroform phase washed with brine together with the organic phase. The combined organic phase was dried with magnesium sulfate, and the solution was filtered and concentrated to give 33 g of 2,3-bis(4-bromophenyl)quinoxaline as a white solid in the yield of 92%.

[Step 2]

A synthetic method of 4,4'-(quinoxaline-2,3-diyl)bis{N-[4-(9-carbazolyl)phenyl]-N-phenylbenzeneamine} (abbreviation: YGAPQ) will be explained. A synthetic scheme of 4,4'-(quinoxaline-2,3-diyl)bis{N-[4-(9-carbazolyl)phenyl]-N-phenylbenzeneamine} (abbreviation: YGAPQ) is shown in (D-2).

formula [147]

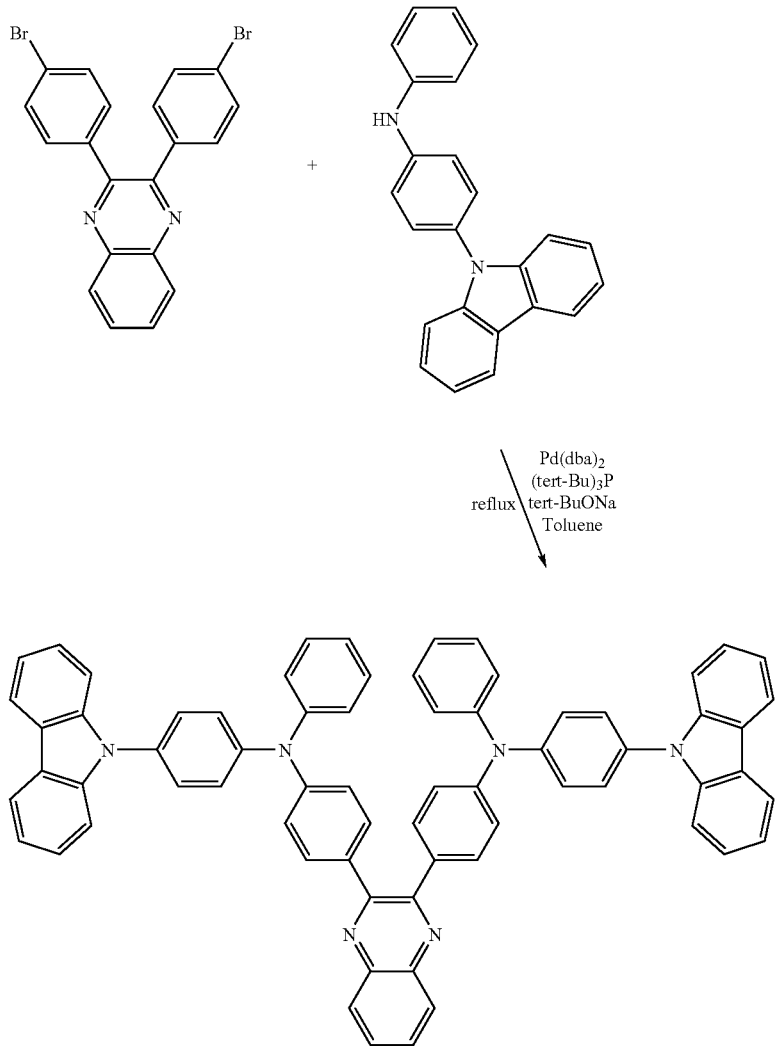

5.0 g (13.51 mmol) of 2,3-bis(4-bromophenyl)quinoxaline, 9.94 g (29.73 mmol) of 4-(carbazol-9-yl)diphenylamine synthesized in Step 2 of Example 1, 0.39 g (0.676 mol) of bis(dibenzylideneacetone)palladium(0), and 6.49 g (67.57 mmol) of sodium tert-butoxide were put into a 300-mL three-neck flask, and nitrogen substitution was carried out. 80 mL of toluene and 1.4 g (0.676 mmol) of tri-tert-butylphosphine (10% hexane solution) were added thereto, and the mixture was stirred at 80° C. for 6 hours. After the reaction, the solution washed with water, and then, a water phase was extracted with toluene. The organic phase was dried with magnesium sulfate. After the drying, the residue that was obtained by filtration and concentration of the organic phase was dissolved into toluene, and the resulting solution was passed through celite, florisil, and alumina. The filtrate was concentrated, and the residue was recrystallized with chloroform/methanol/hexane to provide 9.34 g of a yellow solid in the yield of 73%. It was confirmed by a nuclear magnetic resonance method (NMR) that this compound was 4,4'-(quinoxaline-2,3-diyl)bis{N-[4-(9-carbazolyl)phenyl]-N-phenylbenzeneamine} (abbreviation: YGAPQ).

$^1$H NMR data of this compound is shown below.

$^1$H NMR (CDCl$_3$, 300 MHz): δ=7.02-7.07 (m, 2H), 7.17-7.56 (m, 36H), 7.74-7.77 (m, 2H), 8.12-8.19 (m, 6H).

Figure 14A:
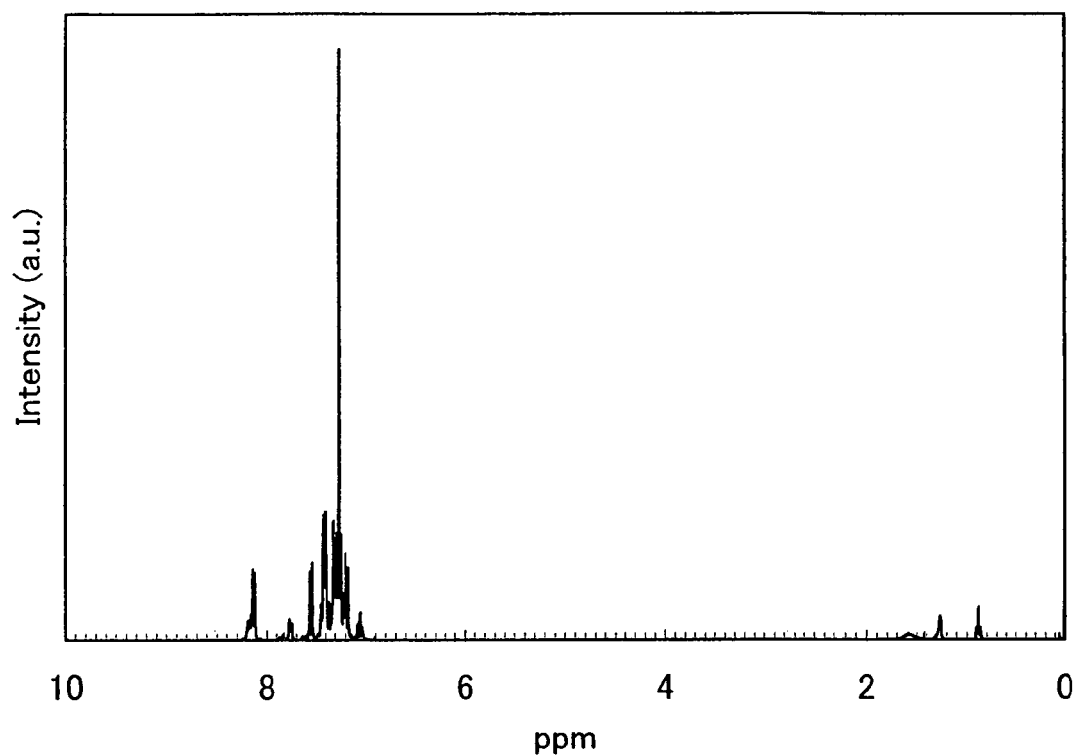
FIGS. 14A and 14B are graphs each showing a $^1$H NMR chart of 4,4'-(quinoxaline-2,3-diyl)bis{N-[4-(9-carbazolyl)phenyl]-N-phenylbenzeneamine} (abbreviation: YGAPQ)
Figure 14B:
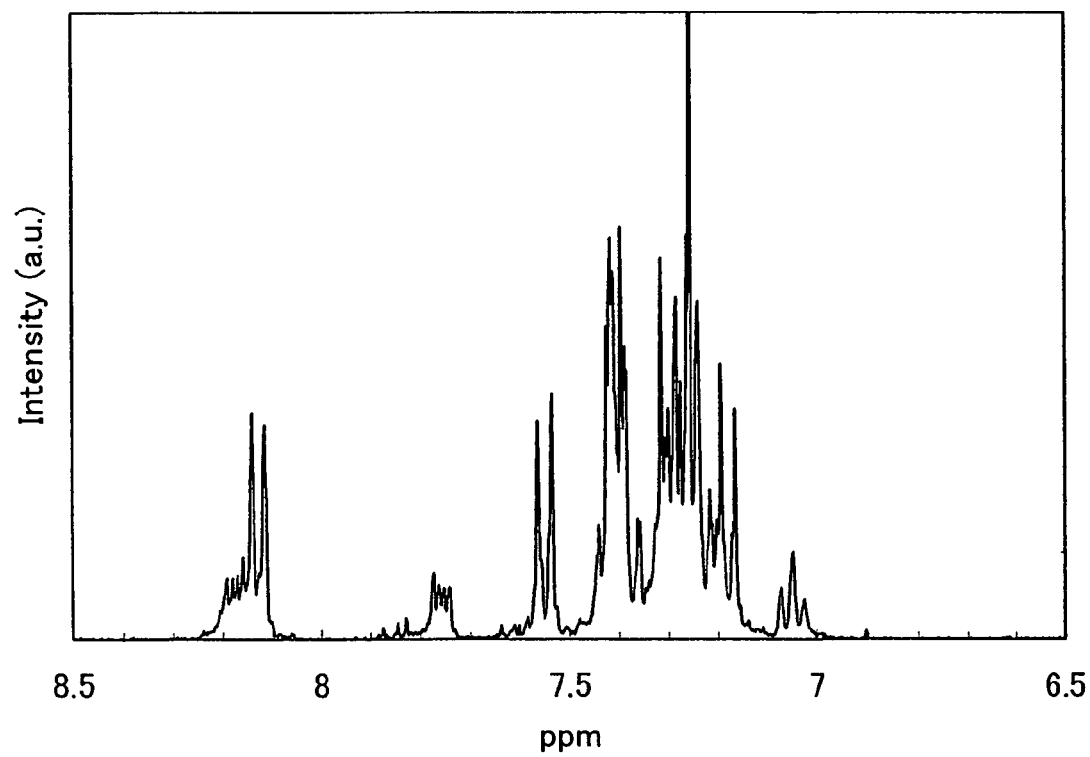

FIGS. 14A and 14B each show a $^1$H NMR chart, and FIG. 14B shows an expanded chart of FIG. 14A in a range of 6.5 ppm to 8.5 ppm.

Further, the decomposition temperature ($T_d$) of YGAPQ measured by a thermo-gravimetric/differential thermal analyzer (TG/DTA 320, manufactured by Seiko Instruments Inc.) was 450° C. Therefore, it was proven that YGAPQ shows high thermal stability.

Figure 28:
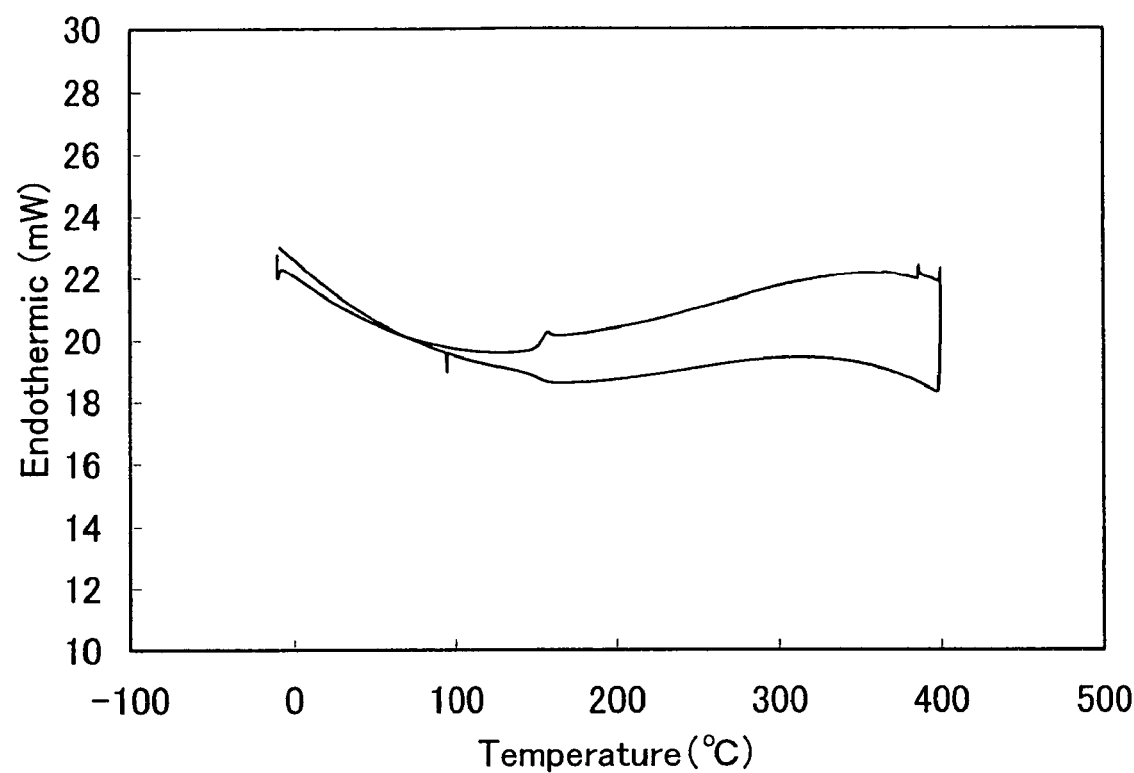
FIG. 28 is a graph showing a DSC chart of 4,4'-(quinoxaline-2,3-diyl)bis{N-[4-(9-carbazolyl)phenyl]-N-phenylbenzeneamine} (abbreviation: YGAPQ)

The glass transition temperature was measured using a differential scanning calorimeter (Pyris 1 DSC, manufactured by PerkinElmer, Inc.). First, the sample was heated to 400° C. at a rate of 40° C./min to melt the sample, and then cooled to room temperature at a rate of 40° C./min. Thereafter, the sample was heated again to 400° C. at a rate of 10° C./min, whereby a DSC chart of FIG. 28 was obtained. The temperature is shown in the X axis and a heat flow is shown in the Y axis in FIG. 28. An upwardness in the Y axis means endothermic. According to this chart, it was found that the glass transition temperature ($T_g$) of YGAPQ is 150° C., and the melting point thereof is higher than or equal to 400° C. Thus, it was found that YGAPQ has a high glass transition temperature.

Figure 15:
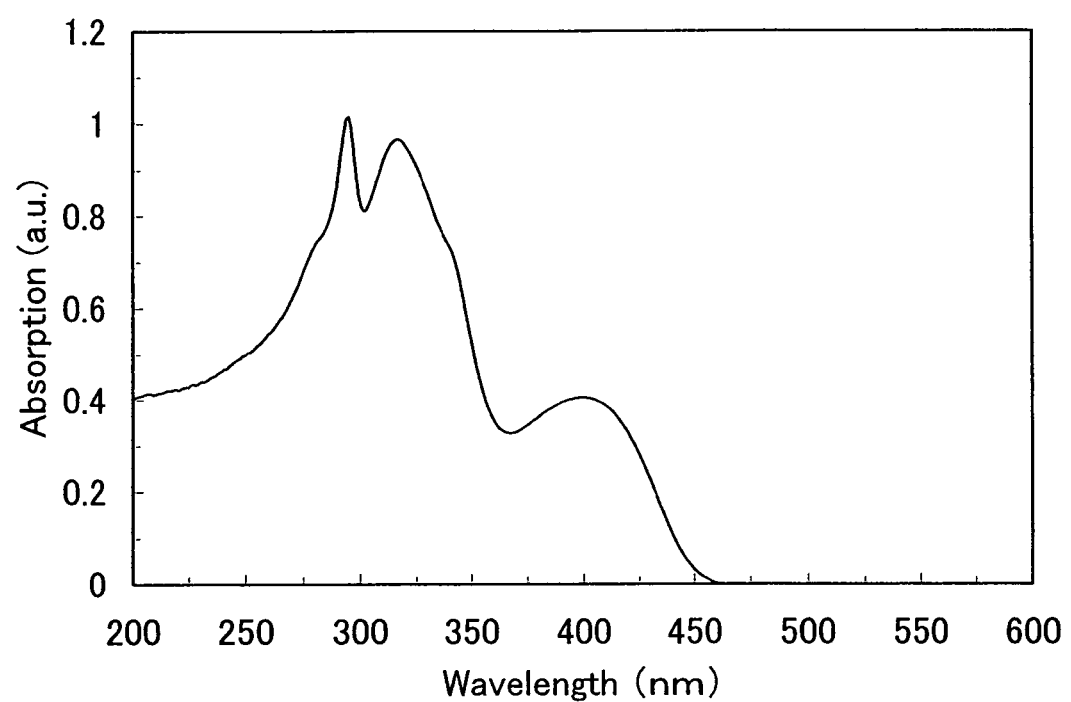
FIG. 15 is a graph showing an absorption spectrum of a toluene solution of 4,4'-(quinoxaline-2,3-diyl)bis{N-[4-(9-carbazolyl)phenyl]-N-phenylbenzeneamine} (abbreviation: YGAPQ)
Figure 16:
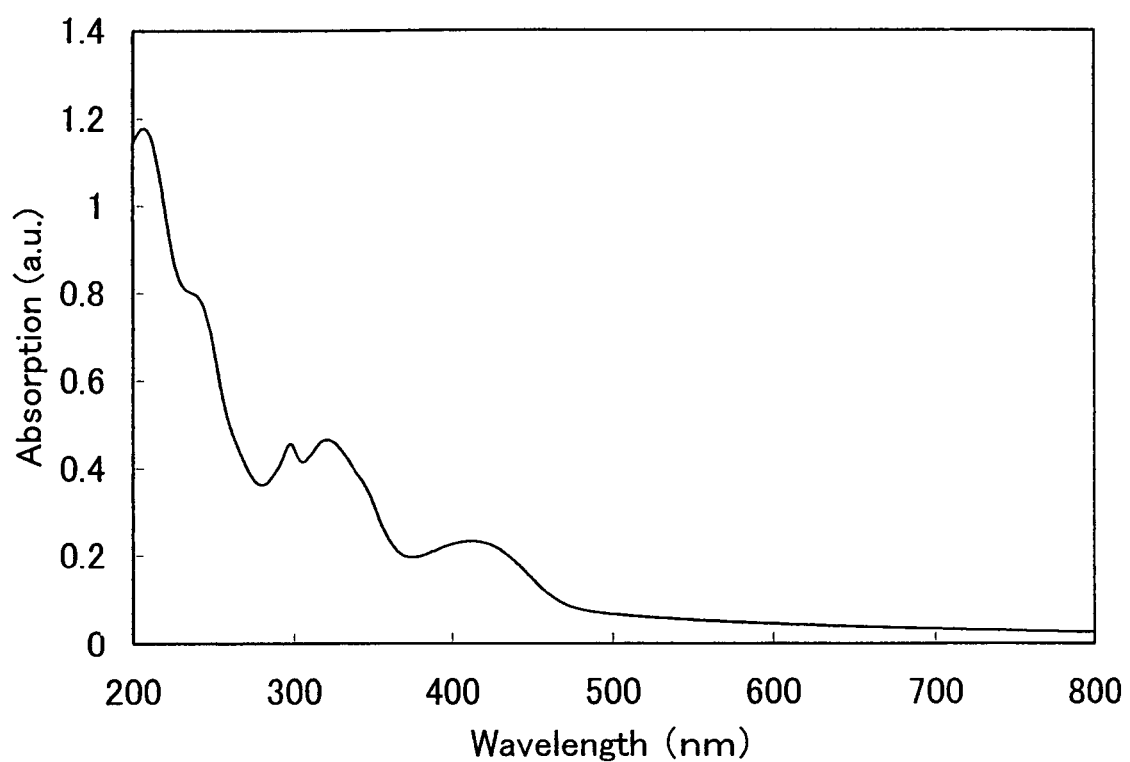
FIG. 16 is a graph showing an absorption spectrum of a thin film of 4,4'-(quinoxaline-2,3-diyl)bis{N-[4-(9-carbazolyl)phenyl]-N-phenylbenzeneamine} (abbreviation: YGAPQ)
Figure 17:
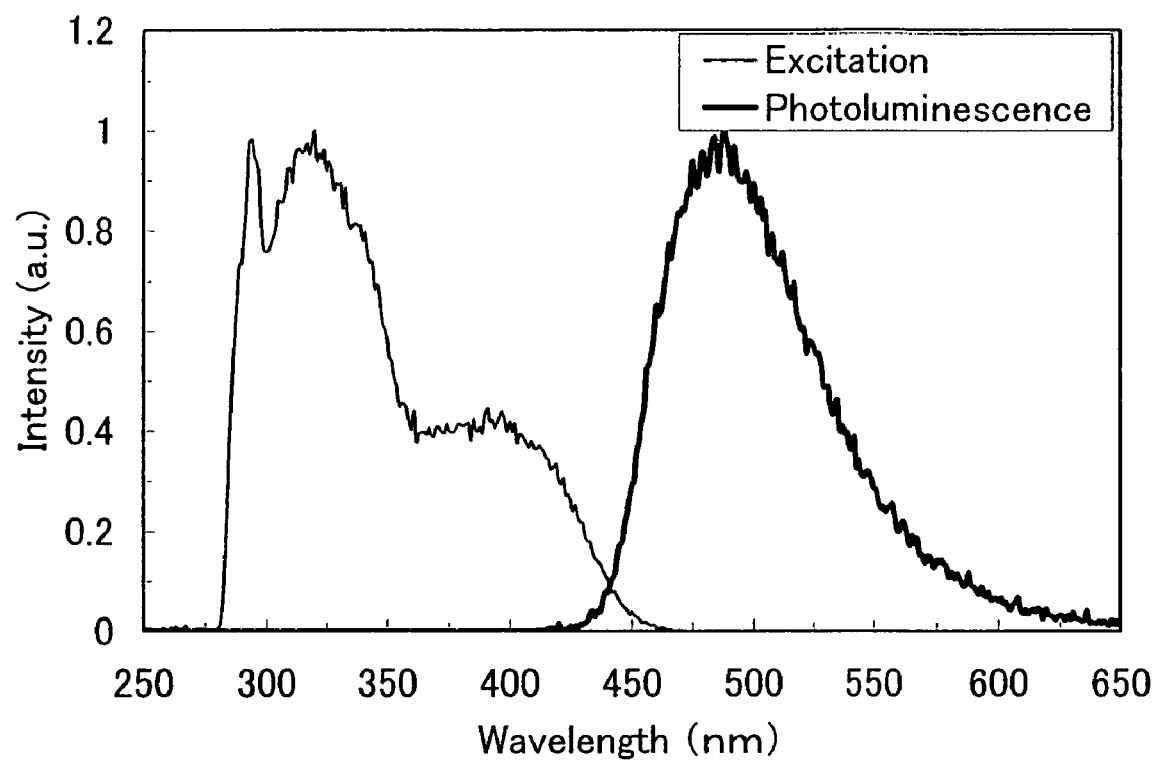
FIG. 17 is a graph showing an emission spectrum of a toluene solution of 4,4'-(quinoxaline-2,3-diyl)bis{N-[4-(9-carbazolyl)phenyl]-N-phenylbenzeneamine} (abbreviation: YGAPQ)
Figure 18:
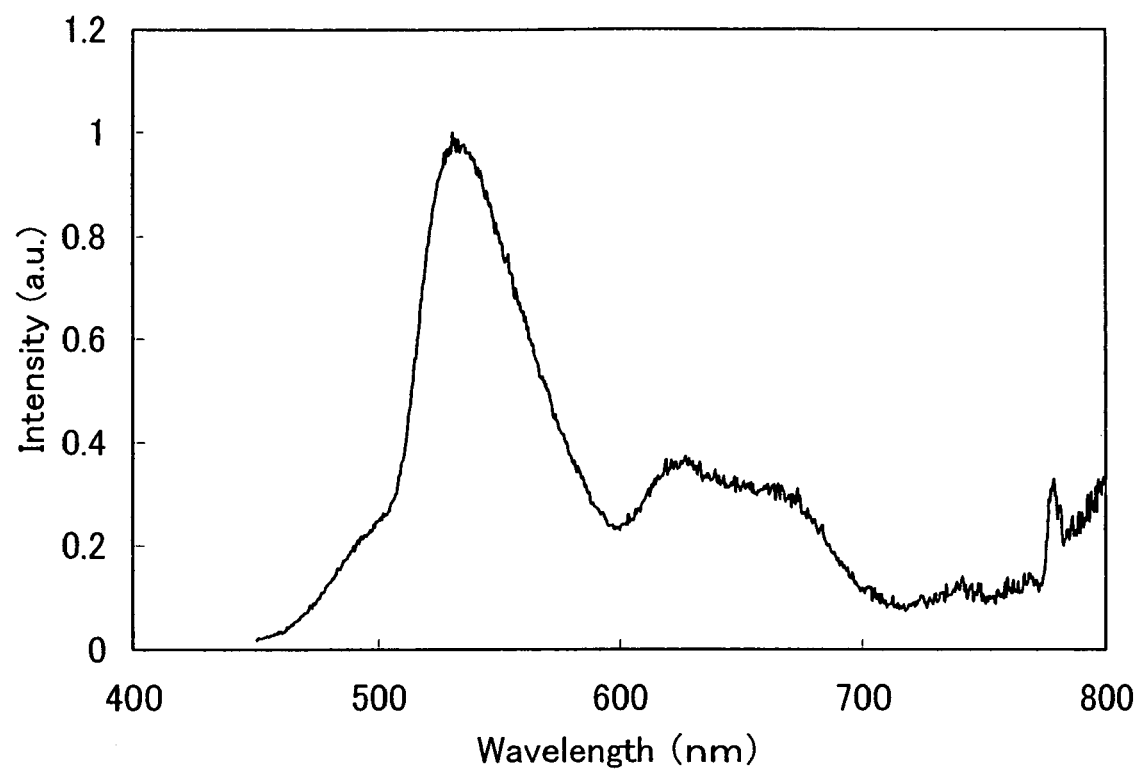
FIG. 18 is a graph showing an emission spectrum of a thin film of 4,4'-(quinoxaline-2,3-diyl)bis{N-[4-(9-carbazolyl)phenyl]-N-phenylbenzeneamine} (abbreviation: YGAPQ)

FIG. 15 shows an absorption spectrum of a toluene solution of YGAPQ. FIG. 16 shows an absorption spectrum of a thin film of YGAPQ. An ultraviolet-visible spectrophotometer (V-550, manufactured by JASCO Corporation) was used for the measurement. The solution was put into a quartz cell and the thin film sample was prepared by vapor deposition of YGAPQ on a quartz substrate. The absorption spectra thereof, from each of which the absorption spectrum of quartz was subtracted, are shown in FIGS. 15 and 16. In FIGS. 15 and 16, the horizontal axis indicates the wavelength (nm) and the vertical axis indicates the absorption intensity (arbitrary unit). The absorption was observed at around 400 nm in the case of the toluene solution, and at around 410 nm in the case of the thin film. FIG. 17 shows the emission spectrum and the excitation spectrum of the toluene solution (the excitation wavelength: 397 nm) of YGAPQ. FIG. 18 shows the emission spectrum of the thin film (the excitation wavelength: 410 nm) of YGAPQ. In FIGS. 17 and 18, the horizontal axis indicates the wavelength (nm), and the vertical axis indicates the emission intensity (arbitrary unit). The maximum emission wavelength was 488 nm (the excitation wavelength: 397 nm) in the case of the toluene solution, and at around 531 nm and 630 nm (the excitation wavelength: 410 nm) in the case of the thin film.

The result of measuring the thin-film using a photoelectron spectrometer (AC-2, manufactured by Riken Keiki Co., Ltd.) under the atmosphere indicated that the HOMO level of YGAPQ in the solid state is −5.42 eV The optical energy gap evaluated by the results of the Tauc plot of the absorption spectrum shown in FIG. 16 revealed that the energy gap of YGAPQ in the solid state was 2.66 eV. This result means that the LUMO level of YGA1PQ in the solid state is −2.76 eV.

An optimal molecular structure of YGAPQ in a ground state was estimated using a density functional theory (DFT) at the B3LYP/6-311 (d, p) level. The accuracy of calculation of the DFT is higher than that of a Hartree-Fock (HF) method which neglects electron correlation. In addition, a calculation cost of the DFT is lower than that of a method of perturbation (MP) which has the same level of accuracy of calculation as that of the DFT. Therefore, the DFT was employed in this calculation. The calculation was performed using a high performance computer (HPC) (Altix3700 DX, manufactured by SGI Japan, Ltd.). The singlet excitation energy (energy gap) of YGAPQ was calculated by applying a time-dependent density functional theory (TDDFT) at the B3LYP/6-311 (d, p) level to the molecular structure optimized by the DFT. The singlet excitation energy of YGAPQ was calculated to be 2.64 eV. The triplet excitation energy of YGAPQ was calculated to be 2.38 eV. From these results, it can be concluded that the quinoxaline derivative of the present invention is a substance having high excitation energy, in particular, a substance having high triplet excitation energy.

Furthermore, the glass transition point ($T_g$) was measured using a differential scanning calorimeter (Pyris 1 DSC, manufactured by PerkinElmer, Inc.). First, a sample was heated to 330° C. at a rate of 40° C./min, and then cooled to room temperature at a rate of 40° C./min. Thereafter, the sample was heated to 330° C. at a rate of 10° C./min, and then cooled to room temperature at a rate of 40° C./min. As a result, it was found that the glass transition temperature ($T_g$) of YGAPQ is 150° C. Thus, it was found that YGAPQ has a high glass transition temperature.

Subsequently, an oxidation profile and a reduction profile of YGAPQ were measured by the cyclic voltammetry (CV) technique. An electrochemical analyzer (ALS model 600A, manufactured by BAS Inc.) was used for the measurement.

The solution for the CV measurement was prepared by using dehydrated N,N-dimethylformamide (DMF) (produced by Sigma-Aldrich Corp., 99.8%, catalog number: 22705-6) as a solvent, dissolving a supporting electrolyte of tetra-n-butylammonium perchlorate (n-Bu$_4$NClO$_4$) (produced by Tokyo Chemical Industry Co., Ltd., catalog number: T0836) at a concentration of 100 mmol/L, and dissolving the sample at a concentration of 1 mmol/L. A platinum electrode (PTE platinum electrode, produced by BAS Inc.) was used as a working electrode, a platinum electrode (Pt counter electrode (5 cm) for VC-3, produced by BAS Inc.) was used as an auxiliary electrode, and an Ag/Ag$^+$ electrode (RE5 non-aqueous solvent reference electrode, produced by BAS Inc.) was used as a reference electrode. The CV measurement of YGAPQ was carried out at room temperature.

The oxidation profile of YGAPQ was examined as follows. A scan, in which the potential of the working electrode with respect to the reference electrode was varied from 1 V to −0.21 V after changing it from −0.21 V to 1 V, was regarded as one cycle, and measurement was performed for 100 cycles. The reduction profile of YGAPQ was examined as follows. A scan, in which the potential of the working electrode with respect to the reference electrode was varied from −2.5 V to −0.3 V after changing it from −0.3 V to −2.5 V, was regarded as one cycle, and measurement was performed for 100 cycles. The scan rate of the CV measurement was set to be 0.1 V/s.

Figure 19:
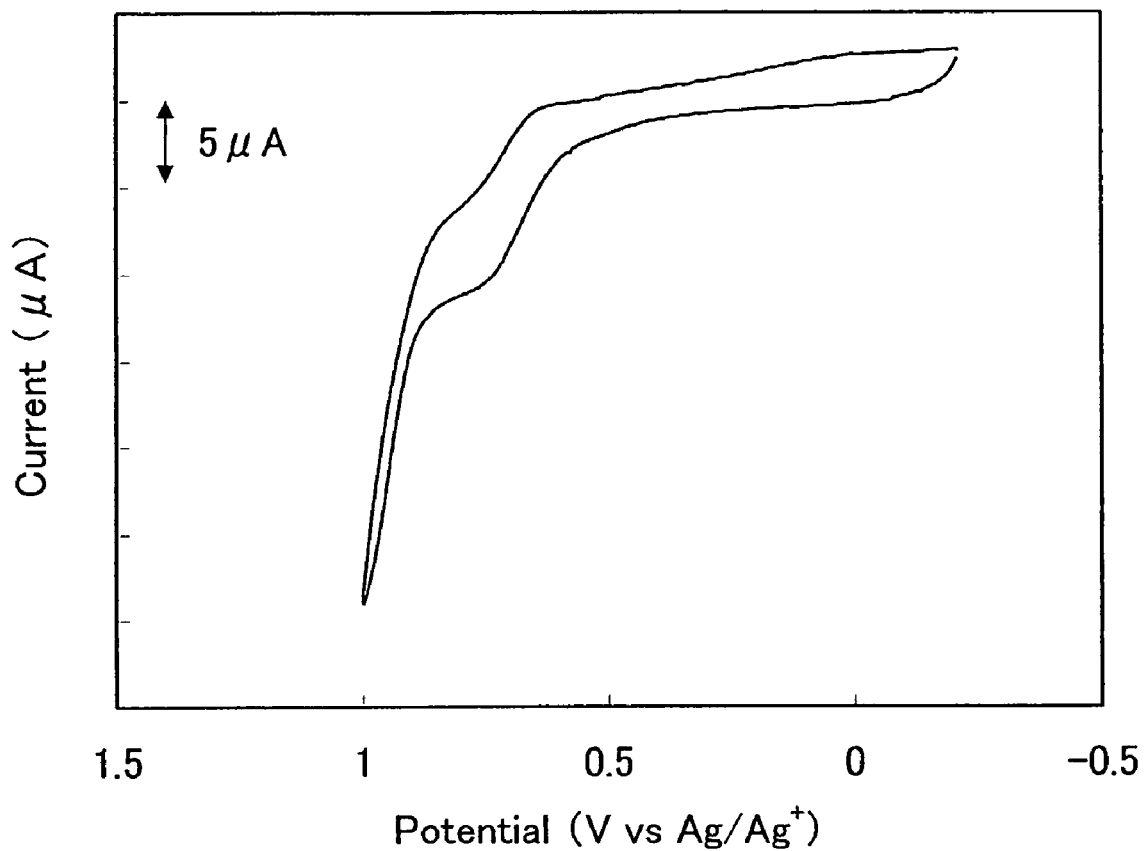
FIG. 19 is a graph showing a result of CV measurement of 4,4'-(quinoxaline-2,3-diyl)bis{N-[4-(9-carbazolyl)phenyl]-N-phenylbenzeneamine} (abbreviation: YGAPQ)
Figure 20:
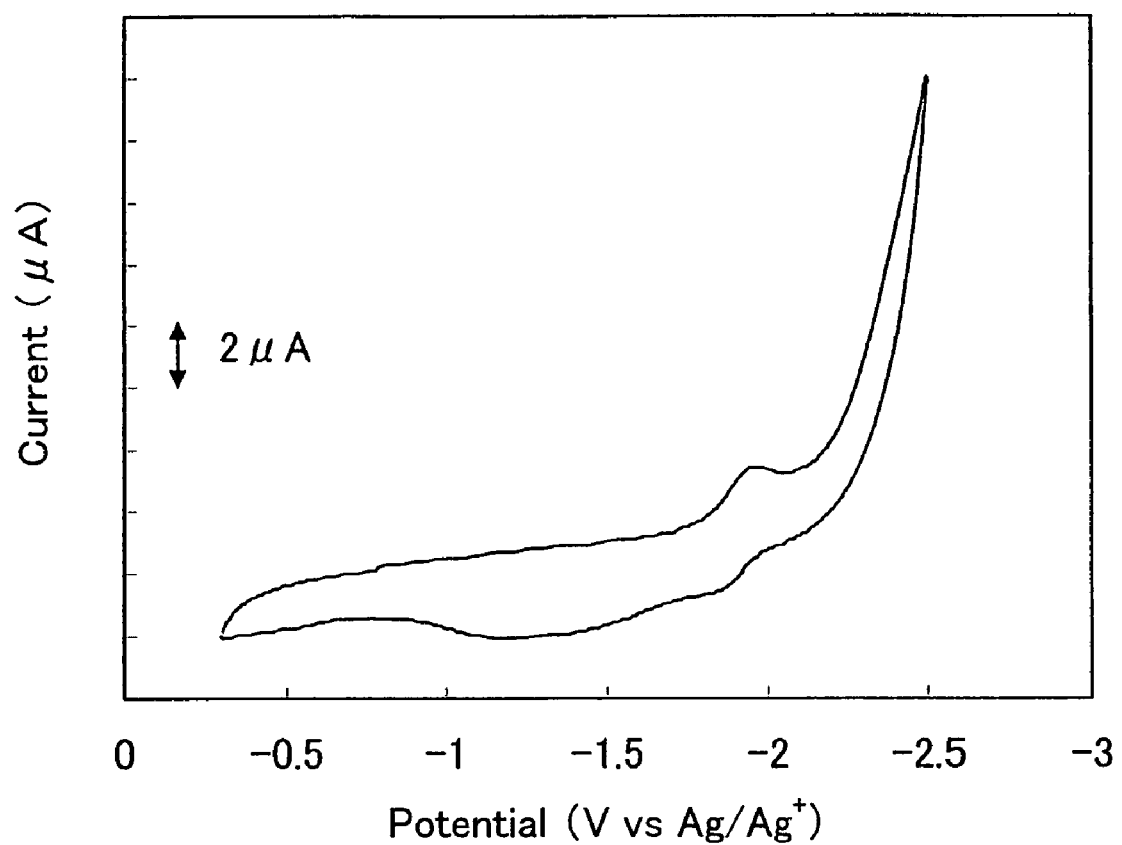
FIG. 20 is a graph showing a result of CV measurement of 4,4'-(quinoxaline-2,3-diyl)bis{N-[4-(9-carbazolyl)phenyl]-N-phenylbenzeneamine} (abbreviation: YGAPQ)

FIG. 19 shows a result of CV measurement of YGAPQ in an oxidation region, and FIG. 20 shows a result of CV measurement of YGAPQ in a reduction region. In each of FIGS. 19 and 20, the horizontal axis indicates a potential (V) of the working electrode with respect to the reference electrode, and the vertical axis indicates a current value (μA) flowing between the working electrode and the auxiliary electrode. According to FIG. 19, currents for oxidation were observed at around 0.7 V to 0.8 V (vs. Ag/Ag$^+$). According to FIG. 20, currents indicating reduction were observed at around −1.94 V (vs. Ag/Ag$^+$).

EXAMPLE 3

In this example, a synthetic method of N,N'-(quinoxaline-2,3-diyldi-4,1-phenylene)bis(N-phenyl-9-phenylcarbazole-3-amine) (abbreviation: PCAPQ) that is a quinoxaline derivative of the present invention represented by a structural formula (271) will be specifically shown.

formula [148]

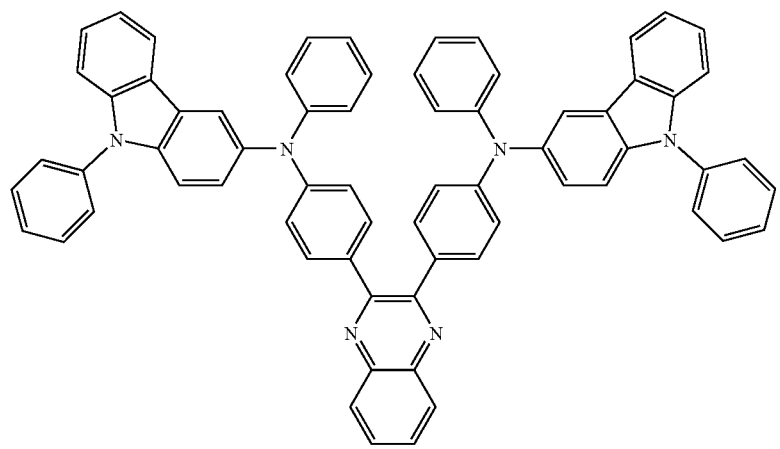

(271)

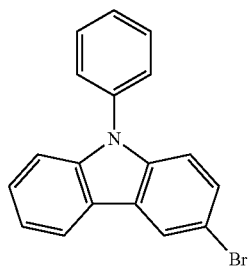

24.3 g (100 mmol) of 9-phenylcarbazole was dissolved into 600 mL of glacial acetic acid, and 17.8 g (100 mmol) of N-bromosuccinimide was slowly added thereto, which was followed by stirring at room temperature for about 15 hours. This glacial acetic acid solution was dropped to 1 L of ice water while being stirred, and a white solid which was precipitated was collected by suction filtration and washed with water three times. The solid was dissolved into 150 mL of diethyl ether, and the solution washed with a saturated sodium hydrogencarbonate aqueous solution and water. The organic layer was dried with magnesium sulfate. After filtration, the obtained filtrate was concentrated, and about 50 mL of methanol was added thereto to homogeneously dissolve the residue. This solution was left at rest, and a white solid was precipitated. This solid was collected and dried, giving 28.4 g of a white powder of 3-bromo-9-phenylcarbazole in the yield of 88%.

[Step 2] Synthesis of N-phenyl-(9-phenylcarbazol-3-yl)amine (Abbreviation: PCA)

A synthetic scheme of PCA is shown in (E-2).

Step 1

A synthetic method of N-phenyl-(9-phenylcarbazol-3-yl)amine (abbreviation: PCA) will be explained.

(i) Synthesis of 3-bromo-9-phenylcarbazole

A synthetic scheme of 3-bromo-9-phenylcarbazole is shown in (E-1).

formula [149]

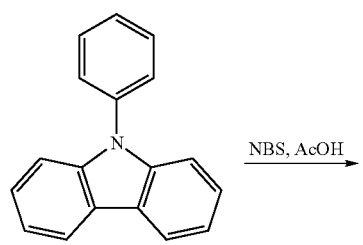

(E-1)

formula [150]

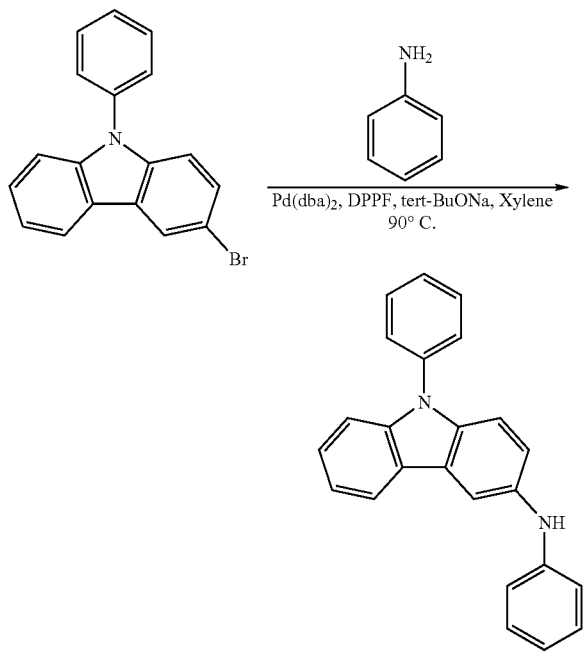

19 g (60 mmol) of 3-bromo-9-phenylcarbazole, 340 mg (0.6 mmol) of bis(dibenzylideneacetone)palladium(0), 1.6 g (3.0 mmol) of 1,1-bis(diphenylphosphino)ferrocene, and 13 g (180 mmol) of sodium tert-butoxide were put into a three-neck flask, and nitrogen substitution was carried out. Then, 110 mL of dehydrated xylene and 7.0 g (75 mmol) of aniline were added thereto. This mixture was heated and stirred at 90° C. for 7.5 hours under a nitrogen atmosphere. After the reaction was completed, about 500 mL of hot toluene was added to the reaction mixture, and the mixture was filtered through florisil, alumina, and celite. The obtained filtrate was concentrated, and hexane and ethyl acetate was added thereto. Then, the mixture was irradiated with ultrasonic waves. The precipitated solid was collected by suction filtration, and the obtained solid was dried. 15 g of a cream-colored powder of N-phenyl-(9-phenylcarbazol-3-yl)amine (abbreviation: PCA) was obtained in the yield of 75%. It was confirmed by a nuclear magnetic resonance method (NMR) that this compound was N-phenyl-(9-phenylcarbazol-3-yl)amine (abbreviation: PCA).

$^1$H NMR data of this compound is shown below.

$^1$H NMR (300 MHz, CDCl$_3$); 6.84 (t, J=6.9, 1H), 6.97 (d, J=7.8, 2H), 7.20-7.61 (m, 13H), 7.90 (s, 1H), 8.04 (d, J=7.8, 1H).

Figure 51A:
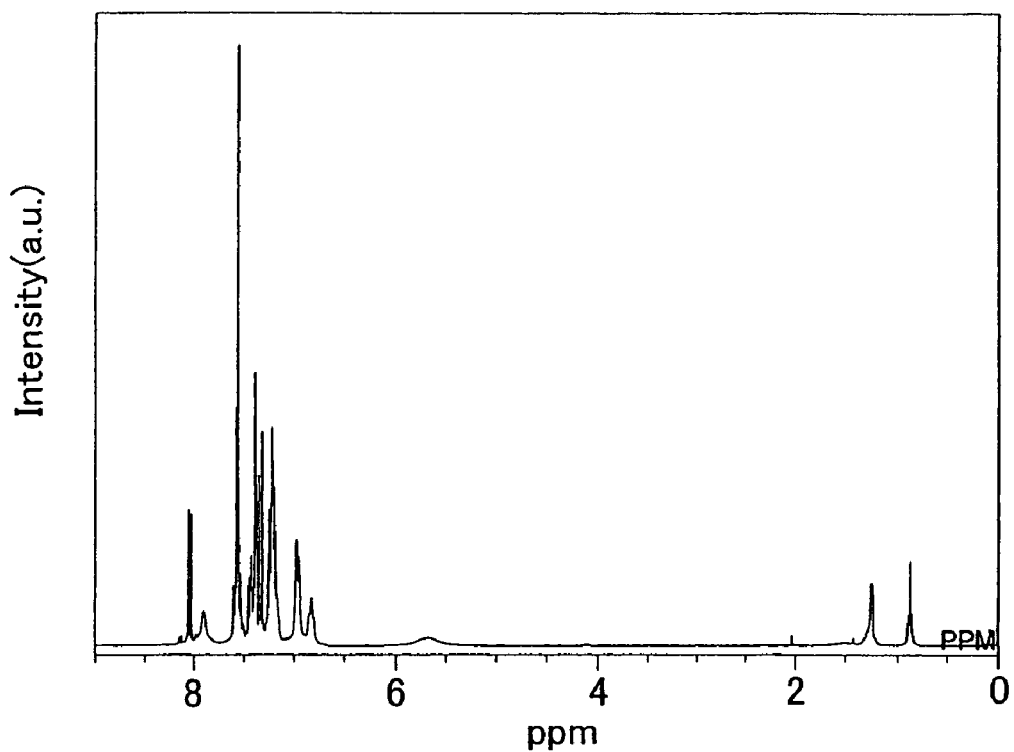
FIGS. 51A and 51B are graphs each showing a $^1$H NMR chart of N-phenyl-(9-phenylcarbazol-3-yl)amine (abbreviation: PCA)
Figure 51B:
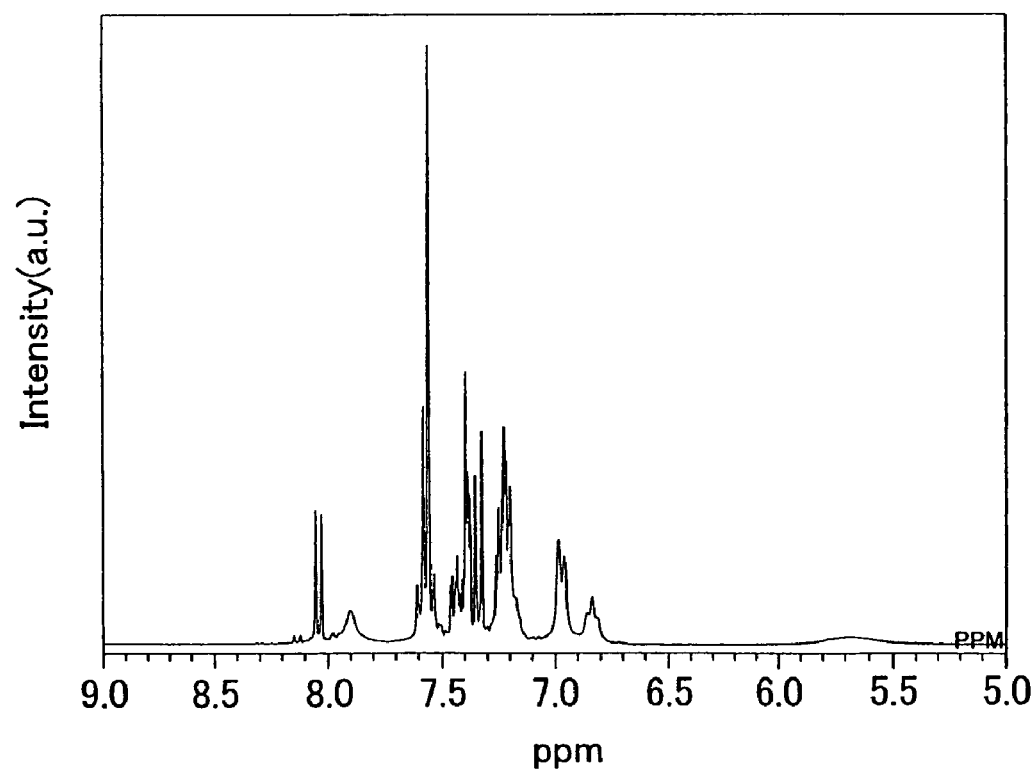

FIG. 51A shows a $^1$H NMR chart, and FIG. 51B shows an expanded chart of FIG. 51A in a range of 5.0 ppm to 9.0 ppm.

[Step 3] Synthesis of N,N-(quinoxaline-2,3-diyldi-4,1-phenylene)bis(N-phenyl-9-phenylcarbazole-3-amine) (Abbreviation: PCAPQ)

A synthetic scheme of N,N'-(quinoxaline-2,3-diyldi-4,1-phenylene)bis(N-phenyl-9-phenylcarbazole-3-amine) (abbreviation: PCAPQ) is shown in (E-3).

formula [151]

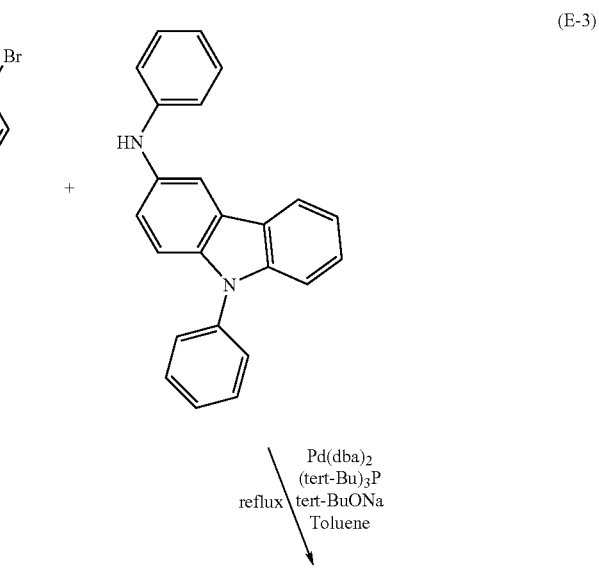

-continued

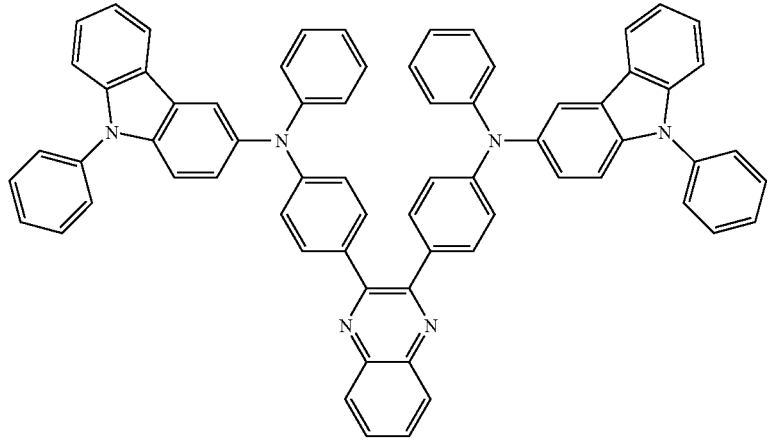

1.79 g (4.08 mmol) of 2,3-bis(4-bromophenyl)quinoxaline, 3.0 g (8.97 mmol) of N-phenyl-(9-phenylcarbazol-3-yl)amine (abbreviation: PCA), 0.117 g (0.204 mol) of bis(dibenzylideneacetone)palladium(0), and 1.96 g (20.39 mmol) of sodium tert-butoxide were put into a 100-mL three-neck flask, and nitrogen substitution was carried out. 30 mL of toluene and 0.5 g (0.245 mmol) of tri-tert-butylphosphine (10% hexane solution) were added thereto, and the mixture was stirred at 80° C. for 6 hours. After the reaction, the mixture washed with water, and then, the water phase was extracted with toluene. The organic phase was dried with magnesium sulfate. After the drying, the residue that was obtained by filtration and concentration was dissolved into toluene, and the solution was passed through celite, florisil, and alumina. The filtrate was concentrated and the resulting solid was recrystallized with ethyl acetate/methanol, giving 2.60 g of a bright yellow solid that was the target product in the yield of 67%. It was confirmed by a nuclear magnetic resonance method (NMR) that this compound was N,N'-(quinoxaline-2,3-diyldi-4,1-phenylene)bis(N-phenyl-9-phenylcarbazole-3-amine) (abbreviation: PCAPQ).

$^1$H NMR data of this compound is shown below.

$^1$H NMR (CDCl$_3$, 300 MHz): δ=6.96-7.01 (m, 2H), 7.06-7.59 (m, 36H), 7.68-7.72 (m, 2H), 7.94-7.97 (m, 4H), 8.10-8.13 (m, 2H).

Figure 21A:
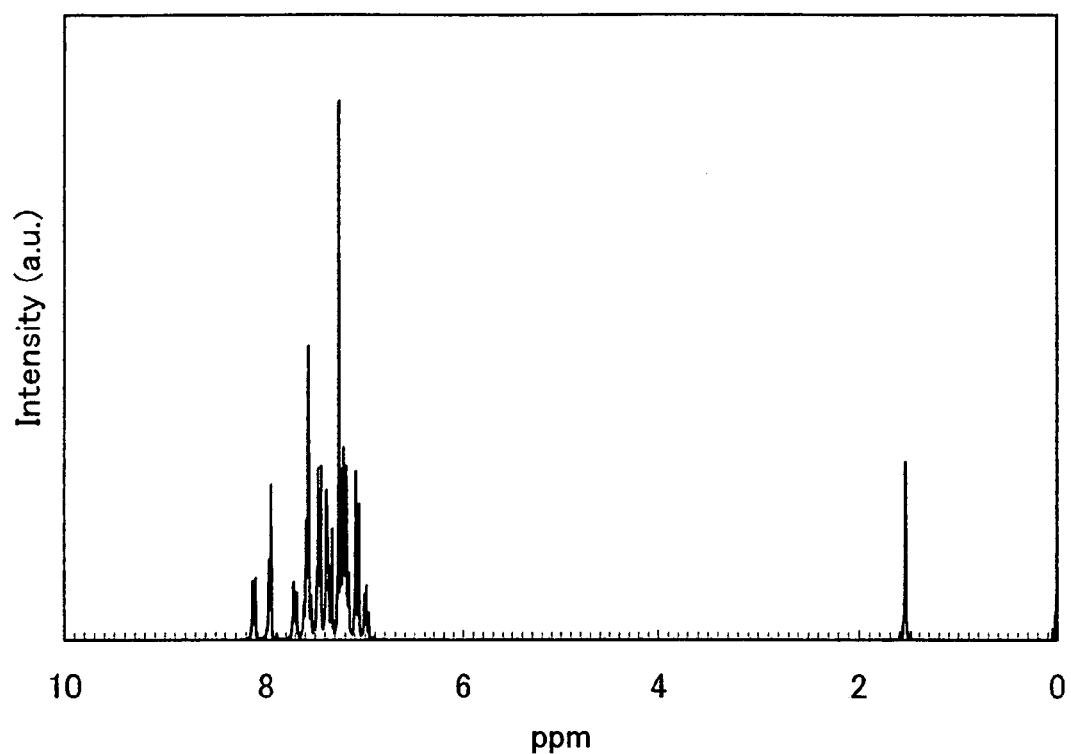
FIGS. 21A and 21B are graphs each showing a $^1$H NMR chart of N,N'-(quinoxaline-2,3-diyldi-4,1-phenylene)bis(N-phenyl-9-phenylcarbazole-3-amine) (abbreviation: PCAPQ)
Figure 21B:
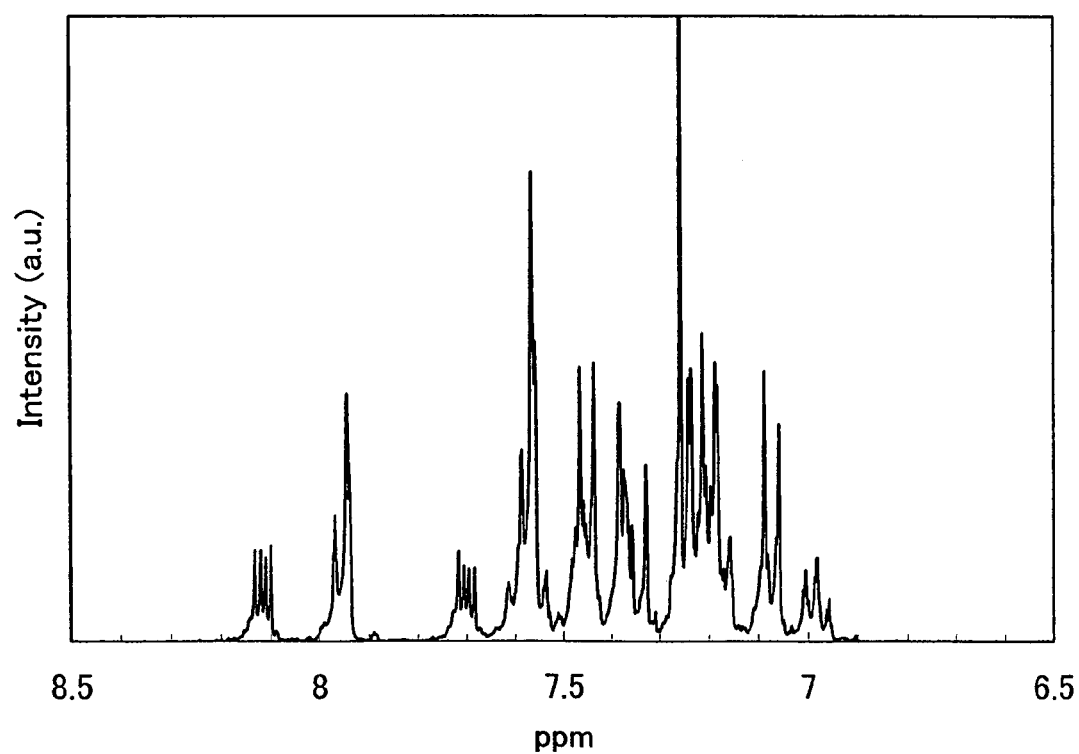

FIGS. 21A and 21B each show a $^1$H NMR chart, and FIG. 21B shows an expanded chart of FIG. 21A in a range of 6.5 ppm to 8.5 ppm.

Figure 22:
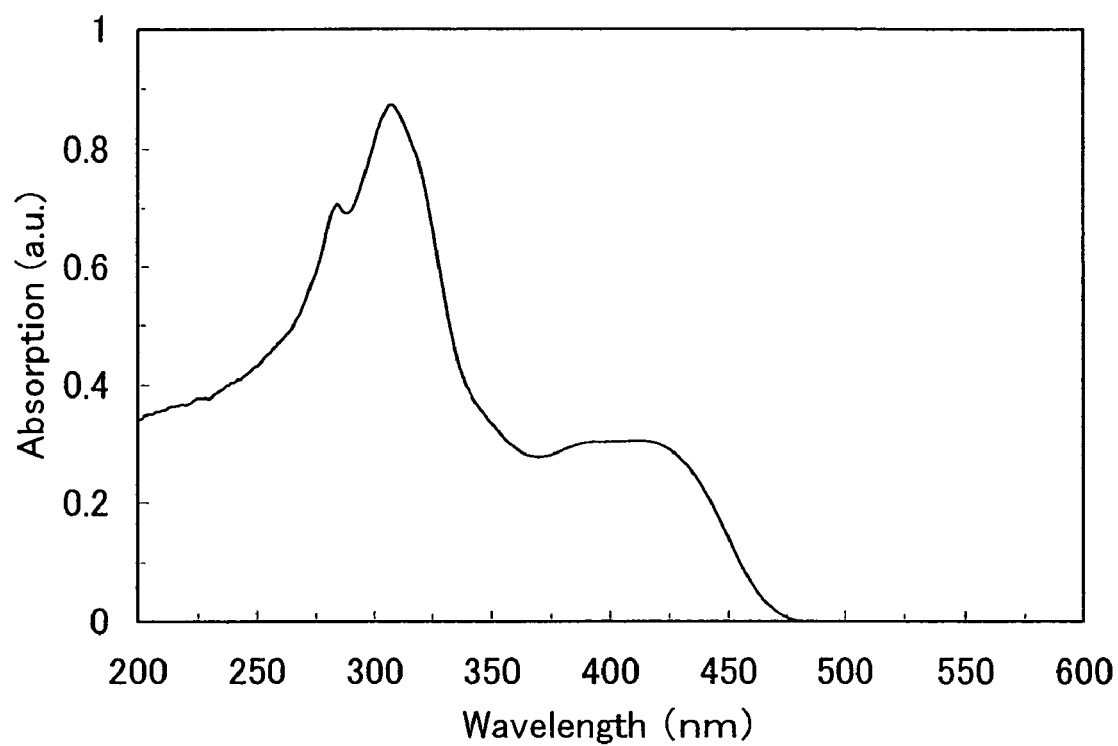
FIG. 22 is a graph showing an absorption spectrum of a toluene solution of N,N'-(quinoxaline-2,3-diyldi-4,1-phenylene)bis(N-phenyl-9-phenylcarbazole-3-amine) (abbreviation: PCAPQ)
Figure 23:
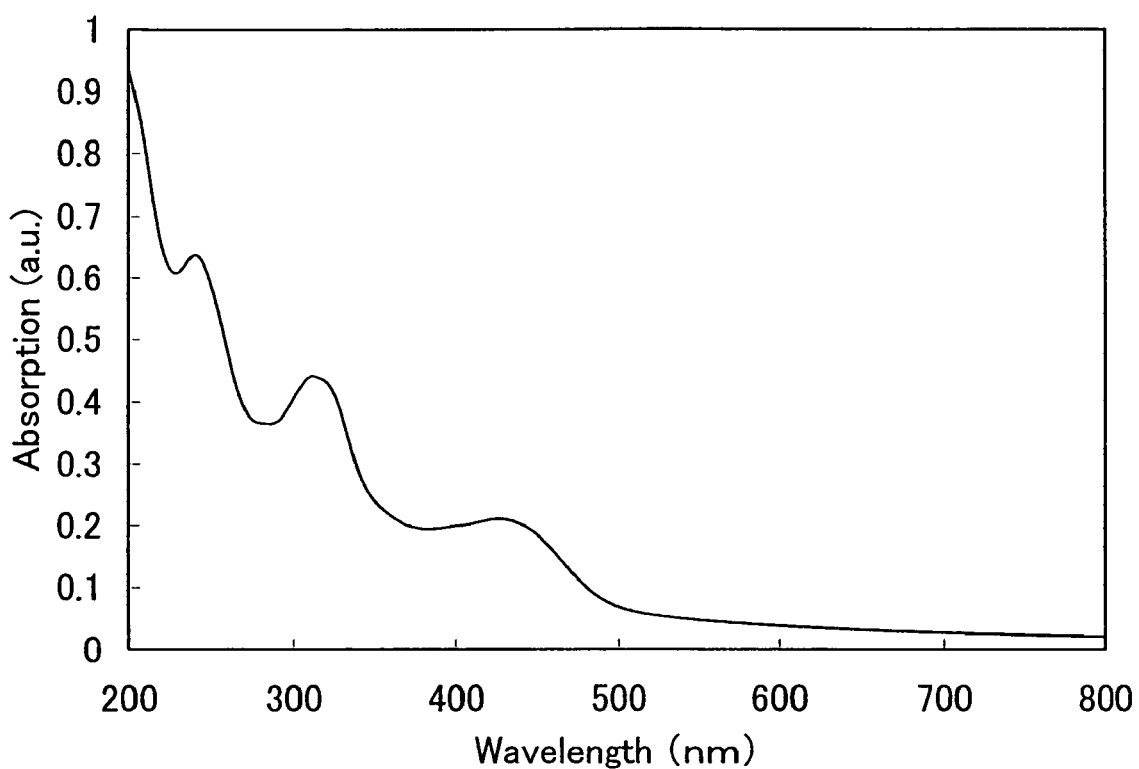
FIG. 23 is a graph showing an absorption spectrum of a thin film of N,N'-(quinoxaline-2,3-diyldi-4,1-phenylene)bis(N-phenyl-9-phenylcarbazole-3-amine) (abbreviation: PCAPQ)
Figure 24:
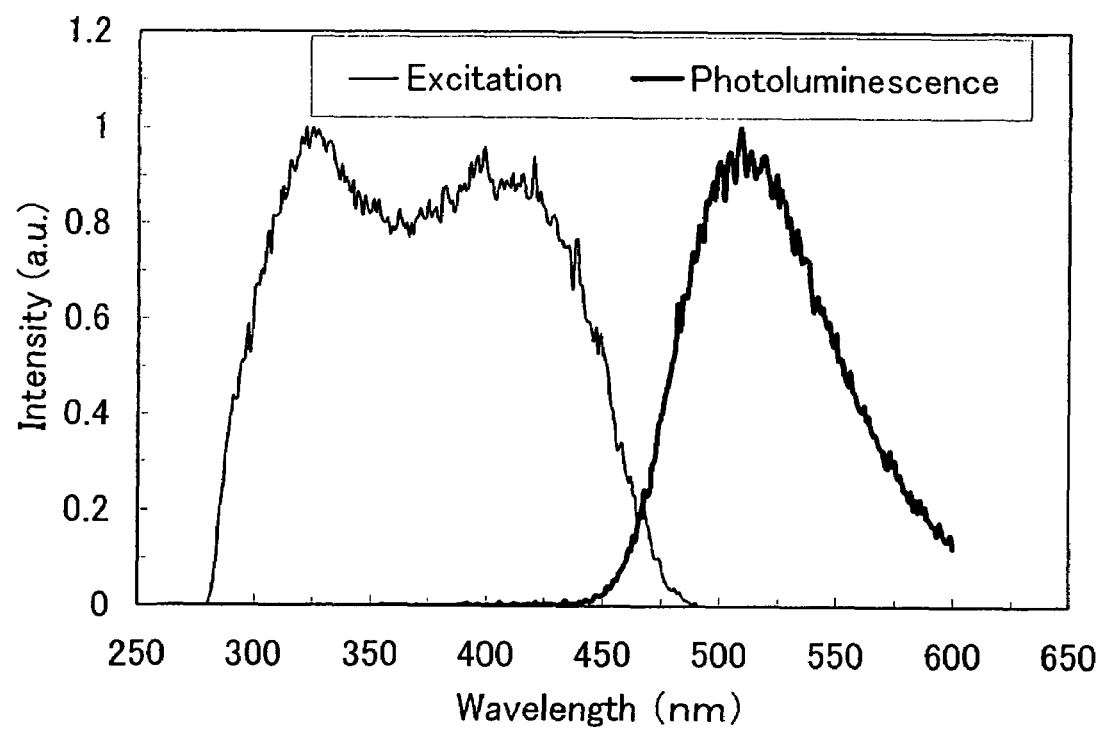
FIG. 24 is a graph showing an emission spectrum of a toluene solution of N,N'-(quinoxaline-2,3-diyldi-4,1-phenylene)bis(N-phenyl-9-phenylcarbazole-3-amine) (abbreviation: PCAPQ)
Figure 25:
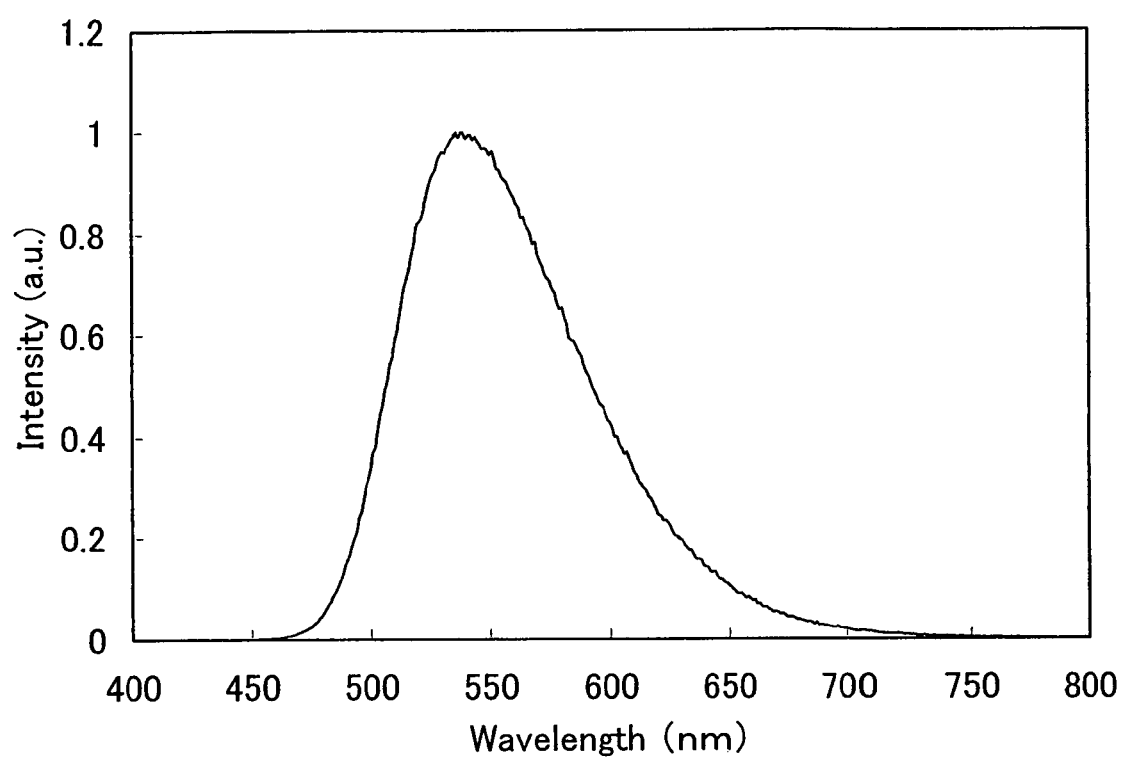
FIG. 25 is a graph showing an emission spectrum of a thin film of N,N'-(quinoxaline-2,3-diyldi-4,1-phenylene)bis(N-phenyl-9-phenylcarbazole-3-amine) (abbreviation: PCAPQ)

The decomposition temperature (T$_d$) of PCAPQ measured by a thermo-gravimetric/differential thermal analyzer (TG/DTA 320, manufactured by Seiko Instruments Inc.) was 477° C. Therefore, it was confirmed that PCAPQ shows high thermal stability FIG. 22 shows an absorption spectrum of a toluene solution of PCAPQ. FIG. 23 shows an absorption spectrum of a thin film of PCAPQ. An ultraviolet-visible spectrophotometer (V-550, manufactured by JASCO Corporation) was used for the measurement. The solution was put into a quartz cell, and the thin film sample was formed by vapor deposition of PCAPQ on a quartz substrate. The absorption spectra thereof, from each of which the absorption spectrum of quartz was subtracted, are shown in FIGS. 22 and 23. In FIGS. 22 and 23, the horizontal axis indicates the wavelength (nm) and the vertical axis indicates the absorption intensity (arbitrary unit). The absorption was observed at around 404 nm in the case of the toluene solution, and at around 426 nm in the case of the thin film. FIG. 24 shows the emission spectrum and the excitation spectrum of the toluene solution (the excitation wavelength: 395 nm) of PCAPQ. FIG. 25 shows the emission spectrum of a thin film (the excitation wavelength: 426 nm) of PCAPQ. In FIGS. 24 and 25, the horizontal axis indicates the wavelength (nm), and the vertical axis indicates the emission intensity (arbitrary unit). The maximum emission wavelength was 508 nm (the excitation wavelength: 395 nm) in the case of the toluene solution and 538 nm (the excitation wavelength: 426 nm) in the case of the thin film.

The result of measuring PCAPQ in a thin-film state using a photoelectron spectrometer (AC-2, manufactured by Riken Keiki Co., Ltd.) under the atmosphere showed that the HOMO level of PCAPQ is −5.29 eV. The optical energy gap evaluated by the results of the Tauc plot of the absorption spectrum shown in FIG. 23 revealed that the energy gap of YGAPQ in the solid state was 2.55 eV. This result means that the LUMO level of YGA1PQ in the solid state is −2.74 eV.

An oxidation profile and a reduction profile of PCAPQ were measured by cyclic voltammetry (CV) technique. An electrochemical analyzer (ALS model 600A, manufactured by BAS Inc.) was used for the measurement.

The solution for the CV measurement was prepared by using dehydrated N,N-dimethylformamide (DMF) (produced by Sigma-Aldrich Corp., 99.8%, catalog number: 22705-6) as a solvent, dissolving a supporting electrolyte of tetra-n-butylammonium perchlorate (n-Bu$_4$NClO$_4$) (produced by Tokyo Chemical Industry Co., Ltd., catalog number: T0836) at the concentration of 100 mmol/L and dissolving the sample at the concentration of 1 mmol/L. A platinum electrode (PTE platinum electrode, produced by BAS Inc.) was used as a working electrode, a platinum electrode (Pt counter electrode (5 cm) for VC-3, produced by BAS Inc.) was used as an auxiliary electrode, and an Ag/Ag$^+$ electrode (RE5 non-aqueous solvent reference electrode, produced by BAS Inc.) was used as a reference electrode. PCAPQ was measured at room temperature.

The oxidation profile of PCAPQ was examined as follows. A scan, in which a potential of the working electrode with respect to the reference electrode was varied from 0.7 V to −0.26 V after changing it from −0.26 V to 0.7 V, was regarded as one cycle, and measurement was performed for 100 cycles. The reduction reaction characteristic of PCAPQ was examined as follows. A scan, in which a potential of the working electrode with respect to the reference electrode was varied from −2.4 V to −0.6 V after changing it from −0.6 V to −2.4 V, was regarded as one cycle, and measurement was performed for 100 cycles. The scan rate of the CV measurement was set to be 0.1 V/s.

Figure 26:
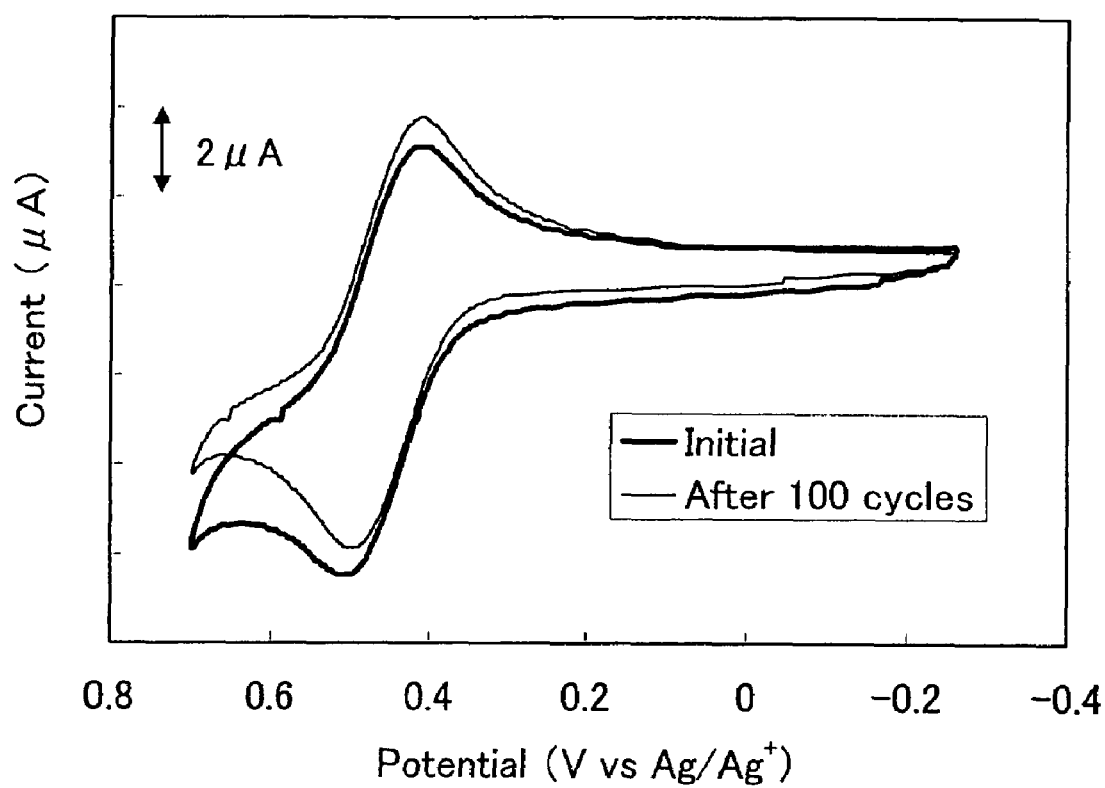
FIG. 26 is a graph showing a result of CV measurement of N,N'-(quinoxaline-2,3-diyldi-4,1-phenylene)bis(N-phenyl-9-phenylcarbazole-3-amine) (abbreviation: PCAPQ)
Figure 27:
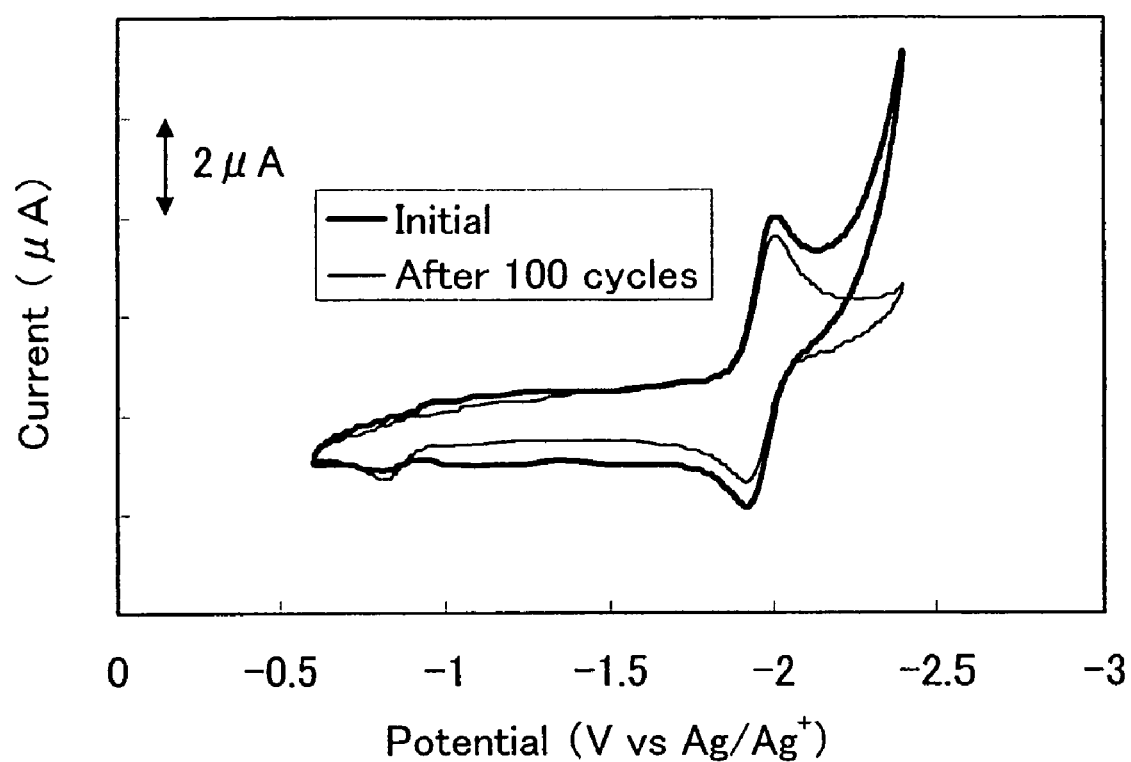
FIG. 27 is a graph showing a result of CV measurement of N,N'-(quinoxaline-2,3-diyldi-4,1-phenylene)bis(N-phenyl-9-phenylcarbazole-3-amine) (abbreviation: PCAPQ)

FIG. 26 shows the result of CV measurement of PCAPQ in an oxidation region and FIG. 27 shows the result of CV measurement of PCAPQ in a reduction region. In each of FIGS. 26 and 27, the horizontal axis indicates a potential (V) of the working electrode with respect to the reference electrode, and the vertical axis indicates a current value (μA) flowing between the working electrode and the auxiliary electrode. According to FIG. 26, currents indicating oxidation were observed at around 0.50 V (vs. Ag/Ag$^+$). According to FIG. 27, currents indicating reduction were observed at around −2.01 V (vs. Ag/Ag$^+$).

FIGS. 26 and 27 show that a reversible peak was obtained in both the oxidation region and reduction region. Further, even when the oxidation or reduction was repeated for 100 times, the cyclic voltamogram hardly changed. This means that PCAPQ is stable with respect to oxidation and reduction, that is, electrochemically stable.

EXAMPLE 4

Figure 29:
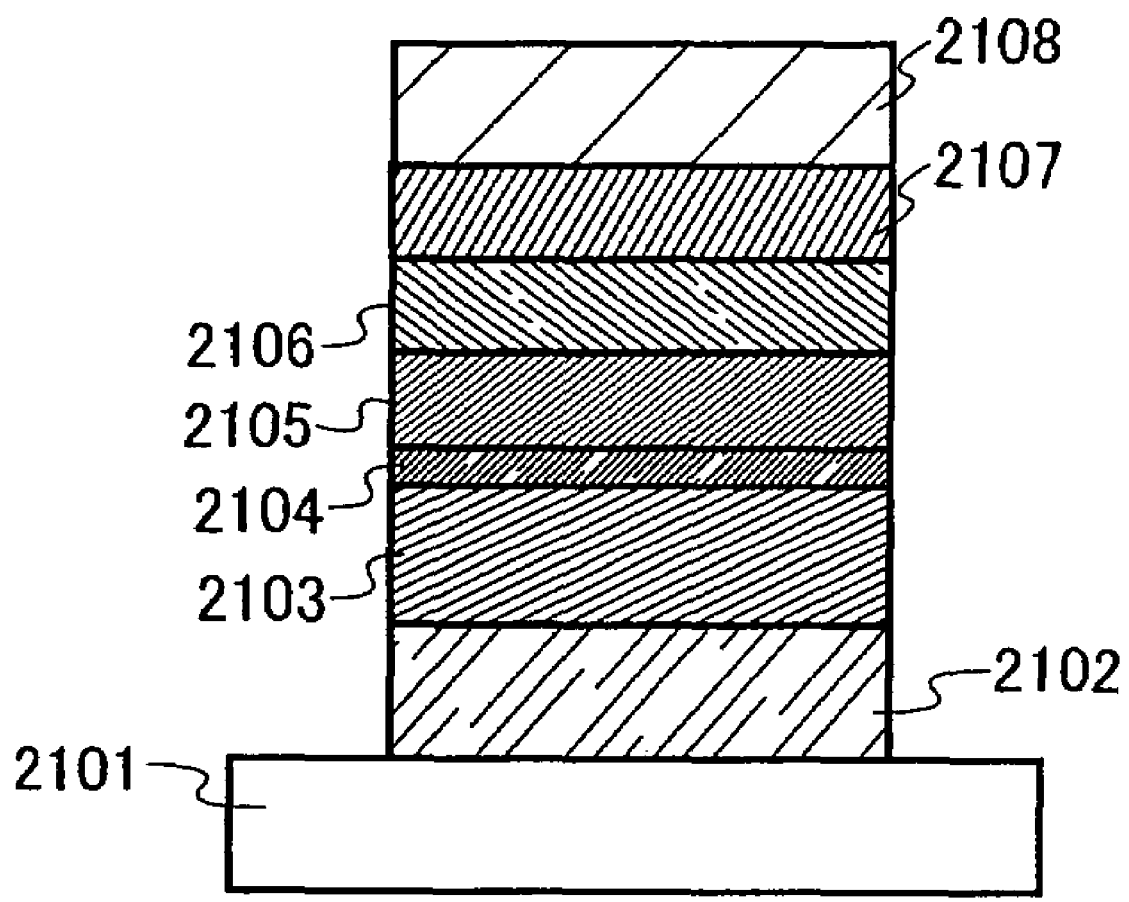
FIG. 29 is an explanatory view of a light-emitting element of examples.

In this example, a light-emitting element of the present invention will be explained with reference to FIG. 29. A chemical formula of the material used in this example, Example 5, and Example 6 is shown below.

formula [152]

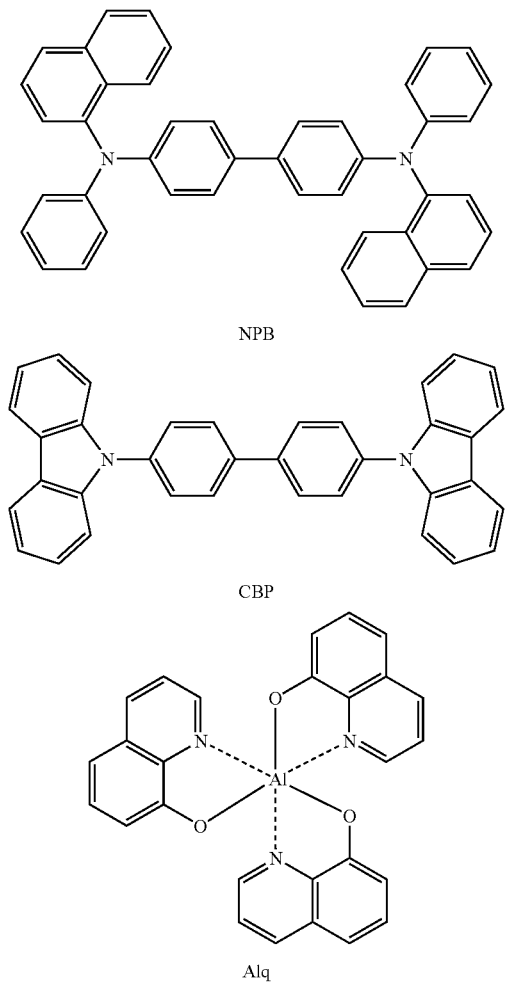

NPB

CBP

Alq

-continued

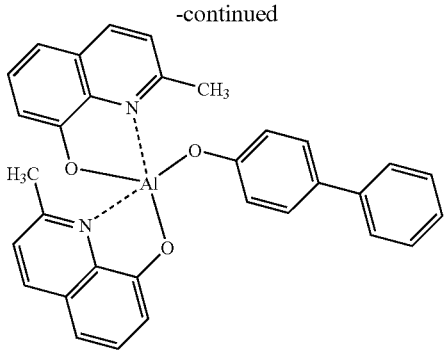

BAlq

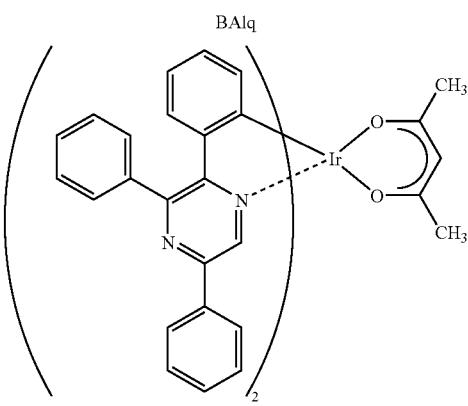

Ir(tppr)$_2$(acac)

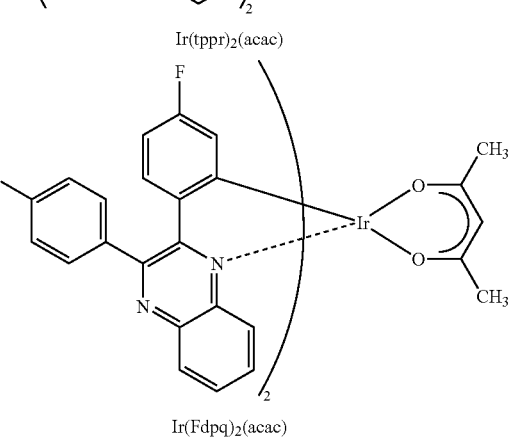

Ir(Fdpq)$_2$(acac)

(Light-Emitting Element 1)

First, indium tin oxide including silicon oxide was formed over a glass substrate 2101 by a sputtering method, thereby forming a first electrode 2102. It is to be noted that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, after the pressure of the evaporation apparatus was reduced to approximately 10$^{-4}$ Pa, a layer 2103 including a composite of an organic compound with an inorganic compound was formed on the first electrode 2102 by co-evaporation of NPB and molybdenum oxide (VI). A thickness thereof was adjusted to be 50 nm and a weight ratio of NPB to molybdenum oxide (VI) was adjusted to be 4:1 (=NPB:molybdenum oxide). It is to be noted that the co-evaporation method is an evaporation method in which evaporation is performed simultaneously from a plurality of evaporation sources in one evaporation chamber.

Next, 4,4'-bis[N-(1-napthyl)-N-phenylamino]biphenyl (abbreviation: NPB) was deposited at the thickness of 10 nm over the composite-including layer 2103 by the vapor deposition technique using resistance heating system, leading to the formation of a hole transporting layer 2104.

Furthermore, a light emitting layer 2105 with a thickness of 30 nm was formed on the hole transporting layer 2104 by co-evaporation of 4,4'-(quinoxaline-2,3-diyl)bis{N-[4-(9-carbazolyl)phenyl]-N-phenylbenzeneamine} (abbreviation: YGAPQ), represented by the structural formula (320), with (acetylacetonato)bis(2,3,5-triphenylpyrazinato)iridium(III) (abbreviation: Ir(tppr)$_2$(acac)). Here, a weight ratio of YGAPQ to Ir(tppr)$_2$(acac) was adjusted to be 1:0.05 (=YGAPQ:Ir(tppr)$_2$(acac)).

After that, bis(2-methyl-8-quinolinolato)(4-phenylphenolato)aluminum (abbreviation: BAlq) was formed at a thickness of 10 nm on the light emitting layer 2105 by the vapor deposition technique using resistance heating system, thereby forming an electron transporting layer 2106.

Moreover, an electron injecting layer 2107 with a thickness of 50 nm was formed on the electron transporting layer 2106 by co-evaporation of tris(8-quinolinolato)aluminum (abbreviation: Alq) with lithium. Here, a weight ratio of Alq to lithium was adjusted to be 1:0.01 (=Alq:lithium).

Finally, aluminum was formed at a thickness of 200 nm on the electron injecting layer 2107 by the vapor deposition technique using resistance heating system, thereby forming a second electrode 2108. Accordingly, a light-emitting element 1 was fabricated.

(Comparative Light-Emitting Element 2)

A light emitting layer 2105 with a thickness of 30 nm was formed by co-evaporation of 4,4'-di(N-carbazolyl)biphenyl (abbreviation: CBP) with (acetylacetonato)bis(2,3,5-triphenylpyrazinato)iridium(III) (abbreviation: Ir(tppr)$_2$(acac)). Here, a weight ratio of CBP to Ir(tppr)$_2$(acac) was adjusted to be 1:0.05 (=CBP:Ir(tppr)$_2$(acac)). The comparative light-emitting element 2 was formed in a same manner as that of the light-emitting element 1 other than the light emitting layer.

Figure 30:
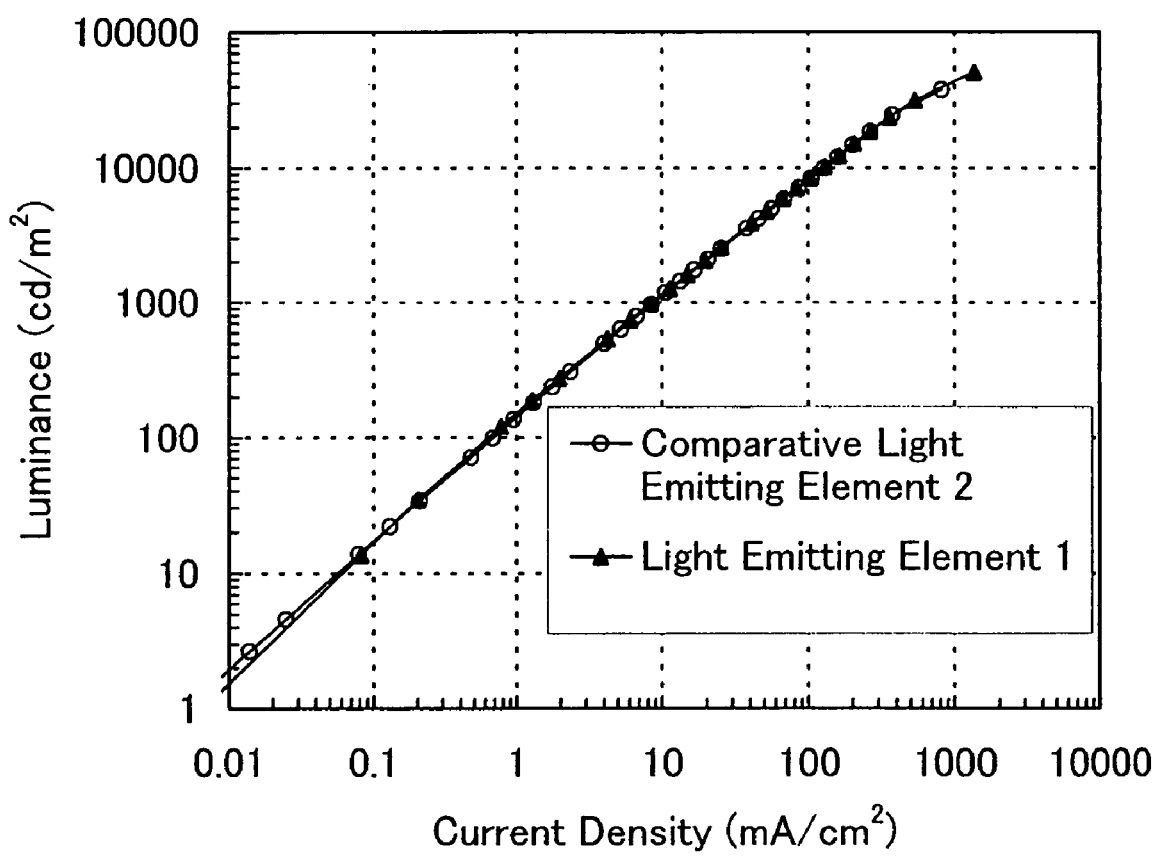
FIG. 30 is a graph showing current density-luminance characteristics of light-emitting elements fabricated in Example 4.
Figure 31:
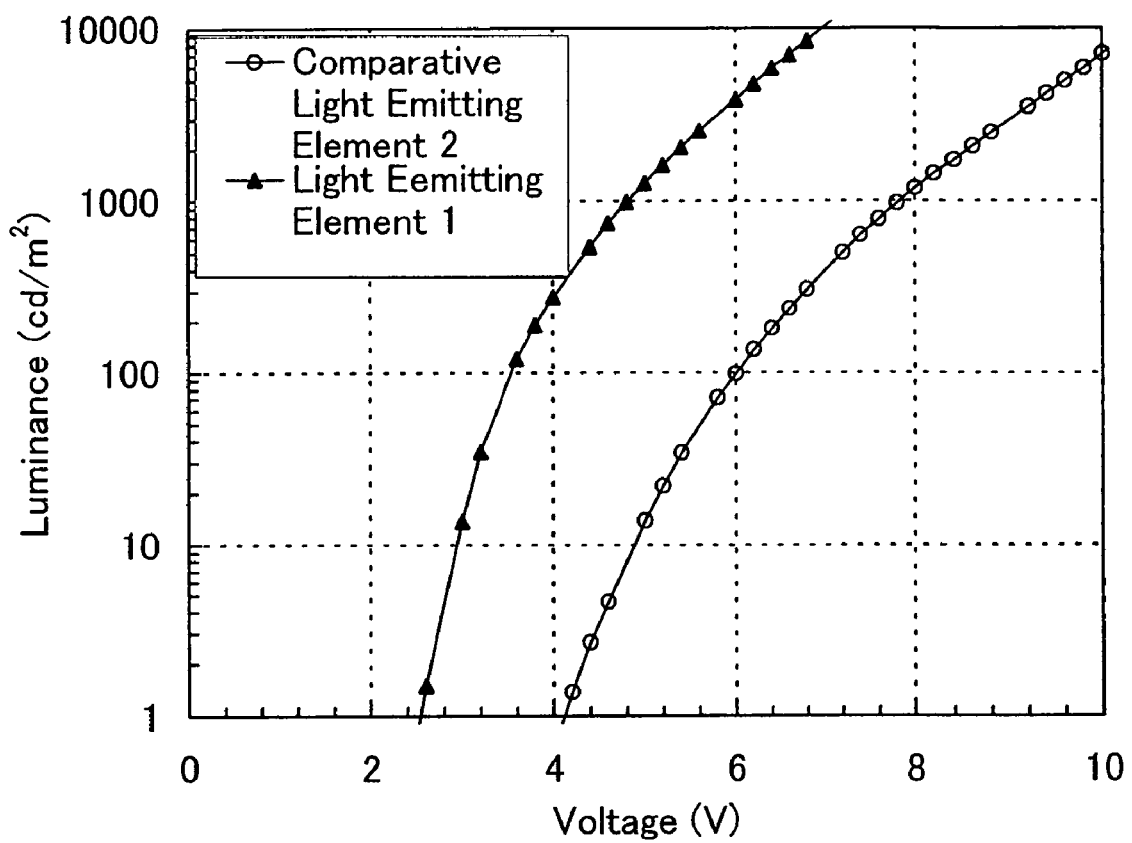
FIG. 31 is a graph showing voltage-luminance characteristics of light-emitting elements fabricated in Example 4.
Figure 32:
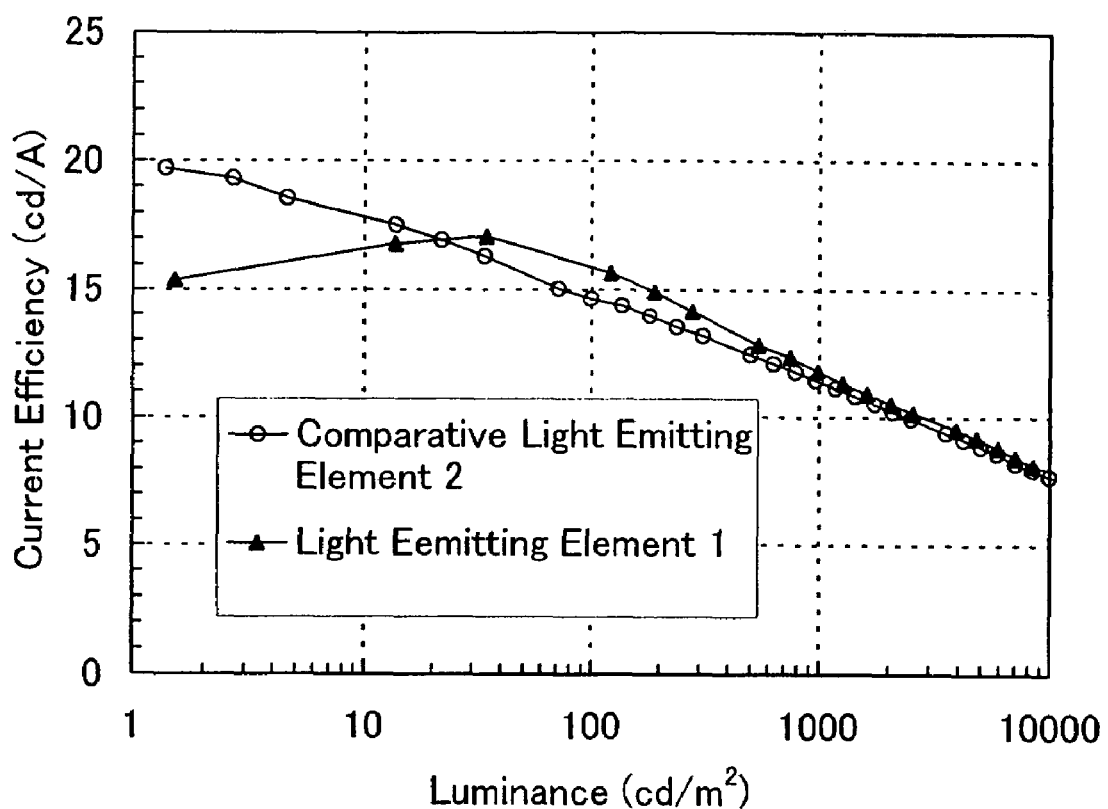
FIG. 32 is a graph showing luminance-current efficiency characteristics of light-emitting elements fabricated in Example 4.
Figure 33:
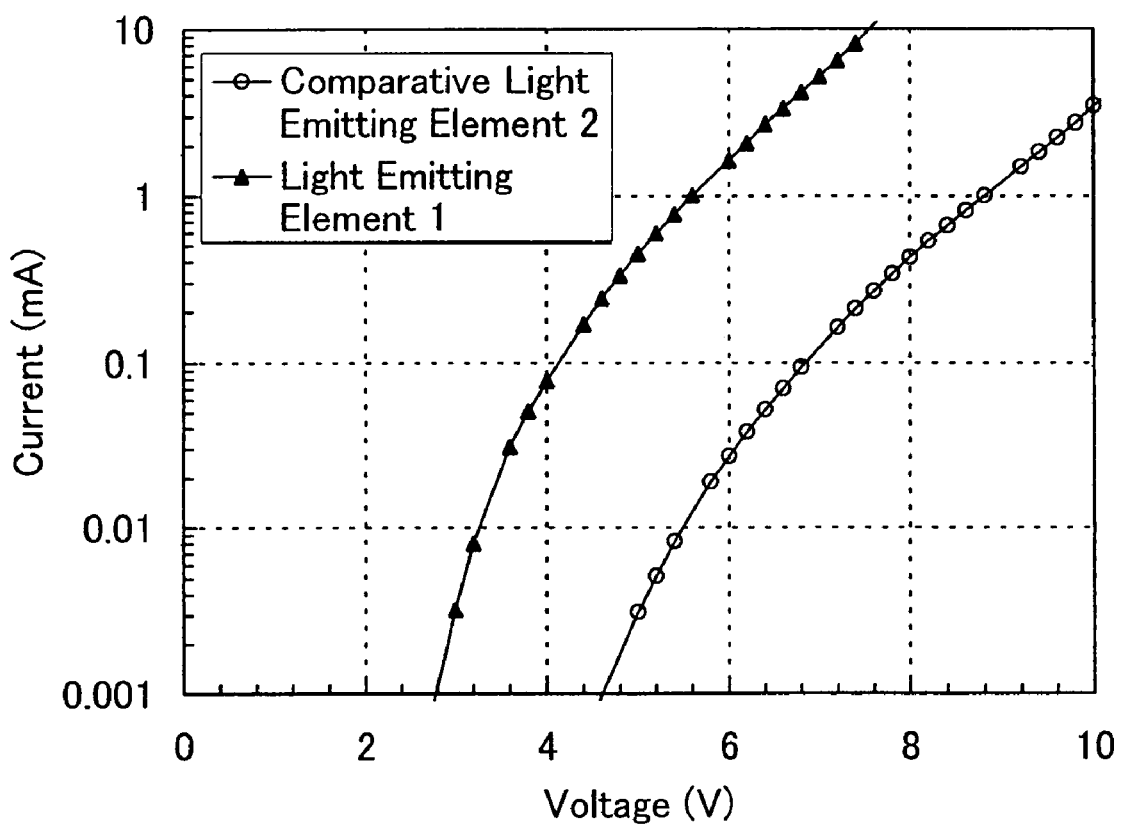
FIG. 33 is a graph showing voltage-current characteristics of light-emitting elements fabricated in Example 4.
Figure 34:
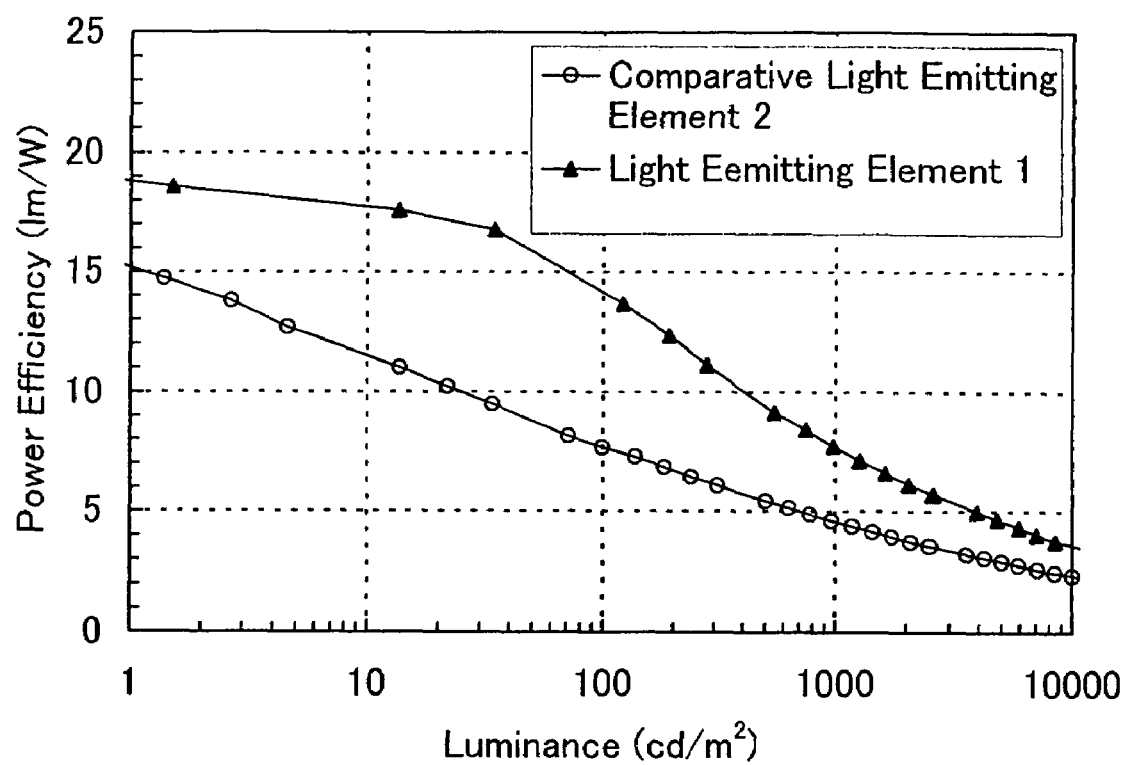
FIG. 34 is a graph showing luminance-power efficiency characteristics of light-emitting elements fabricated in Example 4.
Figure 35:
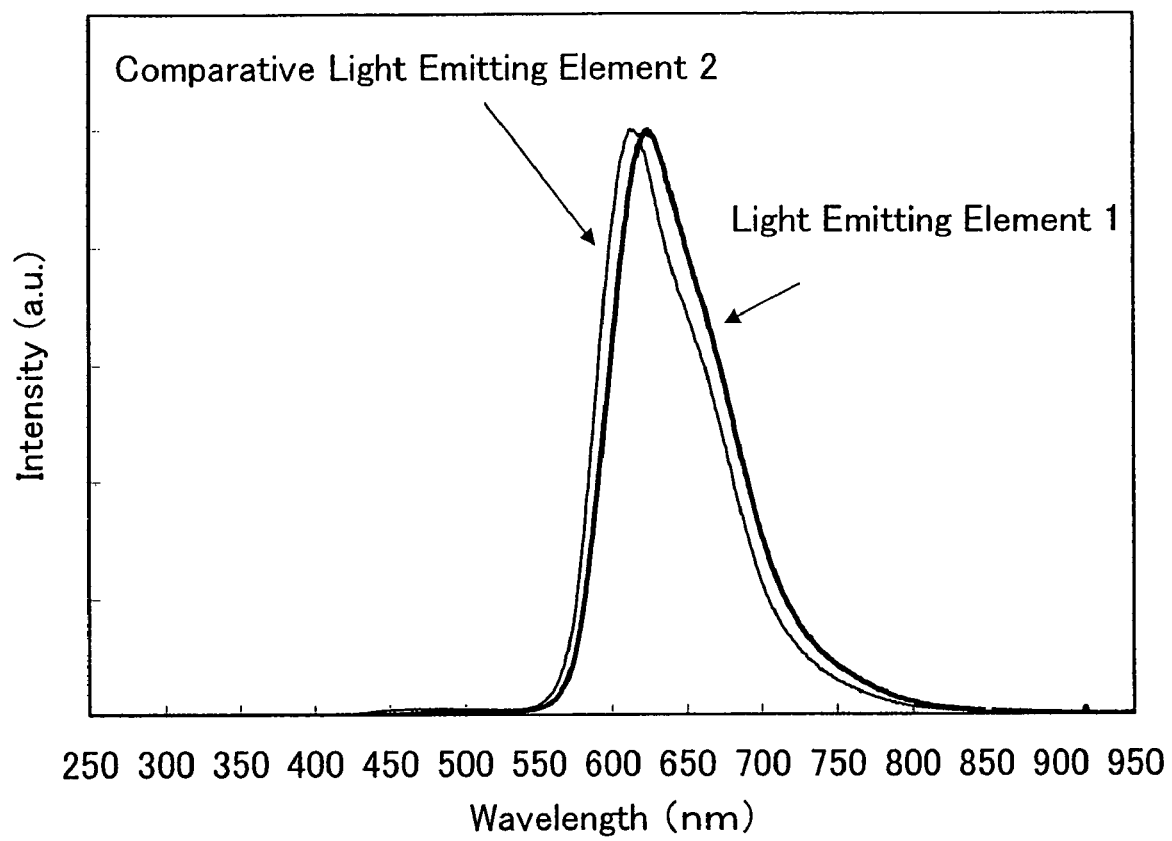
FIG. 35 is a graph showing emission spectra of light-emitting elements fabricated in Example 4.

FIG. 30 shows current density-luminance characteristics of the light-emitting element 1 and the comparative light-emitting element 2. FIG. 31 shows voltage-luminance characteristics. FIG. 32 shows luminance-current efficiency characteristics. FIG. 33 shows voltage-current characteristics. FIG. 34 shows luminance-power efficiency characteristics. FIG. 35 shows emission spectra when a current of 1 mA flows. FIG. 35 indicates that emission of the light-emitting element 1 and the comparative light-emitting element 2 is the emission from Ir(tppr)$_2$(acac).

In the light-emitting element 1, the CIE chromaticity coordinates at luminance of 980 cd/m$^2$ were (x, y)=(0.66, 0.34), and emission of red light was obtained. Current efficiency at luminance of 980 cd/m$^2$ was 12 cd/A, and external quantum efficiency was as high as 11%. Voltage at luminance of 980 cd/m$^2$ was 4.8 V, and current density was 8.3 mA/cm$^2$. The power efficiency was 7.7 lm/W which is an extremely high value.

On the other hand, in the comparative light-emitting element 2, the CIE chromaticity coordinates at luminance of 970 cd/m$^2$ were (x, y)=(0.64, 0.35), and emission of red light was obtained. Current efficiency at luminance of 970 cd/m$^2$ was 11 cd/A, and external quantum efficiency was 8.4%. Voltage at luminance of 970 cd/m$^2$ was 7.8 V; current density, 8.4 mA/cm$^2$; and power efficiency, 4.6 lm/W.

As evidenced by FIG. 32, the light-emitting element 1 and the comparative light-emitting element 2 show almost the same current efficiency. However, as shown in FIGS. 31 and 33, the light-emitting element 1 can be driven at lower voltage than the comparative light-emitting element 2. That is, a voltage required for obtaining a certain luminance is reduced.

As a result, as shown in FIG. 34, power efficiency is improved and power consumption is reduced in the light-emitting element 1 compared with the comparative light-emitting element 2. Therefore, the use of the quinoxaline derivative of the present invention allows the fabrication of a light-emitting element having low driving voltage and low power consumption.

Figure 36:
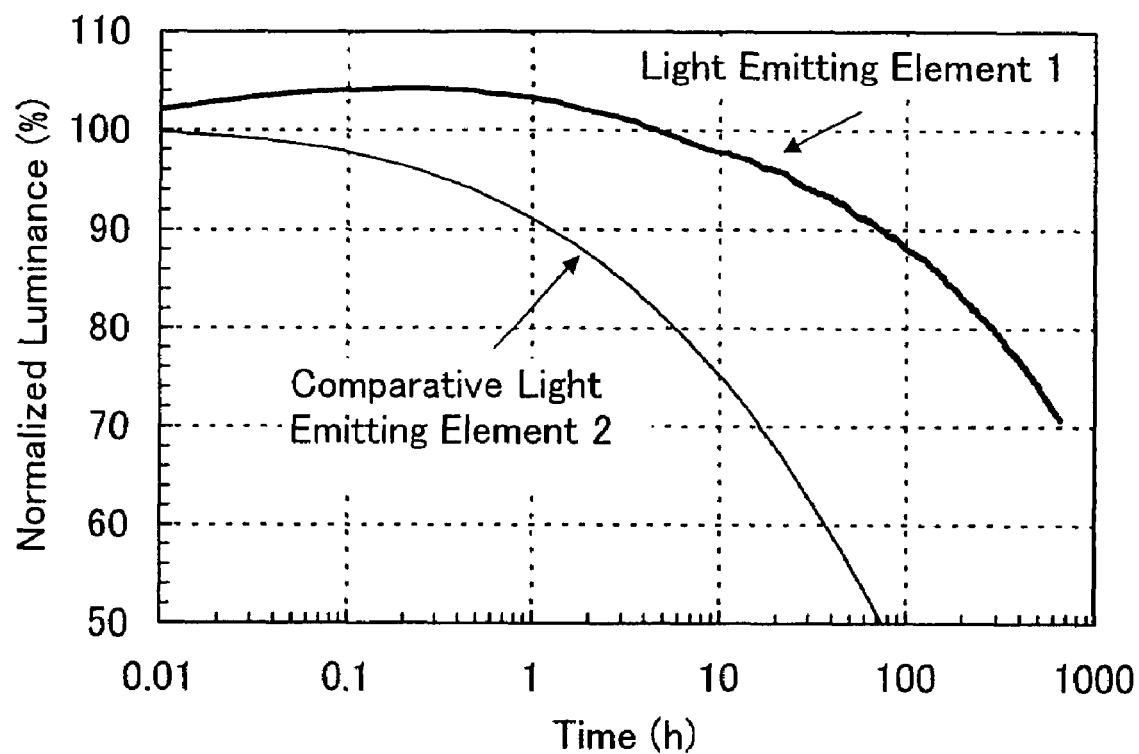
FIG. 36 is a graph showing time-dependence of normalized luminance of light-emitting elements fabricated in Example 4.
Figure 37:
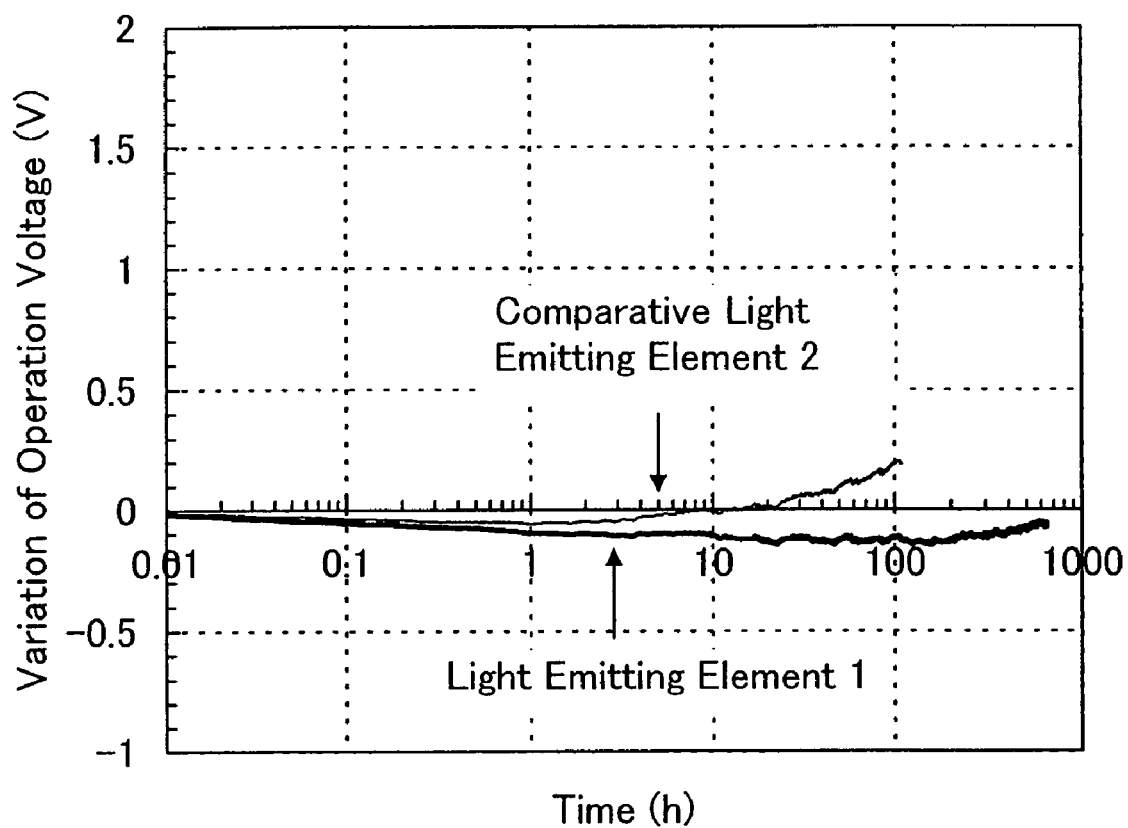
FIG. 37 is a graph showing variation of driving voltage on time for light-emitting elements fabricated in Example 4.

FIG. 36 shows time-dependence of normalized luminance of the light-emitting element 1 and the comparative light-emitting element 2. FIG. 37 shows change of the driving voltage on time. The measurement was carried out at an initial luminance of 1000 cd/m$^2$. FIG. 36 shows that change of luminance on time of the light-emitting element 1 is small compared with that of the comparative light-emitting element 2.

FIG. 37 shows that change of voltage on time of the light-emitting element 1 is small compared with the comparative light-emitting element 2. Accordingly, by using the quinoxaline derivative of the present invention, a long-life light-emitting element can be obtained.

EXAMPLE 5

In this example, a light-emitting element of the present invention will be explained with reference to FIG. 29.

(Light-Emitting Element 3)

First, indium tin oxide including silicon oxide was formed over a glass substrate 2101 by a sputtering method, thereby forming a first electrode 2102. It is to be noted that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 including a composite of an organic compound with an inorganic compound was formed on the first electrode 2102 by co-evaporation of NPB and molybdenum oxide (VI) after a pressure of the evaporation apparatus was reduced to approximately 10$^{-4}$ Pa. A thickness thereof was adjusted to be 50 nm and a weight ratio of NPB to molybdenum oxide (VI) was adjusted to be 4:1 (=NPB:molybdenum oxide). It is to be noted that the co-evaporation method is an evaporation method in which evaporation is performed simultaneously from a plurality of evaporation sources in one evaporation chamber.

Next, 4,4'-bis[N-(1-napthyl)-N-phenylamino]biphenyl (abbreviation: NPB) was deposited at the thickness of 10 nm on the composite-including layer 2103 by the vapor deposition technique using resistance heating system, leading to the formation of a hole transporting layer 2104.

Furthermore, a light emitting layer 2105 with a thickness of 30 nm was formed on the hole transporting layer 2104 by co-evaporation of 4,4'-(quinoxaline-2,3-diyl)bis{N-[4-(9-carbazolyl)phenyl]-N-phenylbenzeneamine} (abbreviation: YGAPQ), represented by the structural formula (320), with (acetylacetonato)bis[2,3-bis(4-fluorophenyl)quinoxalinato] iridium(III) (abbreviation: Ir(Fdpq)$_2$(acac)). Here, a weight ratio of YGAPQ to Ir(Fdpq)$_2$(acac) was adjusted to be 1:0.06 (=YGAPQ:Ir(Fdpq)$_2$(acac)).

After that, bis(2-methyl-8-quinolinolato)(4-phenylphenolato)aluminum (abbreviation: BAlq) was formed at a thickness of 10 nm on the light emitting layer 2105 by the vapor deposition technique using resistance heating system, thereby forming an electron transporting layer 2106.

Moreover, an electron injecting layer 2107 with a thickness of 50 nm was formed on the electron transporting layer 2106 by co-evaporation of tris(8-quinolinolato)aluminum (abbreviation: Alq) with lithium. Here, a weight ratio of Alq to lithium was adjusted to be 1:0.01 (=Alq:lithium).

Finally, aluminum was formed at a thickness of 200 nm on the electron injecting layer 2107 by the vapor deposition technique using resistance heating system, thereby forming a second electrode 2108. Accordingly, a light-emitting element 3 was fabricated.

(Light-Emitting Element 4)

As an electron transporting layer 2106, tris(8-quinolinolato)aluminum (abbreviation: Alq) was formed at a thickness of 10 nm. The light-emitting element 4 was formed in the same manner as the light-emitting element 3 other than the electron transporting layer.

Figure 38:
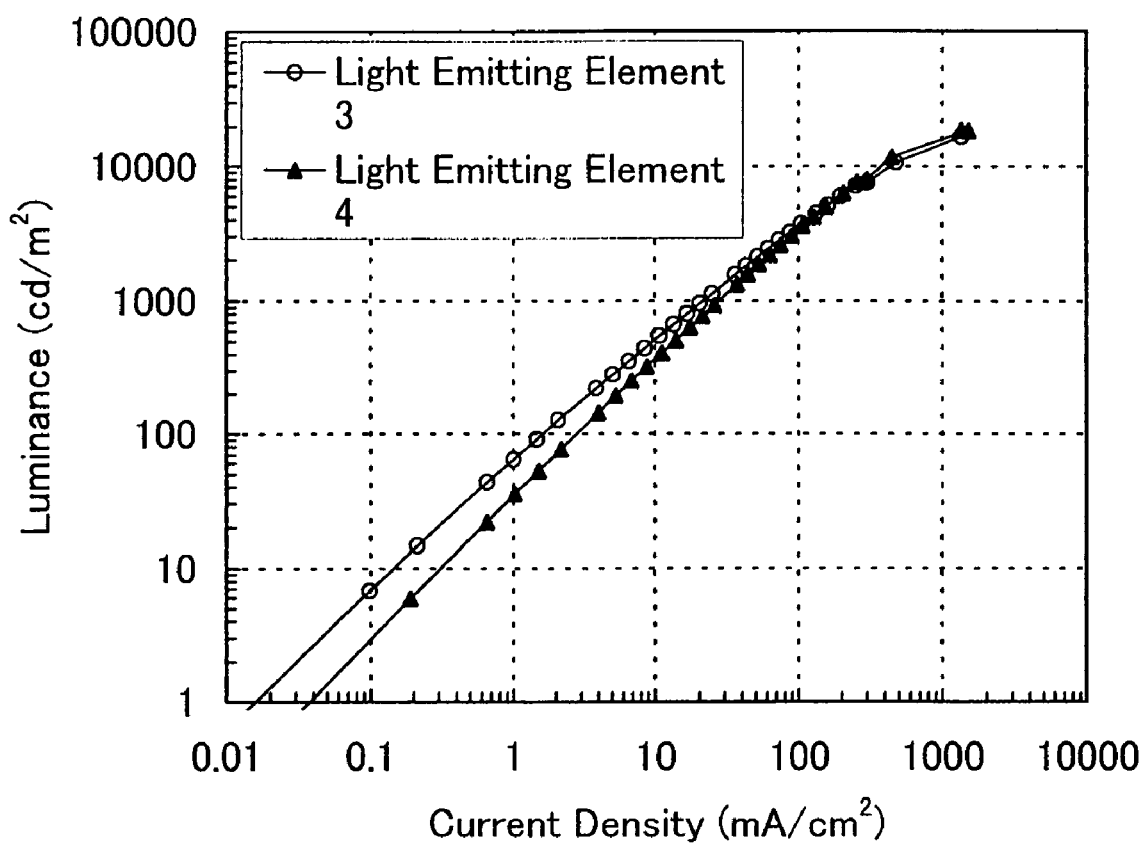
FIG. 38 is a graph showing current density-luminance characteristics of light-emitting elements fabricated in Example 5.
Figure 39:
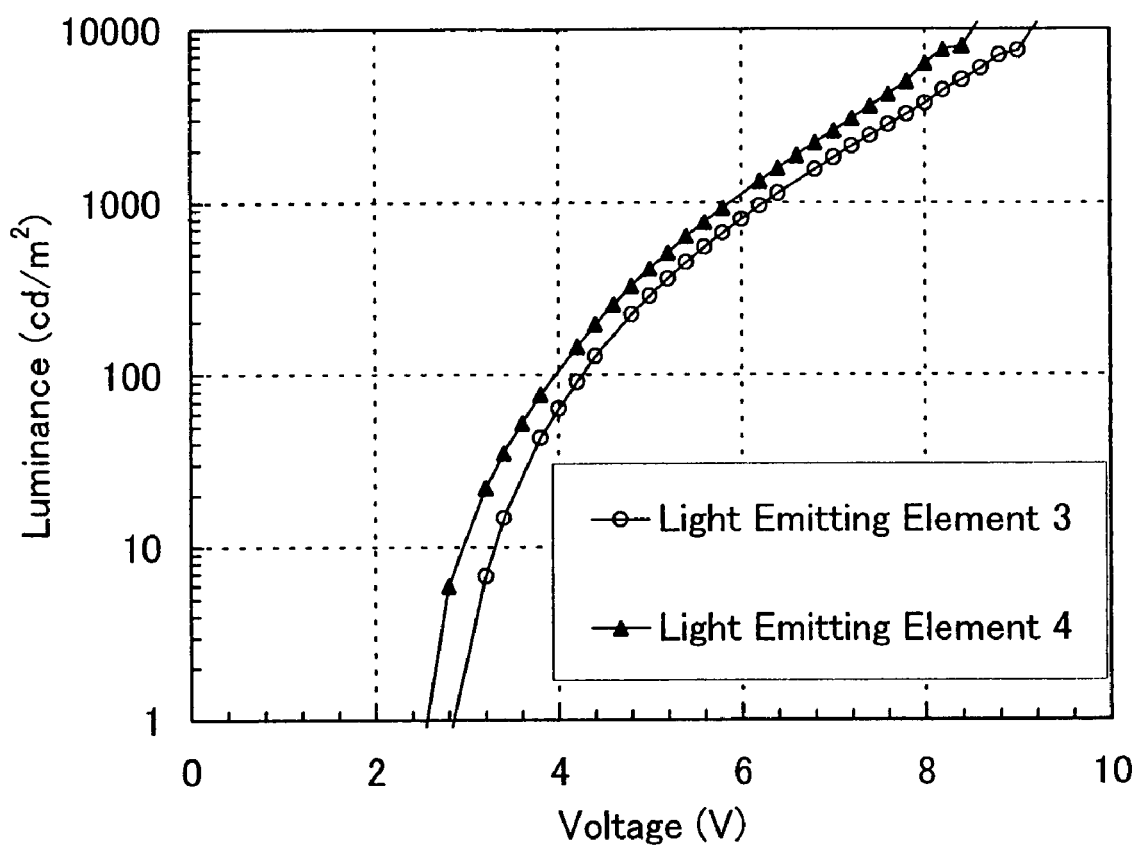
FIG. 39 is a graph showing voltage-luminance characteristics of light-emitting elements fabricated in Example 5.
Figure 40:
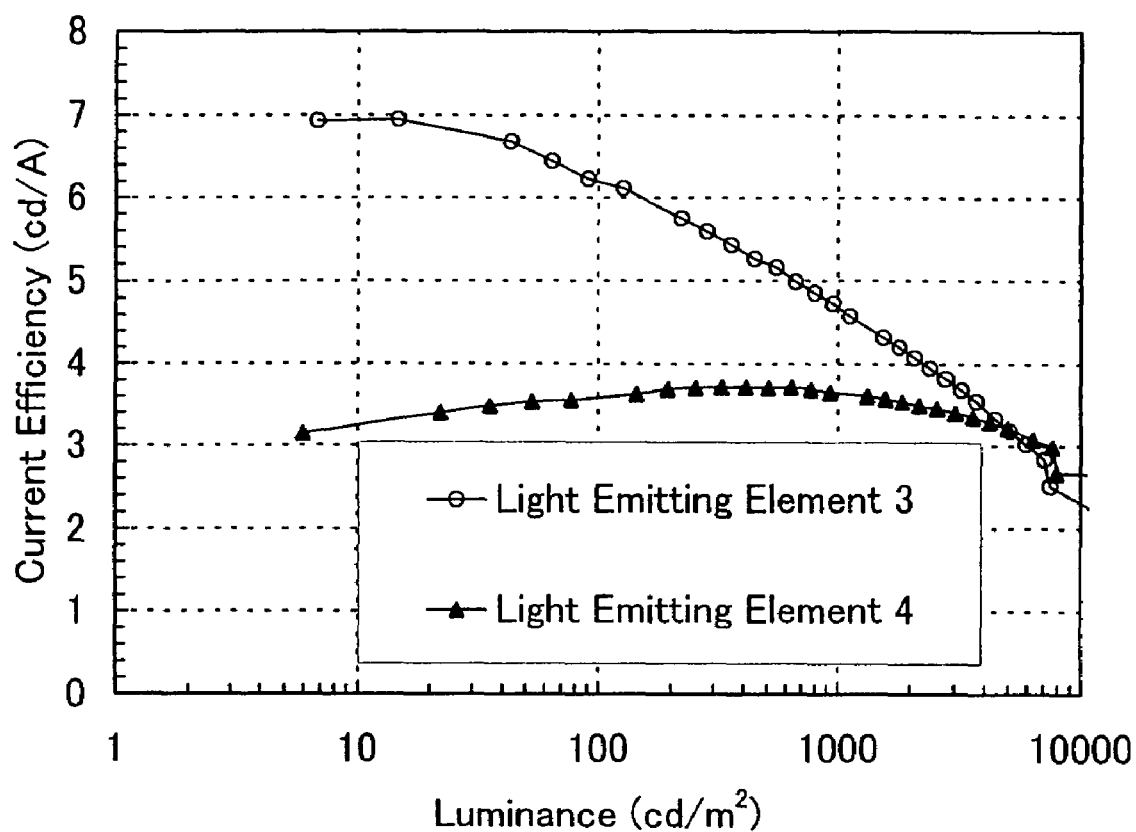
FIG. 40 is a graph showing luminance-current efficiency characteristics of light-emitting elements manufactured in Example 5.
Figure 41:
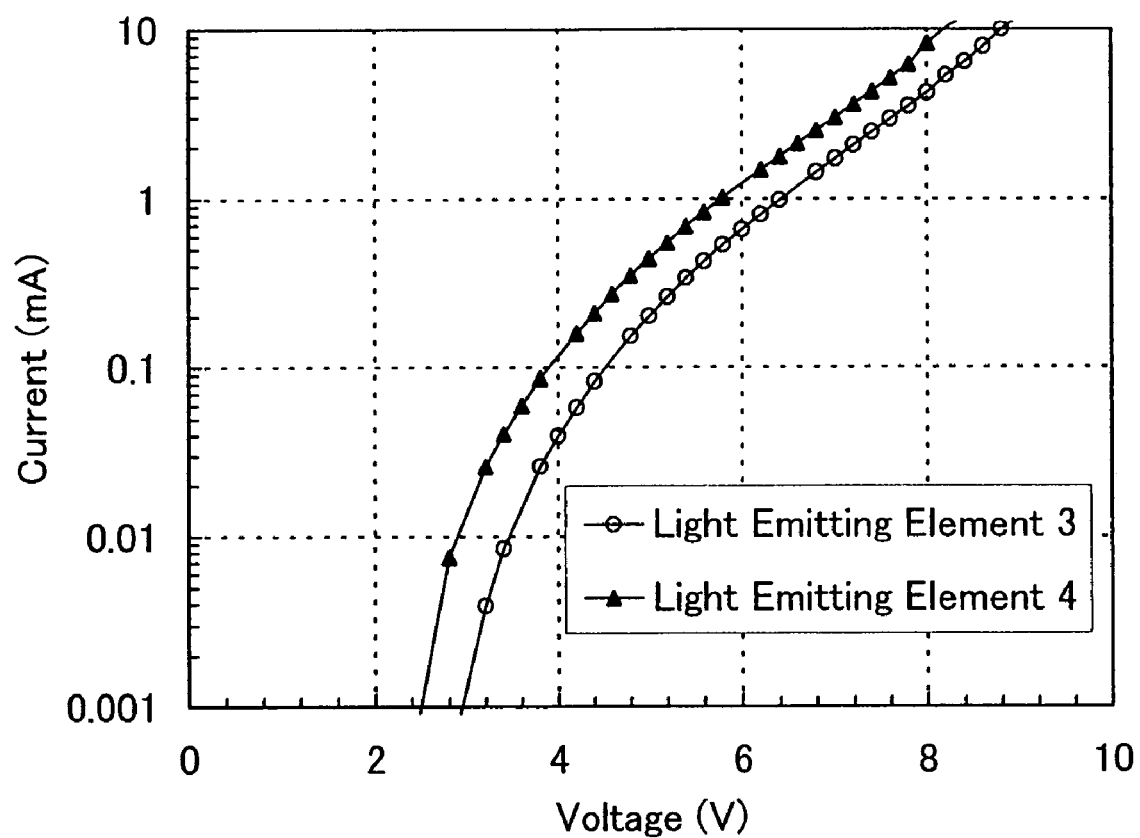
FIG. 41 is a graph showing voltage-current characteristics of light-emitting elements fabricated in Example 5.
Figure 42:
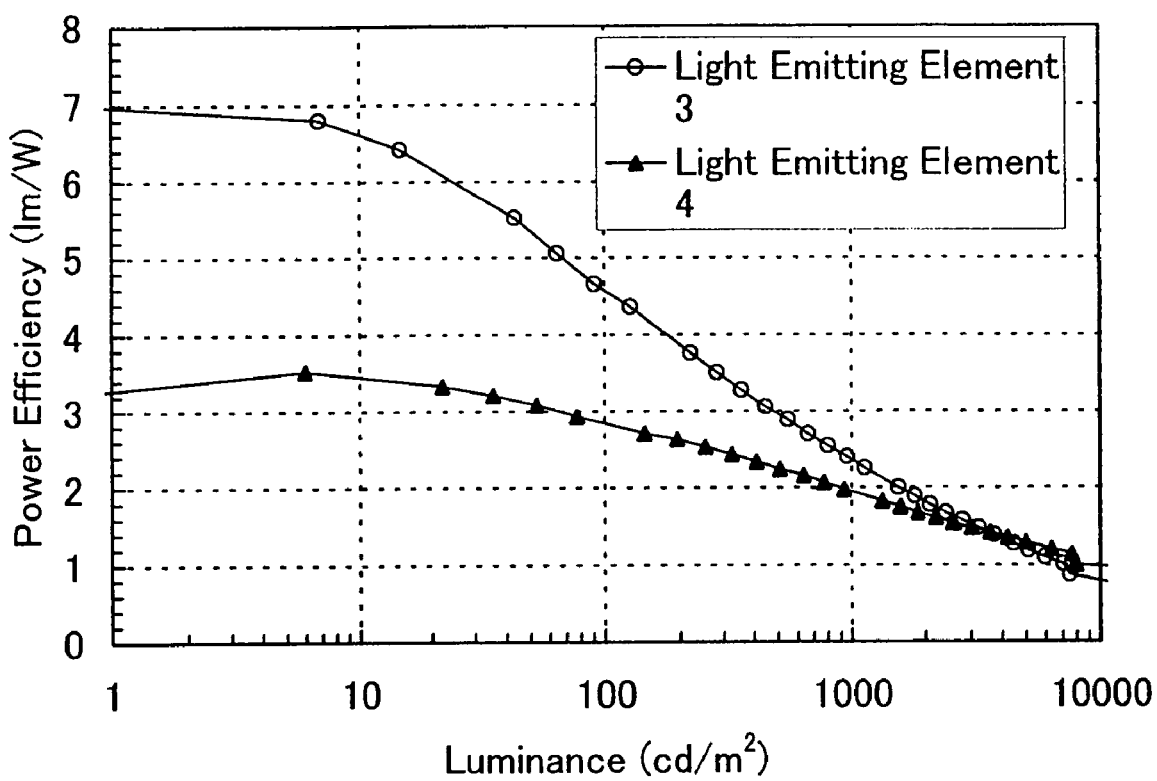
FIG. 42 is a graph showing luminance-power efficiency characteristics of light-emitting elements fabricated in Example 5.
Figure 43:
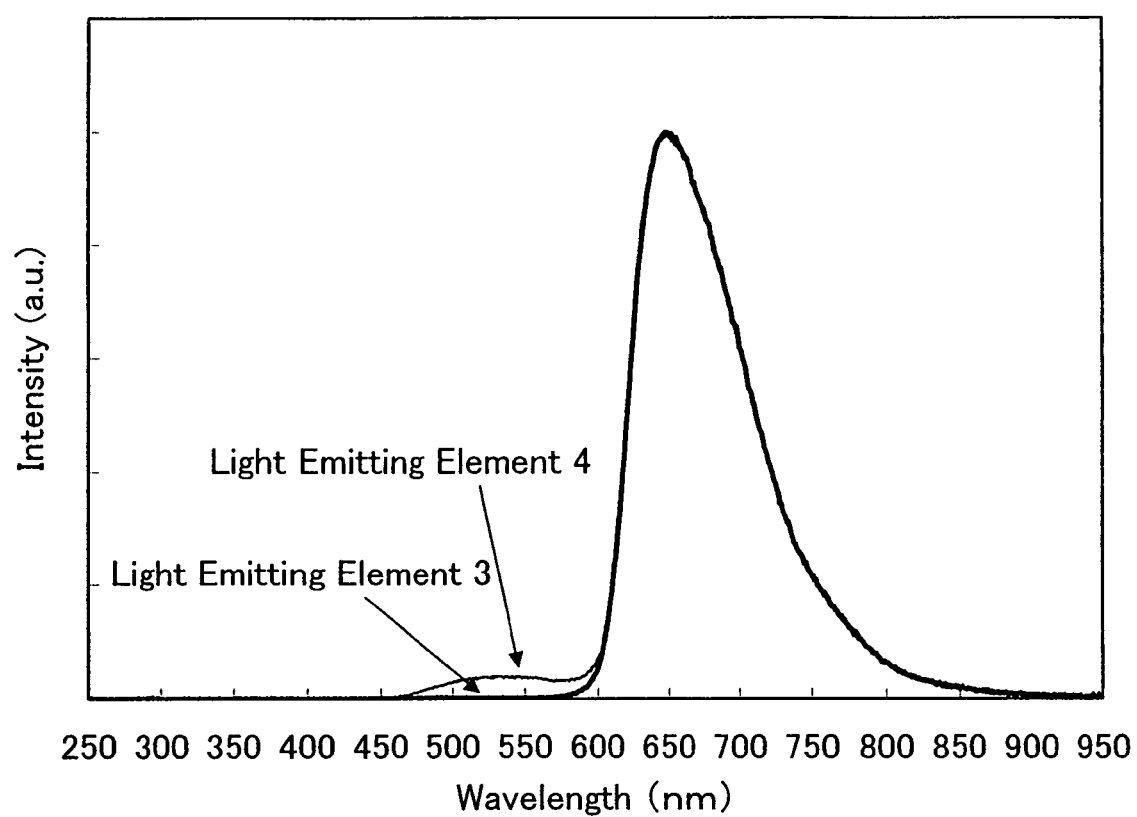
FIG. 43 is a graph showing emission spectra of light-emitting elements fabricated in Example 5.

FIG. 38 shows current density-luminance characteristics of the light-emitting element 3 and the light-emitting element 4. FIG. 39 shows voltage-luminance characteristics. FIG. 40 shows luminance-current efficiency characteristics. FIG. 41 shows voltage-current characteristics. FIG. 42 shows luminance-power efficiency characteristics. FIG. 43 shows emission spectra when a current of 1 mA flows. FIG. 43 demonstrates that emission of the light-emitting element 3 and the light-emitting element 4 is emission of Ir(Fdpq)$_2$(acac).

In the light-emitting element 3, the CIE chromaticity coordinates at luminance of 960 cd/m$^2$ were (x, y)=(0.71, 0.28), and emission of red light with excellent color purity was obtained. Current efficiency at luminance of 960 cd/m$^2$ was 4.7 cd/A, and external quantum efficiency was 12% which were extremely high efficiency. Voltage and current density at luminance of 960 cd/m$^2$ were 6.2 V and 20 mA/cm$^2$; respectively, and power efficiency was 2.4 μm/W which is an extremely high value.

In the light-emitting element 4, the CIE chromaticity coordinates at luminance of 930 cd/m$^2$ were (x, y)=(0.65, 0.33), and emission of red light was obtained. Current efficiency at luminance of 930 cd/m$^2$ was 3.6 cd/A, and external quantum efficiency was 7.2%, which means that high efficiency is realized. Voltage and current density at luminance of 930 cd/m$^2$ were 5.8 V and 26 mA/cm$^2$, respectively, and power efficiency was as high as 2.0 lm/W.

FIGS. 39 and 41 show that a driving voltage is reduced in the light-emitting element 3 and the light-emitting element 4. Accordingly, the use of the quinoxaline derivative of the present invention enables it to provide a light-emitting element having a low driving voltage and reduced power consumption. In particular, in the light-emitting element 3, a driving voltage is further reduced than in the light-emitting element 4. In addition, as evidenced by FIG. 40, higher current efficiency is obtained in the light-emitting element 3 than in the light-emitting element 4. As a result, as shown in FIG. 42, power efficiency is improved and power consumption is reduced in the light-emitting element 3 compared with the light-emitting element 4.

Figure 44:
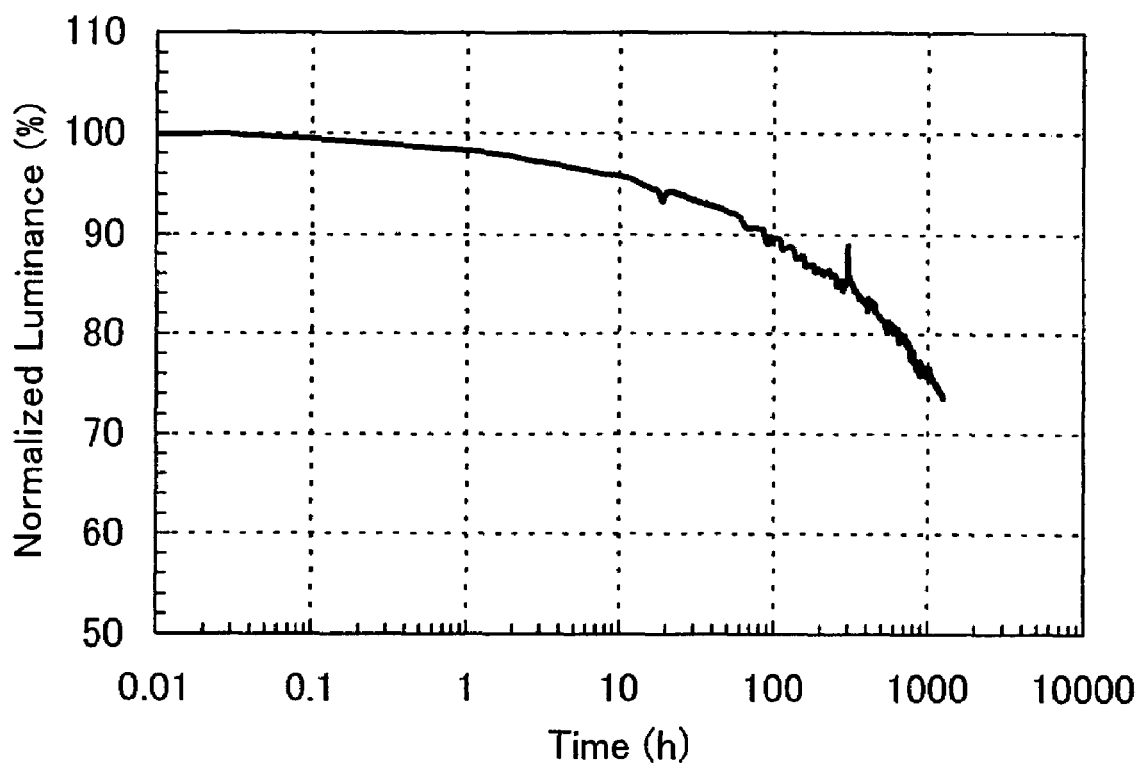
FIG. 44 is a graph showing time-dependence of normalized luminance of light-emitting elements fabricated in Example 5.
Figure 45:
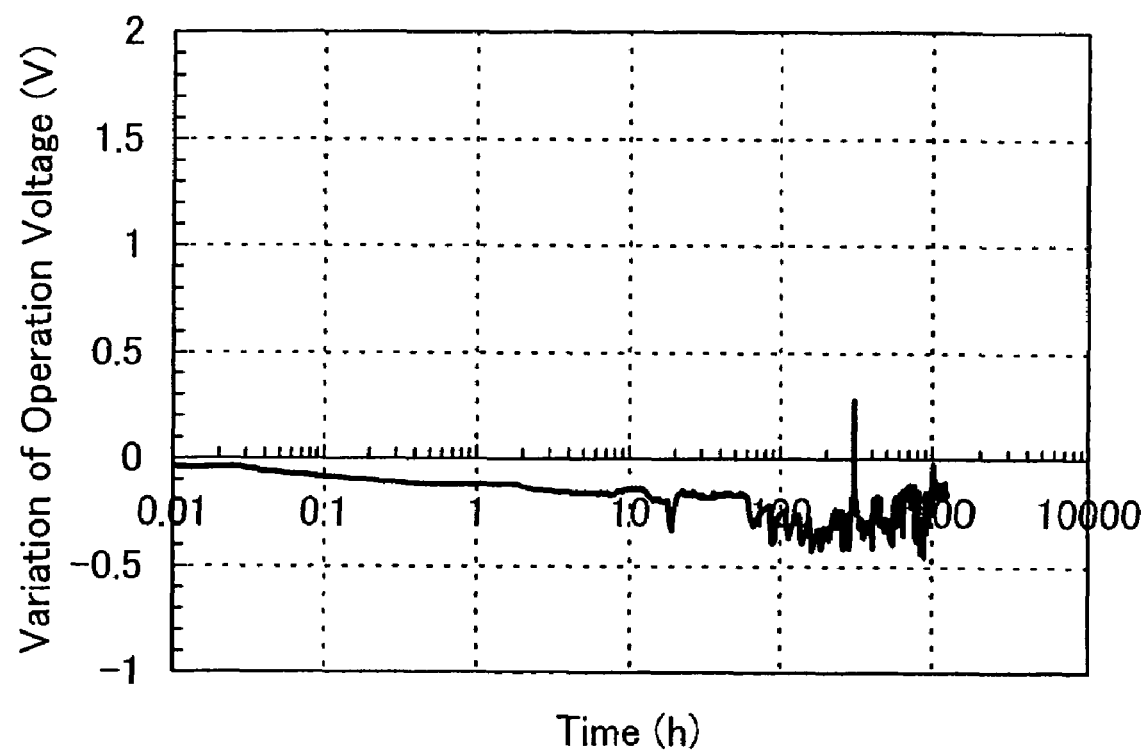
FIG. 45 is a graph showing variation of driving voltage on time for light-emitting elements fabricated in Example 5.

FIG. 44 shows time-dependence of normalized luminance of the light-emitting element 4. FIG. 45 shows change of driving voltage on time. The measurement was carried out at an initial luminance of 1000 cd/m$^2$. FIG. 44 shows that change of luminance on time of the light-emitting element 4 is small. FIG. 45 shows that change of voltage on time of the light-emitting element 4 is small. Therefore, by using the quinoxaline derivative of the present invention, a long-life light-emitting element can be obtained.

EXAMPLE 6

In this example, a light-emitting element of the present invention will be explained with reference to FIG. 29.

(Light-Emitting Element 5)

First, indium tin oxide including silicon oxide was formed over a glass substrate 2101 by a sputtering method, thereby forming a first electrode 2102. It is to be noted that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 including a composite of an organic compound with an inorganic compound was formed on the first electrode 2102 by co-evaporation of NPB with molybdenum oxide (VI) after the pressure of the evaporation apparatus was reduced to approximately 10$^{-4}$ Pa. A thickness thereof was adjusted to be 50 nm and a weight ratio of NPB to molybdenum oxide (VI) was adjusted to be 4:1 (=NPB:molybdenum oxide). It is to be noted that the co-evaporation method is an evaporation method by which evaporation is performed simultaneously from a plurality of evaporation sources in one evaporation chamber.

Next, 4,4'-bis[N-(1-napthyl)-N-phenylamino]biphenyl (abbreviation: NPB) was deposited at the thickness of 10 nm over the composite-including layer 2103 by the vapor deposition technique using resistance heating system, leading to the formation of a hole transporting layer 2104.

Furthermore, a light emitting layer 2105 with a thickness of 30 nm was formed on the hole transporting layer 2104 by co-evaporation of N,N'-(quinoxaline-2,3-diyldi-4,1-phenylene)bis(N-phenyl-9-phenylcarbazole-3-amine) (abbreviation: PCAPQ) with (acetylacetonato)bis[2,3-bis(4-fluorophenyl)quinoxalinato]iridium(III) (abbreviation: Ir(Fdpq)$_2$(acac)). Here, a weight ratio of PCAPQ to Ir(Fdpq)$_2$(acac) was adjusted to be 1:0.08 (=PCAPQ:Ir(Fdpq)$_2$(acac)).

After that, tris(8-quinolinolato)aluminum (abbreviation: Alq) was formed at a thickness of 10 nm on the light emitting layer 2105 by the vapor deposition technique using the resistance heating system, thereby forming an electron transporting layer 2106.

Moreover, an electron injecting layer 2107 with a thickness of 50 nm was formed on the electron transporting layer 2106 by co-evaporation of tris(8-quinolinolato)aluminum (abbreviation: Alq) with lithium. Here, a weight ratio of Alq to lithium was adjusted to be 1:0.01 (=Alq:lithium).

Finally, aluminum Was formed at a thickness of 200 nm on the electron injecting layer 2107 by the vapor deposition technique using the resistance heating system, thereby forming a second electrode 2108. Accordingly, a light-emitting element 5 was fabricated.

Figure 46:
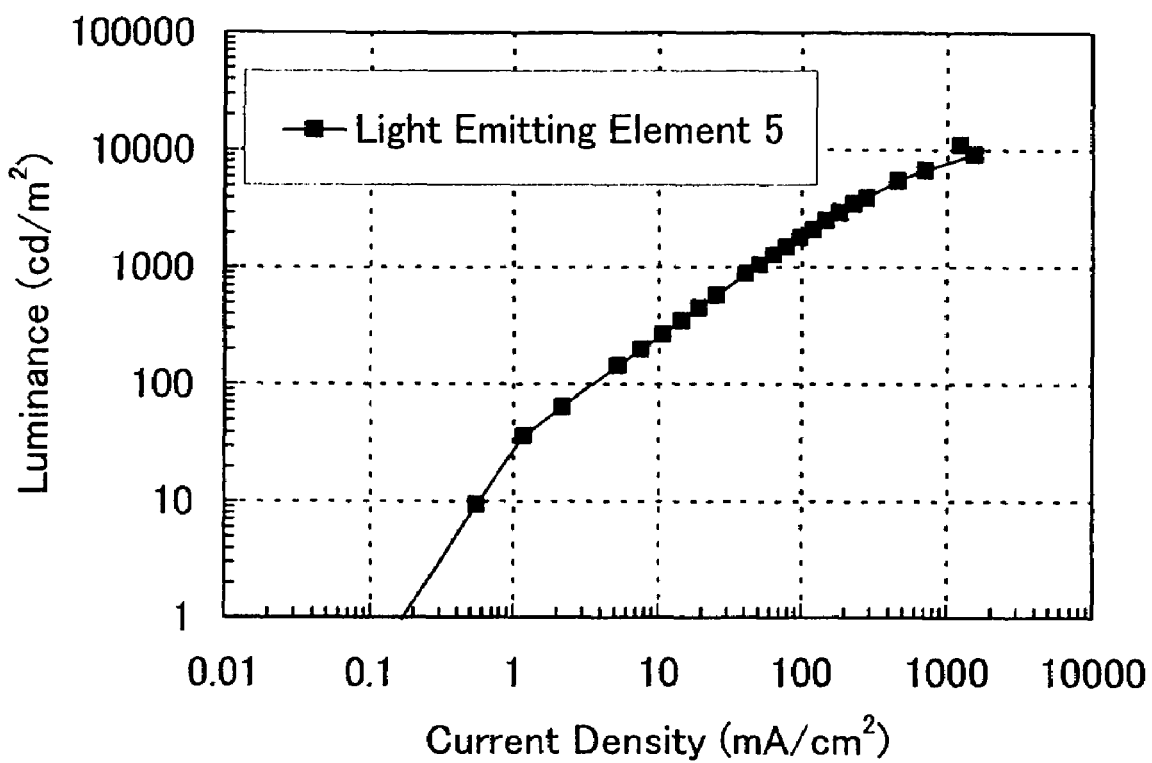
FIG. 46 is a graph showing a current density-luminance characteristic of a light-emitting element fabricated in Example 6.
Figure 47:
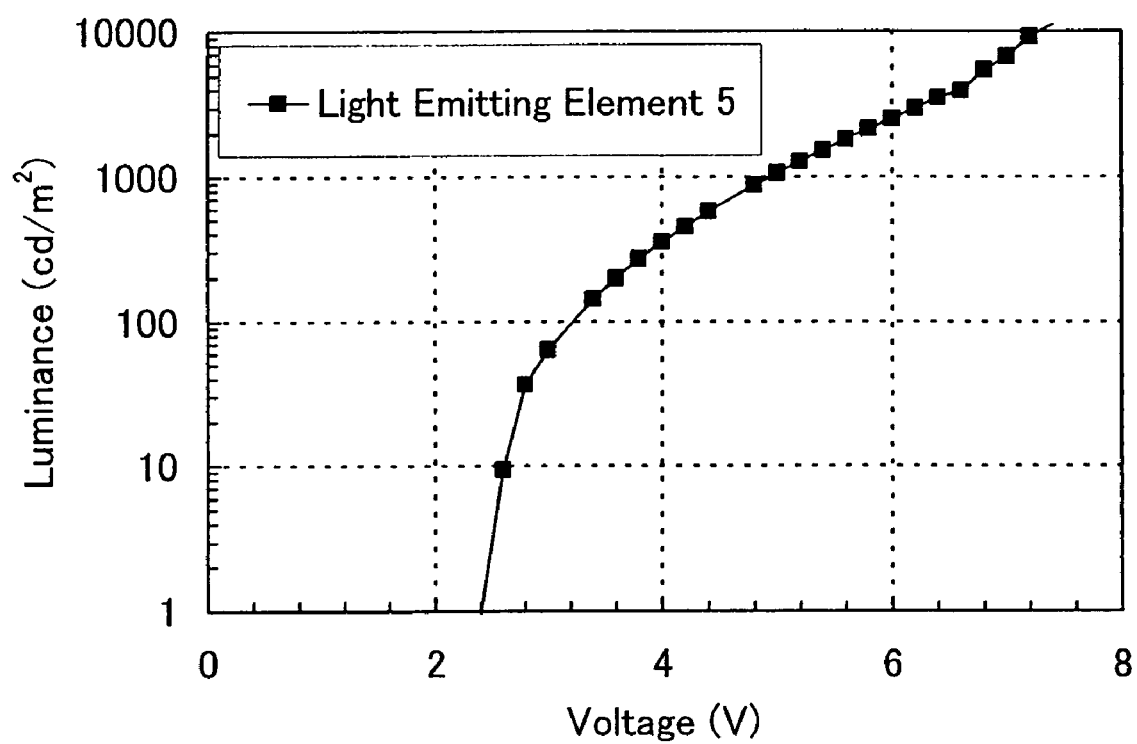
FIG. 47 is a graph showing a voltage-luminance characteristic of a light-emitting element fabricated in Example 6.
Figure 48:
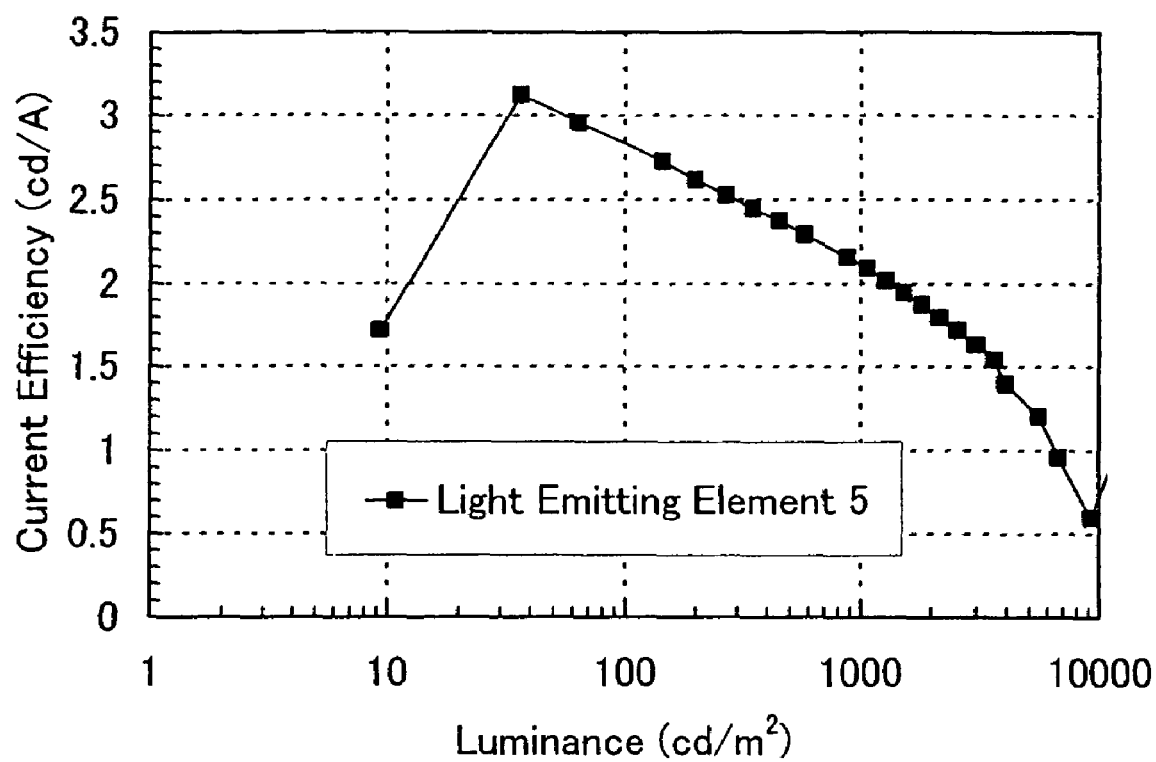
FIG. 48 is a graph showing a luminance-current efficiency characteristic of a light-emitting element fabricated in Example 6.
Figure 49:
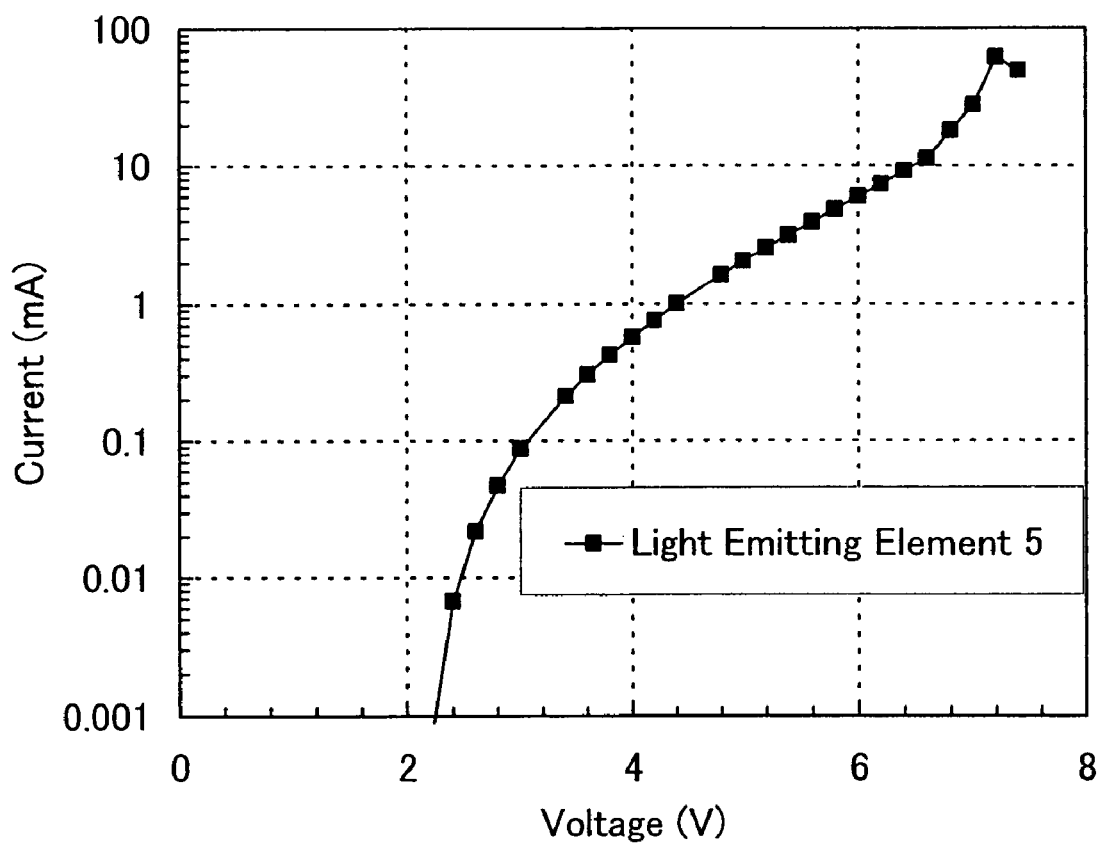
FIG. 49 is a graph showing a voltage-current characteristic of a light-emitting element fabricated in Example 6.
Figure 50:
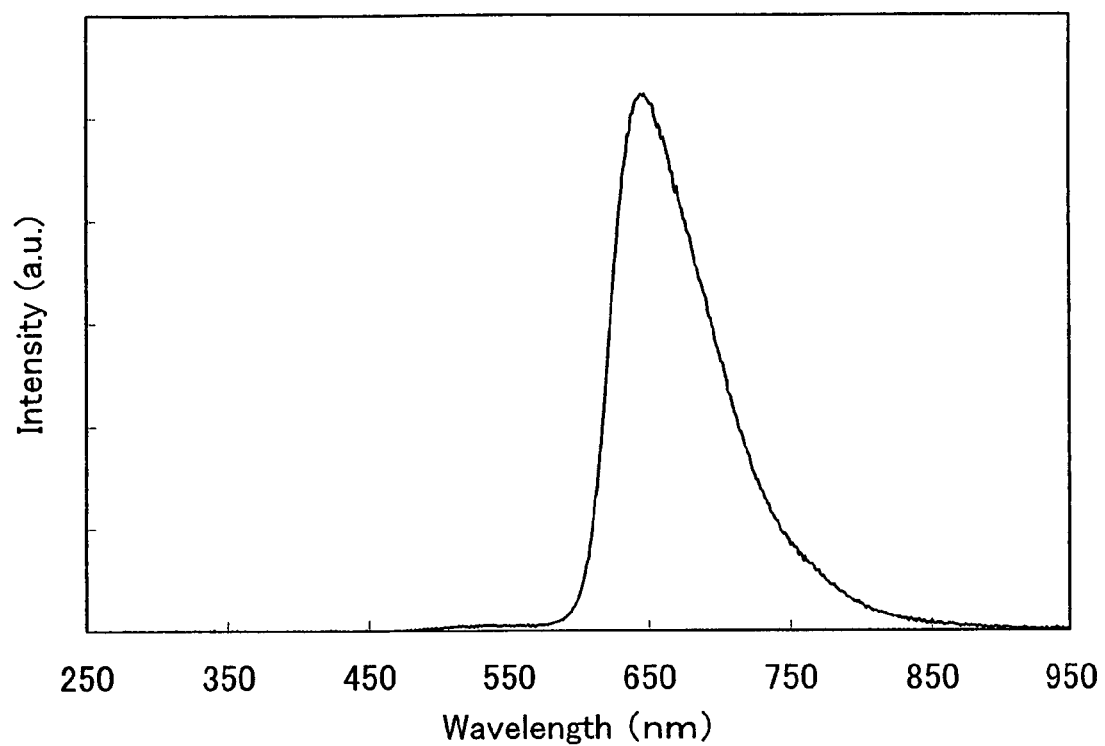
FIG. 50 is a graph showing an emission spectrum of a light-emitting element fabricated in Example 6.

FIG. 46 shows current density-luminance characteristics of the light-emitting element 5. FIG. 47 shows voltage-luminance characteristics. FIG. 48 shows luminance-current efficiency characteristics. FIG. 49 shows voltage-current characteristics. FIG. 50 shows an emission spectrum of the light-emitting element 5 when a current of 1 mA flows. FIG. 50 indicates that emission of the light-emitting element 5 is emission of Ir(Fdpq)$_2$(acac). The CIE chromaticity coordinates at luminance of 1100 cd/m$^2$ were (x, y)=(0.69, 0.30), and emission of red light with excellent color purity was obtained. Current efficiency at luminance of 1100 cd/m$^2$ was as high as 2.1 cd/A. Voltage and current density at luminance of 1100 cd/m$^2$ were 5.0 V and 51 mA/cm$^2$, respectively. The power efficiency, 1.3 lm/W, reveals that high power efficiency is achieved. Further, FIGS. 47 and 49 show that the driving voltage is reduced in the light-emitting element 5. Therefore, the use of the quinoxaline derivative of the present invention makes it possible to fabricate a light-emitting element with low driving voltage and reduced power consumption.

EXAMPLE 7

In this example, a synthetic method of N-phenyl-N-[4-(3-phenylquinoxalin-2-yl)phenyl]-9-phenylcarbazole-3-amine (abbreviation: PCA1PQ) that is a quinoxaline derivative of the present invention represented by a structural formula (86) will be specifically shown.

formula [153]

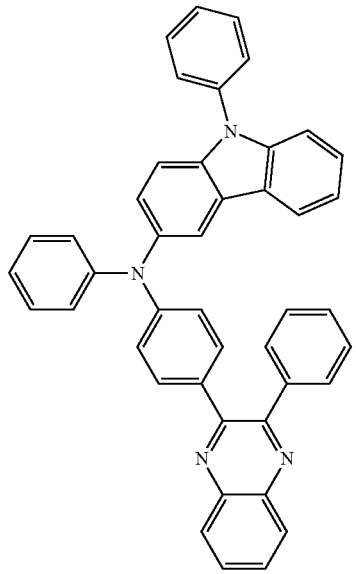

[Step 1]

Synthesis of N-phenyl-N-[4-(3-phenylquinoxalin-2-yl)phenyl]-9-phenylcarbazole-3-amine (Abbreviation: PCA1PQ)

A synthetic scheme of N-phenyl-N-[4-(3-phenylquinoxalin-2-yl)phenyl]-9-phenylcarbazole-3-amine (abbreviation: PCA1PQ) is shown in (H-1).

formula [154]

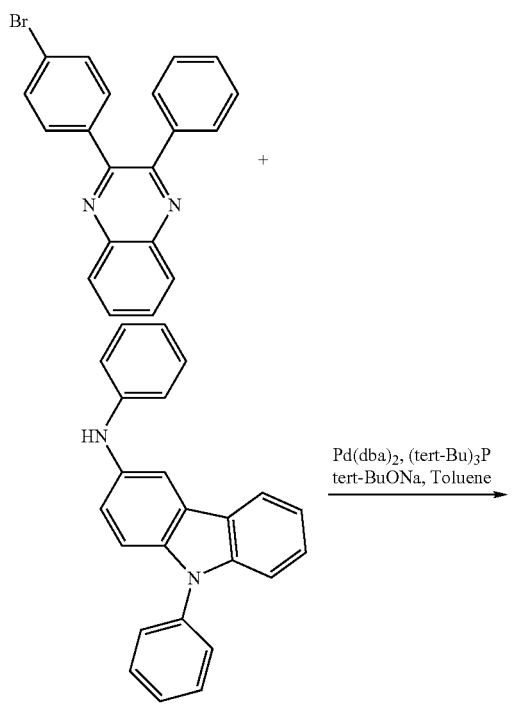

(H-1)

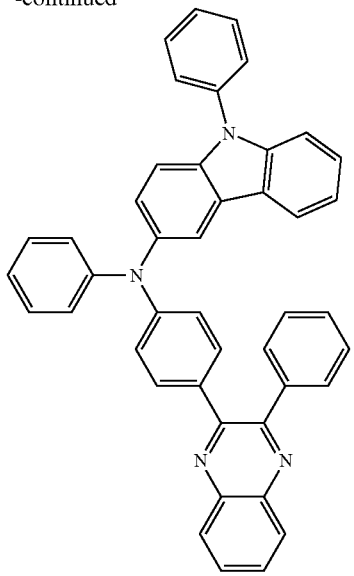

2.0 g (5.5 mmol) of 2-(4-bromophenyl)-3-phenylquinoxaline, 2.0 g of sodium tert-butoxide, 1.9 g (5.5 mmol) of N-phenyl-(9-phenylcarbazol-3-yl)amine (abbreviation: PCA), and 0.1 g (0.2 mmol) of bis(dibenzylideneacetone)palladium(0) were put into a 100-mL three-neck flask, and nitrogen substitution was carried out in the flask. Then, 30 mL of toluene and 0.1 mL of a 10% hexane solution of tri-tert-butylphosphine were added to the mixture, and the mixture was heated and stirred at 80° C. for 3 hours. After the reaction, toluene was added to the reaction mixture, and the suspension was subjected to suction filtration through florisil, celite, and alumina, and the filtrate was obtained. The obtained filtrate washed with water, and then, the water phase and the organic phase were separated from each other. Magnesium sulfate was added to the organic phase for drying. The mixture was subjected to suction filtration to remove magnesium sulfate, the obtained filtrate was concentrated, and a solid was obtained. The obtained solid was recrystallized with a mixed solvent of chloroform and hexane. 2.5 g of a yellow solid was obtained in the yield of 73%. It was confirmed by a nuclear magnetic resonance method (NMR) that this compound was N-phenyl-N-[4-(3-phenylquinoxalin-2-yl)phenyl]-9-phenylcarbazole-3-amine (abbreviation: PCA1PQ).

$^1$H NMR data of this compound is shown below.

$^1$H NMR (CDCl$_3$, 300 MHz): δ=6.96-7.66 (m, 24H), 7.66-7.78 (m, 2H), 7.91-7.96 (m, 1H), 7.98 (d, J=7.8 Hz, 1H), 8.10-8.19 (m, 2H).

Figure 55A:
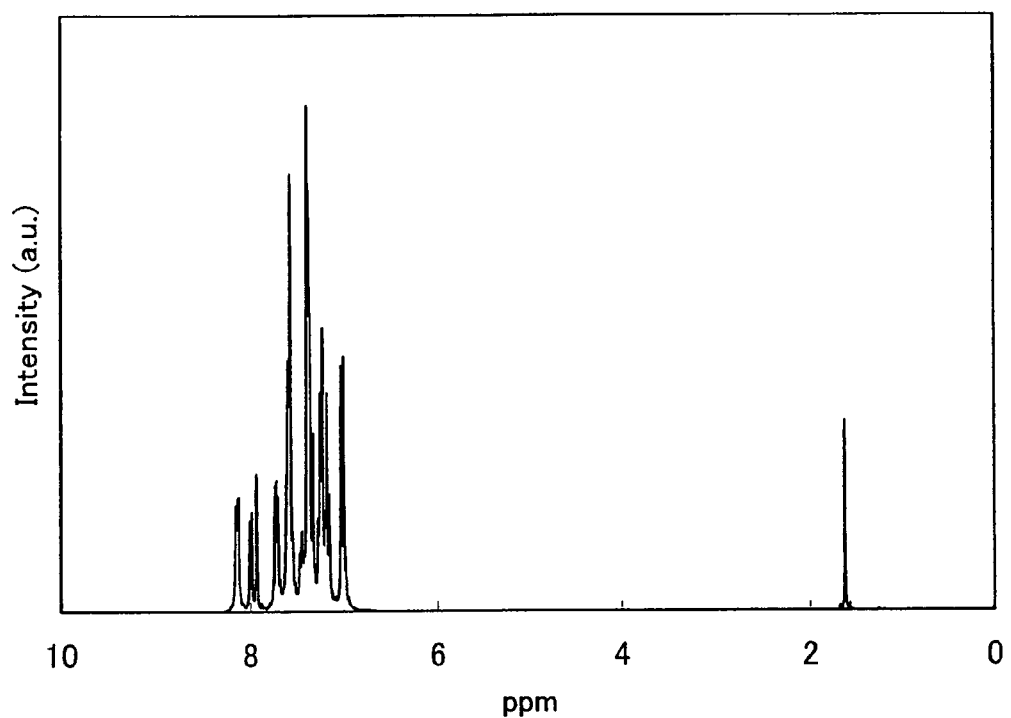
FIGS. 55A and 55B are graphs each showing a $^1$H NMR chart of N-phenyl-N-[4-(3-phenylquinoxalin-2-yl)phenyl]-9-phenylcarbazole-3-amine (abbreviation: PCA1PQ)
Figure 55B:
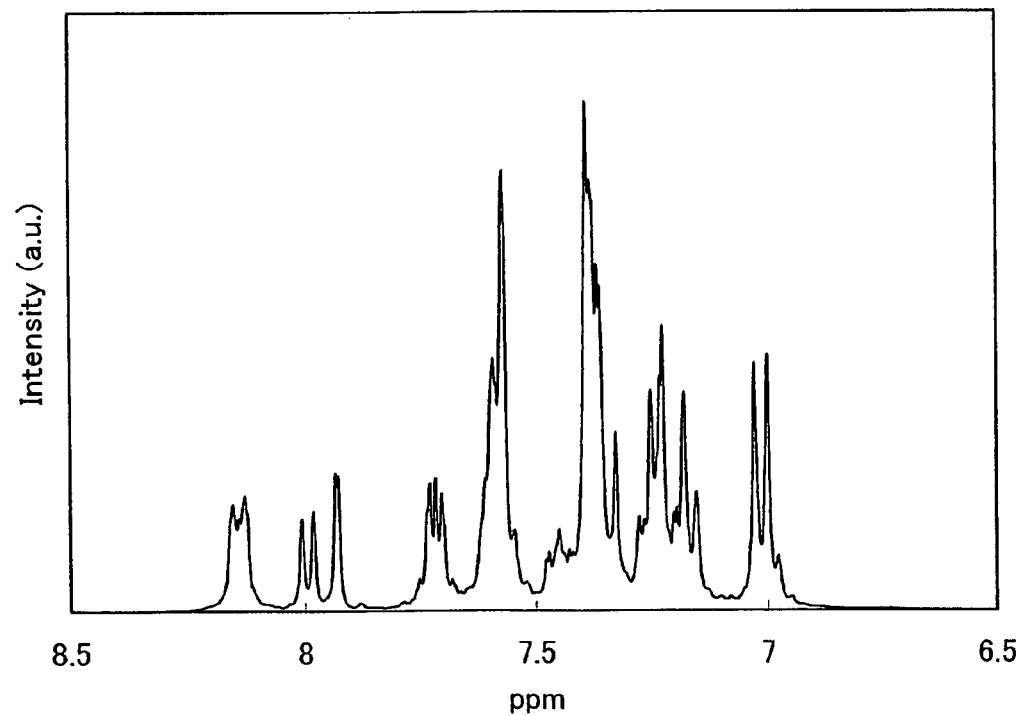

FIGS. 55A and 55B each show a $^1$H NMR chart. FIG. 55B shows an expanded chart of FIG. 55A in a range of 6.5 ppm to 8.5 ppm.

Then, sublimation purification of the obtained yellow solid was performed by a train sublimation method. The sublimation purification was performed at 295° C. for 12 hours under a reduced pressure of 7 Pa, setting the flow rate of argon to be 3 mL/min. When sublimation purification was performed on 2.5 g of charged PCA1PQ, the yield was 2.1 g (84%).

Figure 56:
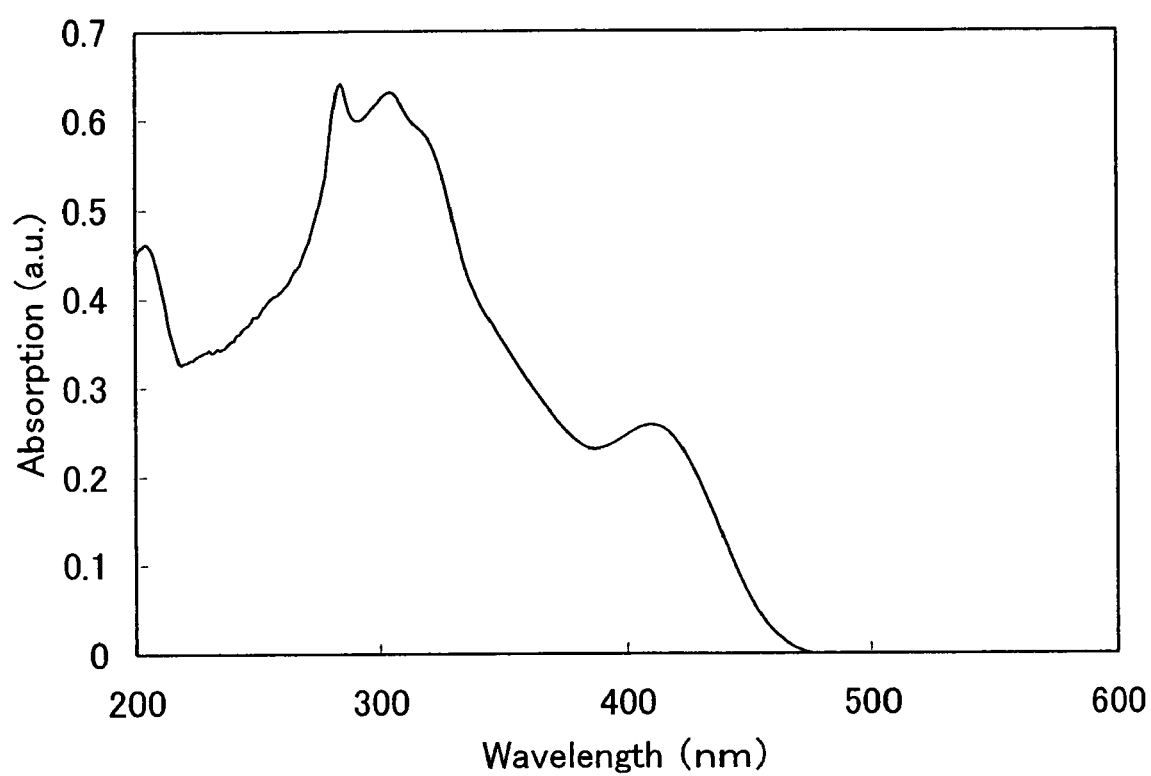
FIG. 56 is a graph showing an absorption spectrum of a toluene solution of N-phenyl-N-[4-(3-phenylquinoxalin-2-yl)phenyl]-9-phenylcarbazole-3-amine (abbreviation: PCA1PQ)
Figure 57:
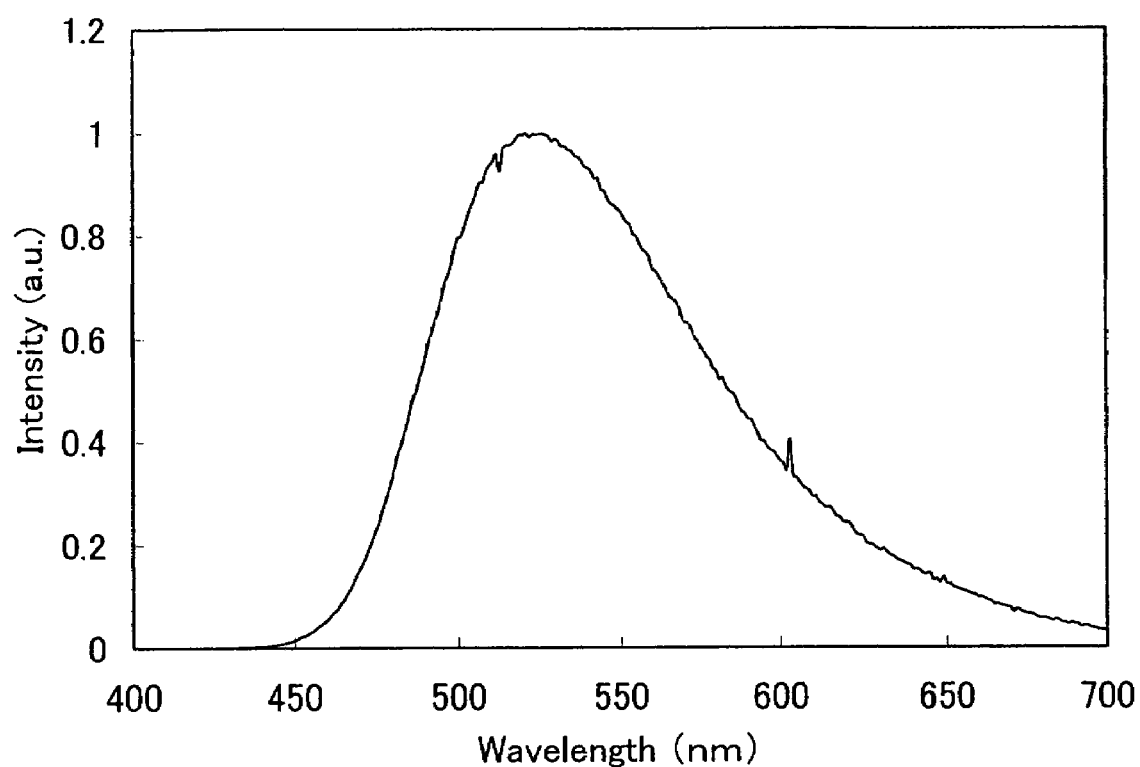
FIG. 57 is a graph showing an emission spectrum of a toluene solution of N-phenyl-N-[4-(3-phenylquinoxalin-2-yl)phenyl]-9-phenylcarbazole-3-amine (abbreviation: PCA1PQ)

FIG. 56 shows an absorption spectrum of a toluene solution of PCA1PQ. An ultraviolet-visible spectrophotometer (V-550, manufactured by JASCO Corporation) was used for the measurement. The solution was put into a quartz cell, and the absorption spectrum thereof, from which the absorption spectrum of quartz was subtracted, is shown in FIG. 56. In FIG. 56, the horizontal axis indicates the wavelength (nm) and the vertical axis indicates the absorption intensity (arbitrary unit). The absorption was observed at around 315 nm and at around 411 nm in the case of the toluene solution. FIG. 57 shows the emission spectrum of the toluene solution (the excitation wavelength: 410 nm) of PCA1PQ. In FIG. 57, the horizontal axis indicates the wavelength (nm) and the vertical axis indicates the emission intensity (arbitrary unit). The maximum emission wavelength was 521 nm (the excitation wavelength: 410 nm) in the case of the toluene solution.

Figure 73:
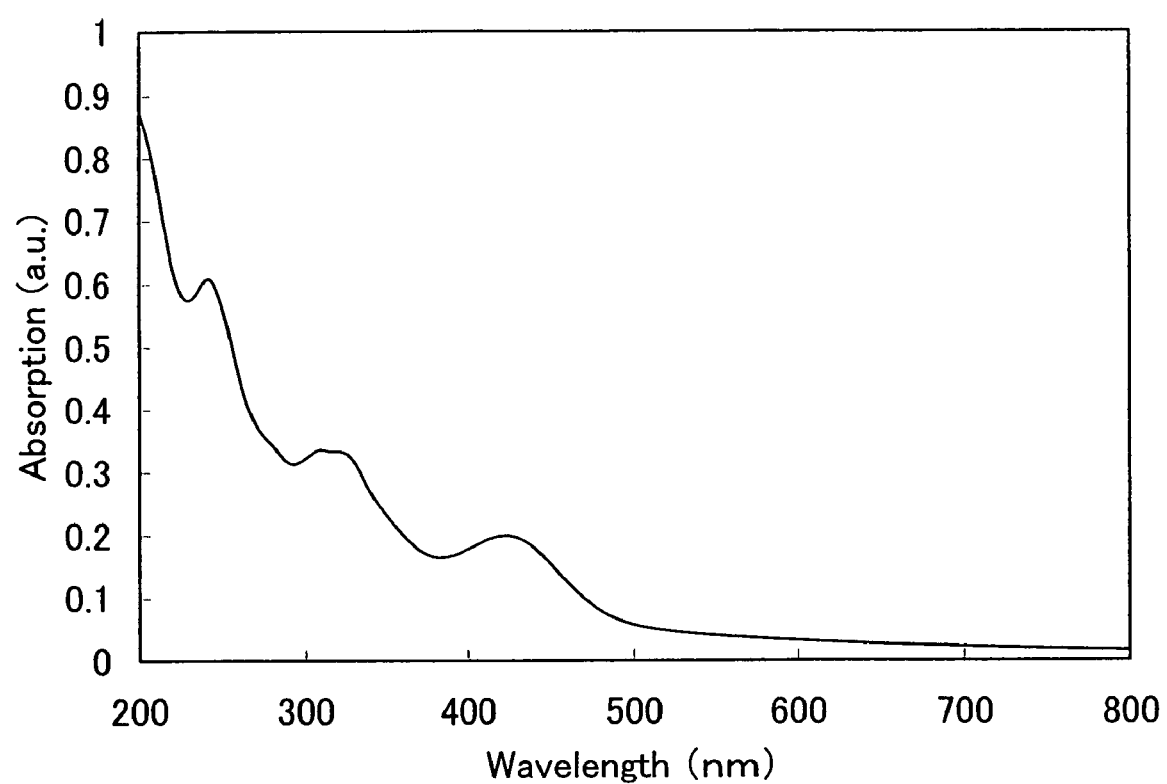
FIG. 73 is a graph showing an absorption spectrum of a thin film of N-phenyl-N-[4-(3-phenylquinoxalin-2-yl)phenyl]-9-phenylcarbazole-3-amine (abbreviation: PCA1PQ)
Figure 74:
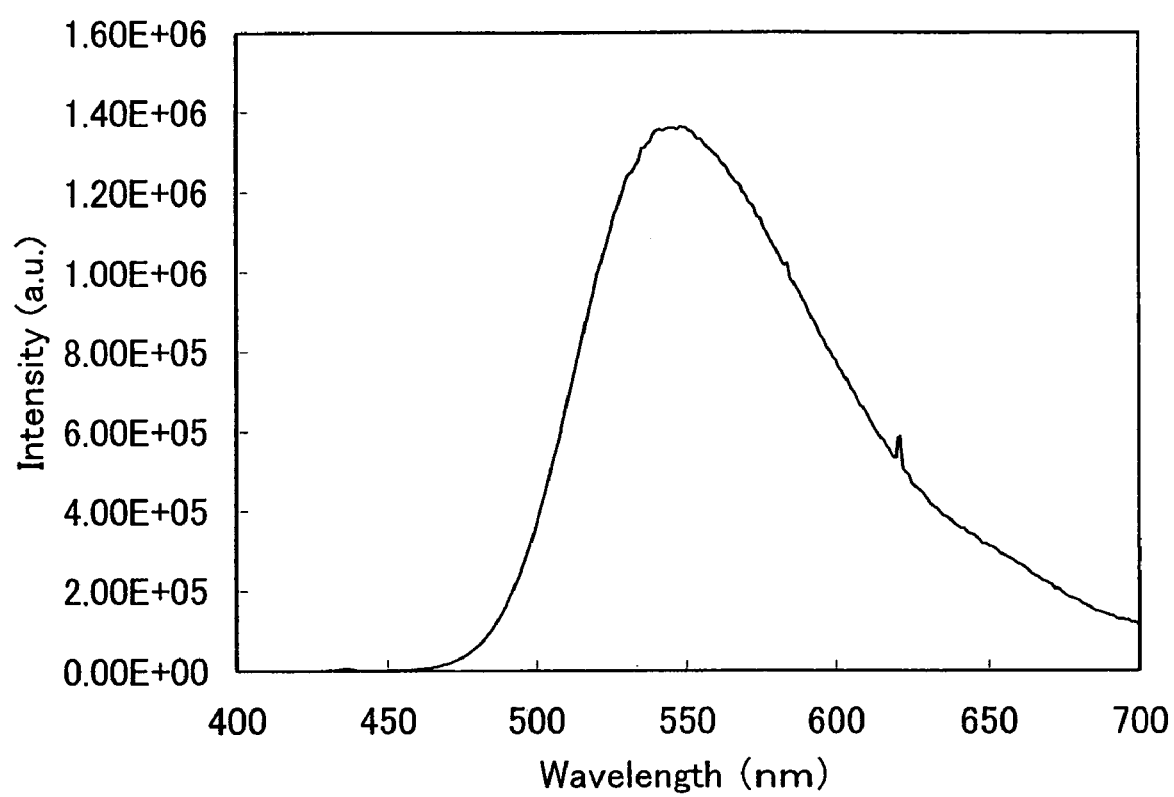
FIG. 74 is a graph showing an emission spectrum of a thin film of N-phenyl-N-[4-(3-phenylquinoxalin-2-yl)phenyl]-9-phenylcarbazole-3-amine (abbreviation: PCA1PQ)

FIG. 73 shows an absorption spectrum of a thin film of PCA1PQ. An ultraviolet-visible spectrophotometer (V-550, manufactured by JASCO Corporation) was used for the measurement. The thin film sample of PCA1PQ was formed on a quartz substrate by the vapor deposition technique, and the absorption spectrum thereof, from which the absorption spectrum of quartz was subtracted, is shown in FIG. 73. In FIG. 73, the horizontal axis indicates the wavelength (nm) and the vertical axis indicates the absorption intensity (arbitrary unit). The absorption was observed at around 423 nm in the case of the thin film. FIG. 74 shows the emission spectrum of the thin film (the excitation wavelength: 423 nm) of PCA1PQ. In FIG. 74, the horizontal axis indicates the wavelength (nm) and the vertical axis indicates the emission intensity (arbitrary unit). The maximum emission wavelength was 552 nm (the excitation wavelength: 423 nm) in the case of the thin film.

The result of measuring the thin-film using a photoelectron spectrometer (AC-2, manufactured by Riken Keiki Co., Ltd.) under the atmosphere indicated that the HOMO level of PCA1PQ in the solid state is −5.22 eV. The Tauc plot of the absorption spectrum shown in FIG. 73 revealed that the absorption edge was 2.59 eV. Thus, the energy gap of PCA1PQ in the solid state was estimated to be 2.59 eV, which means that the LUMO level of PCA1PQ in the solid state is −2.63 eV.

EXAMPLE 8

In this example, a synthetic method of N,N',N'-triphenyl-N-[4-(3-phenylquinoxalin-2-yl)phenyl]benzene-1,4-diamine (abbreviation: DPA1PQ) that is a quinoxaline derivative of the present invention represented by a structural formula (21) will be specifically shown.

formula [155]

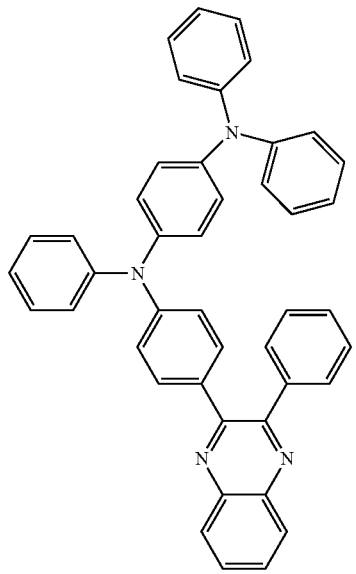

(21)

[Step 1]

Synthesis of N,N',N'-triphenyl-N-[4-(3-phenylquinoxalin-2-yl)phenyl]benzene-1,4-diamine (Abbreviation: DPA1PQ)

A synthetic scheme of N,N',N'-triphenyl-N-[4-(3-phenylquinoxalin-2-yl)phenyl]benzene-1,4-diamine (abbreviation: DPA1PQ) is shown in (J-1).

formula [156]

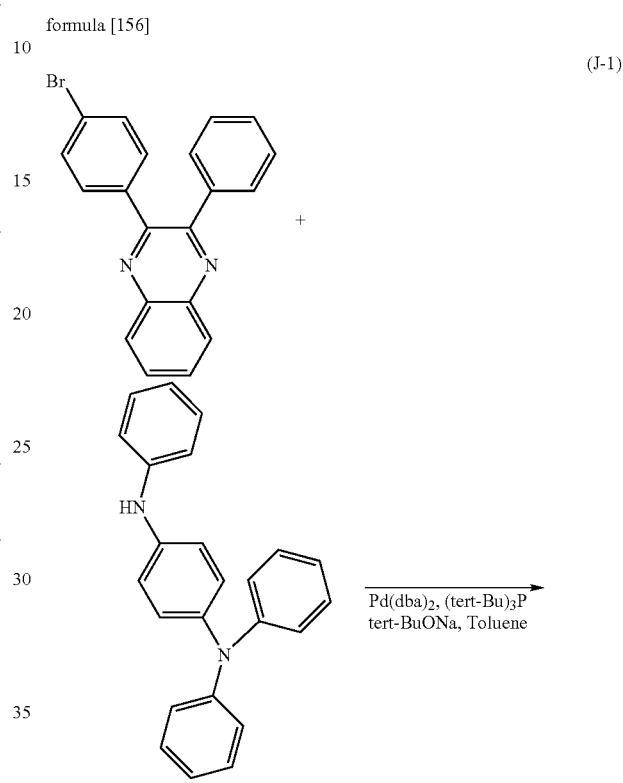

(J-1)

1.0 g (2.8 mmol) of 2-(4-bromophenyl)-3-phenylquinoxaline, 0.3 g of sodium tert-butoxide, 0.93 g (2.8 mmol) of N,N',N'-triphenyl-1,4-phenylenediamine, and 0.05 g (0.1 mmol) of bis(dibenzylideneacetone)palladium(0) were put into a 50-mL three-neck flask, and nitrogen substitution was carried out in the flask. Then, 20 mL of toluene and 0.05 mL of a 10% hexane solution of tri-tert-butylphosphine were added to the mixture, and the mixture was heated and stirred at 80° C. for 3 hours. After the reaction, toluene was added to the reaction mixture, and the suspension was subjected to suction filtration through florisil, celite, and alumina. The obtained filtrate washed with a sodium hydrogencarbonate aqueous solution and brine in this order, and then, a water phase and an organic phase were separated from each other. Magnesium sulfate was added to the organic phase for drying. The mixture was subjected to suction filtration to remove magnesium sulfate, the obtained filtrate was concentrated, and the resulting solid was obtained. The obtained solid was recrystallized with a mixed solvent of chloroform and methanol. 1.4 g of a yellow solid was obtained in the yield of 78%. It was confirmed by a nuclear magnetic resonance method (NMR) that this compound was N,N',N'-triphenyl-N-[4-(3-phenylquinoxalin-2-yl)phenyl]benzene-1,4-diamine (abbreviation: DPA1PQ).

$^1$H NMR data of this compound is shown below.

$^1$H NMR (CDCl$_3$, 300 MHz): δ=6.93-7.43 (m, 26H), 7.55-7.62 (m, 2H), 7.71-7.77 (m, 2H), 8.11-8.19 (m, 2H).

Figure 58A:
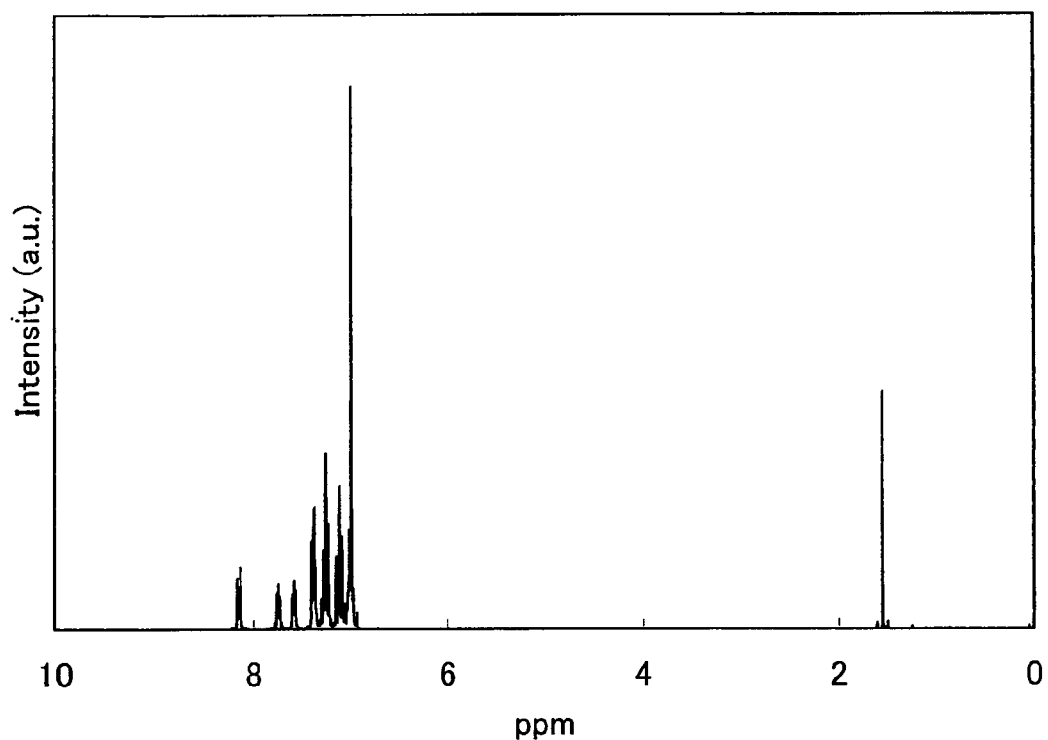
FIGS. 58A and 58B are graphs each showing a $^1$H NMR chart of N,N',N'-triphenyl-N-[4-(3-phenylquinoxalin-2-yl)phenyl]benzene-1,4-diamine (abbreviation: DPA1PQ)
Figure 58B:
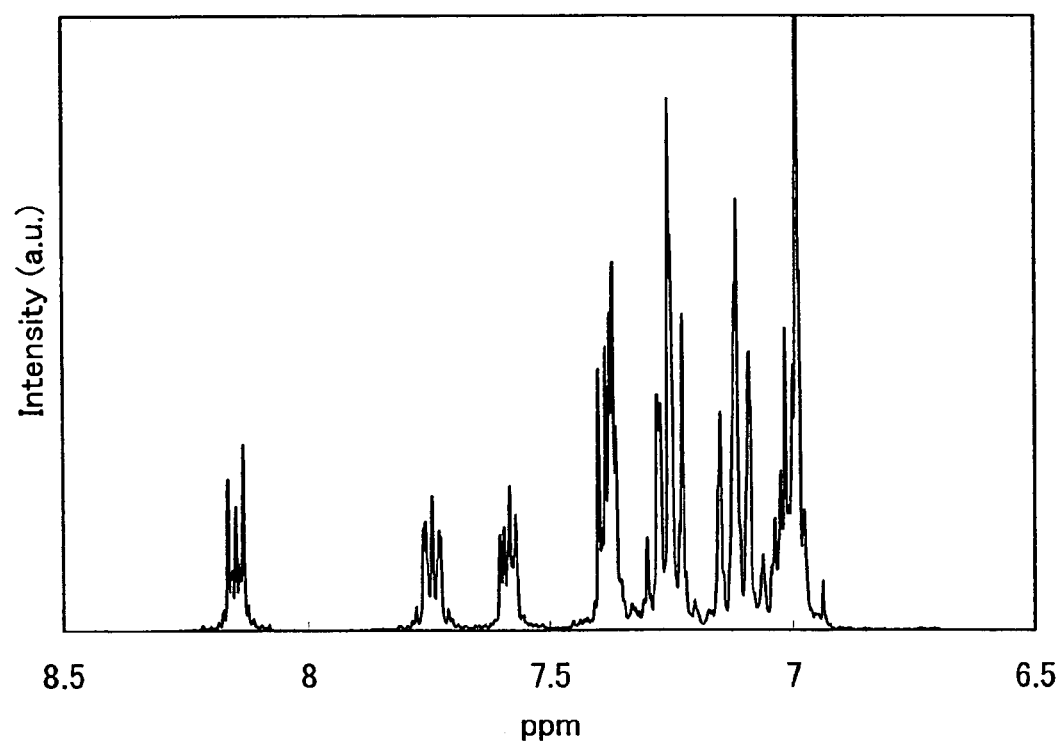

FIGS. 58A and 58B each show a $^1$H NMR chart. FIG. 58B shows an expanded chart of FIG. 58A in a range of 6.5 ppm to 8.5 ppm.

Then, sublimation purification of the obtained yellow solid was performed by a train sublimation method. The sublimation purification was performed at 266° C. for 15 hours under a reduced pressure of 7 Pa, setting the flow rate of argon to be 3 mL/min. When sublimation purification was performed on 1.4 g of charged DPA1PQ, the yield was 1.1 g (79%).

Figure 59:
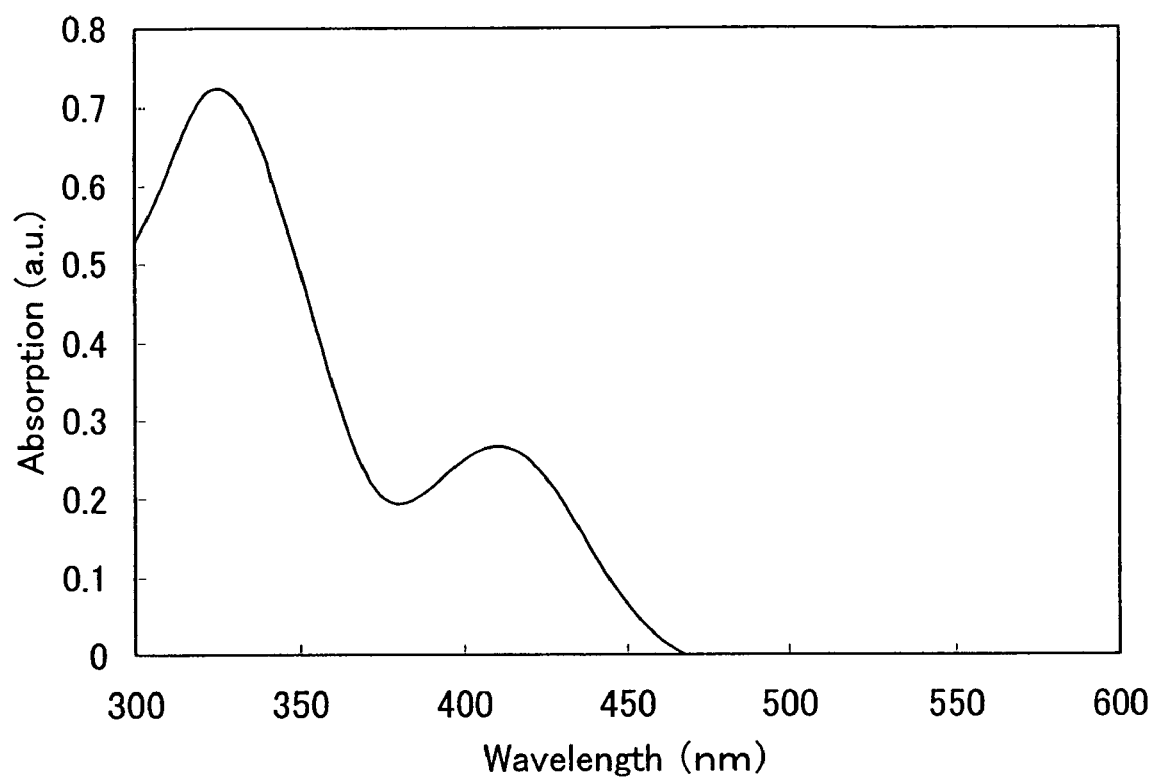
FIG. 59 is a graph showing an absorption spectrum of a toluene solution of N,N',N'-triphenyl-N-[4-(3-phenylqinoxalin-2-yl)phenyl]benzene-1,4-diamine (abbreviation: DPA1PQ)
Figure 60:
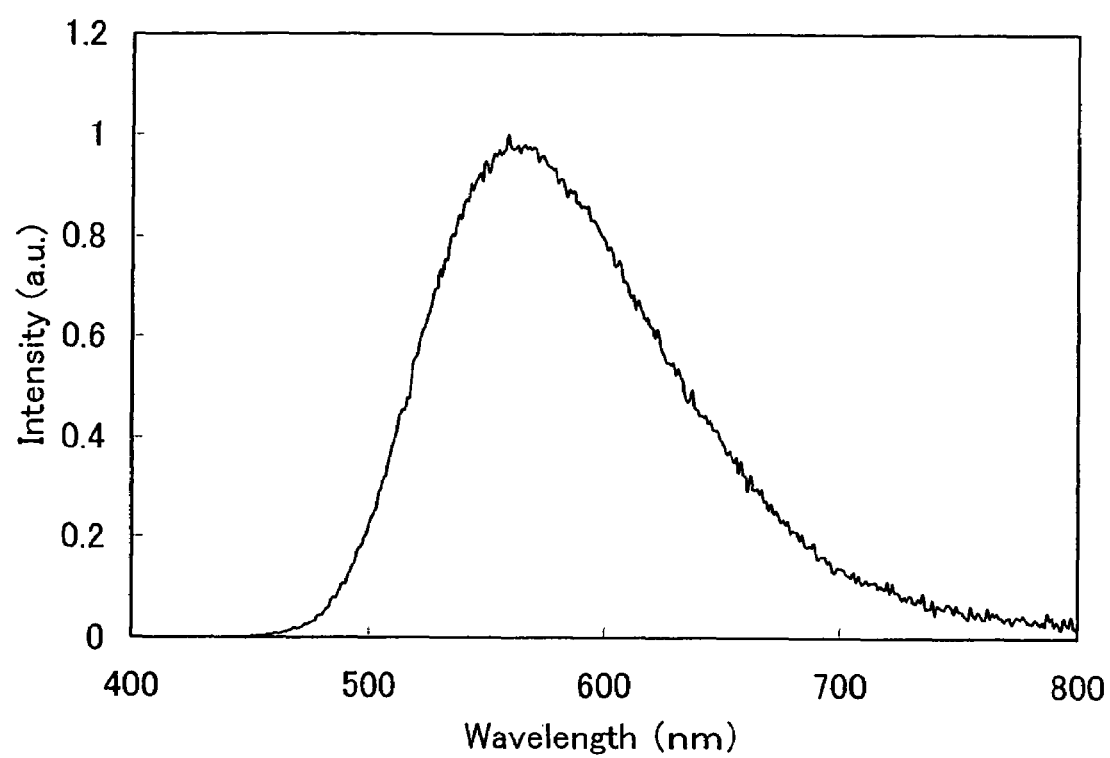
FIG. 60 is a graph showing an emission spectrum of a toluene solution of N,N',N'-triphenyl-N-[4-(3-phenylqinoxalin-2-yl)phenyl]benzene-1,4-diamine (abbreviation: DPA1PQ)

FIG. 59 shows an absorption spectrum of a toluene solution of DPA1PQ. An ultraviolet-visible spectrophotometer (V-550, manufactured by JASCO Corporation) was used for the measurement. The solution was put into a quartz cell, and the absorption spectrum thereof, from which the absorption spectrum of quartz was subtracted, is shown in FIG. 59. In FIG. 59, the horizontal axis indicates the wavelength (nm) and the vertical axis indicates the absorption intensity (arbitrary unit). The absorption was observed at around 325 nm and at around 410 nm in the case of the toluene solution. FIG. 60 shows the emission spectrum of the toluene solution (the excitation wavelength: 410 nm) of DPA1PQ. In FIG. 60, the horizontal axis indicates the wavelength (nm) and the vertical axis indicates the emission intensity (arbitrary unit). The maximum emission wavelength was 559 nm (the excitation wavelength: 410 nm) in the case of the toluene solution.

Figure 75:
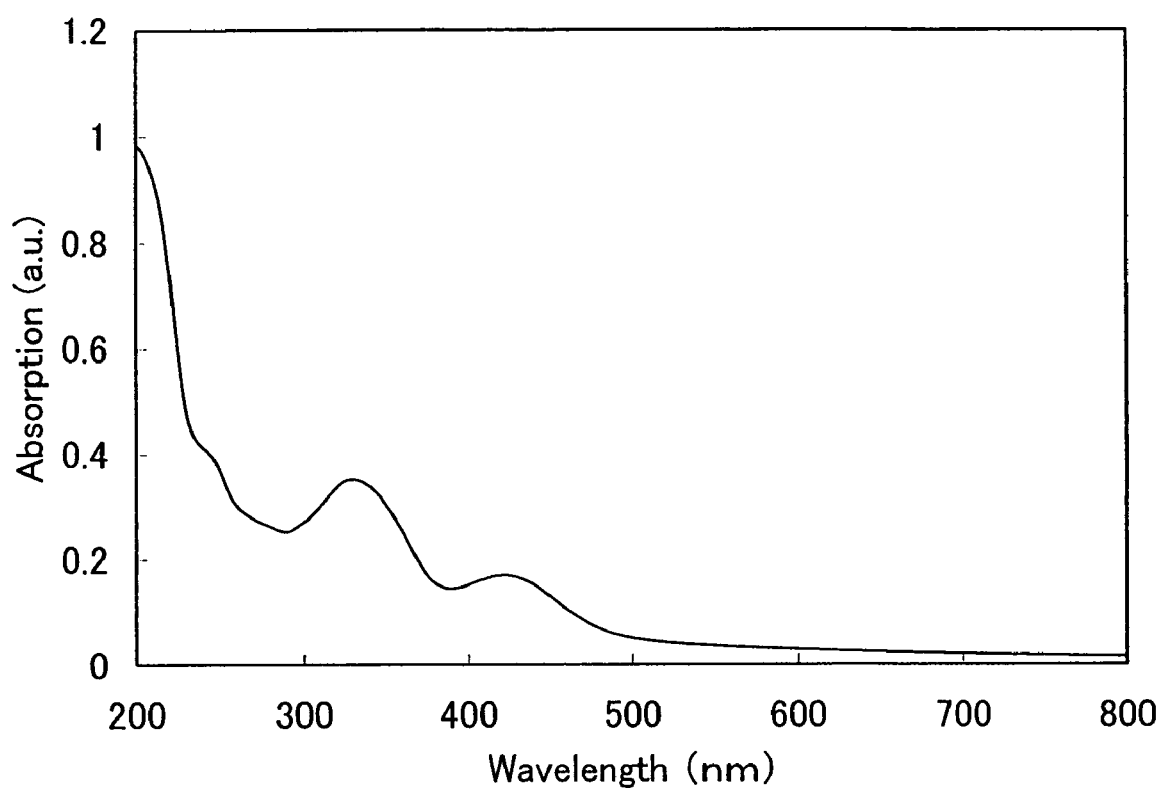
FIG. 75 is a graph showing an absorption spectrum of a thin film of N,N',N'-triphenyl-N-[4-(3-phenylquinoxalin-2-yl)phenyl]benzene-1,4-diamine (abbreviation: DPA1PQ)
Figure 76:
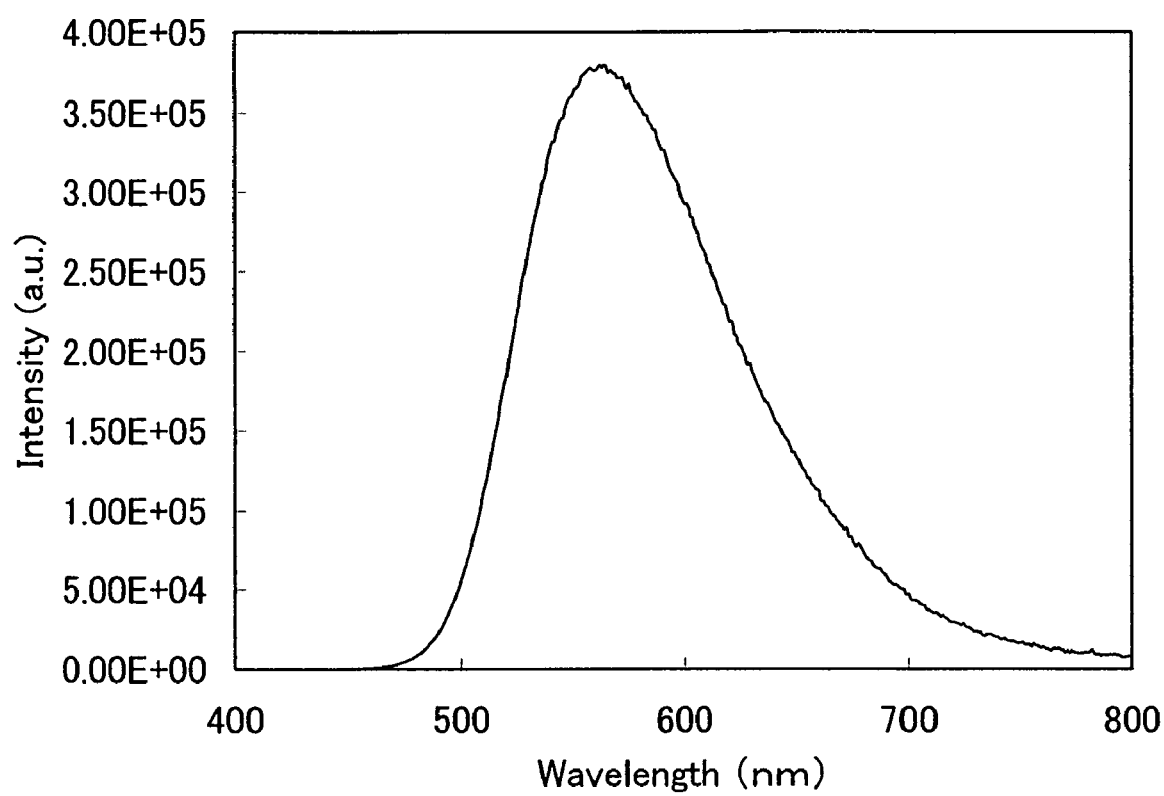
FIG. 76 is a graph showing an emission spectrum of a thin film of N,N',N'-triphenyl-N-[4-(3-phenylquinoxalin-2-yl)phenyl]benzene-1,4-diamine (abbreviation: DPA1PQ).

FIG. 75 shows an absorption spectrum of a thin film of DPA1PQ. An ultraviolet-visible spectrophotometer (V-550, manufactured by JASCO Corporation) was used for the measurement. The thin film was prepared as a sample by the vapor deposition of DPA1PQ on a quartz substrate, and the absorption spectrum thereof, from which the absorption spectrum of quartz was subtracted, is shown in FIG. 75. In FIG. 75, the horizontal axis indicates the wavelength (nm) and the vertical axis indicates the absorption intensity (arbitrary unit). The absorption was observed at around 421 nm in the case of the thin film. FIG. 76 shows the emission spectrum of a thin film (the excitation wavelength: 421 nm) of DPA1PQ. In FIG. 76, the horizontal axis indicates the wavelength (nm) and the vertical axis indicates the emission intensity (arbitrary unit). The maximum emission wavelength was 566 nm (the excitation wavelength: 421 nm) in the case of the thin film.

The result of measuring the thin-film using a photoelectron spectrometer (AC-2, manufactured by Riken Keiki Co., Ltd.) under the atmosphere indicated that the HOMO level of DPA1PQ in the solid state is −5.31 eV. The Tauc plot of the absorption spectrum shown in FIG. 75 revealed that the absorption edge was 2.60 eV. Thus, the energy gap of DPA1PQ in the solid state was estimated to be 2.60 eV, which means that the LUMO level of PCA1PQ in the solid state is −2.71 eV.

EXAMPLE 9

In this example, a light-emitting element of the present invention will be explained with reference to FIG. 29.

(Light-Emitting Element 6)

First, indium tin oxide including silicon oxide was formed over a glass substrate 2101 by a sputtering method, thereby forming a first electrode 2102. It is to be noted that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 including a composite of an organic compound with an inorganic compound was formed on the first electrode 2102 by co-evaporation of NPB and molybdenum oxide (VI) after a pressure of the vacuum evaporation apparatus was reduced to approximately $10^{-4}$ Pa. A thickness thereof was adjusted to be 50 nm and a weight ratio of NPB to molybdenum oxide (VI) was adjusted to be 4:1 (=NPB:molybdenum oxide). It is to be noted that the co-evaporation method is an evaporation method in which evaporation is performed simultaneously from a plurality of evaporation sources in one evaporation chamber.

Next, 4,4'-bis[N-(1-napthyl)-N-phenylamino]biphenyl (abbreviation: NPB) was deposited at the thickness of 10 nm over the composite-including layer 2103 by the vapor deposition technique using resistance heating system, leading to the formation of a hole transporting layer 2104.

Further, a light emitting layer 2105 with a thickness of 30 nm was formed on the hole transporting layer 2104 by co-evaporation of 4-(carbazol-9-yl)-4'-(3-phenylquinoxalin-2-yl)triphenylamine (abbreviation: YGA1PQ) represented by the structural formula (159) with (acetylacetonato)bis[2,3-bis (4-fluorophenyl)quinoxalinato]iridium(III) (abbreviation: Ir(Fdpq)$_2$(acac)). Here, a weight ratio of YGA1PQ and Ir(Fdpq)$_2$(acac) was adjusted to be 1:0.06 (=YGA1PQ:Ir(Fdpq)$_2$(acac)).

After that, bis(2-methyl-8-quinolinolato)(4-phenylphenolato)aluminum (abbreviation: BAlq) was formed at a thickness of 10 nm on the light emitting layer 2105 by the vapor deposition technique using resistance heating system, thereby forming an electron transporting layer 2106.

Moreover, an electron injecting layer 2107 with a thickness of 50 nm was formed on the electron transporting layer 2106 by co-evaporation of tris(8-quinolinolato)aluminum (abbreviation: Alq) with lithium. Here, a weight ratio of Alq to lithium was adjusted to be 1:0.01 (=Alq:lithium).

Finally, aluminum was formed at a thickness of 200 nm on the electron injecting layer 2107 by the vapor deposition technique using resistance heating system, thereby forming a second electrode 2108. Accordingly, a light-emitting element 6 was fabricated.

Figure 61:
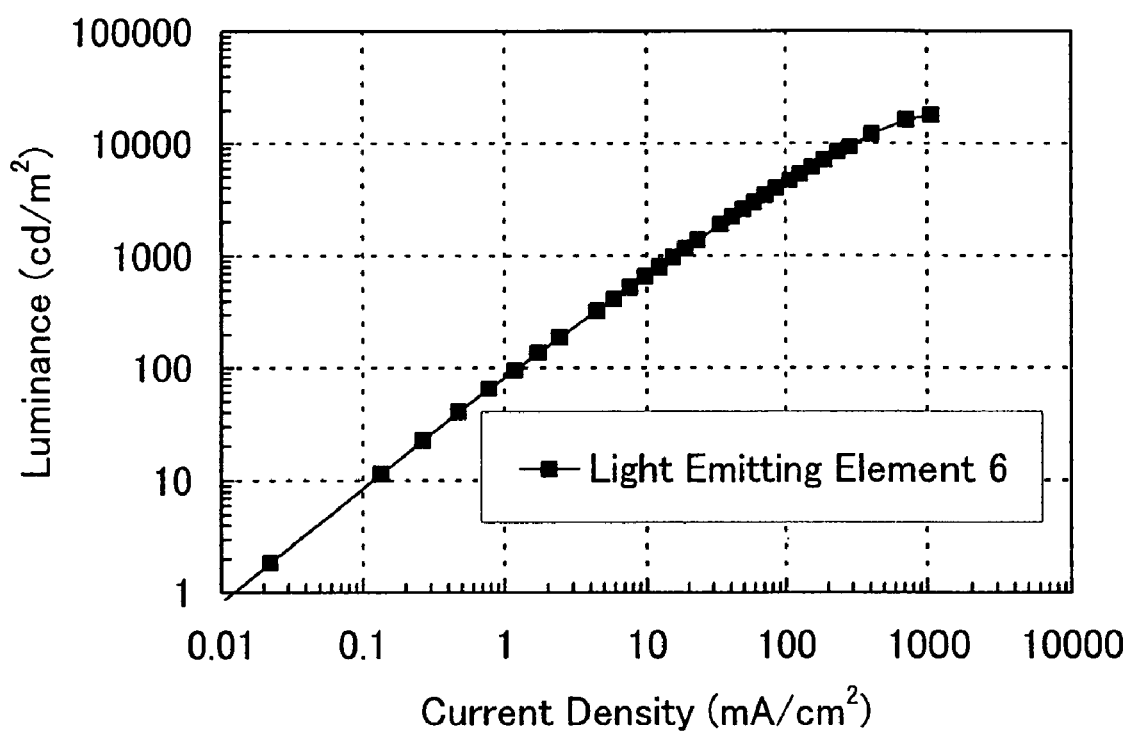
FIG. 61 is a graph showing a current density-luminance characteristic of a light-emitting element fabricated in Example 9.
Figure 62:
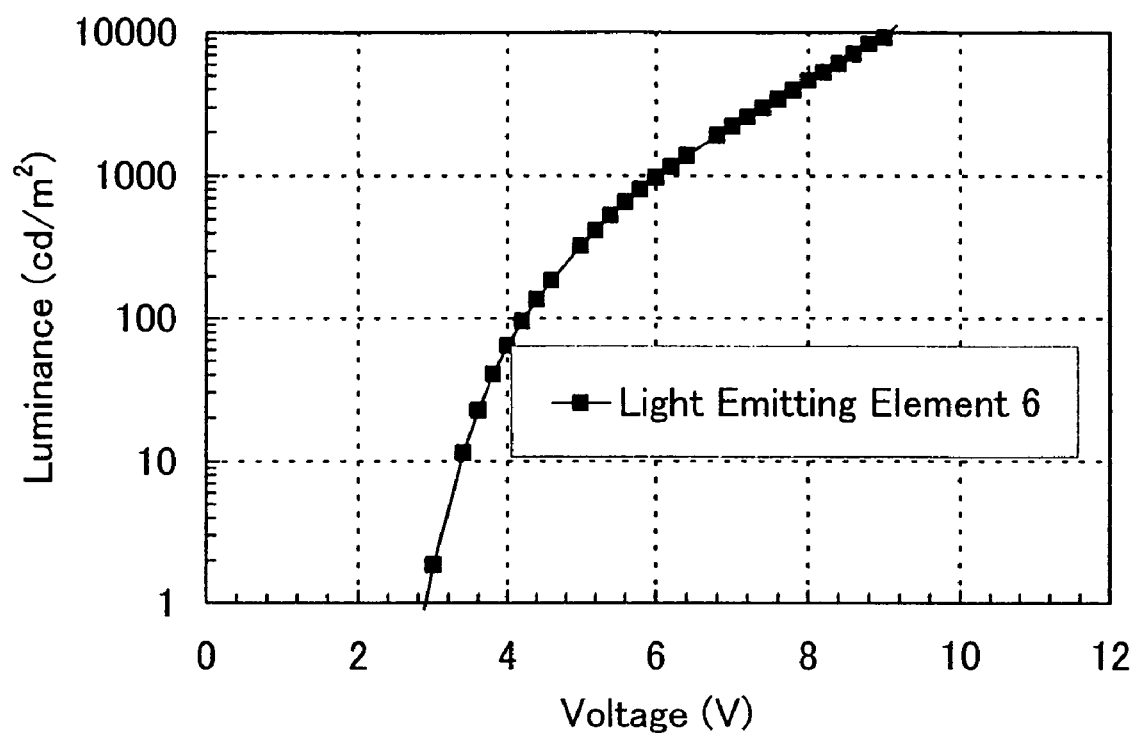
FIG. 62 is a graph showing a voltage-luminance characteristic of a light-emitting element fabricated in Example 9.
Figure 63:
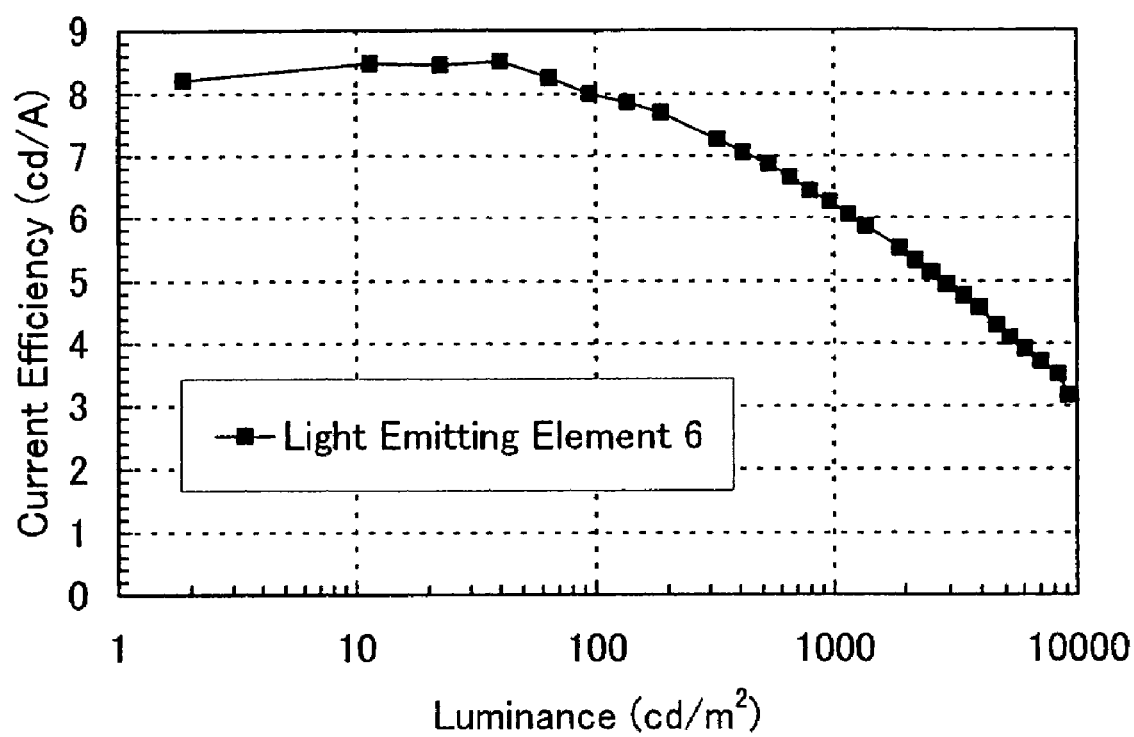
FIG. 63 is a graph showing a luminance-current efficiency characteristic of a light-emitting element fabricated in Example 9.
Figure 64:
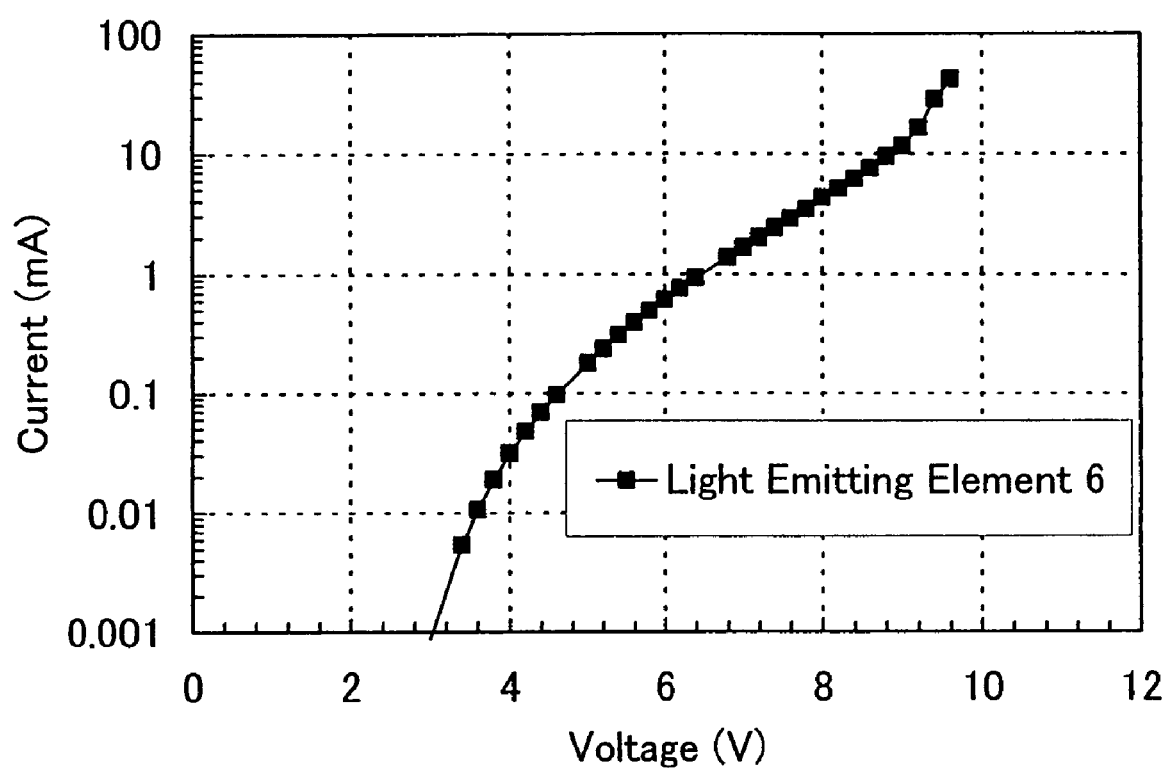
FIG. 64 is a graph showing a voltage-current characteristic of a light-emitting element fabricated in Example 9.
Figure 65:
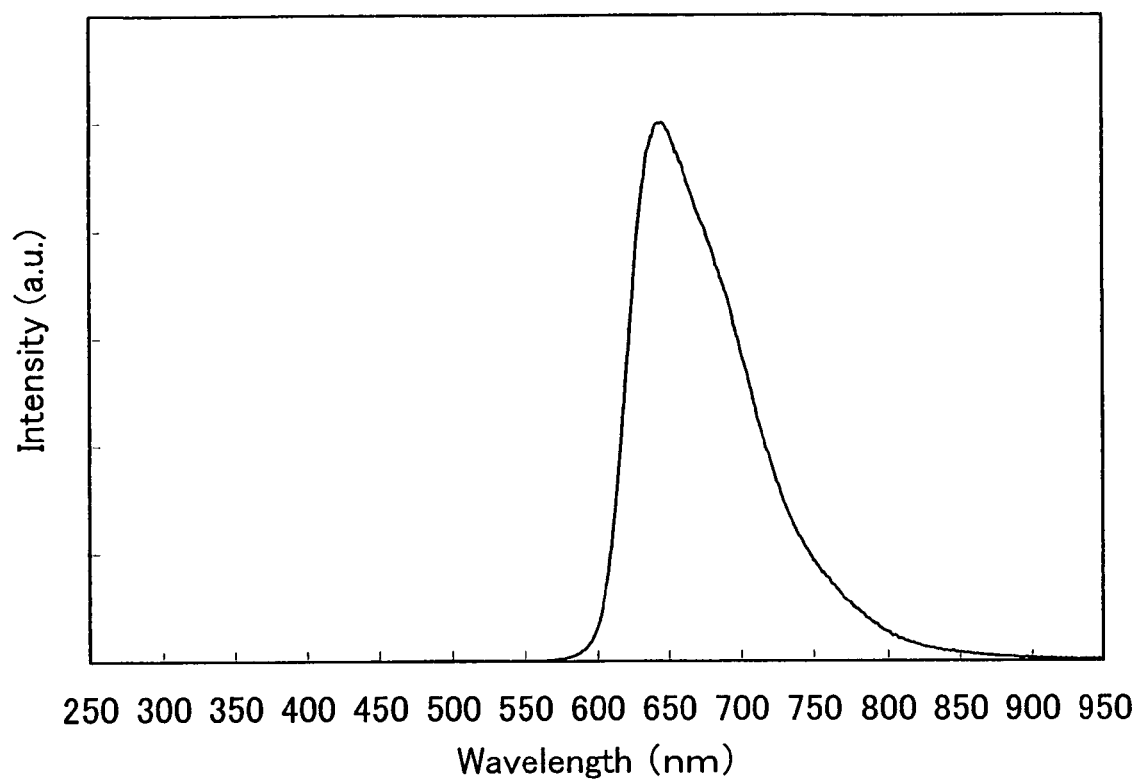
FIG. 65 is a graph showing an emission spectrum of a light-emitting element fabricated in Example 9.

FIG. 61 shows current density-luminance characteristics of the light-emitting element 6. FIG. 62 shows voltage-luminance characteristics. FIG. 63 shows luminance-current efficiency characteristics. FIG. 64 shows voltage-current characteristics. FIG. 65 shows an emission spectrum of the light emitting element 6 when a current of 1 mA flows. FIG. 65 indicates that emission of the light-emitting element 6 is emission of Ir(Fdpq)$_2$(acac). The CIE chromaticity coordinates at luminance of 960 cd/m$^2$ were (x, y)=(0.71, 0.29), and emission of red light with excellent color purity was obtained. Current efficiency at luminance of 960 cd/m$^2$ was 6.3 cd/A, and external quantum efficiency was as high as 14%. Voltage and current density at luminance of 960 cd/m$^2$ were 6.0 V and 15 mA/cm$^2$, respectively, and power efficiency was 3.3 lm/W which was an extremely high value. Further, FIGS. 62 and 64 show that a driving voltage is reduced in the light-emitting element 6. Therefore, the use of the quinoxaline derivative of the present invention allows the fabrication of a light-emitting element having a low driving voltage and reduced power consumption.

EXAMPLE 10

In this example, a light-emitting element of the present invention will be explained with reference to FIG. 29.

(Light-Emitting Element 7)
First, indium tin oxide including silicon oxide was formed over a glass substrate 2101 by a sputtering method, thereby forming a first electrode 2102. It is to be noted that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 including a composite of an organic compound with an inorganic compound was formed on the first electrode 2102 by co-evaporation of NPB and molybdenum oxide (VI) after a pressure of the vacuum evaporation apparatus was reduced to approximately $10^{-4}$ Pa. A thickness thereof was adjusted to be 50 nm and a weight ratio of NPB to molybdenum oxide (VI) was adjusted to be 4:1 (=NPB:molybdenum oxide). It is to be noted that the co-evaporation method is an evaporation method in which evaporation is performed simultaneously from a plurality of evaporation sources in one treatment chamber.

Next, 4,4'-bis[N-(1-napthyl)-N-phenylamino]biphenyl (abbreviation: NPB) was deposited at the thickness of 10 nm over the composite-including layer 2103 by the vapor deposition technique using resistance heating system, leading to the formation of a hole transporting layer 2104.

Further, a light emitting layer 2105 with a thickness of 30 nm was formed on the hole transporting layer 2104 by co-evaporation of N-phenyl-N-[4-(3-phenylquinoxalin-2-yl)phenyl]-9-phenylcarbazole-3-amine (abbreviation: PCA1PQ) represented by the structural formula (86) with (acetylacetonato)bis[2,3-bis(4-fluorophenyl)quinoxalinato]iridium(III) (abbreviation: Ir(Fdpq)$_2$(acac)). Here, a weight ratio of PCA1PQ and Ir(Fdpq)$_2$(acac) was adjusted to be 1:0.06 (=PCA1PQ:Ir(Fdpq)$_2$(acac)).

After that, bis(2-methyl-8-quinolinolato)(4-phenylphenolato)aluminum (abbreviation: BAlq) was formed at a thickness of 10 nm on the light emitting layer 2105 by the vapor deposition technique using resistance heating system, thereby forming an electron transporting layer 2106.

Moreover, an electron injecting layer 2107 with a thickness of 50 nm was formed on the electron transporting layer 2106 by co-evaporation of tris(8-quinolinolato)aluminum (abbreviation: Alq) with lithium. Here, a weight ratio of Alq to lithium was adjusted to be 1:0.01 (=Alq:lithium).

Finally, aluminum was formed at a thickness of 200 nm on the electron injecting layer 2107 by the vapor deposition technique using resistance heating system, thereby forming a second electrode 2108. Accordingly, a light-emitting element 6 was manufactured.

Figure 66:
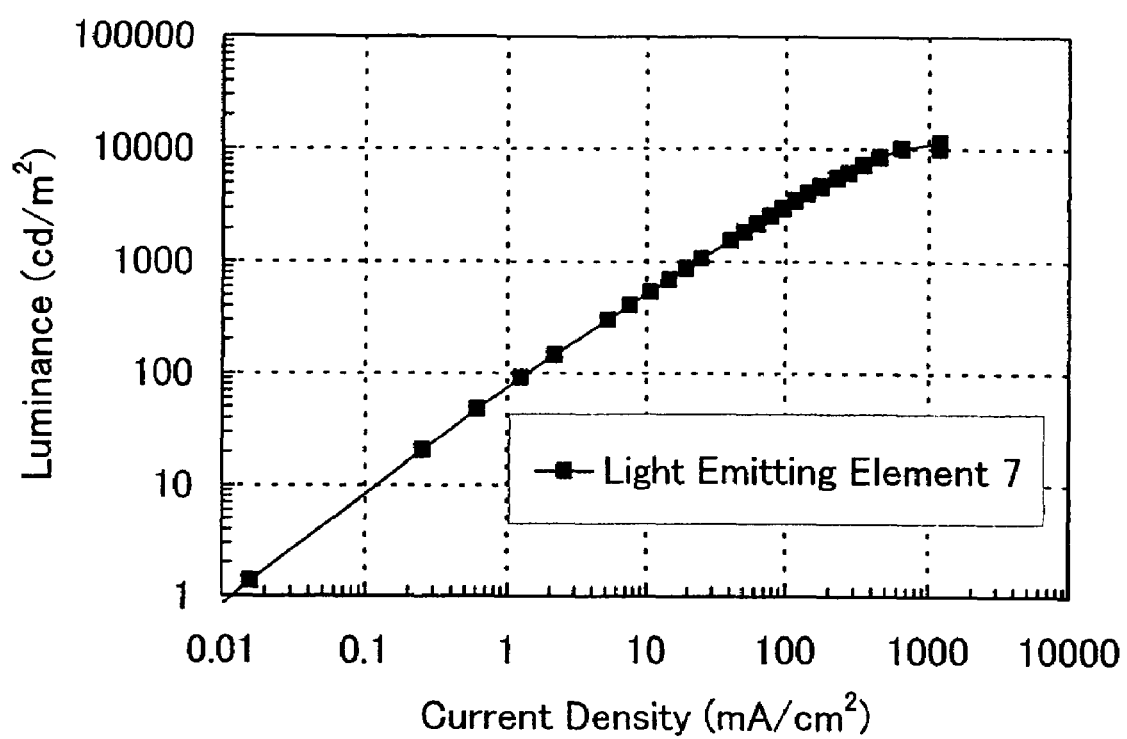
FIG. 66 is a graph showing a current density-luminance characteristic of a light-emitting element fabricated in Example 10.
Figure 67:
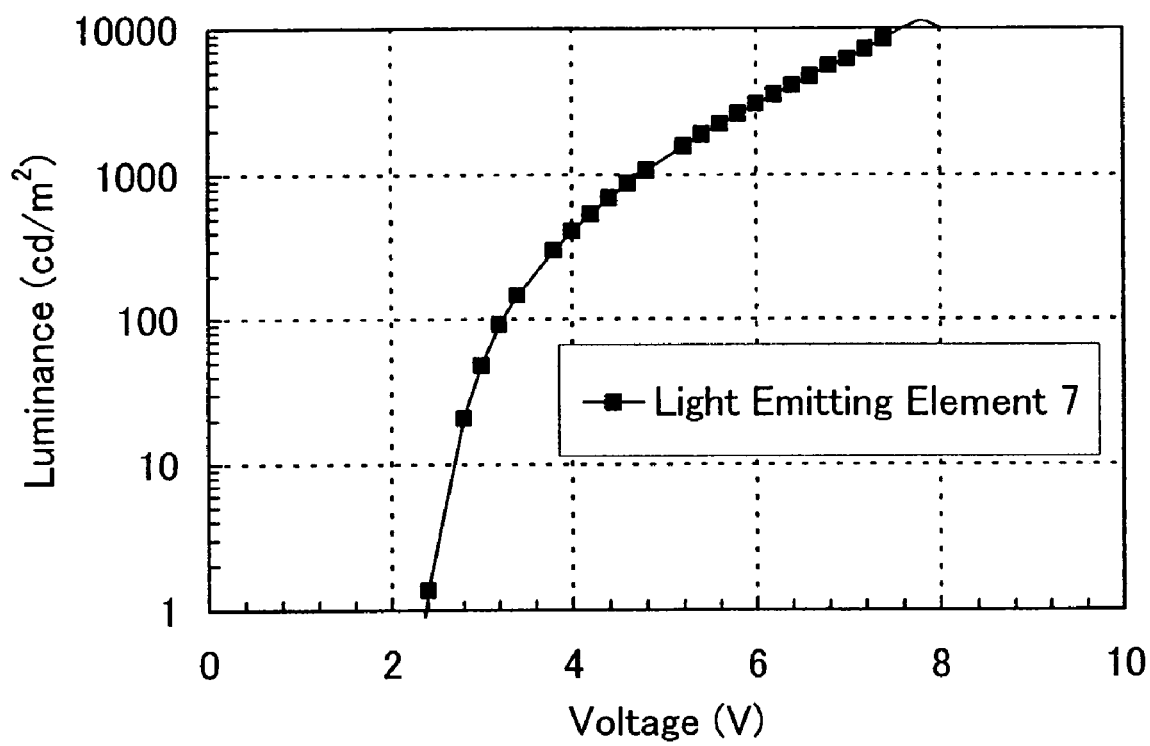
FIG. 67 is a graph showing a voltage-luminance characteristic of a light-emitting element fabricated in Example 10.
Figure 68:
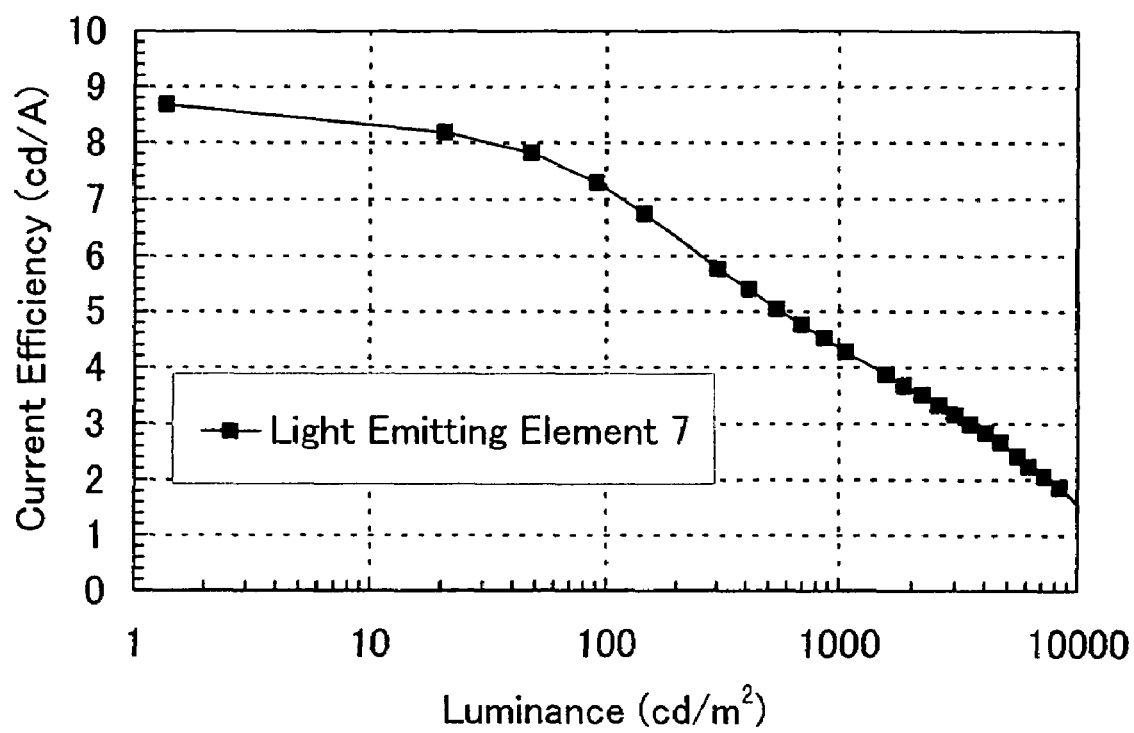
FIG. 68 is a graph showing a luminance-current efficiency characteristic of a light-emitting element fabricated in Example 10.
Figure 69:
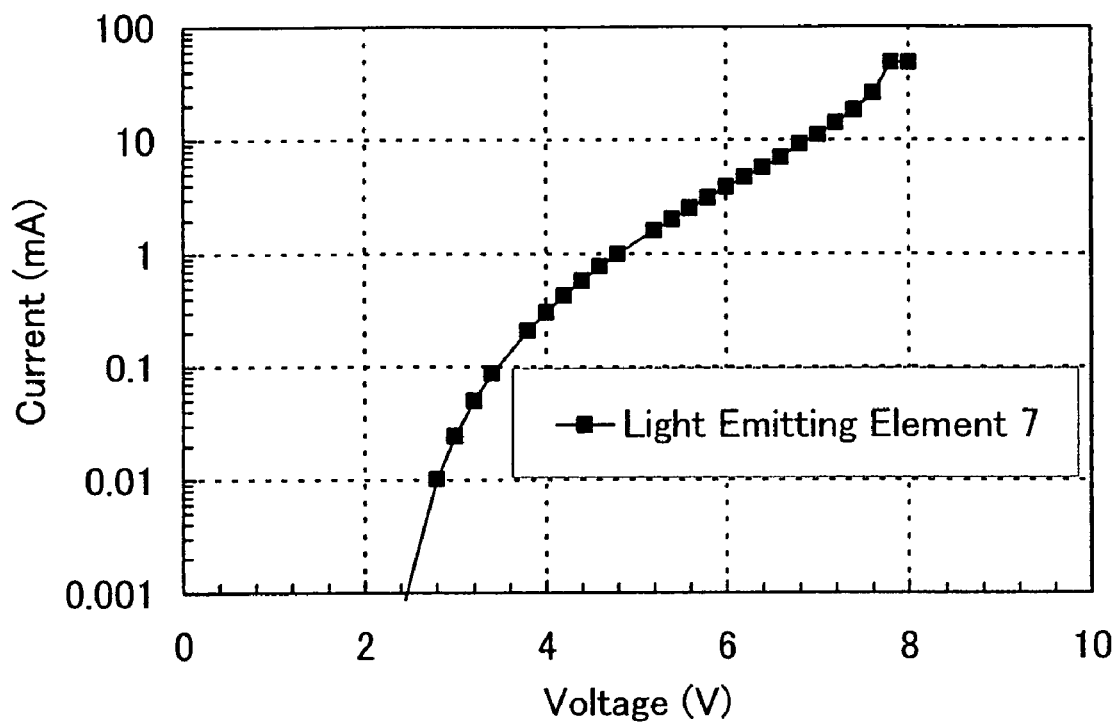
FIG. 69 is a graph showing a voltage-current characteristic of a light-emitting element fabricated in Example 10.
Figure 70:
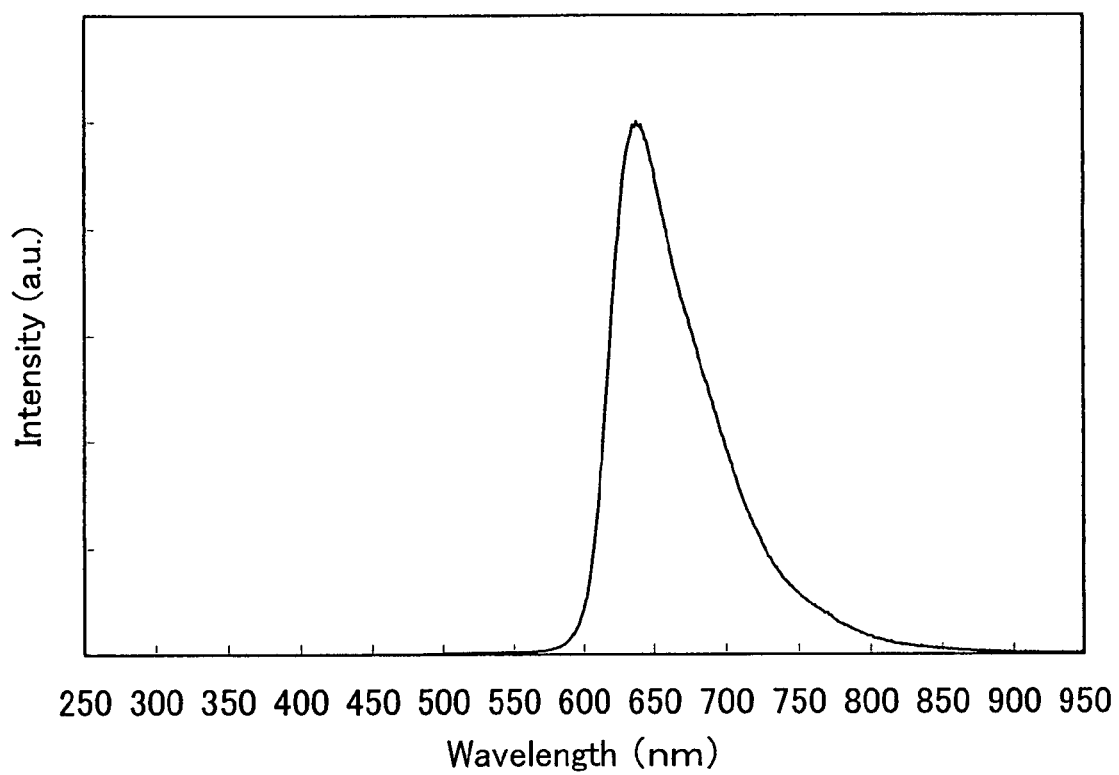
FIG. 70 is a graph showing an emission spectrum of a light-emitting element fabricated in Example 10.

FIG. 66 shows current density-luminance characteristics of the light-emitting element 7. FIG. 67 shows voltage-luminance characteristics. FIG. 68 shows luminance-current efficiency characteristics. FIG. 69 shows voltage-current characteristics. FIG. 70 shows an emission spectrum of the light-emitting element 7 when a current of 1 mA flows. FIG. 70 indicates that emission of the light-emitting element 7 is emission of Ir(Fdpq)$_2$(acac). The CIE chromaticity coordinates at luminance of 1100 cd/m were (x, y)=(0.70, 0.30), and emission of red light with excellent color purity was obtained. Current efficiency at luminance of 1100 cd/m$^2$ was 4.3 cd/A, and external quantum efficiency was 7.4%, which means that high efficiency is attainable. Voltage and current density at luminance of 1100 cd/m$^2$ were 4.8 V and 25 mA/cm$^2$, respectively, and power efficiency was 2.8 lm/W which was an extremely high value. Further, FIGS. 67 and 69 show that a driving voltage is reduced in the light-emitting element 7. Therefore, by using the quinoxaline derivative of the present invention, a light-emitting element with a low driving voltage and reduced and power consumption can be obtained.

EXAMPLE 11

In this example, a material used in the aforementioned examples will be explained.

<<Synthesis of Ir(tppr)$_2$(acac)>>

Hereinafter, an example for the synthesis of (acetylacetonato)bis(2,3,5-triphenylpyrazinato)iridium(III) (abbreviation: [Ir(tppr)$_2$(acac)]) represented by a structural formula (402) will be specifically exemplified.

formula [157]

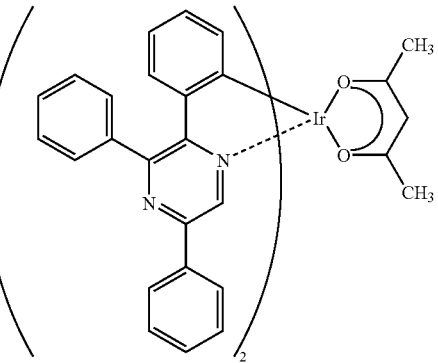

(402)

[Step 1]
Synthesis of 2,3,5-triphenylpyrazine (abbreviation: Htppr) will be explained.

First, in a nitrogen atmosphere, 5.5 mL of a dibutyl ether solution of phenyl lithium (produced by Wako Pure Chemical Industries, Ltd., 2.1 mol/L) and 50 mL of diethyl ether were mixed to prepare a solution. Then, 2.43 g of 2,3-diphenylpyrazine was dropwised into this solution while the solution was being cooled with ice, and the mixture was stirred at room temperature for 24 hours. After the stirring, water was added to the mixture and the organic phase was extracted with diethyl ether. The extracted organic phase washed with water and dried with magnesium sulfate. After the drying, to the organic layer was added an excess amount of activated manganese dioxide, and the mixture was stirred sufficiently, and then filtered. After a solvent of the filtrate was distilled off, the obtained residue was recrystallized with ethanol to give a pyrazine derivative, Htppr (yellow powder), in the yield of 56%. A synthetic scheme of Step 1 is shown in the following (G-1).

formula [158]

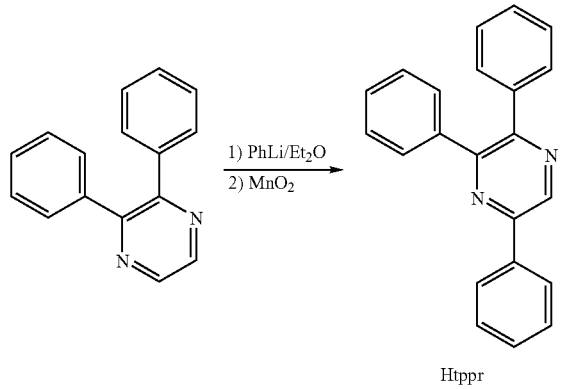

[Step 2]

Synthesis of di-μ-chloro-bis[bis(2,3,5-triphenylpyrazinato)iridium(III)] (abbreviation: [Ir(tppr)$_2$Cl]$_2$) will be explained.

1.08 g of the pyrazine derivative Htppr obtained in the above Step 1 and 0.73 g of iridium chloride hydrate (IrCl$_3$·H$_2$O) (produced by Sigma-Aldrich Corp.) were mixed in a mixed solvent of 30 mL of 2-ethoxyethanol and 10 mL of water, and the mixture was refluxed in a nitrogen atmosphere for 16 hours. The precipitated powder was filtered and washed with ethanol, ether, and then hexane, giving a dinuclear complex [Ir(tppr)$_2$Cl]$_2$ (orange powder) in the yield of 97%. A synthetic scheme of Step 2 is shown in the following (G-2).

formula [159]

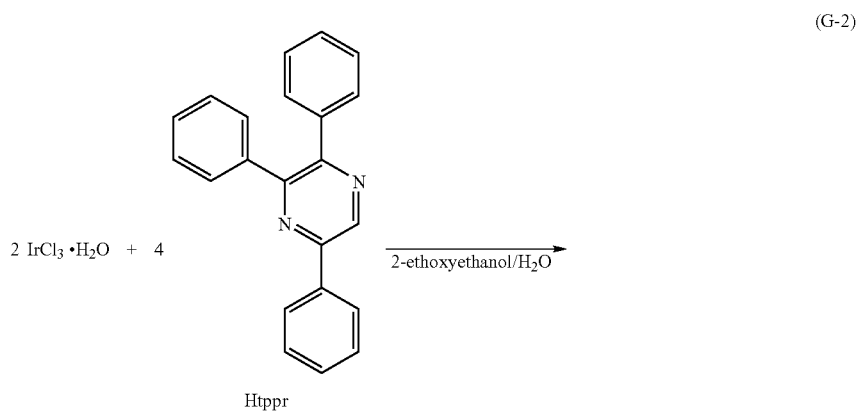

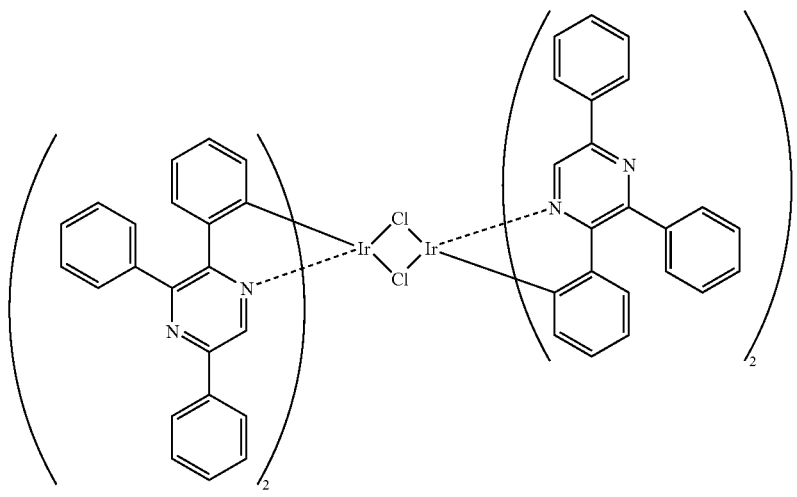

[Step 3]

Synthesis of (acetylacetonato)bis(2,3,5-triphenylpyrazinato)iridium(III) (abbreviation: [Ir(tppr)$_2$(acac)]) will be explained.

2.00 g of the dinuclear complex [Ir(tppr)$_2$Cl]$_2$ obtained in the above Step 2, 0.37 mL of acetylacetone, and 1.26 g of sodium carbonate were mixed in a solvent of 40 mL of 2-ethoxyethanol, and the mixture was refluxed under a nitrogen atmosphere for 18 hours. After the reflux, the mixture was filtered and the filtrate was left for one week. Then, the precipitated crystal was removed by filtration and the solvent of the filtrate was distilled off. The obtained residue was recrystallized with a mixed solvent of dichloromethane and ethanol. A powder obtained by the recrystallization washed with ethanol and then ether, giving the organometallic complex [Ir(tppr)$_2$(acac)] (orange powder) in the yield of 16%. A synthetic scheme of Step 3 is shown in the following (G-3).

Further, a decomposition temperature, $T_d$, of the obtained organometallic complex [Ir(tppr)$_2$(acac)] measured by a thermo-gravimetric/differential thermal analyzer (TG/DTA 320, manufactured by Seiko Instruments Inc.) was 331° C. Therefore, it was found that [Ir(tppr)$_2$(acac)] shows excellent thermal stability.

Figure 54:
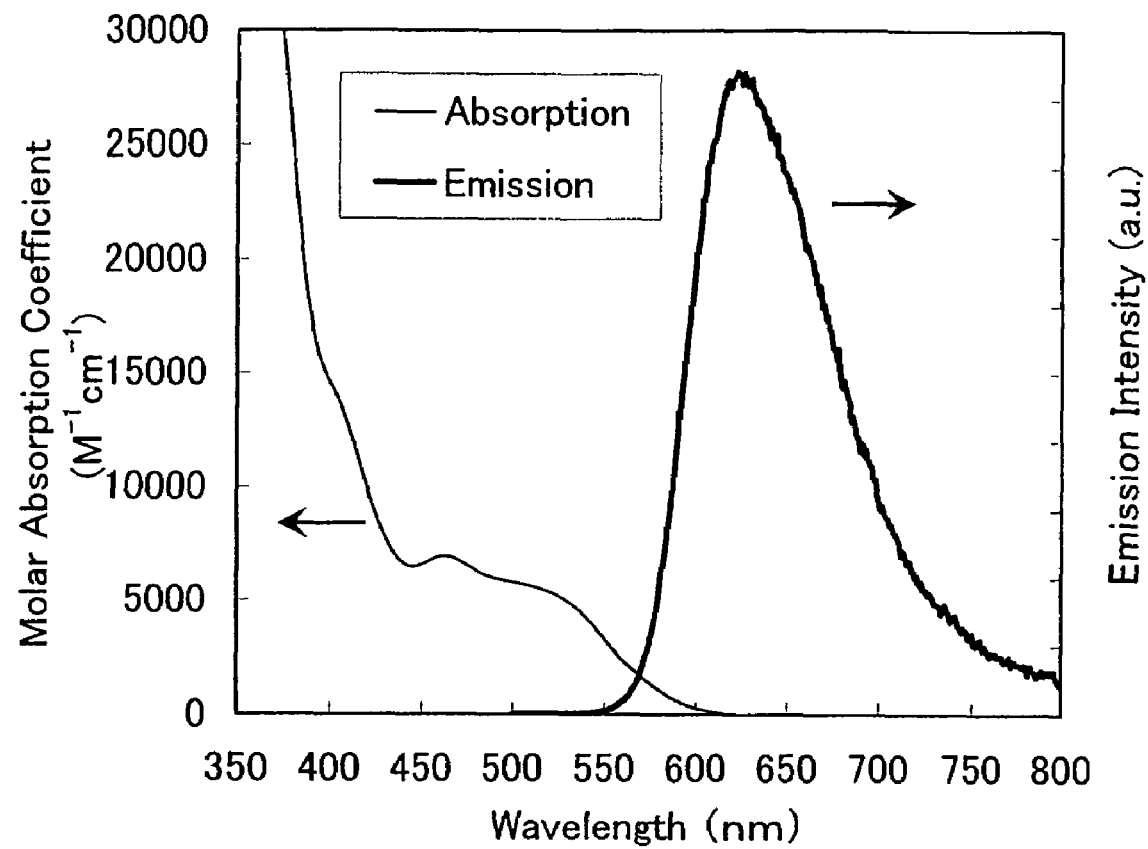
FIG. 54 is a graph showing an absorption spectrum and an emission spectrum of (acetylacetonato)bis(2,3,5-triphenylpyrazinato) iridium(III)

Next, an absorption spectrum of [Ir(tppr)$_2$(acac)] was measured using an ultraviolet-visible spectrophotometer (V-550, manufactured by JASCO Corporation). The measurement was conducted by using a degassed dichloromethane solution (0.10 mmol/L) at a room temperature. In addition, an emission spectrum of [Ir(tppr)$_2$(acac)] was measured using a fluorescence spectrophotometer (FS920, manufactured by Hamamatsu Photonics Corporation). The measurement was conducted by using a degassed dichloromethane solution (0.35 mmol/L) at room temperature. FIG. 54 shows the meaformula [160]

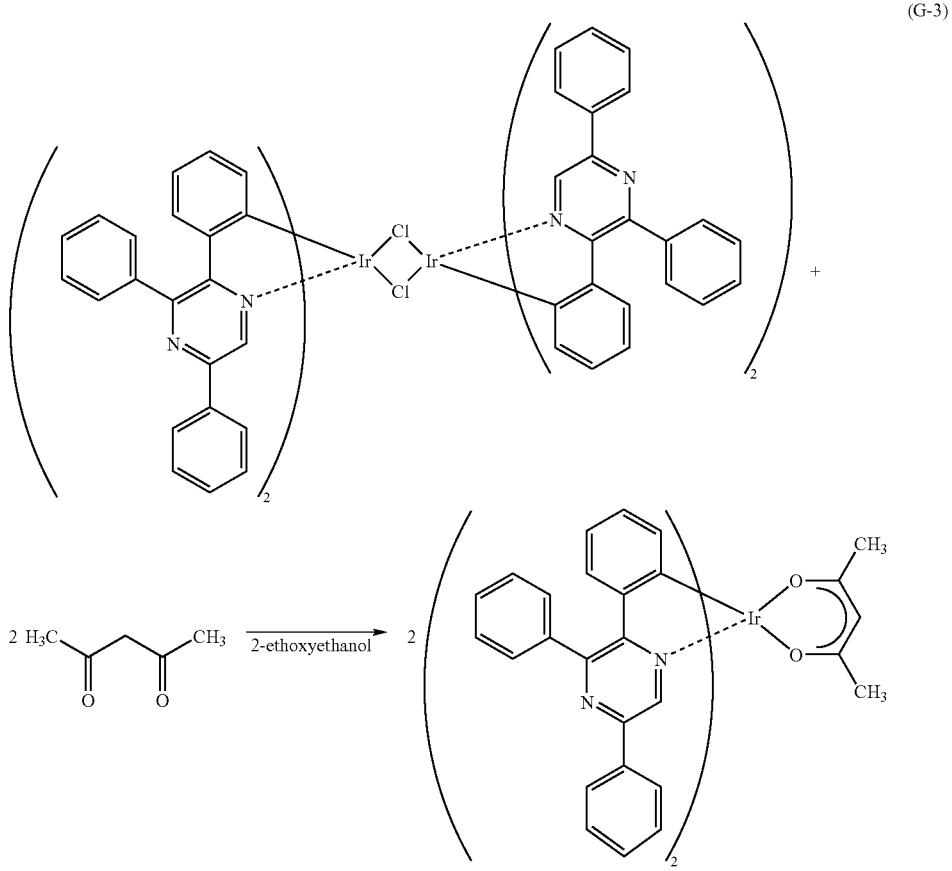

(G-3)

Figure 53A:
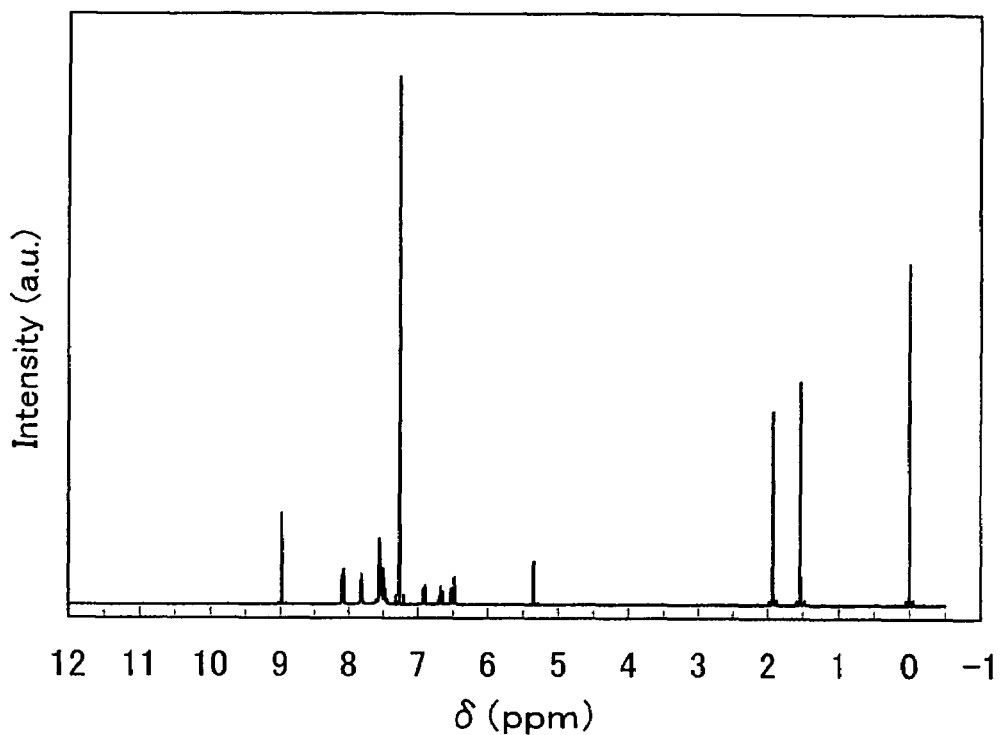
FIGS. 53A and 53B are graphs each showing a $^1$H NMR chart of (acetylacetonato)bis(2,3,5-triphenylpyrazinato)iridium (III)
Figure 53B:
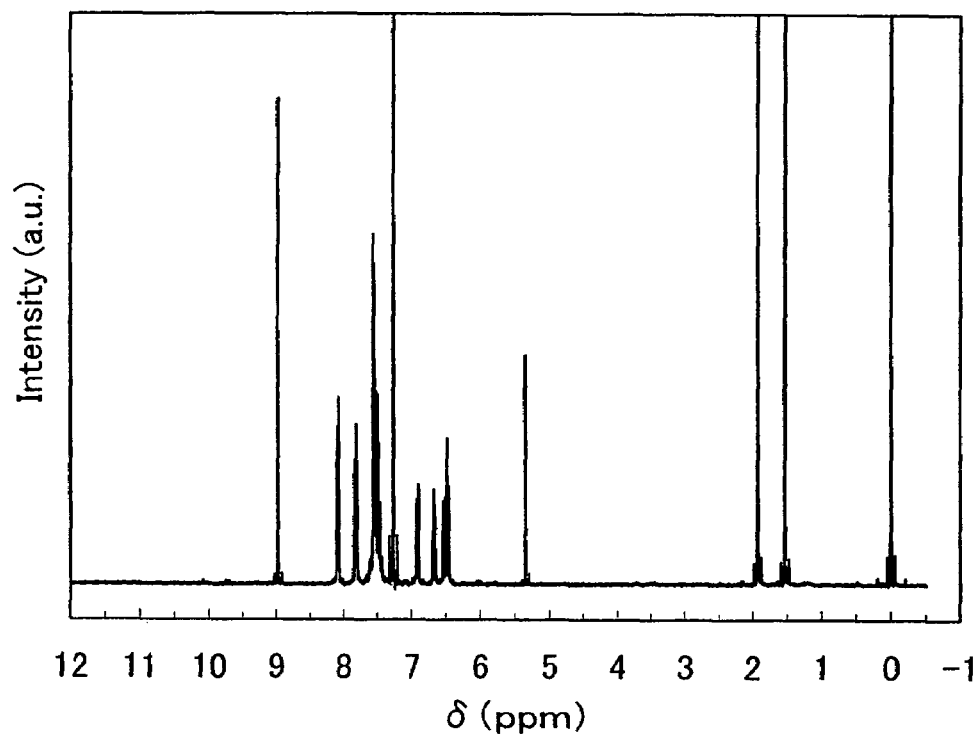

An analysis result of the orange powder obtained in the above Step 3 by nuclear magnetic resonance spectrometry ($^1$H NMR) is shown below. FIGS. 53A and 53B each show a $^1$H NMR chart. FIG. 53B shows an expanded view of FIG. 53A in the vertical axis direction. From FIGS. 53A and 53B, it was confirmed that the organometallic complex [Ir(tppr)$_2$(acac)] represented by the above structural formula (402) was obtained in this Synthesis Example 1.

$^1$H NMR (CDCl$_3$, 300 MHz): δ=1.92 (s, 6H), 5.35 (s, 1H), 6.45-6.54 (m, 4H), 6.67 (td, 2H), 6.91 (d, 2H), 7.41-7.57 (m, 12H), 7.81 (m, 4H), 8.08 (dd, 4H), 8.98 (s, 2H).

surement results. The horizontal axis indicates a wavelength and the vertical axis indicates a molar absorption coefficient and emission intensity.

As shown in FIG. 54, the organometallic complex [Ir(tppr)$_2$(acac)] has a peak of emission at 622 nm, and emission of red-orange light was observed from the solution.

It was revealed that the organometallic complex [Ir(tppr)$_2$(acac)] has several absorption peaks in the visible light region. This is absorption unique to some organometallic complexes such as an ortho-metalated complex, and is considered to correspond to singlet MLCT transition, triplet π-π* transition, triplet MLCT transition, or the like. In particular, the absorption on the longest wavelength side is tailing toward the long-wavelength region. Thus, this absorption is considered to correspond to the triplet MLCT transition. In other words, it was confirmed that the organometallic complex [Ir(tppr)$_2$(acac)] was a compound capable of direct photo-excitation to a triplet excited state and intersystem crossing. Therefore, it can be considered that obtained emission was light emission from the triplet excited state, in other words, phosphorescence.

[Step 4]

A synthetic method of 2,3,5-triphenylpyrazine (abbreviation: Htppr), which was synthesized in the above Step 1, different from Step 1 will be exemplified.

First, 4.60 g of phenylglyoxal (produced by Tokyo Chemical Industries Co., Ltd.) and 7.28 g of meso-1,2-diphenylethylenediamine were mixed in a solvent of 200 mL of ethanol, and the mixture was refluxed in a nitrogen atmosphere for 6 hours. After the reflux, the solvent of this mixture was distilled off, and the obtained residue was recrystallized with ethanol. An ocher powder obtained by the recrystallization was dissolved into dichloromethane, and an excess amount of manganese dioxide was added to the solution. The mixture was stirred sufficiently, and then filtered. After a solvent of the filtrate was distilled off, the obtained residue was recrystallized with ethanol, giving a pyrazine derivative, Htppr (yellow powder), in the yield of 37%. A synthetic scheme of Step 4 is shown in the following (G-1-2).

formula [161]

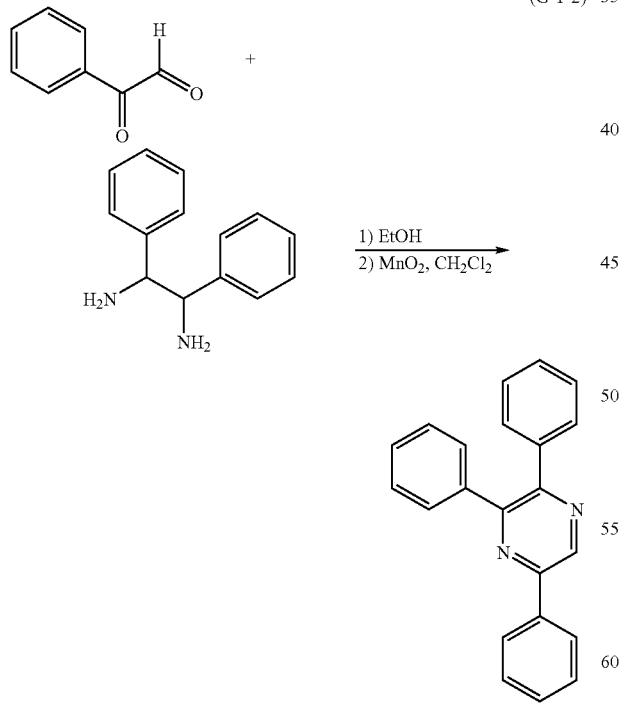

(G-1-2)

This application is based on Japanese Patent Application serial No. 2006-077900 filed in Japan Patent Office on Mar. 21, 2006, the contents of which are hereby incorporated by reference.

EXPLANATION OF REFERENCE

101: substrate, 102: first electrode, 103: first layer, 104: second layer, 105: third layer, 106: fourth layer, 107: second electrode, 301: substrate, 302: first electrode, 303: first layer, 304: second layer, 305: third layer, 306: fourth layer, 307: second electrode, 501: first electrode, 502: second electrode, 511: first light-emitting unit, 512: second light-emitting unit, 513: charge generation layer, 601: source side driver circuit, 602: pixel portion, 603: gate side driver circuit, 604: sealing substrate, 605: sealing material, 607: space, 608: wiring, 609: FPC (flexible printed circuit), 610: element substrate, 611: switching TFT, 612: current control TFT, 613: first electrode, 614: insulator, 616: layer including light-emitting substance, 617: second electrode, 618: light-emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: layer including light-emitting substance, 956: electrode, 1201: source electrode, 1202: active layer, 1203: drain electrode, 1204: gate electrode, 2001: housing, 2002: light source, 2101: substrate, 2102: first electrode, 2103: layer including composite material, 2104: hole transporting layer, 2105: light emitting layer, 2106: electron transporting layer, 2107: electron injecting layer, 2108: second electrode, 9101: housing, 9102: supporting base, 9103: display portion, 9104: speaker portion, 9105: video input terminal, 9201: main body, 9202: housing, 9203: display portion, 9204: keyboard, 9205: external connection port, 9206: pointing mouse, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: a remote control receiving portion, 9506: image receiving portion, 9507: battery, 9508: audio input portion, 9509: operation key, 9510: eye piece portion

The invention claimed is:

1. A compound represented by the structure:

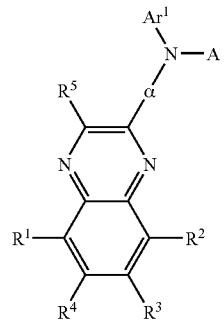

wherein:

R$^1$ to R$^4$ each represent any of a hydrogen atom, an alkyl group having 1 to 4 carbon atoms, or an aryl group having 6 to 25 carbon atoms;

R$^5$ represents any of a hydrogen atom, an alkyl group having 1 to 4 carbon atoms, or an aryl group having 6 to 25 carbon atoms;

Ar$^1$ represents an aryl group having 6 to 25 carbon atoms, α represents an arylene group having 6 to 25 carbon atoms;

A is represented by the structure:

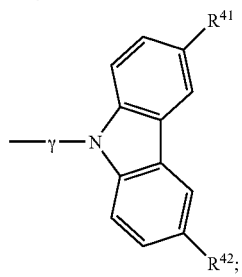

γ represents an arylene group having 6 to 25 carbon atoms; and $R^{41}$ and $R^{42}$ each represent any of a hydrogen atom, an alkyl group having 1 to 4 carbon atoms, or an aryl group having 6 to 25 carbon atoms.

2. A compound according to claim 1, wherein:
A is represented by the structure:

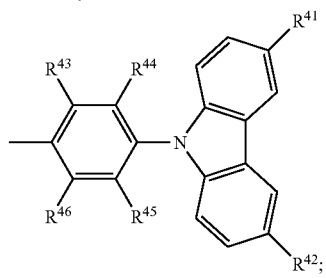

$R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

3. A compund according to claim 1,
wherein:
$Ar^1$ is represented by the structure:

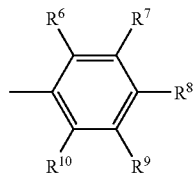

$R^6$ to $R^{10}$ each represent any of a hydrogen atom, an alkyl group having 1 to 4 carbon atoms, or an aryl group having 6 to 15 carbon atoms;
A is represented by the structure:

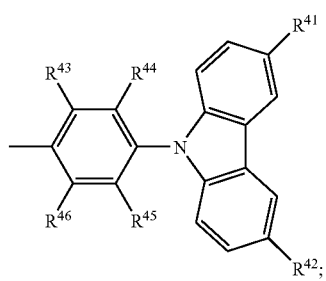

$R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

4. A compund according to claim 1,
wherein:
α is represented by the structure:

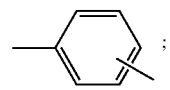

$Ar^1$ is represented by the structure:

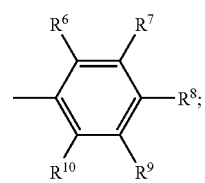

$R^6$ to $R^{10}$ each represent any of a hydrogen atom, an alkyl group having 1 to 4 carbon atoms, or an aryl group having 6 to 15 carbon atoms;
A is represented by the structure:

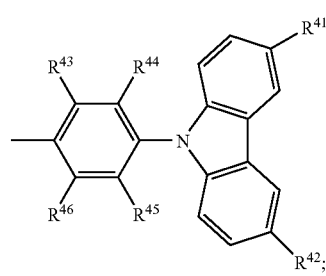

$R^{41}$ and $R^{42}$ each represent any of a hydrogen atom, an alkyl group having 1 to 4 carbon atoms, or an aryl group having 6 to 25 carbon atoms; and $R^{43}$ to $R^{46}$ each represent any of a hydrogen atom, an alkyl group having 1 to 4 carbon atoms, or an aryl group having 6 to 15 carbon atoms.

5. A compound according to claim 1,
wherein:
$R^1$ to $R^4$ each represent a hydrogen atom;
$R^5$ represents any of a hydrogen atom, an alkyl group having 1 to 4 carbon atoms, or an aryl group having 6 to 25 carbon atoms;
α is represented by the structure:

425
Ar¹ is represented by the structure:
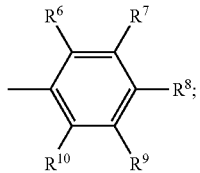
$R^6$ to $R^{10}$ each represent any of a hydrogen atom, an alkyl group having 1 to 4 carbon atoms, or an aryl group having 6 to 15 carbon atoms;
426
A is represented by the structure:
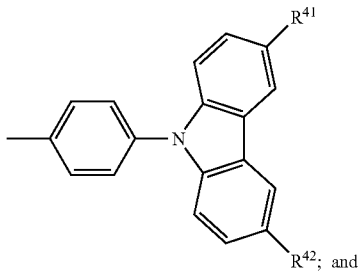
$R^{41}$ and $R^{42}$ each represent any of a hydrogen atom, an alkyl group having 1 to 4 carbon atoms, or an aryl group having 6 to 25 carbon atoms.
* * * * *

UNITED STATES PATENT AND TRADEMARK OFFICE
CERTIFICATE OF CORRECTION

PATENT NO. : 7,696,348 B2
APPLICATION NO. : 11/723385
DATED : April 13, 2010
INVENTOR(S) : Masakazu Egawa et al.

It is certified that error appears in the above-identified patent and that said Letters Patent is hereby corrected as shown below:

in the specification, column 387, line 22, "After the reaction, the reaction mixture washed" should read "After the reaction, the reaction mixture was washed"

in the specification, column 387, line 25, "organic phase washed" should read "organic phase was washed"

in the specification, column 388, line 32, "washed with ethanol" should read "was washed with ethanol"

in the specification, column 391, line 8, "the mixture washed with water," should read "the mixture was washed with water,"

in the specification, column 397, line 45, "Step 1" should read "[Step 1]"

in the specification, column 398, line 52, ", and the solution washed with" should read ", and the solution was washed with"

in the specification, column 408, line 37, "Was" should read "was"

in the specification, column 413, line 5, "obtained filtrate washed with a sodium" should read "obtained filtrate was washed with a sodium"

in the specification, column 416, line 59, "extracted organic phase washed with water" should read "extracted organic phase was washed with water"

in the claims, claim 3, line 1, "A compund;" should read "A compound"

in the claims, claim 4, line 1, "A compund;" should read "A compound"

Signed and Sealed this

Twenty-fourth Day of August, 2010

David J. Kappos
*Director of the United States Patent and Trademark Office*